US012649727B2

(12) United States Patent
Yang et al.

(10) Patent No.: US 12,649,727 B2
(45) Date of Patent: Jun. 9, 2026

(54) EFGR INHIBITOR, PREPARATION METHOD THEREFOR AND APPLICATION THEREOF

(71) Applicant: Abbisko Therapeutics Co., Ltd, Shanghai (CN)

(72) Inventors: Fei Yang, Shanghai (CN); Shuqun Yang, Shanghai (CN); Hongping Yu, Shanghai (CN); Zhui Chen, Shanghai (CN); Yaochang Xu, Shanghai (CN)

(73) Assignee: Abbisko Therapeutics Co., Ltd

( * ) Notice: Subject to any disclaimer, the term of this patent is extended or adjusted under 35 U.S.C. 154(b) by 566 days.

(21) Appl. No.: 18/040,598

(22) PCT Filed: Aug. 9, 2021

(86) PCT No.: PCT/CN2021/111411

§ 371 (c)(1),
(2) Date: Feb. 3, 2023

(87) PCT Pub. No.: WO2022/033410

PCT Pub. Date: Feb. 17, 2022

(65) Prior Publication Data

US 2023/0271936 A1 Aug. 31, 2023

(30) Foreign Application Priority Data

| | | |
|---|---|---|
| Aug. 10, 2020 | (CN) | 202010794066.8 |
| Dec. 24, 2020 | (CN) | 202011546021.5 |
| Jun. 18, 2021 | (CN) | 202110676156.1 |

(51) Int. Cl.

| | |
|---|---|
| ***C07D 401/12*** | (2006.01) |
| ***C07D 239/94*** | (2006.01) |
| ***C07D 401/14*** | (2006.01) |
| ***C07D 403/12*** | (2006.01) |
| ***C07D 405/12*** | (2006.01) |
| ***C07D 405/14*** | (2006.01) |

(52) U.S. Cl.

CPC ......... *C07D 401/12* (2013.01); *C07D 239/94* (2013.01); *C07D 401/14* (2013.01); *C07D 403/12* (2013.01); *C07D 405/12* (2013.01); *C07D 405/14* (2013.01)

(58) Field of Classification Search

CPC .............. A61K 31/192; A61K 2300/00; A61K 31/706; A61K 31/455; A61K 31/405; A61K 31/7088; A61K 39/00; A61P 3/04; A61P 3/10; A61P 9/00; A61P 9/04; A61P 9/10; A61P 9/12

See application file for complete search history.

(56) References Cited

FOREIGN PATENT DOCUMENTS

| | | | | |
|---|---|---|---|---|
| CN | 101304978 B | | 12/2012 | |
| WO | WO-2007055514 A1 | * | 5/2007 | ............. A61P 43/00 |
| WO | WO 2007/082434 A1 | | 7/2007 | |
| WO | WO 2020/009156 A1 | | 1/2020 | |
| WO | WO 2020/068867 A1 | | 4/2020 | |
| WO | WO-2021030711 A1 | * | 2/2021 | ........... C07D 403/06 |

OTHER PUBLICATIONS

International Search Report for corresponding International application PCT/CN2021/111411, mailed Nov. 9, 2021, 4 pgs., with English translation, 2 pgs.

Written Opinion of the International Searching Authority for corresponding International application PCT/CN2021/111411, mailed Nov. 9, 2021, 6 pgs.

* cited by examiner

*Primary Examiner* — Pierre Paul Eleniste

(74) *Attorney, Agent, or Firm* — Crowell & Moring LLP; Yuezhong Feng

(57) ABSTRACT

An EGFR inhibitor having the structure of formula (I), a preparation method therefor, a pharmaceutical composition containing same, a use of same as an EGFR inhibitor, and a use of same in preparing a drug for treating and/or preventing a cancer, a tumor, or a metastatic disease at least partially related to an EGFR exon 20 insertion, deletion, or other mutation, and in particular a use in preparing a drug for treating and/or preventing a hyperproliferative disease and an induced cell death disorder. Each substituent of formula (I) has the same definition as in the description.

(I)

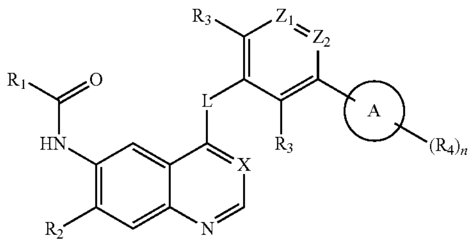

3 Claims, No Drawings

EFGR INHIBITOR, PREPARATION METHOD THEREFOR AND APPLICATION THEREOF

RELATED APPLICATIONS

This application is a U.S. National Phase entry under 35 U.S.C. § 371 of International Application No. PCT/CN2021/111411, filed 9 Aug. 2021, which claims the benefit of Chinese Patent Application No. 202010794066.8, filed 10 Aug. 2020, Chinese Patent Application No. 202011546021.5, filed 24 Dec. 2020, and Chinese Patent Application No. 202110676156.1, filed 18 Jun. 2021, the contents of which are incorporated herein by reference in their entireties.

TECHNICAL FIELD

The present invention belongs to the field of pharmaceutical synthesis, and particularly relates to an EGFR inhibitor, preparation method therefor and application thereof.

BACKGROUND

Lung cancer is the leading cause of cancer death worldwide, with non-small cell lung cancer (NSCLC) accounting for 85%. Multi-target therapies against epidermal growth factor receptor (EGFR) mutations, anaplastic lymphoma kinase (ALK) translocations, ROS1 proto-oncogene receptor tyrosine kinase (ROS1) rearrangements and B-raf proto-oncogenes, serine/threonine kinases (BRAF) have been successfully developed and clinically validated. Inhibitors against EGFR can significantly improve progression-free survival of adenocarcinoma in NSCLC, while acquired resistance mutations of these inhibitors can be targeted by the third generation EGFR inhibitors.

Although classical EGFR activating mutations (Exons 19 and 21) and drug resistance mutation (T790M) can be inhibited by existing medicaments, but insertion mutation of Exon 20 also results in structural activation of EGFR signaling and is insensitive to all of existing EGFR inhibitors. The mutation of Exon 20 is heterogeneous and includes insertions or repeats of 1-7 amino acids between amino acids at positions 762-774 of the EGFR protein. In NSCLC, the mutation frequency of Exon 20 in EGFR is 4-10% of all mutations in EGFR. These mutations are mutually exclusive with other known oncogene-driven mutations and are enriched in adenocarcinomas of women, non-smokers, Asian populations, and non-small cell lung cancer patients. In addition to NSCLC, the insertion mutation of EGFR Exon 20 is also seen in a rare head and neck cancer, namely sinonasal squamous cell carcinoma (SNSCC). In addition, a structurally-similar insertion mutation of Exon 20 is also found in HER2, another member of the EGFR family.

Several retrospective analytical studies have shown that currently-available first, second and third-generation EGFR inhibitors have limited the therapeutic effect against the insertion mutation of Exon 20, with the exception of the mutation of A763-Y764insFQEA. An irreversible inhibitor Poziotinib and an EGFR/MET bispecific antibody Amivantamab are in clinical trials. Several small-molecule inhibitors, including TAK-788 and TAS-6417, have shown clinically-significant efficacy in non-small cell lung cancer patients with EGFR Exon 20. However, due to their limited selectivity for EGFR wild type, adverse effects in clinical use are unavoidable and may lead to dose limiting toxicity. Meanwhile, the existing compounds may exist clinically the problem of insufficient exposure. Thus, there is an urgent need for small-molecule inhibitors with higher exposure and/or high selectivity against the insertion mutation of EGFR Exon 20 for these patients.

SUMMARY

The object of the present invention is to provide an EGFR inhibitor, preparation method therefor and application thereof. A series of compounds of the present invention have a strong inhibition effect on the cytological activity of an insertion, deletion or other mutation of EGFR Exon 20, have a high selectivity for EGFR wild type, and can be widely applied to the preparation of medicaments for treating and/or preventing cancer, tumor or metastatic disease at least partially associated with an insertion, deletion or other mutation of EGFR Exon 20, particularly medicaments for treating hyperproliferative diseases and diseases for inducing cell death disorder, so that a new generation of EGFR inhibitors is expected to be developed.

The first aspect of the present invention provides a compound of formula (I), a stereoisomer or pharmaceutically acceptable salt thereof:

(I)

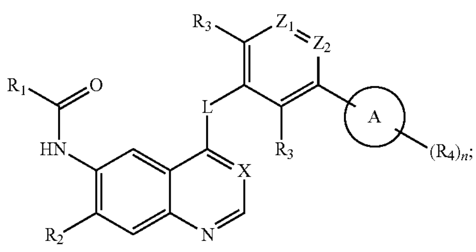

wherein ring A is $C_{6-10}$ aryl or 5-10 membered heteroaryl;

L is —NR— or —O—;

X is N or $CR_5$;

$Z_1$ and $Z_2$ are each independently N or $CR_3$;

R is selected from the group consisting of hydrogen, deuterium, hydroxy, $C_{1-10}$ alkyl, $C_{1-10}$ haloalkyl, $C_{1-10}$ deuterioalkyl, —$C_{0-8}$ alkyl-C(O)O$R_{10}$, —$C_{0-8}$ alkyl-C(O)$R_{11}$, —$C_{0-8}$ alkyl-C(=N$R_{12}$)$R_{11}$ and —$C_{0-8}$ alkyl-C(O)N$R_{12}R_{13}$;

$R_1$ is vinyl or ethynyl, the vinyl or ethynyl is optionally further substituted with one or more substituents selected from the group consisting of deuterium, halogen, cyano, hydroxy, $C_{1-10}$ alkyl, $C_{1-10}$ haloalkyl, $C_{1-10}$ deuterioalkyl, $C_{3-6}$ cycloalkyl, 3-6 membered heterocyclyl and —$C_{0-4}$ alkyl-N$R_6R_7$;

$R_2$ is selected from the group consisting of hydrogen, deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, —$C_{0-8}$ alkyl-$SF_5$, —$C_{0-8}$ alkyl-S(O)$_r R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$, the above groups are independently optionally further substituted with one or more substituents selected from the group consisting of deuterium, halogen, cyano, nitro, azido, $C_{1-10}$ alkyl, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r R_8$, —$C_{0-8}$ alkyl-O—$R_9$, —$C_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$, the above groups are independently optionally more further substituted with one or more substituents selected from the group consisting of deuterium, halogen, cyano, nitro, azido, C$_{1-10}$ alkyl, C$_{1-10}$ haloalkyl, C$_{1-10}$ deuterioalkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, ═O, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$;

each R$_3$ is independently selected from the group consisting of hydrogen, deuterium, halogen, cyano, nitro, azido, C$_{1-10}$ alkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$, or wherein 2 adjacent R$_3$, together with the moiety to which they are directly attached, form a C$_{6-10}$ cycloalkyl, 5-10 membered heterocyclyl, C$_{6-10}$ aryl or 5-10 membered heteroaryl, the above groups are independently optionally further substituted with one or more substituents selected from the group consisting of deuterium, halogen, cyano, nitro, azido, C$_{1-10}$ alkyl, C$_{1-10}$ haloalkyl, C$_{1-10}$ deuterioalkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, ═O, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$;

each R$_4$ is independently selected from the group consisting of hydrogen, deuterium, halogen, cyano, nitro, azido, C$_{1-10}$ alkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$, or when n≥2, wherein 2 adjacent R$_4$, together with the moiety to which they are directly attached, form a C$_{6-10}$ cycloalkyl, 5-10 membered heterocyclyl, C$_{6-10}$ aryl or 5-10 membered heteroaryl, the above groups are independently optionally further substituted with one or more substituents selected from the group consisting of deuterium, halogen, cyano, nitro, azido, C$_{1-10}$ alkyl, C$_{1-10}$ haloalkyl, C$_{1-10}$ deuterioalkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, ═O, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$;

R$_5$ is selected from the group consisting of hydrogen, deuterium, halogen, cyano, nitro, azido, C$_{1-10}$ alkyl, C$_{1-10}$ haloalkyl, C$_{1-10}$ deuterioalkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$;

R$_6$ and R$_7$ are each independently selected from the group consisting of hydrogen, deuterium, hydroxy, C$_{1-10}$ alkyl, —C$_{0-8}$ alkyl-C(O)OR$_{10}$, —C$_{0-8}$ alkyl-C(O)R$_{11}$, —C$_{0-8}$ alkyl-C(═NR$_2$)R$_{11}$ and —C$_{0-8}$ alkyl-C(O)NR$_{12}$R$_{13}$, the above groups are independently optionally further substituted with one or more substituents selected from the group consisting of deuterium, halogen, cyano, nitro, azido, C$_{1-10}$ alkyl, C$_{1-10}$ haloalkyl, C$_{1-10}$ deuterioalkyl, C$_{2-10}$ alkenyl, C$_{2-10}$ alkynyl, C$_{3-12}$ cycloalkyl, 3-12 membered heterocyclyl, C$_{6-10}$ aryl, 5-10 membered heteroaryl, ═O, —C$_{0-8}$ alkyl-SF$_5$, —C$_{0-8}$ alkyl-S(O)$_r$R$_8$, —C$_{0-8}$ alkyl-O—R$_9$, —C$_{0-8}$ alkyl-C(O)OR$_{10}$, —C$_{0-8}$ alkyl-C(O)R$_{11}$, —C$_{0-8}$ alkyl-O—C(O)R$_{11}$, —C$_{0-8}$ alkyl-NR$_{12}$R$_{13}$, —C$_{0-8}$ alkyl-C(═NR$_{12}$)R$_{11}$, —C$_{0-8}$ alkyl-N(R$_{12}$)—C(═NR$_{13}$)R$_{11}$, —C$_{0-8}$ alkyl-C(O)NR$_{12}$R$_{13}$ and —C$_{0-8}$ alkyl-N(R$_{12}$)—C(O)R$_{11}$;

each R$_8$ is independently selected from the group consisting of hydrogen, deuterium, hydroxy, C$_{1-10}$ alkyl, C$_{2-10}$ alkenyl, C$_{3-12}$ cycloalkyl, 3-12 membered heterocyclyl, C$_6$-10 aryl, 5-10 membered heteroaryl and —NR$_{12}$R$_{13}$, the above groups are independently optionally further substituted with one or more substituents selected from the group consisting of deuterium, halogen, hydroxy, oxo, C$_{1-10}$ alkyl, C$_{1-10}$ alkoxy, C$_{3-12}$ cycloalkyl, C$_{3-12}$ cycloalkyloxy, 3-12 membered heterocyclyl, 3-12 membered heterocyclyloxy, C$_{6-10}$ aryl, C$_{6-10}$ aryloxy, 5-10 membered heteroaryl, 5-10 membered heteroaryloxy and —NR$_{12}$R$_{13}$;

each of R$_9$ and R$_{10}$ is independently selected from the group consisting of hydrogen, deuterium, C$_{1-10}$ alkyl, C$_{2-10}$ alkenyl, C$_{3-12}$ cycloalkyl, 3-12 membered heterocyclyl, C$_6$-10 aryl and 5-10 membered heteroaryl, the above groups are independently optionally further substituted with one or more substituents selected from the group consisting of deuterium, halogen, hydroxy, oxo, cyano, C$_{1-10}$ alkyl, C$_{1-10}$ alkoxy, C$_{3-12}$ cycloalkyl, C$_{3-12}$ cycloalkyloxy, 3-12 membered heterocyclyl, 3-12 membered heterocyclyloxy, C$_{6-10}$ aryl, C$_{6-10}$ aryloxy, 5-10 membered heteroaryl, 5-10 membered heteroaryloxy and —NR$_{12}$R$_{13}$;

each R$_{11}$ is independently selected from the group consisting of hydrogen, deuterium, hydroxy, C$_{1-10}$ alkyl, C$_{1-10}$ alkoxy, C$_{2-10}$ alkenyl, C$_{2-10}$ alkynyl, C$_{3-12}$ cycloalkyl, C$_{3-12}$ cycloalkyloxy, 3-12 membered heterocyclyl, 3-12 membered heterocyclyloxy, C$_{6-10}$ aryl, C$_{6-10}$ aryloxy, 5-10 membered heteroaryl, 5-10 membered heteroaryloxy and —NR$_{12}$R$_{13}$, the above groups are independently optionally further substituted with one or more substituents selected from the group consisting of deuterium, halogen, hydroxy, cyano, C$_{1-10}$ alkyl, C$_{1-10}$ alkoxy, C$_{3-12}$ cycloalkyl, C$_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy and —$NR_{12}R_{13}$;

each of $R_{12}$ and $R_{13}$ is independently selected from the group consisting of hydrogen, deuterium, hydroxy, $C_{1-10}$ alkoxy, $C_{2-10}$ alkenyl, $C_{2-10}$ alkynyl, $C_{3-12}$ cycloalkyl, 3-12 membered heterocyclyl, $C_{6-10}$ aryl, 5-10 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-10}$ alkylamino, di$C_{1-10}$ alkylamino and $C_{1-10}$ alkanoyl, the above groups are independently optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$alkylamino, di$C_{1-10}$ alkylamino and $C_{1-10}$ alkanoyl, or, $R_{12}$ and $R_{13}$, together with the nitrogen atom to which they are directly attached thereto, form a 4-10 membered heterocyclyl or 5-10 membered heteroaryl, the 4-10 membered heterocyclyl or 5-10 membered heteroaryl is optionally further substituted with one or more substituents selected from the group consisting of deuterium, halogen, hydroxy, $C_{1-10}$ alkyl, $C_{2-10}$ alkenyl, $C_{2-10}$ alkynyl, $C_{1-10}$ haloalkyl, $C_{1-10}$ deuterioalkyl, $C_{1-10}$ alkoxy, $C_{3-12}$ cycloalkyl, $C_{3-12}$ cycloalkyloxy, 3-12 membered heterocyclyl, 3-12 membered heterocyclyloxy, $C_{6-10}$ aryl, $C_{6-10}$ aryloxy, 5-10 membered heteroaryl, 5-10 membered heteroaryloxy, amino, mono$C_{1-10}$ alkylamino, di$C_{1-10}$ alkylamino and $C_{1-10}$ alkanoyl;

n is 0, 1, 2, 3 or 4; and each r is independently 0, 1 or 2.

As a preferred embodiment, in the compound of formula (I), the stereoisomer or pharmaceutically acceptable salt thereof, $R_5$ is selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-g}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(═$NR_{12}$)$R_{11}$, —$C_{0-4}$ alkyl-N($R_{12}$)—C(═$NR_{13}$)$R_{11}$, —$C_{0-4}$ alkyl-C(O)$NR_{12}R_{13}$ and —$C_{0-4}$ alkyl-N($R_{12}$)—C(O)$R_{11}$;

preferably, $R_5$ is selected from the group consisting of hydrogen, deuterium, fluoro, chloro, cyano, $C_{1-4}$ alkyl, $C_{1-4}$ haloalkyl, $C_{1-4}$ deuterioalkyl, —$SF_5$, —O—$R_9$, —C(O)$OR_{10}$, —C(O)$R_{11}$, —O—C(O)$R_{11}$, —$NR_{12}R_{13}$ and —C(O)$NR_{12}R_{13}$;

wherein, $R_8$, $R_9$, $R_{10}$, $R_{11}$, $R_{12}$, $R_{13}$ and r are described as those in the compound of formula (I).

As a preferred embodiment, in the compound of formula (I), the stereoisomer or pharmaceutically acceptable salt thereof, R is selected from the group consisting of hydrogen, deuterium, hydroxy, $C_{1-4}$ alkyl, $C_{1-4}$ haloalkyl, $C_{1-4}$ deuterioalkyl, —$C_{0-4}$ alkyl-C(O)$OR_{10}$, —$C_{0-4}$ alkyl-C(O)$R_{11}$, —$C_{0-4}$ alkyl-C(═$NR_{12}$)$R_{11}$ and —$C_{0-4}$ alkyl-C(O)$NR_{12}R_{13}$;

$R_1$ is vinyl or ethynyl, the vinyl or ethynyl is optionally further substituted with one or more substituents selected from the group consisting of deuterium, fluoro, cyano, hydroxy, $C_{1-4}$ alkyl, $C_{1-4}$ haloalkyl, $C_{1-4}$ deuterioalkyl, $C_{3-6}$ cycloalkyl, 3-6 membered heterocyclyl and —$C_{0-4}$ alkyl-$NR_6R_7$;

$R_6$ and $R_7$ are each independently selected from the group consisting of hydrogen, deuterium, hydroxy, $C_{1-4}$ alkyl, —$C_{0-4}$ alkyl-C(O)$OR_{10}$, —$C_{0-4}$ alkyl-C(O)$R_{11}$, —$C_{0-4}$ alkyl-C(═$NR_{12}$)$R_{11}$ and —$C_{0-4}$ alkyl-C(O)$NR_{12}R_{13}$, the above groups are independently optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-g}$ aryl, 5-8 membered heteroaryl, ═O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(═$NR_{12}$)$R_{11}$, —$C_{0-4}$ alkyl-N($R_{12}$)—C(═$NR_{13}$)$R_{11}$, —$C_{0-4}$ alkyl-C(O)$NR_{12}R_{13}$ and —$C_{0-4}$ alkyl-N($R_{12}$)—C(O)$R_{11}$;

wherein, $R_8$, $R_9$, $R_{10}$, $R_{11}$, $R_{12}$, $R_{13}$ and r are described as those in the compound of formula (I).

As a preferred embodiment, in the compound of formula (I), the stereoisomer or pharmaceutically acceptable salt thereof, each $R_3$ is independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-g}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(═$NR_{12}$)$R_{11}$, —$C_{0-4}$ alkyl-N($R_{12}$)—C(═$NR_{13}$)$R_{11}$, —$C_{0-4}$ alkyl-C(O)$NR_{12}R_{13}$ and —$C_{0-4}$ alkyl-N($R_{12}$)—C(O)$R_{11}$, or wherein 2 adjacent $R_3$, together with the moiety to which they are directly attached, form a $C_{5-6}$ cycloalkyl, 5-6 membered heterocyclyl, phenyl or 5-6 membered heteroaryl, the above groups are independently optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, ═O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(═$NR_{12}$)$R_{11}$, —$C_{0-4}$ alkyl-N($R_{12}$)—C(═$NR_{13}$)$R_{11}$, —$C_{0-4}$ alkyl-C(O)$NR_{12}R_{13}$ and —$C_{0-4}$ alkyl-N($R_{12}$)—C(O)$R_{11}$;

preferably, each $R_3$ is independently selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(═$NR_{12}$)$R_{11}$, —$C_{0-4}$ alkyl-N($R_{12}$)—C(═$NR_{13}$)$R_{11}$, —$C_{0-4}$ alkyl-C(O)$NR_{12}R_{13}$ and —$C_{0-4}$ alkyl-N($R_{12}$)—C(O)$R_{11}$, or wherein 2 adjacent $R_3$, together with the moiety to which they are directly attached, form a $C_{5-6}$ cycloalkyl, 5-6 membered heterocyclyl, phenyl or 5-6 membered heteroaryl;

wherein, $R_8$, $R_9$, $R_{10}$, $R_{11}$, $R_{12}$, $R_{13}$ and r are described as those in the compound of formula (I).

As a preferred embodiment, in the compound of formula (I), the stereoisomer or pharmaceutically acceptable salt thereof, each $R_4$ is independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $-C_{0-4}$ alkyl-$SF_5$, $-C_{0-4}$ alkyl-$S(O)_rR_8$, $-C_{0-4}$ alkyl-O—$R_9$, $-C_{0-4}$ alkyl-$C(O)OR_{10}$, $-C_{0-4}$ alkyl-$C(O)R_{11}$, $-C_{0-4}$ alkyl-O—$C(O)R_{11}$, $-C_{0-4}$ alkyl-$NR_{12}R_{13}$, $-C_{0-4}$ alkyl-C($=NR_{12}$)$R_{11}$, $-C_{0-4}$ alkyl-N($R_{12}$)—C($=NR_{13}$)$R_{11}$, $-C_{0-4}$ alkyl-$C(O)NR_{12}R_{13}$ and $-C_{0-4}$ alkyl-N($R_{12}$)—$C(O)R_{11}$, or when n≥2, wherein 2 adjacent $R_4$, together with the moiety to which they are directly attached, form a $C_{6-8}$ cycloalkyl, 5-8 membered heterocyclyl, $C_{6-8}$ aryl or 5-8 membered heteroaryl, the above groups are independently optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $-C_{0-4}$ alkyl-$SF_5$, $-C_{0-4}$ alkyl-$S(O)_rR_8$, $-C_{0-4}$ alkyl-O—$R_9$, $-C_{0-4}$ alkyl-C(O)$OR_{10}$, $-C_{0-4}$ alkyl-$C(O)R_{11}$, $-C_{0-4}$ alkyl-O—$C(O)R_{11}$, $-C_{0-4}$ alkyl-$NR_{12}R_{13}$, $-C_{0-4}$ alkyl-C($=NR_{12}$)$R_{11}$, $-C_{0-4}$ alkyl-N($R_{12}$)—C($=NR_{13}$)$R_{11}$, $-C_{0-4}$ alkyl-$C(O)NR_{12}R_{13}$ and $-C_{0-4}$ alkyl-N($R_{12}$)—$C(O)R_{11}$;

wherein, $R_8$, $R_9$, $R_{10}$, $R_{11}$, $R_{12}$, $R_{13}$ and r are described as those in the compound of formula (I).

As a preferred embodiment, in the compound of formula (I), the stereoisomer or pharmaceutically acceptable salt thereof, ring A is $C_{6-8}$ aryl or 5-8 membered heteroaryl;

preferably, ring A is selected from the group consisting of phenyl, pyridyl, pyridazinyl, pyrimidinyl, pyrazinyl, triazinyl, pyrrolyl, pyrazolyl, imidazolyl, triazolyl, furyl, thiophenyl, oxazolyl, isoxazolyl and thiazolyl.

As a preferred embodiment, in the compound of formula (I), the stereoisomer or pharmaceutically acceptable salt thereof, $R_2$ is selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $-C_{0-4}$ alkyl-$SF_5$, $-C_{0-4}$ alkyl-$S(O)_rR_8$, $-C_{0-4}$ alkyl-O—$R_9$, $-C_{0-4}$ alkyl-C(O)$OR_{10}$, $-C_{0-4}$ alkyl-$C(O)R_{11}$, $-C_{0-4}$ alkyl-O—$C(O)R_{11}$, $-C_{0-4}$ alkyl-$NR_{12}R_{13}$, $-C_{0-4}$ alkyl-C($=NR_{12}$)$R_{11}$, $-C_{0-4}$ alkyl-N($R_{12}$)—C($=NR_{13}$)$R_{11}$, $-C_{0-4}$ alkyl-$C(O)NR_{12}R_{13}$ and $-C_{0-4}$ alkyl-N($R_{12}$)—$C(O)R_{11}$, the above groups are independently optionally further substituted with one or more substituents selected from the group consisting of deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $-C_{0-4}$ alkyl-$SF_5$, $-C_{0-4}$ alkyl-$S(O)_rR_8$, $-C_{0-4}$ alkyl-O—$R_9$, $-C_{0-4}$ alkyl-C(O)$OR_{10}$, $-C_{0-4}$ alkyl-$C(O)R_{11}$, $-C_{0-4}$ alkyl-O—$C(O)R_{11}$, $-C_{0-4}$ alkyl-$NR_{12}R_{13}$, $-C_{0-4}$ alkyl-C($=NR_{12}$)$R_{11}$, $-C_{0-4}$ alkyl-N($R_{12}$)—C($=NR_{13}$)$R_{11}$, $-C_{0-4}$ alkyl-$C(O)NR_{12}R_{13}$ and $-C_{0-4}$ alkyl-N($R_{12}$)—$C(O)R_{11}$, the above groups are independently optionally more further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $-C_{0-4}$ alkyl-$SF_5$, $-C_{0-4}$ alkyl-$S(O)_rR_8$, $-C_{0-4}$ alkyl-O—$R_9$, $-C_{0-4}$ alkyl-$C(O)OR_{10}$, $-C_{0-4}$ alkyl-$C(O)R_{11}$, $-C_{0-4}$ alkyl-O—$C(O)R_{11}$, $-C_{0-4}$ alkyl-$NR_{12}R_{13}$, $-C_{0-4}$ alkyl-C($=NR_{12}$)$R_{11}$, $-C_{0-4}$ alkyl-N($R_{12}$)—C($=NR_{13}$)$R_{11}$, $-C_{0-4}$ alkyl-$C(O)NR_{12}R_{13}$ and $-C_{0-4}$ alkyl-N($R_{12}$)—$C(O)R_{11}$;

wherein, $R_8$, $R_9$, $R_{10}$, $R_{11}$, $R_{12}$, $R_{13}$ and r are described as those in the compound of formula (I).

As a further preferred embodiment, in the compound of formula (I), the stereoisomer or pharmaceutically acceptable salt thereof, the compound of formula (I) is a compound of formula (IIa), formula (IIb) or formula (IIc):

(IIa)

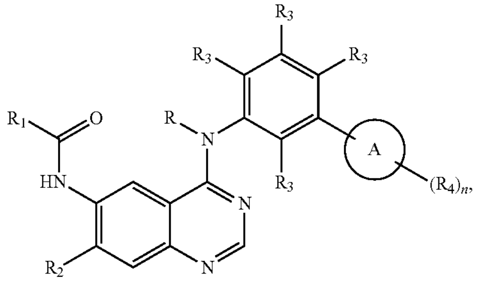

(IIb)

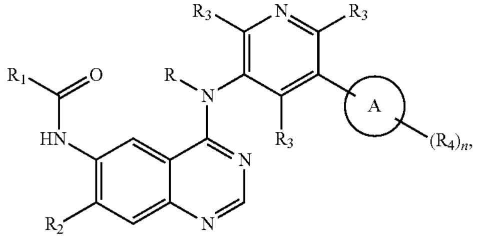

(IIc)

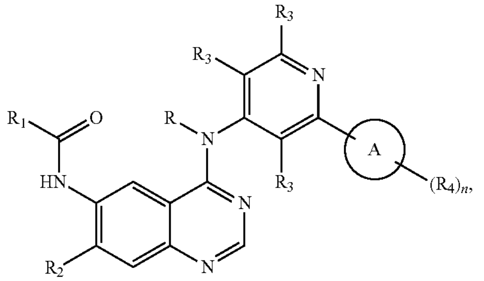

wherein each ring A is independently selected from the group consisting of phenyl, pyridyl, pyrrolyl, pyrazolyl, imidazolyl and triazolyl;

each R is independently selected from the group consisting of hydrogen, deuterium, hydroxy, $C_{1-4}$ alkyl, $C_{1-4}$ haloalkyl and $C_{1-4}$ deuterioalkyl;

each $R_1$ is independently vinyl or ethynyl, the vinyl or ethynyl is optionally further substituted with one or more substituents selected from the group consisting of deuterium, fluoro, cyano, $C_{1-4}$ alkyl, $C_{1-4}$ haloalkyl, $C_{1-4}$ deuterioalkyl, $C_{3-6}$ cycloalkyl, 3-6 membered heterocyclyl and $-C_{0-2}$ alkyl-$NR_6R_7$;

each $R_2$ is independently selected from the group consisting of hydrogen, deuterium, halogen, cyano, $C_{1-4}$ alkyl, $C_{2-4}$ alkenyl, $C_{2-4}$ alkynyl, 3-6 membered heterocyclyl, $-C_{0-4}$ alkyl-O—$R_9$, $-C_{0-4}$ alkyl-O—$C(O)R_{11}$ and $-C_{0-4}$ alkyl-$NR_{12}R_{13}$, the above groups are independently optionally further substituted with one or more substituents selected from the group consisting of deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, $-C_{0-4}$ alkyl-$SF_5$, $-C_{0-4}$ alkyl-$S(O)_rR_8$, $-C_{0-4}$ alkyl-O—$R_9$, $-C_{0-4}$ alkyl-$C(O)OR_{10}$, $-C_{0-4}$ alkyl-$C(O)R_{11}$, $-C_{0-4}$ alkyl-O—$C(O)R_{11}$, $-C_{0-4}$ alkyl-$NR_{12}R_{13}$, $-C_{0-4}$ alkyl-C($=NR_{12}$)$R_{11}$, $-C_{0-4}$ alkyl-N($R_{12}$)—C($=NR_{13}$)$R_{11}$, $-C_{0-4}$ alkyl-$C(O)NR_{12}R_{13}$ and $-C_{0-4}$ alkyl-N($R_{12}$)—$C(O)R_{11}$, the above groups are independently optionally more further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(=$NR_{12}$)$R_{11}$, —$C_{0-4}$ alkyl-N($R_{12}$)—C(=$NR_{13}$)$R_{11}$, —$C_{0-4}$ alkyl-C(O)$NR_{12}R_{13}$ and —$C_{0-4}$ alkyl-N($R_{12}$)—C(O)$R_{11}$;

each $R_3$ is independently selected from the group consisting of hydrogen, deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(=$NR_{12}$)$R_{11}$, —$C_{0-4}$ alkyl-N($R_{12}$)—C(=$NR_{13}$)$R_{11}$, —$C_{0-4}$ alkyl-C(O)$NR_{12}R_{13}$ and —$C_{0-4}$ alkyl-N($R_{12}$)—C(O)$R_{11}$, or wherein 2 adjacent $R_3$, together with the moiety to which they are directly attached, form a $C_{5-6}$ cycloalkyl, 5-6 membered heterocyclyl, phenyl or 5-6 membered heteroaryl;

each $R_4$ is independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(=$NR_{12}$)$R_{11}$, —$C_{0-4}$ alkyl-N($R_{12}$)—C(=$NR_{13}$)$R_{11}$, —$C_{0-4}$ alkyl-C(O)$NR_{12}R_{13}$ and —$C_{0-4}$ alkyl-N($R_{12}$)—C(O)$R_{11}$, or when n≥2, wherein 2 adjacent $R_4$, together with the moiety to which they are directly attached, form a $C_{6-8}$ cycloalkyl, 5-8 membered heterocyclyl, $C_{6-8}$ aryl or 5-8 membered heteroaryl, the above groups are independently optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, =O, —$C_{0-4}$ alkyl-$SF_5$, —$C_{0-4}$ alkyl-$S(O)_rR_8$, —$C_{0-4}$ alkyl-O—$R_9$, —$C_{0-4}$ alkyl-C(O)$OR_{10}$, —$C_{0-4}$ alkyl-C(O)$R_{11}$, —$C_{0-4}$ alkyl-O—C(O)$R_{11}$, —$C_{0-4}$ alkyl-$NR_{12}R_{13}$, —$C_{0-4}$ alkyl-C(=$NR_{12}$)$R_{11}$, —$C_{0-4}$ alkyl-N($R_{12}$)—C(=$NR_{13}$)$R_{11}$, —$C_{0-4}$ alkyl-C(O)$NR_{12}R_{13}$ and —$C_{0-4}$ alkyl-N($R_{12}$)—C(O)$R_{11}$;

$R_6$ and $R_7$ are each independently selected from the group consisting of hydrogen, deuterium, hydroxy, $C_{1-4}$ alkyl, $C_{1-4}$ haloalkyl, $C_{1-4}$ deuterioalkyl, —$C_{0-4}$ alkyl-C(O)$OR_{10}$, —$C_{0-4}$ alkyl-C(O)$R_{11}$, —$C_{0-4}$ alkyl-C(=$NR_{12}$)$R_{11}$ and —$C_{0-4}$ alkyl-C(O)$NR_{12}R_{13}$;

each $R_8$ is independently selected from the group consisting of hydrogen, deuterium, hydroxy, $C_{1-4}$ alkyl, $C_{2-4}$ alkenyl, $C_{3-6}$ cycloalkyl, 3-6 membered heterocyclyl, $C_{6-8}$ aryl, 5-8 membered heteroaryl and —$NR_{12}R_{13}$, the above groups are independently optionally further substituted with one or more substituents selected from the group consisting of deuterium, halogen, hydroxy, oxo, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{12}R_{13}$;

each of $R_9$ and $R_{10}$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{6-8}$ aryl and 5-8 membered heteroaryl, the above groups are independently optionally further substituted with one or more substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{12}R_{13}$;

each $R_{11}$ is independently selected from the group consisting of hydrogen, deuterium, hydroxy, $C_{1-4}$ alkyl, $C_{1-4}$ alkoxy, $C_{2-4}$ alkenyl, $C_{2-4}$ alkynyl, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{12}R_{13}$, the above groups are independently optionally further substituted with one or more substituents selected from the group consisting of deuterium, halogen, hydroxy, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy and —$NR_{12}R_{13}$;

each of $R_{12}$ and $R_{13}$ is independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-4}$ alkylamino, di$C_{1-4}$ alkylamino and $C_{1-4}$ alkanoyl, the above groups are independently optionally further substituted with one or more substituents selected from the group consisting of deuterium, halogen, hydroxy, $C_1$. 4 alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino and $C_{1-4}$ alkanoyl, or, $R_{12}$ and $R_{13}$, together with the nitrogen atom to which they are directly attached, form a 4-8 membered heterocyclyl or 5-8 membered heteroaryl, the 4-8 membered heterocyclyl or 5-8 membered heteroaryl is optionally further substituted with one or more substituents selected from the group consisting of deuterium, halogen, hydroxy, $C_1$. 4 alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino and $C_{1-4}$ alkanoyl;

n is 0, 1, 2, 3 or 4; and each r is independently 0, 1 or 2.

As a more further preferred embodiment, in the compound of formula (I), the stereoisomer or pharmaceutically acceptable salt thereof, R is selected from the group consisting of hydrogen, deuterium, $C_{1-4}$ alkyl, $C_{1-4}$ haloalkyl and $C_{1-4}$ deuterioalkyl;

$R_1$ is vinyl or ethynyl, the vinyl or ethynyl is optionally further substituted with one or more substituents selected from the group consisting of deuterium, fluoro, cyano, methyl, ethyl, isopropyl, difluoromethyl, trifluoromethyl, dideuteriomethyl, trideuteriomethyl, cyclopropyl, amino, dimethylamino and dimethylaminomethyl.

As a still more further preferred embodiment, in the compound of formula (I), the stereoisomer or pharmaceutically acceptable salt thereof, R is hydrogen.

As a still more further preferred embodiment, in the compound of formula (I), the stereoisomer or pharmaceutically acceptable salt thereof, $R_1$ is vinyl, the vinyl is optionally further substituted with one or more substituents selected from the group consisting of deuterium, fluoro, cyano, methyl and dimethylaminomethyl.

As a more further preferred embodiment, in the compound of formula (I), the stereoisomer or pharmaceutically acceptable salt thereof, each $R_3$ is independently selected from the group consisting of hydrogen, deuterium, fluoro, chloro, cyano, methyl, ethyl, isopropyl, difluoromethyl, trifluoromethyl, dideuteriomethyl, trideuteriomethyl, methoxy, ethoxy, isopropoxy, trifluoromethoxy, difluoromethoxy, trideuteriomethoxy, dideuteriomethoxy, cyclopropyl, cyclobutyloxy and amino.

As a more further preferred embodiment, in the compound of formula (I), the stereoisomer or pharmaceutically acceptable salt thereof, ring A, together with $-(R_4)_n$, forms the following structure:

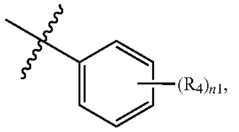
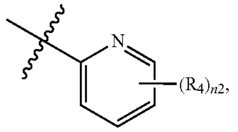
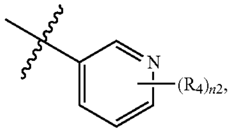
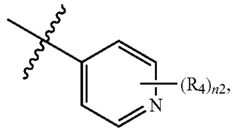
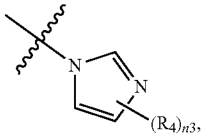
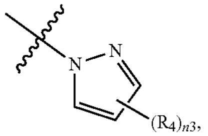
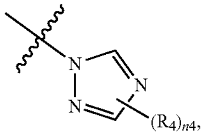
or
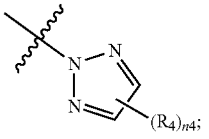

each $R_4$ is independently selected from the group consisting of hydrogen, deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-g}$ aryl, 5-8 membered heteroaryl, $-SF_5$, $-S(O)_rR_8$, $-O-R_9$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$, or when $n_1 \geq 2$ or $n_2 \geq 2$, wherein 2 adjacent $R_4$, together with the moiety to which they are directly attached, form a $C_{6-8}$ cycloalkyl, 5-8 membered heterocyclyl, $C_{6-8}$ aryl or 5-8 membered heteroaryl, the above groups are independently optionally further substituted with one or more substituents selected from the group consisting of deuterium, halogen, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $=O$, $-SF_5$, $-S(O)_rR_8$, $-O-R_9$, $-C(O)OR_{10}$, $-C(O)R_{11}$, $-O-C(O)R$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$;

$n_1$ is 0, 1, 2, 3 or 4;

$n_2$ is 0, 1, 2 or 3;

$n_3$ is 0, 1 or 2;

$n_4$ is 0, 1 or 2;

wherein, $R_8$, $R_9$, $R_{10}$, $R_{11}$, $R_{12}$, $R_{13}$ and r are described as those in the compound of formula (IIa), formula (IIb) or formula (IIc).

As a still more further preferred embodiment, in the compound of formula (I), the stereoisomer or pharmaceutically acceptable salt thereof, ring A, together with $-(R_4)_n$, forms the following structure:

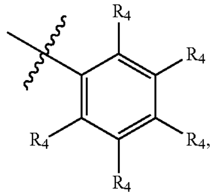
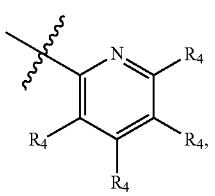
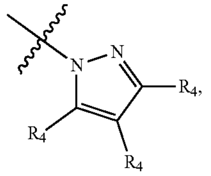
or
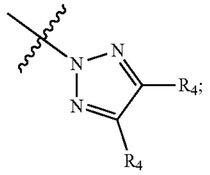

each $R_4$ is independently selected from the group consisting of hydrogen, deuterium, fluoro, chloro, bromo, cyano, $C_{1-4}$ alkyl, $C_{3-6}$ cycloalkyl and 3-6 membered heterocyclyl, the $C_{1-4}$ alkyl, $C_{3-6}$ cycloalkyl and 3-6 membered heterocyclyl are independently optionally further substituted with one or more substituents selected from the group consisting of deuterium, fluoro, chloro, bromo, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl and 3-6 membered heterocyclyl.

As a more further preferred embodiment, in the compound of formula (I), the stereoisomer or pharmaceutically acceptable salt thereof, $R_2$ is selected from the group consisting of hydrogen, deuterium, fluoro, chloro, bromo, cyano, $C_{1-4}$ alkyl, $C_{2-4}$ alkenyl, $C_{2-4}$ alkynyl, 3-6 membered heterocyclyl, $-O-R_9$, $-O-C(O)R_1$ and $-NR_{12}R_{13}$, the above groups are independently optionally further substituted with one or more substituents selected from the group consisting of deuterium, halogen, cyano, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $=O$, $-SF_5$, $-S(O)_rR_8$, $-O-R_9$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$, the above groups are independently optionally more further substituted with one or more substituents selected from the group consisting of deuterium, fluoro, chloro, bromo, cyano, $C_{1-4}$ alkyl, $C_{1-4}$ haloalkyl, $C_{1-4}$ deuterioalkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, $=O$, $-S(O)_rR_8$, $-O-R_9$, $-C(O)OR_{10}$, $-C(O)R_{11}$, $-O-C(O)R_{11}$, $-NR_{12}R_{13}$, $-C(=NR_{12})R_{11}$, $-N(R_{12})-C(=NR_{13})R_{11}$, $-C(O)NR_{12}R_{13}$ and $-N(R_{12})-C(O)R_{11}$;

wherein, $R_8$, $R_9$, $R_{10}$, $R_{11}$, $R_{12}$, $R_{13}$ and r are described as those in the compound of formula (IIa), formula (IIb) or formula (IIc).

As a still more further preferred embodiment, in the compound of formula (I), the stereoisomer or pharmaceutically acceptable salt thereof, $R_2$ is selected from the group consisting of hydrogen, deuterium, fluoro, chloro, bromo, $C_{1-4}$ alkyl, $C_{2-4}$ alkynyl, 3-6 membered heterocyclyl, —O—$R_9$ and —$NR_{12}R_{13}$, the above groups are independently optionally further substituted with one or more substituents selected from the group consisting of deuterium, fluoro, chloro, bromo, cyano, $C_{1-4}$ alkyl, $C_{3-6}$ cycloalkyl, 3-6 membered heterocyclyl, =O, —O—$R_9$ and —$NR_{12}R_{13}$, the above groups are independently optionally more further substituted with one or more substituents selected from the group consisting of deuterium, fluoro, chloro, bromo, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, —O—$R_9$ and —$NR_{12}R_{13}$;

wherein $R_9$, $R_{12}$ and $R_{13}$ are described as those in the compound of formula (IIa), formula (IIb) or formula (IIc).

As the most preferred embodiment, the compound of formula (I), the stereoisomer or pharmaceutically acceptable salt thereof include, but are not limited to, the following compounds:

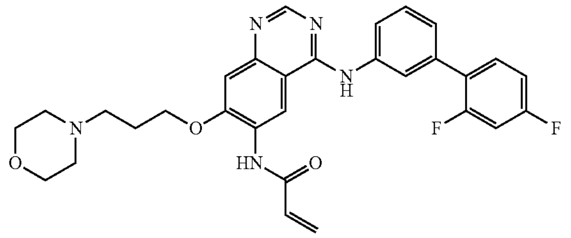

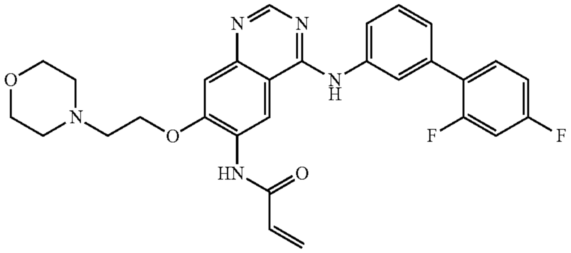

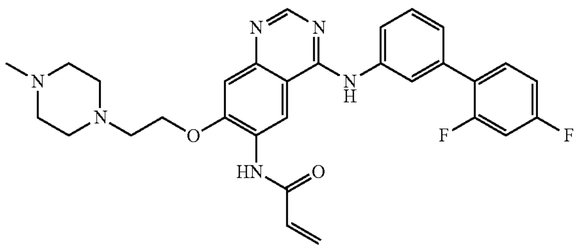

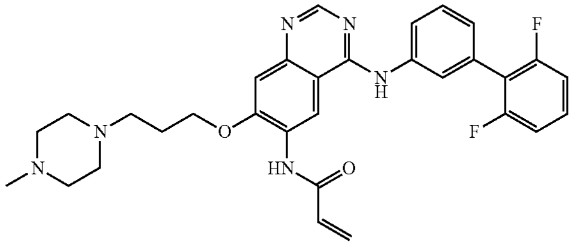

-continued

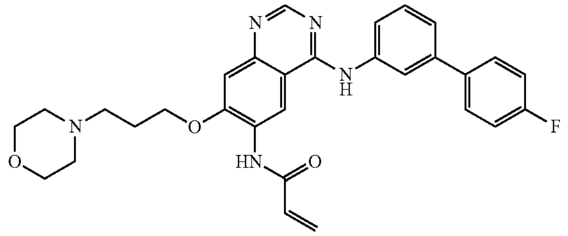

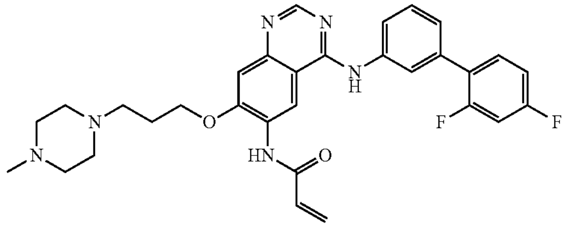

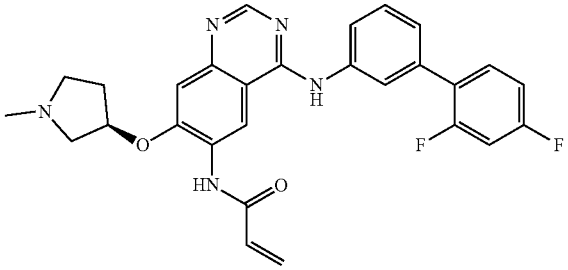

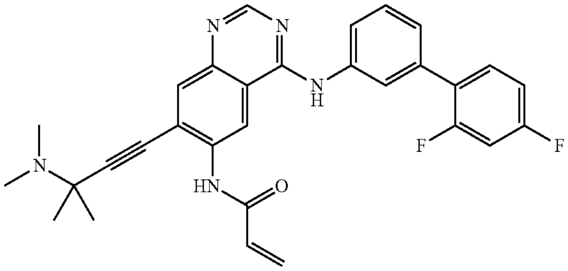

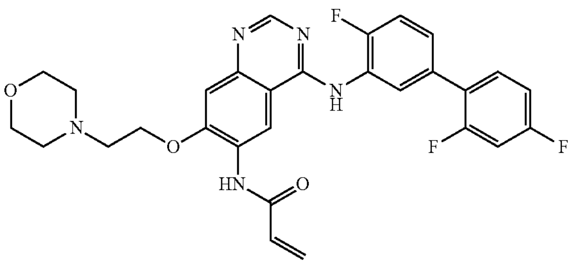

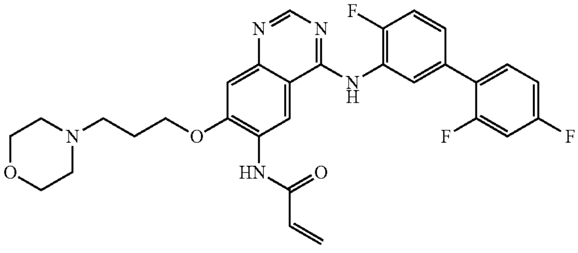

-continued
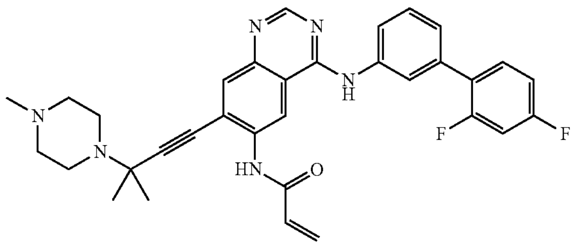
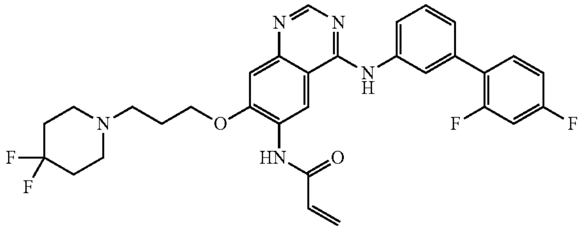
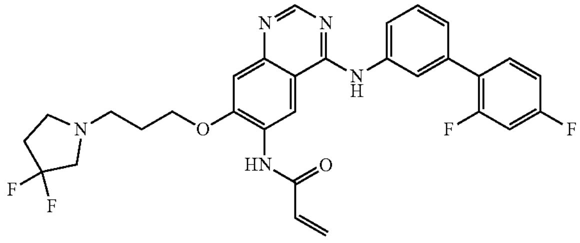
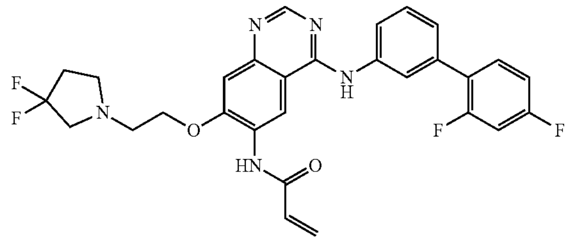
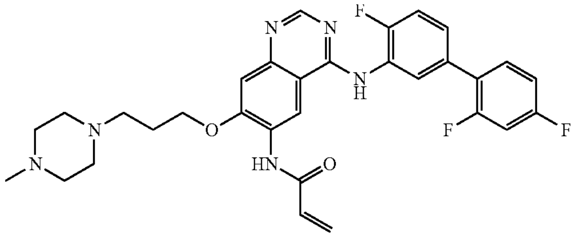
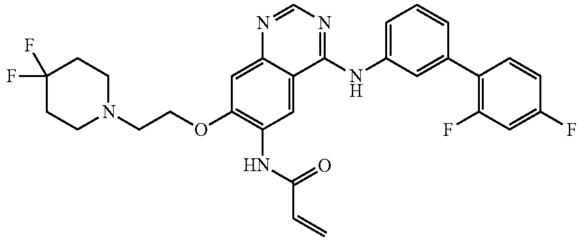
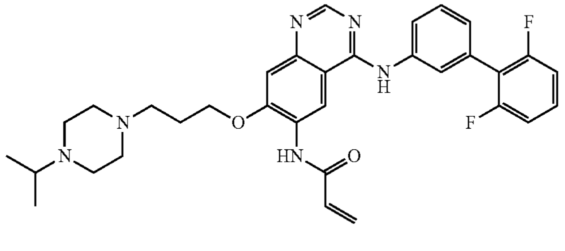
-continued
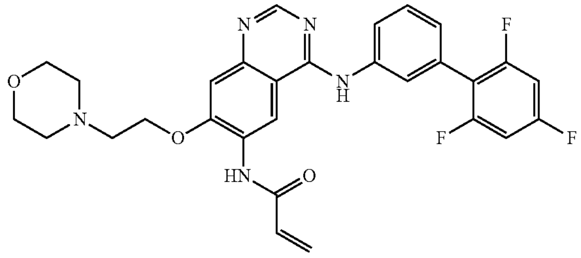
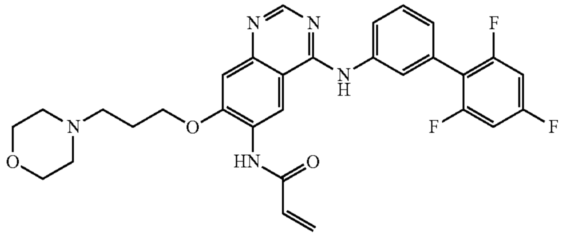
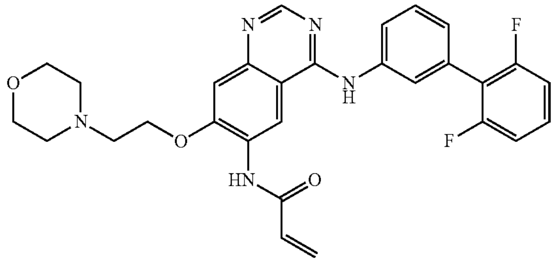
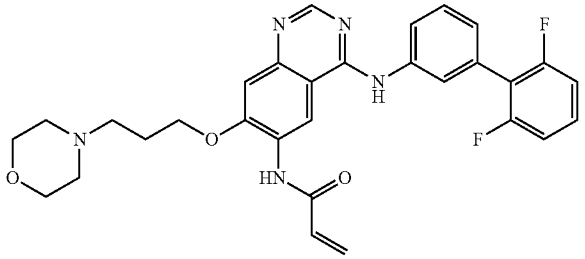
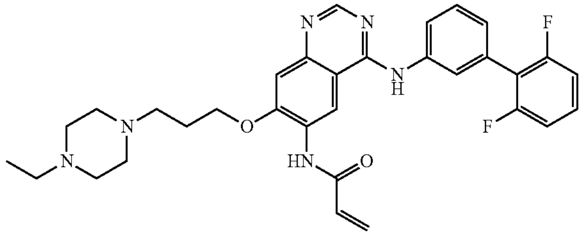
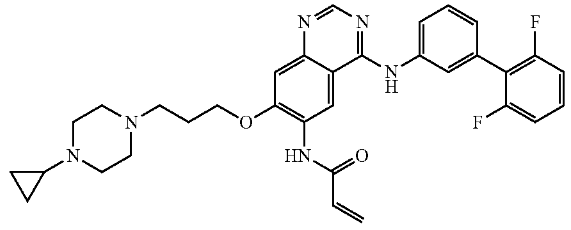
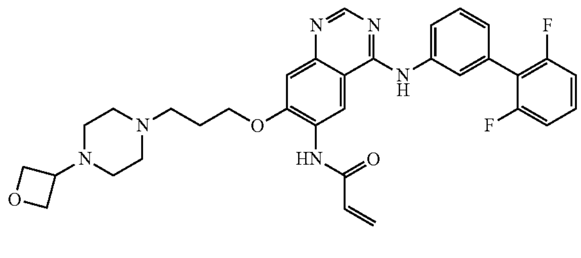

-continued
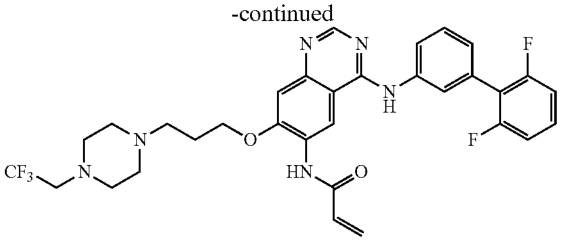
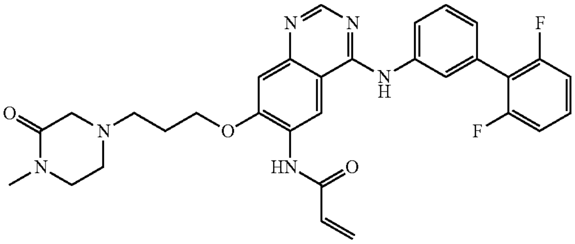
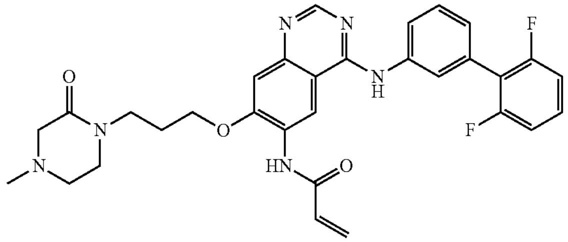
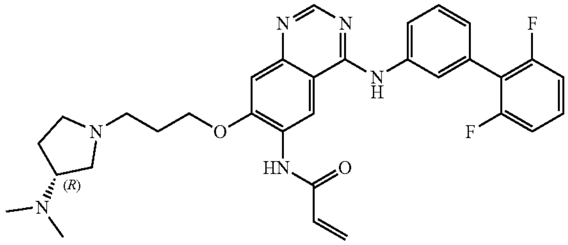
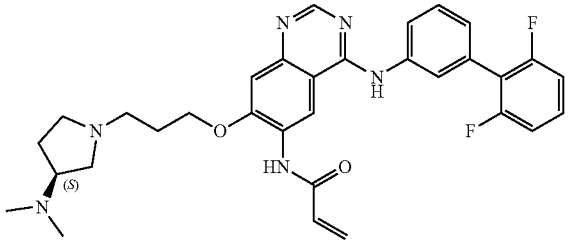
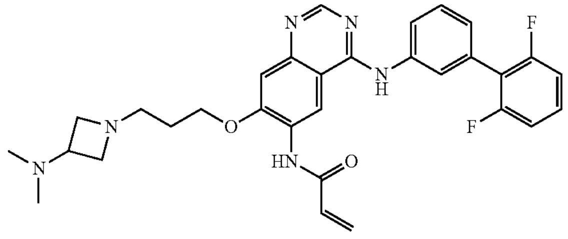
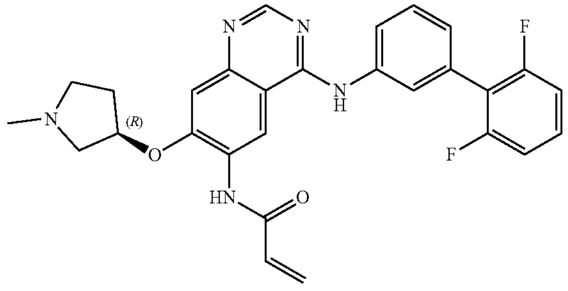
-continued
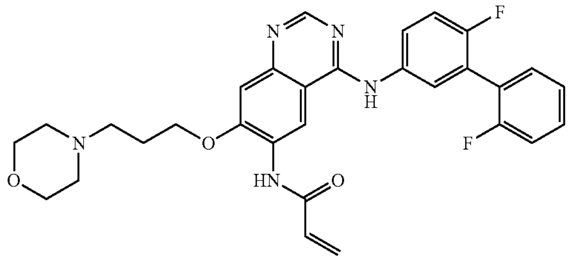
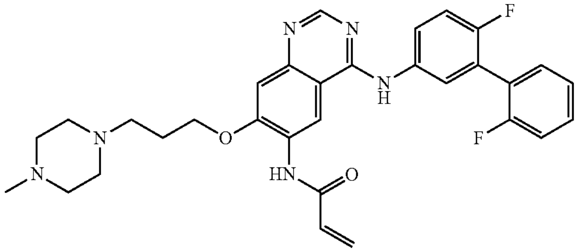
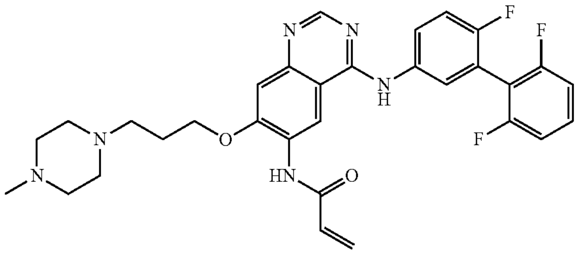
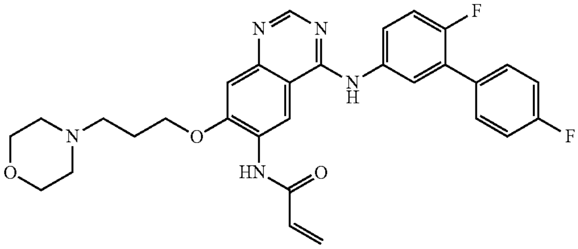
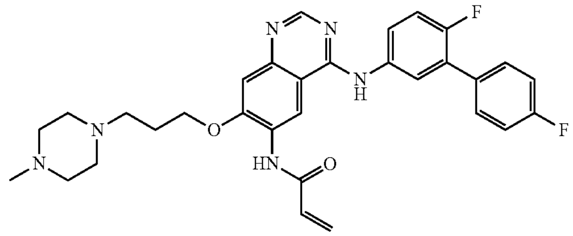
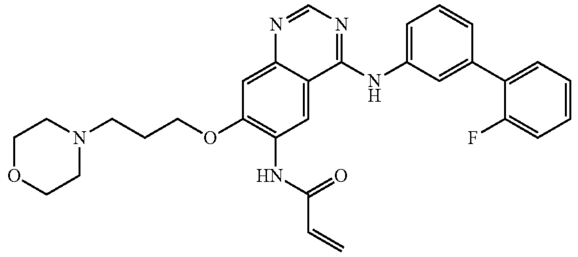

-continued
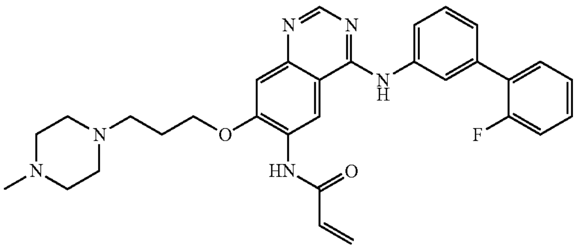
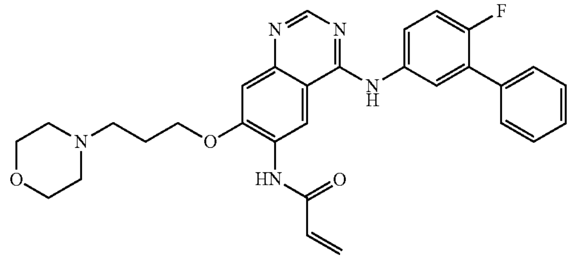
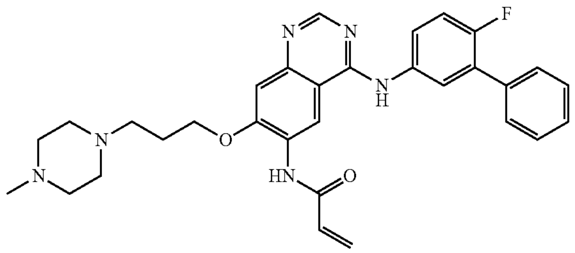
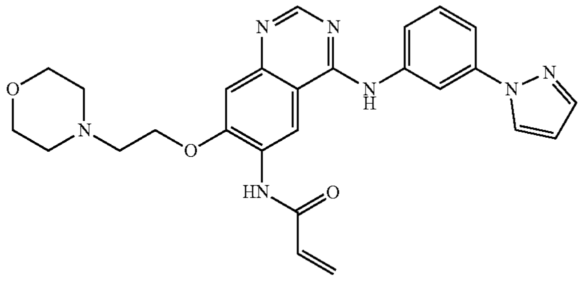
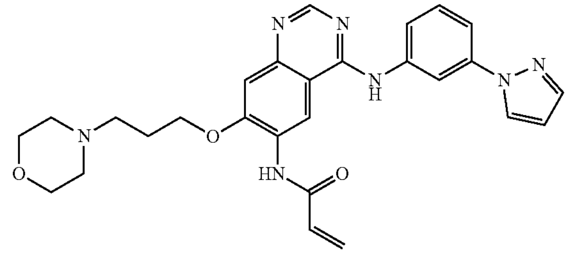
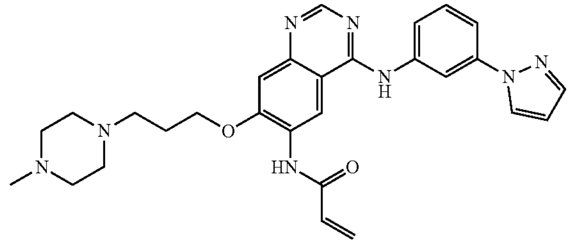
-continued
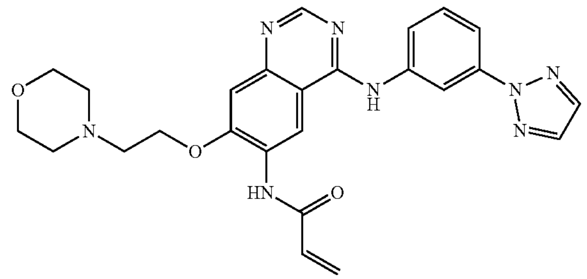
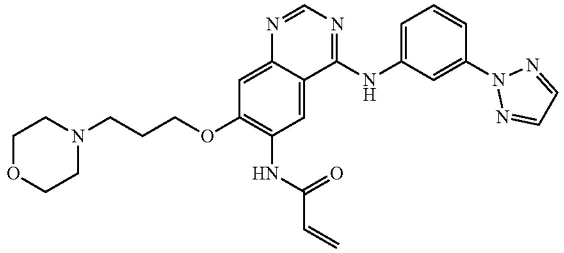
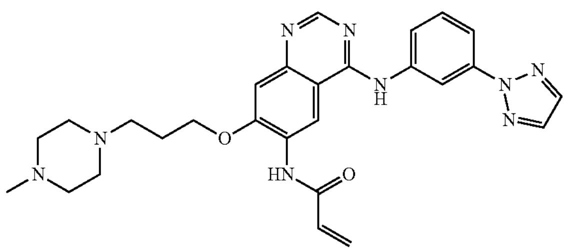
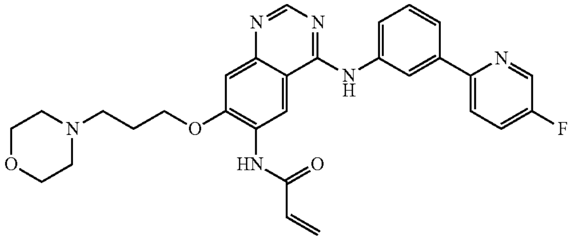
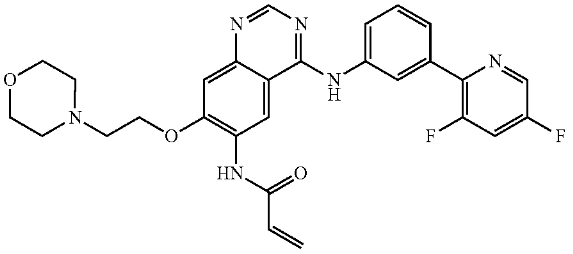
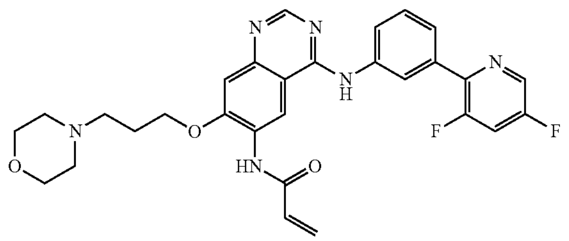

-continued
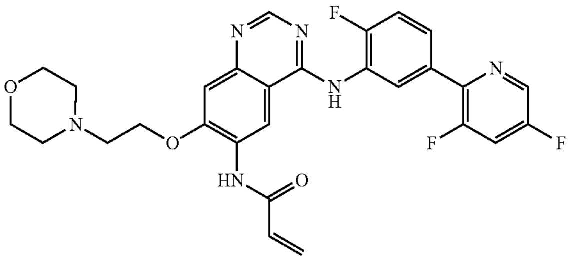
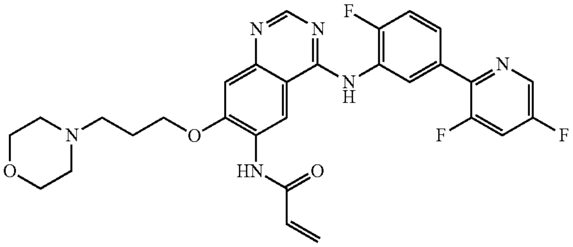
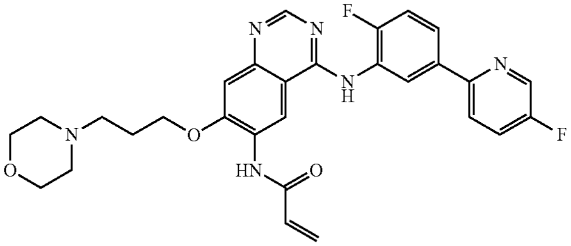
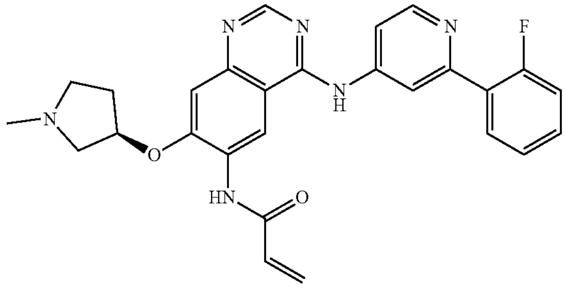
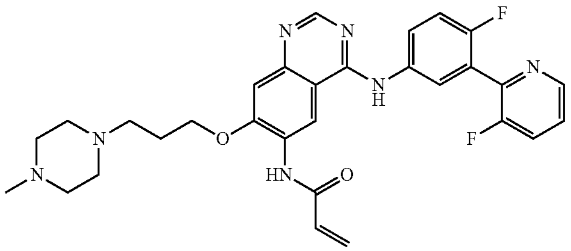
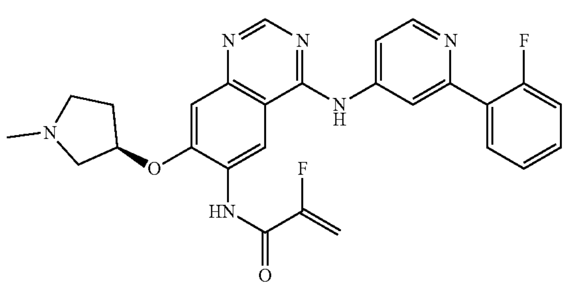
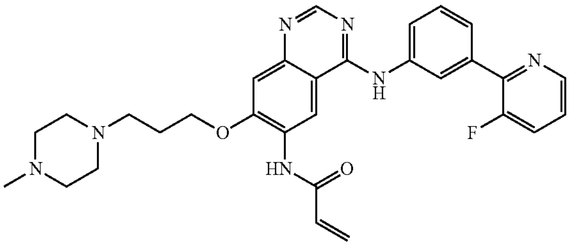
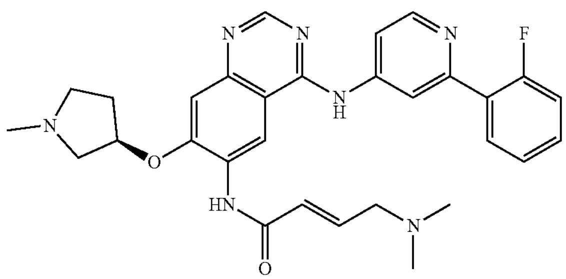
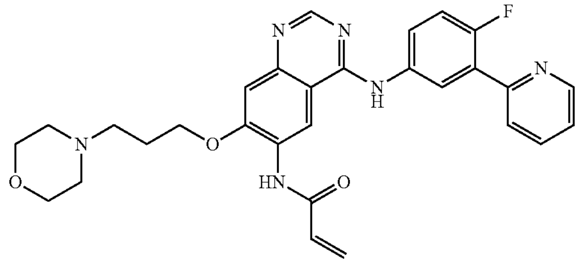
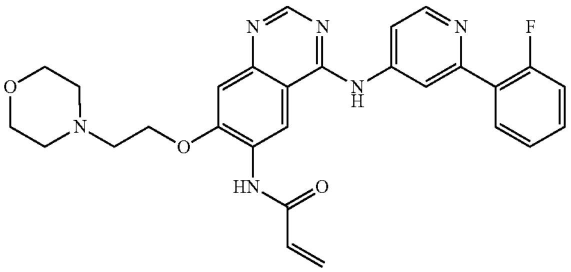
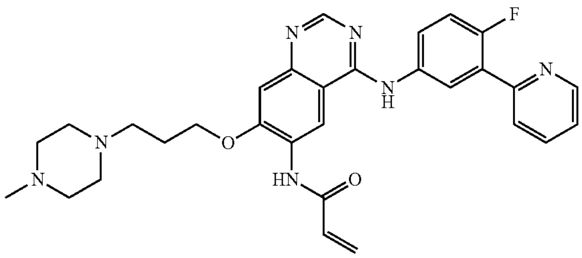
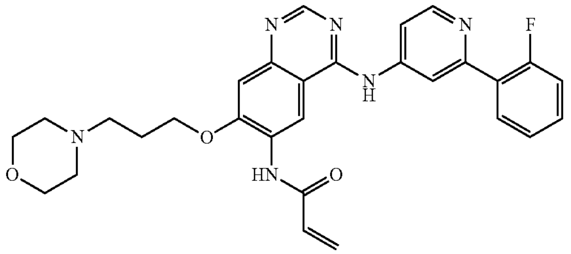
-continued -continued
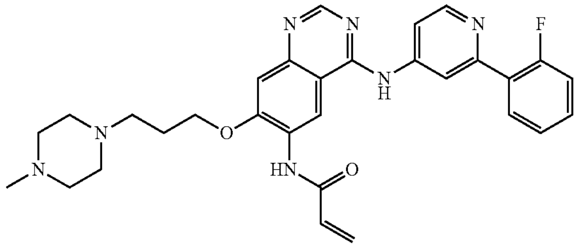
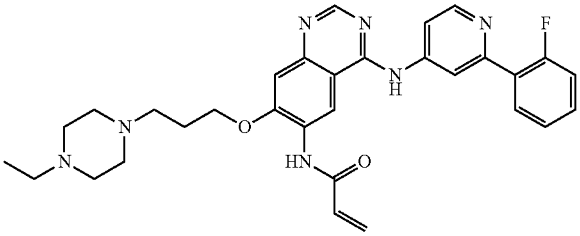
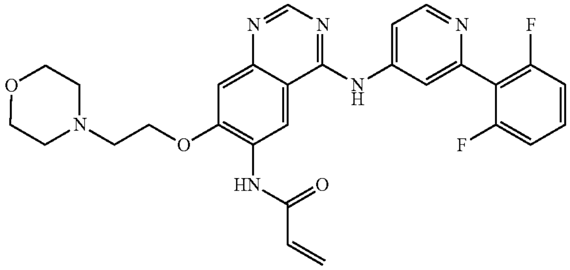
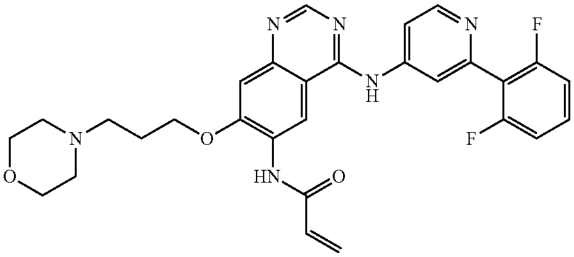
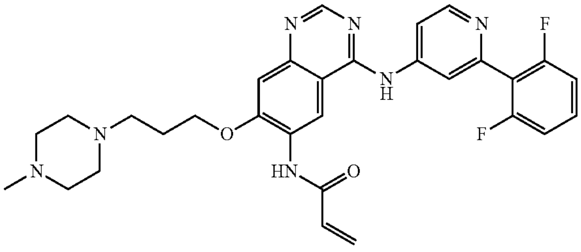
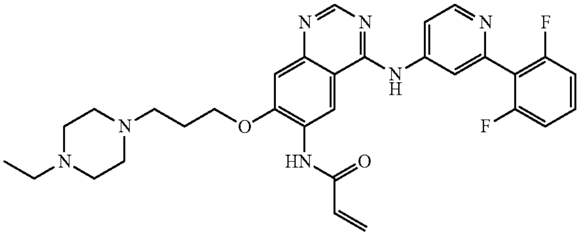
-continued
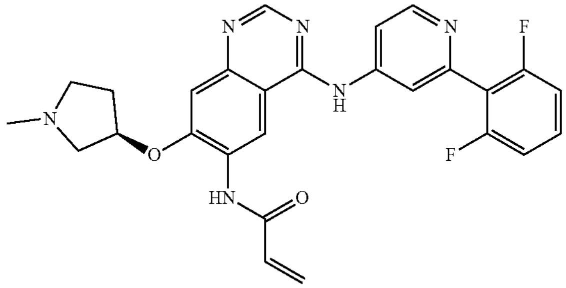
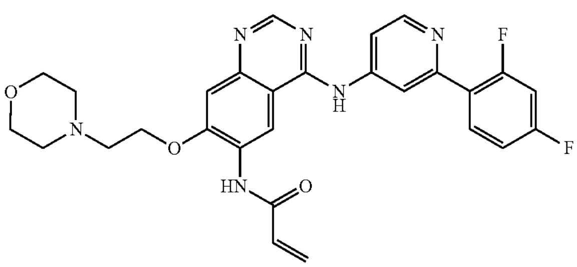
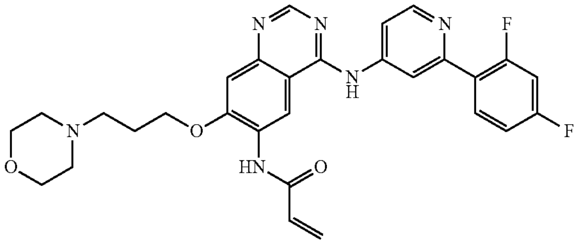
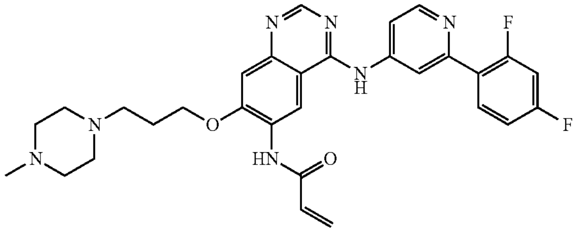
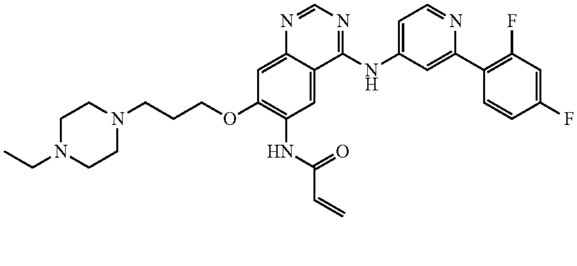
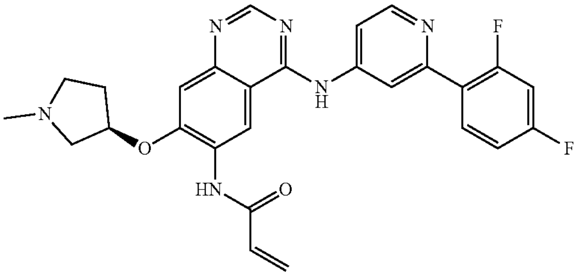

-continued
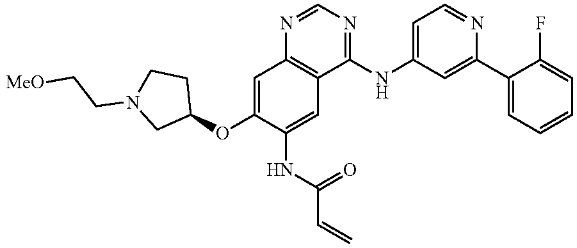
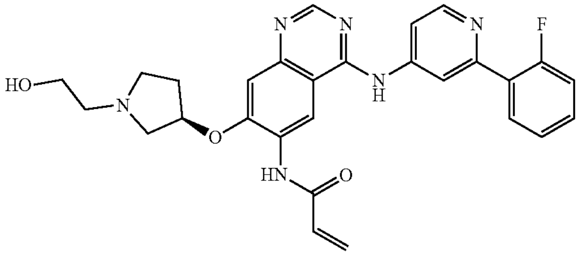
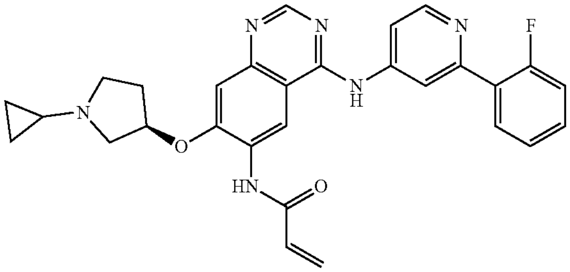
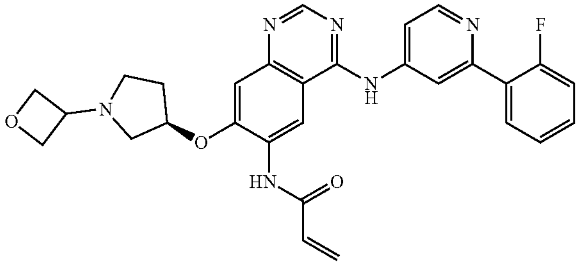
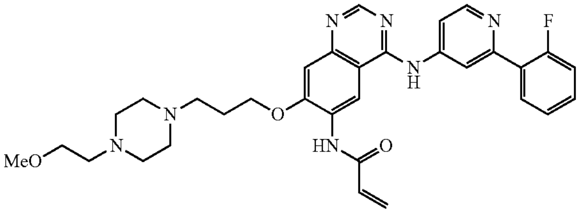
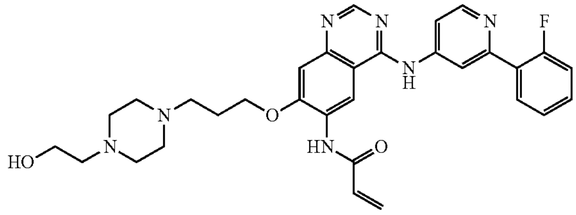
-continued
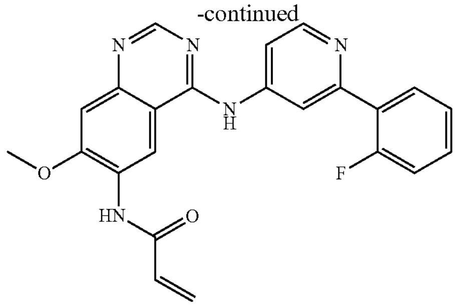
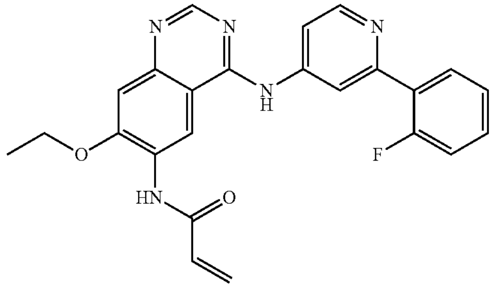
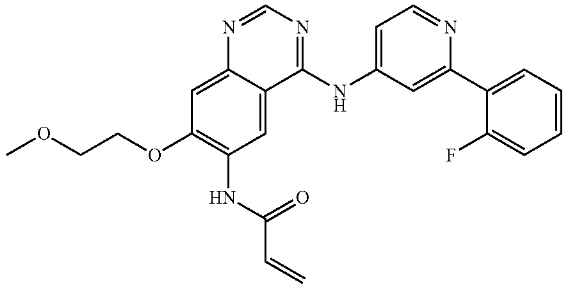
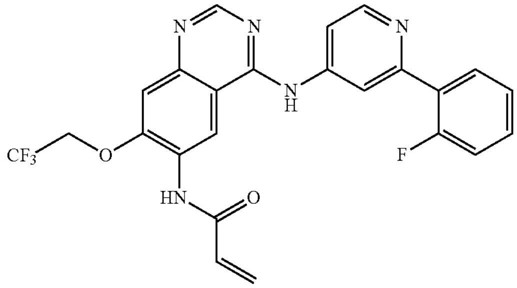
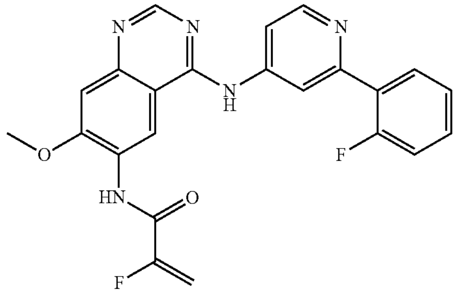
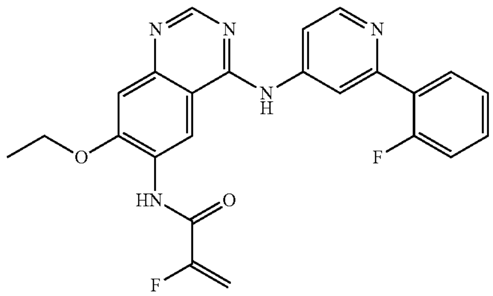

-continued
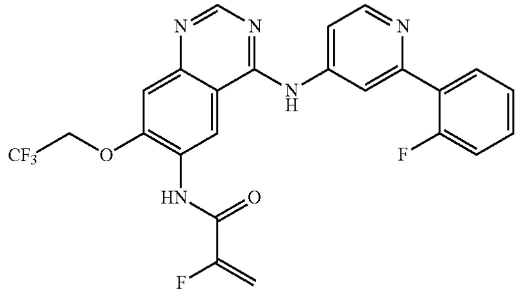
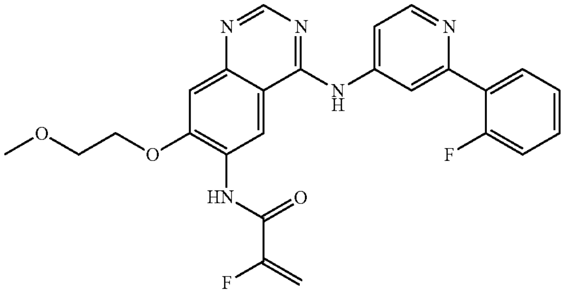
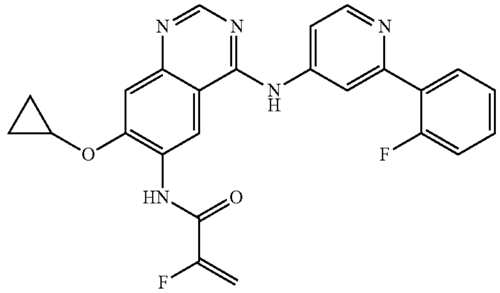
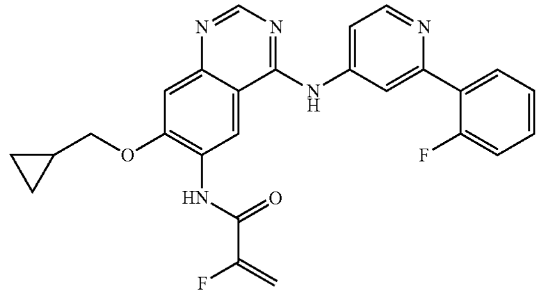
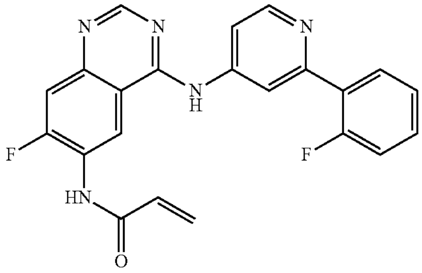
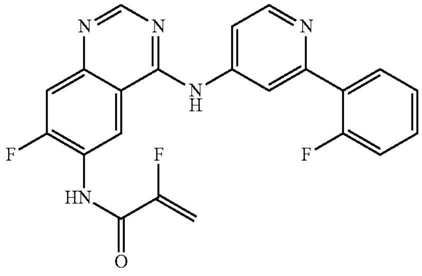
-continued
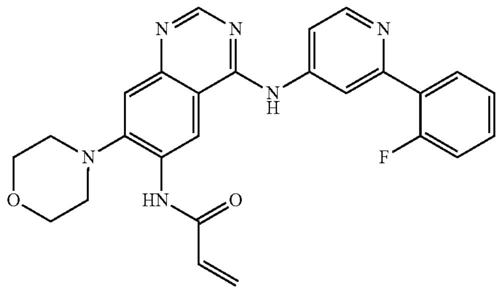
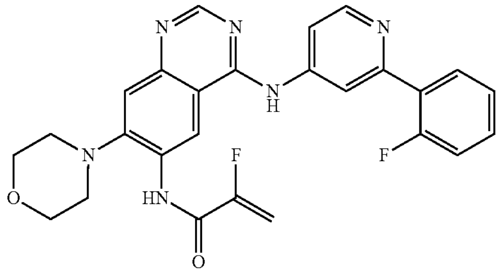
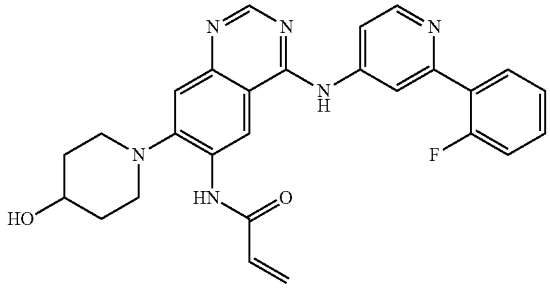
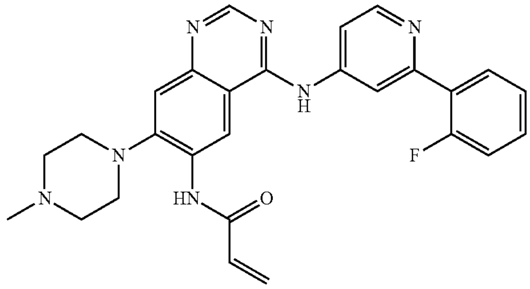
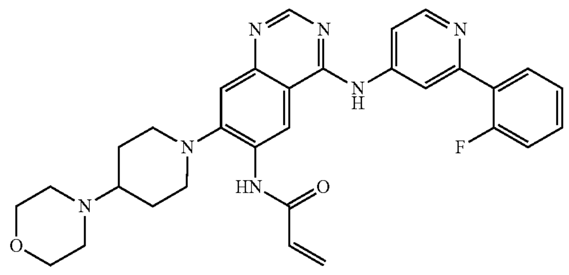
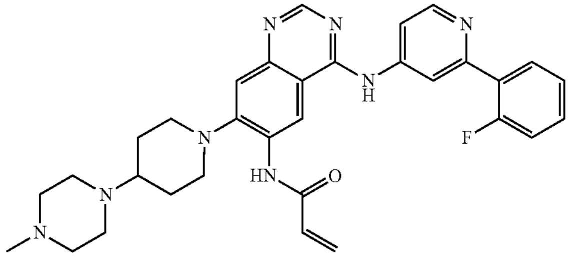

-continued
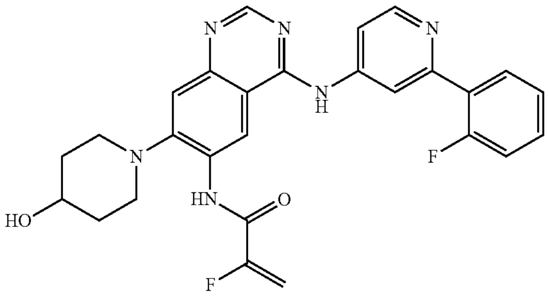
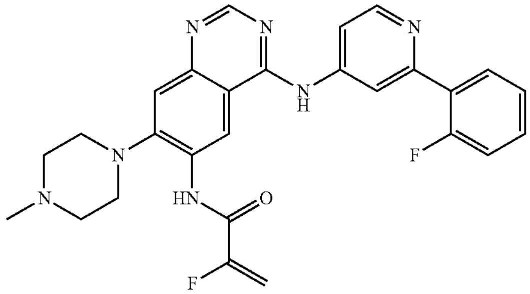
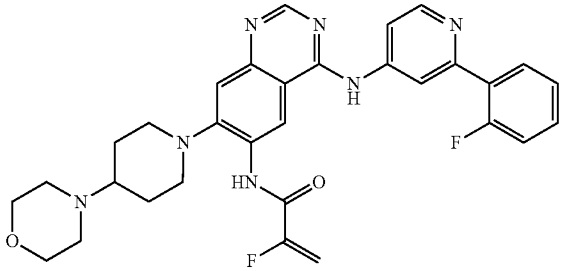
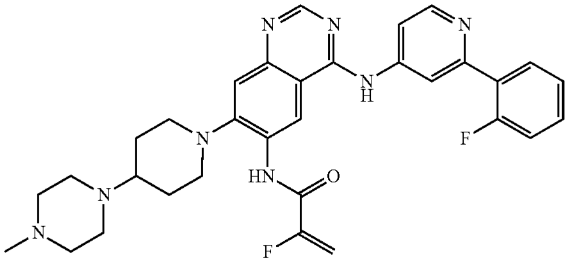
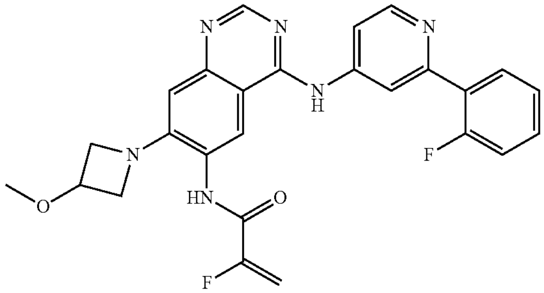
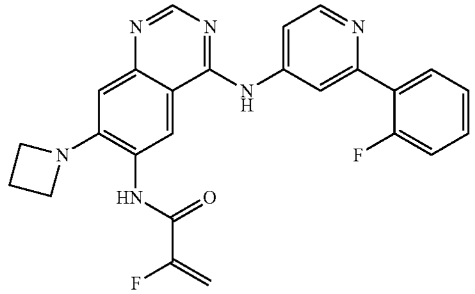
-continued
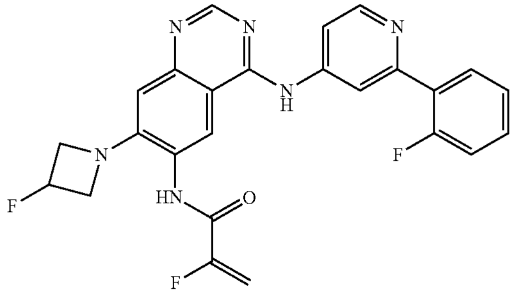
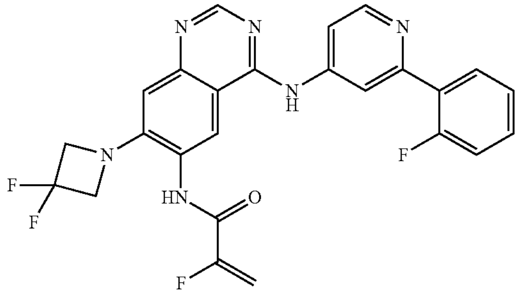
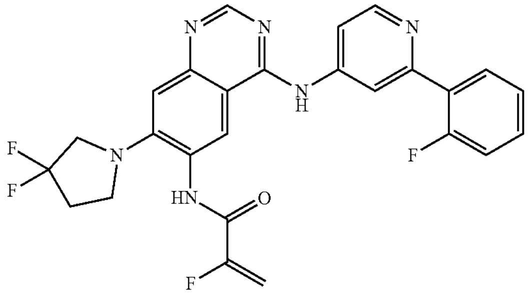
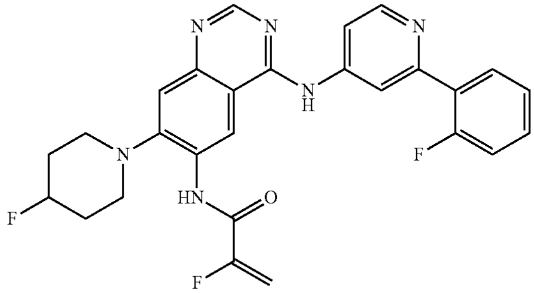
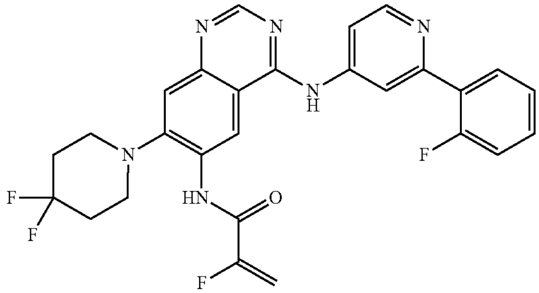
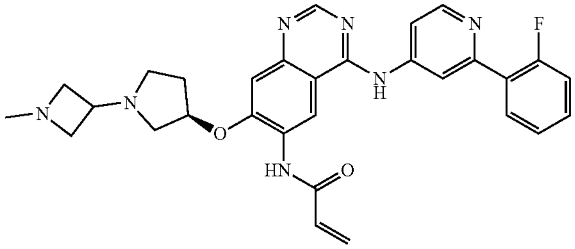

-continued
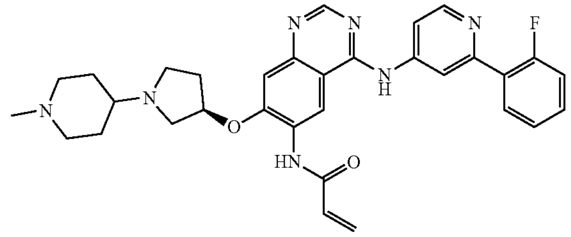
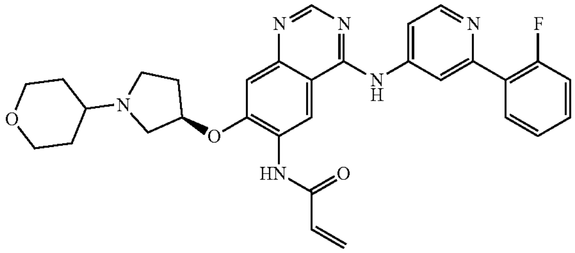
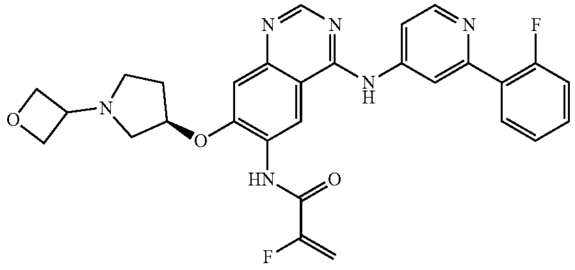
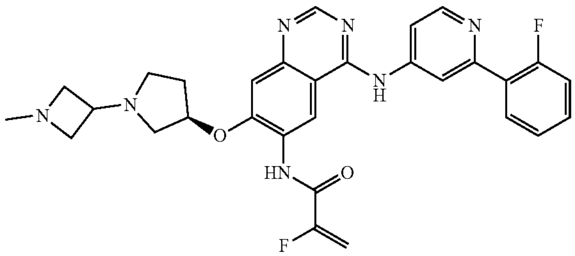
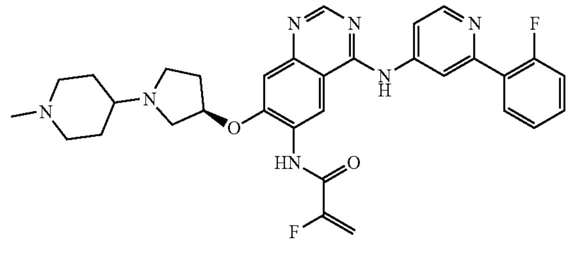
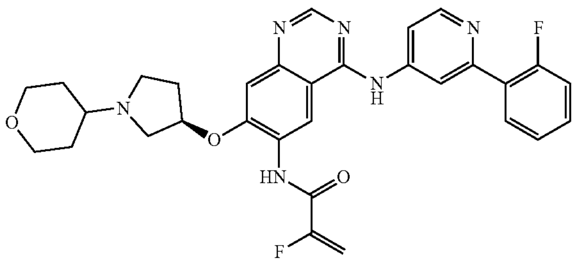
-continued
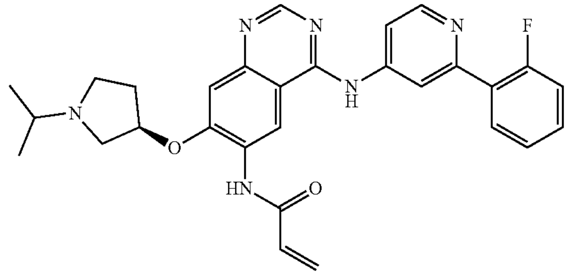
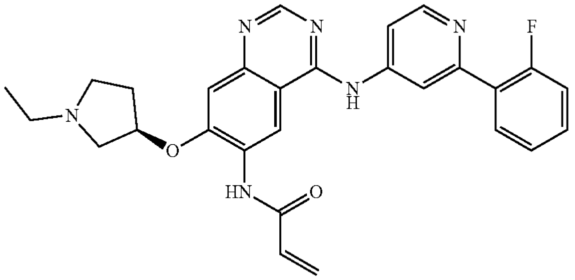
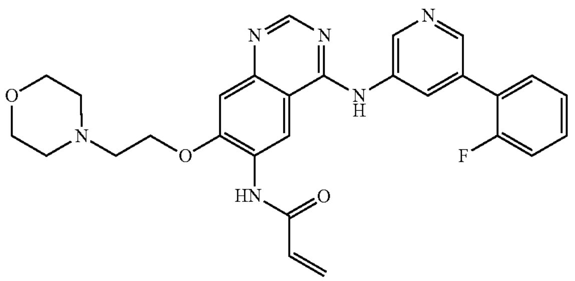
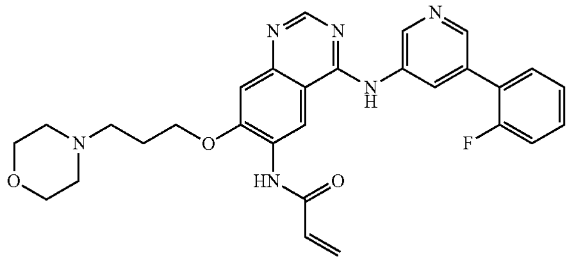
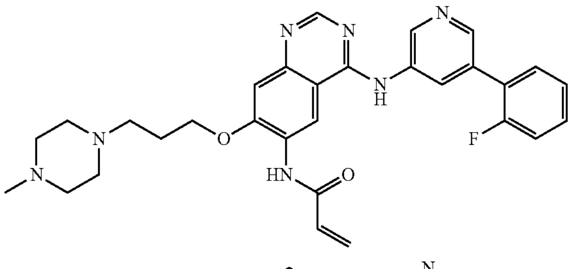
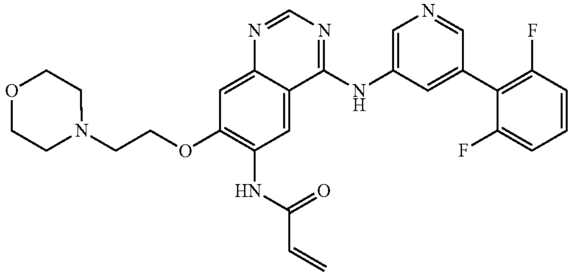

-continued

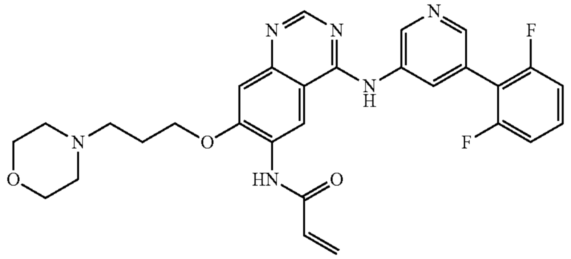

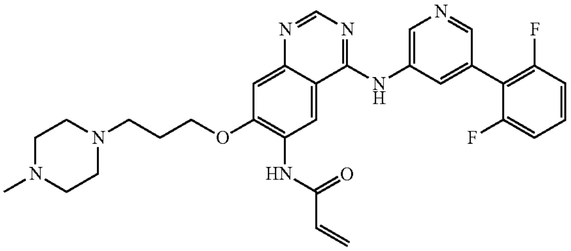

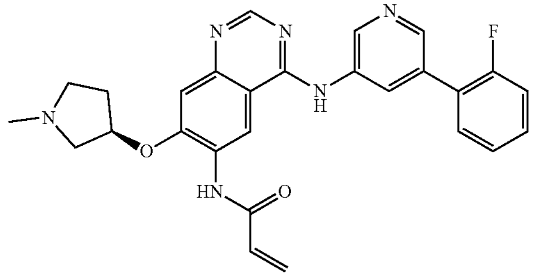

or

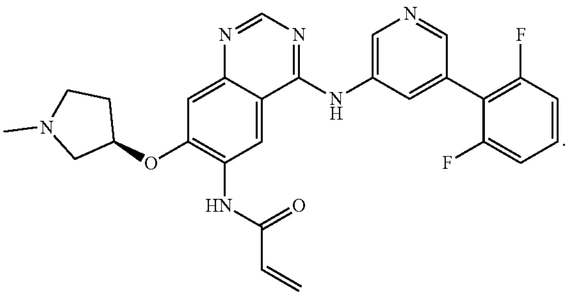

The second aspect of the present invention provides a process for preparing the compound of formula (I), the stereoisomer or pharmaceutically acceptable salt thereof, which comprises the following steps:

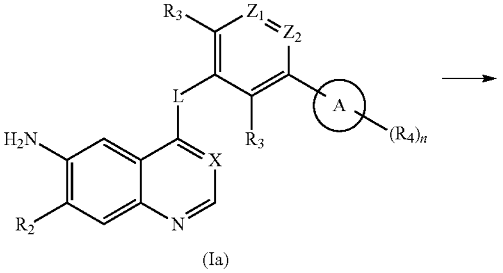

(Ia)

-continued

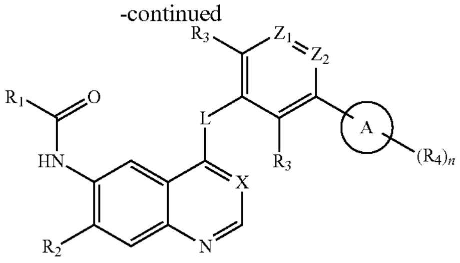

(I)

wherein, ring A, X, $Z_1$, $Z_2$, L, $R_1$, $R_2$, $R_3$, $R_4$ and n are described as those in the compound of formula (I).

The third aspect of the present invention provides a pharmaceutical composition, which comprises the compound of formula (I), the stereoisomer or pharmaceutically acceptable salt thereof, and a pharmaceutically acceptable carrier.

The present invention also relates to use of the compound of formula (I), the stereoisomer or pharmaceutically acceptable salt thereof in preparation of a medicament for treating and/or preventing cancer, tumor or metastatic disease at least partially associated with an insertion, deletion or other mutation of EGFR Exon 20.

The present invention also relates to use of the compound of formula (I), the stereoisomer or pharmaceutically acceptable salt thereof in preparation of a medicament for preventing and/or treating tumor, cancer and/or metastatic disease caused by hyperproliferation and dysfunction in cell death induction.

The present invention also relates to use of the above compound of formula (I), the stereoisomer or pharmaceutically acceptable salt thereof in preparation a medicament for preventing and/or treating lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, sinonasal inverted papilloma or sinonasal squamous cell carcinoma associated with sinonasal inverted papilloma at least partially associated with an insertion, deletion or other mutation of EGFR Exon 20.

The present invention also relates to the compound of formula (I), the stereoisomer or pharmaceutically acceptable salt thereof for use in treatment and/or prevention of cancer, tumor or metastatic disease at least partially associated with an insertion, deletion or other mutation of EGFR Exon 20.

The present invention also relates to the compound of formula (I), the stereoisomer or pharmaceutically acceptable salt thereof for use in prevention and/or treatment of tumor, cancer and/or metastatic disease caused by hyperproliferation and dysfunction in cell death induction.

The present invention also relates to the compound of formula (I), the stereoisomer or pharmaceutically acceptable salt thereof for use in treatment and/or prevention of lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, inverted sinonasal papilloma or inverted sinonasal papilloma associated sinonasal squamous cell carcinoma at least partially associated with an insertion, deletion or other mutation of EGFR Exon 20.

The present invention also relates to a method for treating and/or preventing cancer, tumor or metastatic disease at least partially associated with an insertion, deletion or other mutation of EGFR Exon 20, which comprises administering to a patient in need thereof a therapeutically effective amount of the compound of formula (I), the stereoisomer or pharmaceutically acceptable salt thereof.

The present invention also relates to a method for preventing and/or treating tumor, cancer and/or metastatic disease caused by hyperproliferation and dysfunction in cell death induction, which comprises administering to a patient in need thereof a therapeutically effective amount of the compound of formula (I), the stereoisomer or pharmaceutically acceptable salt thereof.

The present invention also relates to a method for treating and/or preventing lung cancer, colon cancer, pancreatic cancer, head and neck cancer, breast cancer, ovarian cancer, uterine cancer, gastric cancer, non-small cell lung cancer, leukemia, myelodysplastic syndrome, malignant lymphoma, head and neck tumor, thoracic tumor, gastrointestinal tumor, endocrine tumor, breast and other gynecological tumors, urological tumor, skin tumor, sarcoma, inverted sinonasal papilloma or inverted sinonasal papilloma associated sinonasal squamous cell carcinoma at least partially associated with an insertion, deletion or other mutation of EGFR Exon 20, which comprises administering to a patient in need thereof a therapeutically effective amount of the compound of formula (I), the stereoisomer or pharmaceutically acceptable salt thereof.

DETAILED DESCRIPTION OF THE INVENTION

After an extensive and intensive research, the inventors of the present application have developed, for the first time, an EGFR inhibitor with a structure shown as formula (I). A series of compounds of the present invention can be widely applied to the preparation of medicaments for treating and/or preventing cancer, tumor or metastatic disease at least partially associated with an insertion, deletion or other mutation of EGFR Exon 20, particularly medicaments for treating hyperproliferative diseases and diseases for inducing cell death disorder, so that a new generation of EGFR inhibitors is expected to be developed. The present invention is achieved on this basis.

Detailed description: unless otherwise stated or specified, the following terms used in the specification and claims have the following meanings.

"Alkyl" refers to linear or branched saturated aliphatic alkyl groups, preferably linear or branched alkyl groups containing 1 to 10, 1 to 6 or 1 to 4 carbon atoms, including but not limited to methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl or various branched isomers thereof, and the like. "$C_{1-10}$ alkyl" refers to linear alkyl and branched alkyl containing 1 to 10 carbon atoms, "$C_{1-4}$ alkyl" refers to linear alkyl and branched alkyl containing 1 to 4 carbon atoms, "$C_{0-8}$ alkyl" refers to linear alkyl and branched alkyl containing 0 to 8 carbon atoms, and "$C_{0-4}$ alkyl" refers to linear alkyl and branched alkyl containing 0 to 4 carbon atoms.

Alkyl may be optionally substituted or unsubstituted, and when alkyl is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Cycloalkyl" or "carbocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated π-electron system; cycloalkyl is classified into monocyclic cycloalkyl and polycyclic cycloalkyl, and is preferably cycloalkyl containing 3 to 12, 3 to 8, or 3 to 6 carbon atoms. For example, "$C_{3-12}$ cycloalkyl" refers to cycloalkyl containing 3 to 12 carbon atoms, "$C_{3-6}$ cycloalkyl" refers to cycloalkyl containing 3 to 6 carbon atoms, "$C_{6-10}$ cycloalkyl" refers to cycloalkyl containing 6 to 10 carbon atoms, "$C_{5-8}$ cycloalkyl" refers to cycloalkyl containing 5 to 8 carbon atoms, and "$C_{5-6}$ cycloalkyl" refers to cycloalkyl containing 5 to 6 carbon atoms, wherein:

monocyclic cycloalkyl includes, but is not limited to, cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like;

polycyclic cycloalkyl includes spirocycloalkyl, fused cycloalkyl and bridged cycloalkyl. "Spirocycloalkyl" refers to a polycyclic group in which a carbon atom (called a spiro-atom) is shared among monocyclic rings, wherein those rings may contain one or more (preferably, 1, 2 or 3) double bonds, but none of them has a fully conjugated π-electron system. According to the number of the spiro-atoms shared among the rings, the spirocycloalkyl may be monospirocycloalkyl, bispirocycloalkyl or polyspirocycloalkyl, including but not limited to:

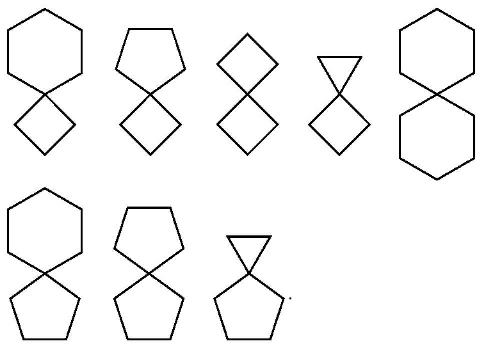

"Fused cycloalkyl" refers to an all-carbon polycyclic group in which each ring shares a pair of adjacent carbon atoms with the other rings in the system, wherein one or more of the rings may contain one or more (preferably, 1, 2 or 3) double bonds, but none of them has a fully conjugated π-electron system. According to the number of formed rings, the fused cycloalkyl may be bicyclic, tricyclic, tetracyclic or polycyclic, including but not limited to:

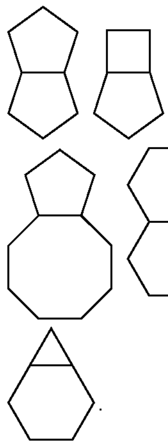

"Bridged cycloalkyl" refers to an all-carbon polycyclic group in which any two rings share two carbon atoms that are not directly connected to each other, wherein these rings may contain one or more (preferably, 1, 2 or 3) double bonds, but none of them has a fully conjugated π-electron system. According to the number of formed rings, the bridged cycloalkyl may be bicyclic, tricyclic, tetracyclic or polycyclic, including but not limited to:

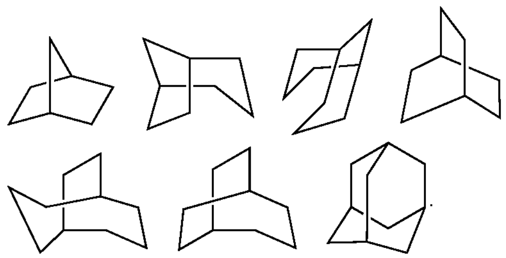

The cycloalkyl ring can be fused to an aryl, heteroaryl or heterocycloalkyl ring, wherein the ring attached to the parent structure is cycloalkyl, which includes, but is not limited to, indanyl, tetrahydronaphthyl, benzocycloheptyl, and the like.

Cycloalkyl may be optionally substituted or unsubstituted, and when cycloalkyl is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_{10}$, —$C_{0-8}$ alkyl-C(O)$R_{11}$, —$C_{0-8}$ alkyl-O—C(O)$R_{11}$, —$C_{0-8}$ alkyl-$NR_{12}R_{13}$, —$C_{0-8}$ alkyl-C(=$NR_{12}$)$R_{11}$, —$C_{0-8}$ alkyl-N($R_{12}$)—C(=$NR_{13}$)$R_{11}$, —$C_{0-8}$ alkyl-C(O)$NR_{12}R_{13}$ and —$C_{0-8}$ alkyl-N($R_{12}$)—C(O)$R_{11}$.

"Heterocyclyl" or "heterocycle" refers to a monocyclic or polycyclic hydrocarbon substituent that is saturated or partially unsaturated. The partially unsaturated cyclic hydrocarbon means that the cyclic hydrocarbon may contain one or more (preferably 1, 2 or 3) double bonds, but none of the rings has a fully conjugated R-electron system; in heterocyclyl, one or more (preferably 1, 2, 3 or 4) ring atoms are heteroatoms selected from nitrogen, oxygen, S(O)(=NH) and $S(O)_r$ (where r is an integer of 0, 1 or 2), excluding ring moiety of —O—O—, —O—S— or —S—S—, and the remaining ring atoms are carbon atoms. Preferably, heterocyclyl is one containing 3 to 12, 3 to 8, 3 to 6 or 5 to 6 ring atoms; for example, "3-6 membered heterocyclyl" refers to a cyclic group containing 3 to 6 ring atoms, "5-6 membered heterocyclyl" refers to a cyclic group containing 5 to 6 ring atoms, "4-8 membered heterocyclyl" refers to a cyclic group containing 4 to 8 ring atoms, "5-10 membered heterocyclyl" refers to a cyclic group containing 5 to 10 ring atoms, "5-8 membered heterocyclyl" refers to a cyclic group containing 5 to 8 ring atoms, "4-10 membered heterocyclyl" refers to a cyclic group containing 4 to 10 ring atoms, and "3-12 membered heterocyclyl" refers to a cyclic group containing 3 to 12 ring atoms.

Monocyclic heterocyclyl includes, but is not limited to, pyrrolidinyl, piperidinyl, piperazinyl, morpholinyl, thiomorpholinyl, homopiperazinyl, and the like.

Polycyclic heterocyclyl includes spiroheterocyclyl, fused heterocyclyl and bridged heterocyclyl. "Spiroheterocyclyl" refers to a polycyclic heterocyclyl group in which an atom (called a spiro-atom) is shared among monocyclic rings, wherein one or more (preferably 1, 2, 3 or 4) ring atoms are heteroatoms selected from nitrogen, oxygen, S(O)(=NH) and $S(O)_r$ (wherein r is an integer of 0, 1 or 2), and the remaining ring atoms are carbon atoms. These rings may contain one or more (preferably, 1, 2 or 3) double bonds, but none of them has a fully conjugated π-electron system. According to the number of spiro-atoms shared among the rings, the spiroheterocyclyl may be monospiroheterocyclyl, bispiroheterocyclyl or polyspiroheterocyclyl. Spiroheterocyclyl includes but is not limited to:

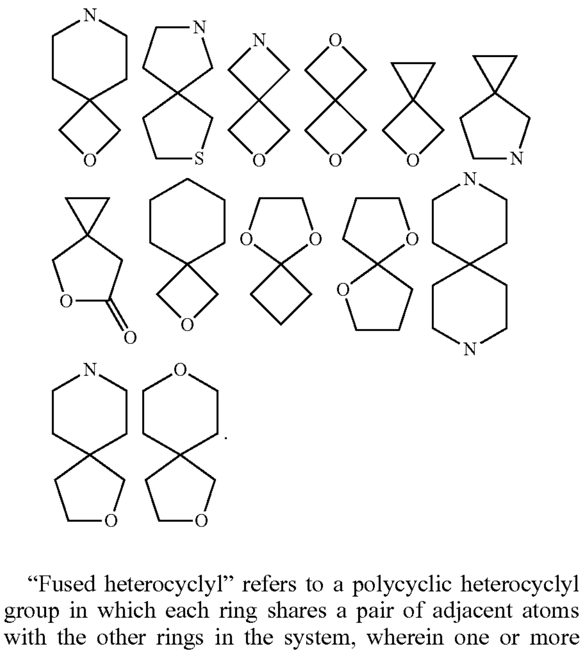

"Fused heterocyclyl" refers to a polycyclic heterocyclyl group in which each ring shares a pair of adjacent atoms with the other rings in the system, wherein one or more (preferably, 1, 2, 3 or 4) of the rings may contain one or more (preferably, 1, 2 or 3) double bonds, but none of them has a fully conjugated π-electron system, wherein one or more (preferably, 1, 2, 3 or 4) ring atoms are heteroatoms selected from nitrogen, oxygen, S(O)(=NH) and $S(O)_r$ (wherein r is an integer of 0, 1 or 2), and the remaining ring atoms are carbon atoms. According to the number of formed rings, the fused heterocycloalkyl may be bicyclic, tricyclic, tetracyclic or polycyclic, including but not limited to:

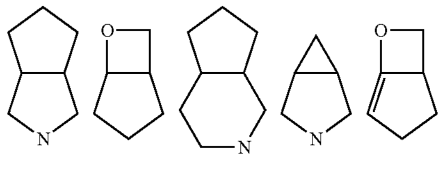
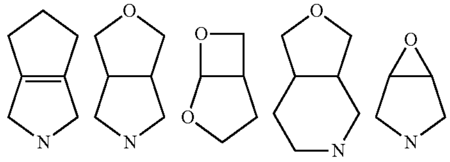
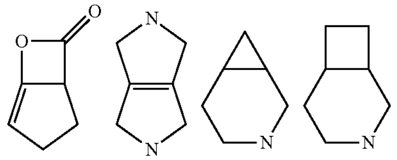
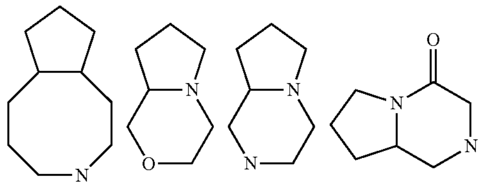
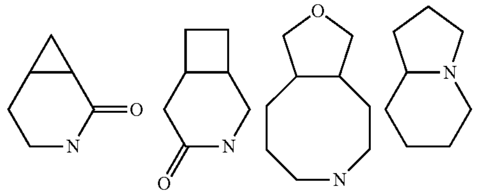
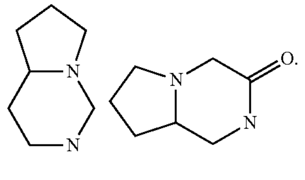

"Bridged heterocyclyl" refers to a polycyclic heterocyclyl group in which any two rings share two atoms that are not directly connected to each other, wherein these rings may contain one or more (preferably, 1, 2 or 3) double bonds, but none of them has a fully conjugated π-electron system, wherein one or more (preferably, 1, 2, 3 or 4) ring atoms are heteroatoms selected from nitrogen, oxygen, S(O)(=NH) and $S(O)_r$ (wherein r is an integer of 0, 1 or 2), and the remaining ring atoms are carbon atoms. According to the number of formed rings, the bridged heterocyclyl may be bicyclic, tricyclic, tetracyclic or polycyclic, including but not limited to:

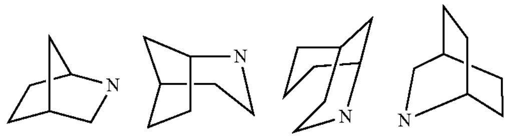
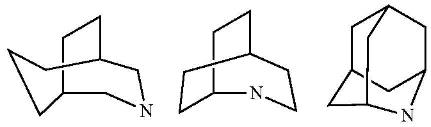
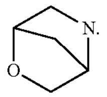

The heterocyclyl ring may be fused to an aryl, heteroaryl or cycloalkyl ring, wherein the ring attached to the parent structure is heterocyclyl, including but not limited to:

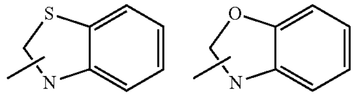
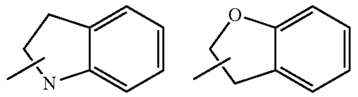
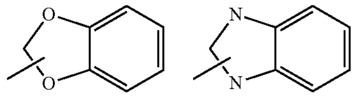
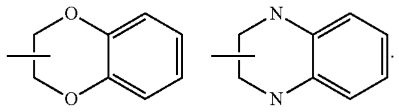

Heterocyclyl may be optionally substituted or unsubstituted, and when heterocyclyl is substituted, the substituents are preferably one or more (preferably 1, 2, 3 or 4) groups independently selected from the group consisting of the deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-$S(O)_rR_8$, —$C_{0-8}$ alkyl-O—$R_9$, —$C_{0-8}$ alkyl-C(O)$OR_{10}$, —$C_{0-8}$ alkyl-C(O)$R_{11}$, —$C_{0-8}$ alkyl-O—C(O)$R_{11}$, —$C_{0-8}$ alkyl-$NR_{12}R_{13}$, —$C_{0-8}$ alkyl-C(=$NR_{12}$)$R_{11}$, —$C_{0-8}$ alkyl-N($R_{12}$)—C(=$NR_{13}$)$R_{11}$, —$C_{0-8}$ alkyl-C(O)$NR_{12}R_{13}$ and —$C_{0-8}$ alkyl-N($R_{12}$)—C(O)$R_{11}$.

"Aryl" or "aromatic ring" refers to an all-carbon monocyclic or fused-polycyclic group (i.e., rings that share a pair of adjacent carbon atoms) and a polycyclic group having a conjugated π-electron system (i.e., rings with adjacent pairs of carbon atoms), and is preferably all-carbon aryl containing 6 to 10, 6 to 8 or 6 carbons atoms. For example, "$C_{6-10}$ aryl" refers to all-carbon aryl containing 6 to 10 carbon atoms, and "$C_{6-8}$ aryl" refers to all-carbon aryl containing 6 to 8 carbon atoms. The aryl or aromatic ring includes, but is not limited to, phenyl and naphthyl. The aryl ring can be fused to a heteroaryl, heterocyclyl or cycloalkyl ring, wherein the ring attached to the parent structure is the aryl ring, including but not limited to:

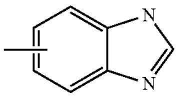
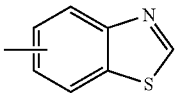
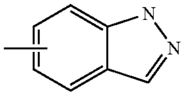
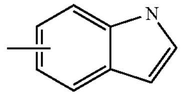
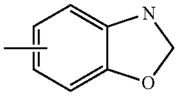
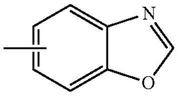
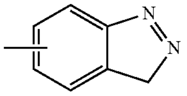
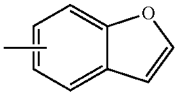
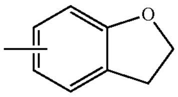
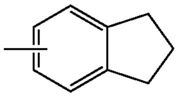
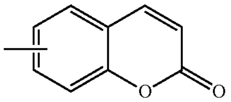
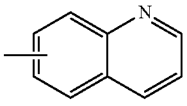
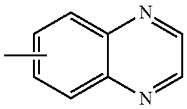
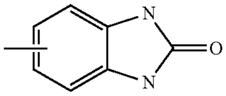
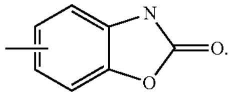

"Aryl" may be substituted or unsubstituted, and when aryl is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Heteroaryl" refers to a heteroaromatic system containing one or more (preferably 1, 2, 3 or 4) heteroatoms including nitrogen, oxygen and S(O)$_r$ (wherein r is an integer of 0, 1 or 2), and is preferably a heteroaromatic system containing 5 to 10, 5 to 8 or 5 to 6 ring atoms. For example, "5-6 membered heteroaryl" refers to a heteroaromatic system containing 5 to 6 ring atoms, "5-8 membered heteroaryl" refers to a heteroaromatic system containing 5 to 8 ring atoms, and "5-10 membered heteroaryl" refers to a heteroaromatic system containing 5 to 10 ring atoms. The heteroaryl includes, but is not limited to, furyl, thiophenyl, pyridyl, pyrrolyl, N-alkylpyrrolyl, pyrimidinyl, pyrazinyl, imidazolyl, tetrazolyl, etc. The heteroaryl ring can be fused to an aryl, heterocyclyl or cycloalkyl ring, wherein the ring attached to the parent structure is the heteroaryl ring, including but not limited to:

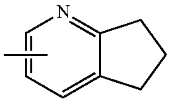
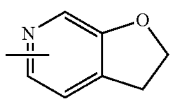

-continued

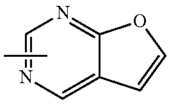
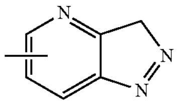
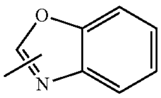
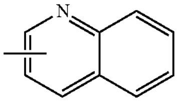
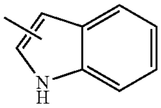
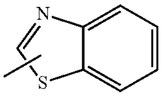
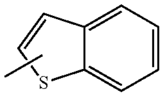
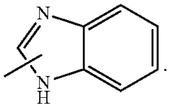

"Heteroaryl" may be optionally substituted or unsubstituted, and when heteroaryl is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Alkenyl" refers to alkyl defined as above consisting of at least two carbon atoms and at least one carbon-carbon double bond, and is preferably linear or branched alkenyl containing 2 to 10 or 2 to 4 carbon atoms. For example, "$C_{2-10}$ alkenyl" refers to linear or branched alkenyl containing 2 to 10 carbon atoms, and "$C_{2-4}$ alkenyl" refers to linear or branched alkenyl containing 2 to 4 carbon atoms. The alkenyl includes, but is not limited to, vinyl, 1-propenyl, 2-propenyl, 1-, 2- or 3-butenyl, and the like.

"Alkenyl" may be substituted or unsubstituted, and when alkenyl is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Alkynyl" refers to alkyl defined as above consisting of at least two carbon atoms and at least one carbon-carbon triple bond, and is preferably linear or branched alkynyl containing 2 to 10 or 2 to 4 carbon atoms. For example, "$C_{2-10}$ alkynyl" refers to linear or branched alkynyl containing 2 to 10 carbon atoms, and "$C_{2-4}$ alkynyl" refers to linear or branched alkynyl containing 2 to 4 carbon atoms. The alkynyl includes, but is not limited to, ethynyl, 1-propynyl, 2-propynyl, 1-, 2- or 3-butynyl, and the like.

"Alkynyl" may be substituted or unsubstituted, and when alkynyl is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Alkoxy" refers to —O-alkyl, wherein the alkyl is defined as above. For example, "$C_{1-10}$ alkoxy" refers to alkoxy containing 1 to 10 carbon atoms, and "$C_{1-4}$ alkoxy" refers to alkoxy containing 1 to 4 carbon atoms. The alkoxy includes, but is not limited to, methoxy, ethoxy, propoxy, butoxy and the like.

"Alkoxy" may be optionally substituted or unsubstituted, and when alkoxy is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Cycloalkyloxy" refers to —O-cycloalkyl, wherein the cycloalkyl is defined as above. For example, "$C_{3-12}$ cycloalkyloxy" refers to cycloalkyloxy containing 3 to 12 carbon atoms, and "$C_{3-8}$ cycloalkyloxy" refers to cycloalkyloxy containing 3 to 8 carbon atoms. The cycloalkyloxy includes, but is not limited to, cyclopropyloxy, cyclobutyloxy, cyclopentyloxy, cyclohexyloxy, etc.

"Cycloalkyloxy" may be optionally substituted or unsubstituted, and when cycloalkyloxy is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"Heterocyclyloxy" refers to —O-heterocyclyl, wherein heterocyclyl is defined as above, and heterocyclyloxy includes, but is not limited to, azacyclobutyloxy, oxacyclobutyloxy, azacyclopentyloxy, nitrogen, oxacyclohexyloxy, etc.

"Heterocyclyloxy" may be optionally substituted or unsubstituted, and when heterocyclyloxy is substituted, the substituents are preferably one or more (preferably 1, 2, 3 or 4) groups independently selected from the group consisting of deuterium, halogen, cyano, nitro, azido, $C_{1-10}$ alkyl, $C_{2-10}$ alkenyl, $C_{2-10}$ alkynyl, $C_{1-10}$ haloalkyl, $C_{1-10}$ deuterioalkyl, $C_{3-12}$ cycloalkyl, 3-12 membered heterocyclyl, $C_{6-10}$ aryl, 5-10 membered heteroaryl, =O, —$C_{0-8}$ alkyl-$SF_5$, —$C_{0-8}$ alkyl-S(O)$_r$$R_8$, —$C_{0-8}$ alkyl-O—$R_9$, —$C_{0-8}$ alkyl-C(O)O$R_{10}$, —$C_{0-8}$ alkyl-C(O)$R_{11}$, —$C_{0-8}$ alkyl-O—C(O)$R_{11}$, —$C_{0-8}$ alkyl-N$R_{12}R_{13}$, —$C_{0-8}$ alkyl-C(=N$R_{12}$)$R_{11}$, —$C_{0-8}$ alkyl-N($R_{12}$)—C(=N$R_{13}$)$R_{11}$, —$C_{0-8}$ alkyl-C(O)N$R_{12}R_{13}$ and —$C_{0-8}$ alkyl-N($R_{12}$)—C(O)$R_{11}$.

"$C_{1-10}$ alkanoyl" refers to a monovalent atomic group which is obtained after hydroxy is removed from $C_{1-10}$ alkyl acid, and is also generally referred to as "$C_{0-9}$ alkyl-C(O)—". For example, "$C_1$ alkyl-C(O)—" refers to acetyl; "$C_2$ alkyl-C(O)—" refers to propionyl; and "$C_3$ alkyl-C(O)—" refers to butyryl or isobutyryl.

"$C_{1-4}$" refers to "$C_{1-4}$ alkyl", "$C_{0-4}$" refers to "$C_{0-4}$ alkyl", "$C_{1-8}$" refers to "$C_{1-8}$ alkyl", and "$C_{0-8}$" refers to "$C_{0-8}$ alkyl", which are defined as above.

"—$C_{0-8}$ alkyl-S(O)$_r$$R_8$" means that the sulfur atom in —S(O)$_r$$R_8$ is connected to $C_{0-8}$ alkyl, wherein $C_{0-8}$ alkyl is defined as above.

"—$C_{0-8}$ alkyl-O—$R_9$" means that the oxygen atom in —O—$R_9$ is connected to $C_{0-8}$ alkyl, wherein $C_{0-8}$ alkyl is defined as above.

"—$C_{0-8}$ alkyl-C(O)O$R_{10}$" means that the carbonyl in —C(O)O$R_{10}$ is connected to $C_{0-8}$ alkyl, wherein $C_{0-8}$ alkyl is defined as above.

"—$C_{0-8}$ alkyl-C(O)$R_{11}$" means that the carbonyl in —C(O)$R_{11}$ is connected to $C_{0-8}$ alkyl, wherein $C_{0-8}$ alkyl is defined as above.

"—$C_{0-8}$ alkyl-O—C(O)$R_{11}$" means that the oxygen atom in —O—C(O)$R_1$ is connected to $C_{0-8}$ alkyl, wherein $C_{0-8}$ alkyl is defined as above.

"—$C_{0-8}$ alkyl-N$R_{12}R_{13}$" means that the nitrogen atom in —N$R_{12}R_{13}$ is connected to $C_{0-8}$ alkyl, wherein $C_{0-8}$ alkyl is defined as above.

"—$C_{0-8}$ alkyl-C(=N$R_{12}$)$R_{11}$" means that the carbon atom in —C(=N$R_{12}$)$R_{11}$ is connected to $C_{0-8}$ alkyl, wherein $C_{0-8}$ alkyl is defined as above.

"—$C_{0-8}$ alkyl-N($R_{12}$)—C(=N$R_{13}$)$R_{11}$" means that the nitrogen atom in —N($R_{12}$)—C(=N$R_{13}$)$R_{11}$ is connected to $C_{0-8}$ alkyl, wherein $C_{0-8}$ alkyl is defined as above.

"—$C_{0-8}$ alkyl-C(O)N$R_{12}R_{13}$" means that the carbonyl in —C(O)N$R_{12}R_{13}$ is connected to $C_{0-8}$ alkyl, wherein $C_{0-8}$ alkyl is defined as above.

"—$C_{0-8}$ alkyl-N($R_{12}$)—C(O)$R_{11}$" means that the nitrogen atom in —N($R_{12}$)—C(O)$R_{11}$ is connected to $C_{0-8}$ alkyl, wherein $C_{0-8}$ alkyl is defined as above.

"$C_{1-10}$ haloalkyl" refers to an alkyl group having 1 to 10 carbon atoms in which hydrogens on the alkyl are optionally substituted with a fluorine, chlorine, bromine or iodine atom, including but not limited to, difluoromethyl (—$CHF_2$), dichloromethyl (—$CHCl_2$), dibromomethyl (—$CHBr_2$), trifluoromethyl (—$CF_3$), trichloromethyl (—$CCl_3$), tribromomethyl (—$CBr_3$), etc.

"$C_{1-10}$ haloalkoxy" refers to an alkoxy group having 1 to 10 carbon atoms in which hydrogens on the alkyl are optionally substituted with a fluorine, chlorine, bromine or iodine atom, including but not limited to, difluoromethoxy, dichloromethoxy, dibromomethoxy, trifluoromethoxy, trichloromethoxy, tribromomethoxy, etc.

"$C_{1-10}$ deuterioalkyl" refers to an alkyl group having 1 to 10 carbon atoms in which hydrogens on the alkyl are optionally substituted with a deuterium atom, including but not limited to, monodeuteriomethyl (—$CH_2D$), dideuteriomethyl (—$CHD_2$), trideuteriomethyl (—$CD_3$), etc.

"$C_{1-10}$ deuterioalkyl" refers to an alkyl group having 1 to 10 carbon atoms in which hydrogens on the alkyl are optionally substituted with a deuterium atom, including but not limited to, monodeuteriomethoxy, dideuteriomethoxy, trideuteriomethoxy, etc.

"Halogen" refers to fluorine, chlorine, bromine or iodine. "EtOAc" refers to ethyl acetate. "PE" refers to petroleum ether. "DMF" refers to dimethylformamide.

The term "optional" or "optionally" means that the event or circumstance subsequently described may, but not necessarily, occur, and that the description includes instances where the event or circumstance occurs or does not occur, that is, instances where substitution occurs or does not occur. For example, "heterocyclyl group optionally substituted with alkyl" means that alkyl may be, but not necessarily, present, and that the description includes instances where the heterocyclyl group is or is not substituted with alkyl.

The term "substituted" means that one or more hydrogen atoms in the group are each independently substituted by a corresponding number of substituents. It goes without saying that a substituent is only in its possible chemical position and consistent with chemical valence bond theory, and those skilled in the art will be able to determine (by studies or theories) possible or impossible substitution without undue efforts. For example, it may be unstable when amino or hydroxy having free hydrogen is bound to a carbon atom having an unsaturated bond (such as olefin).

"Stereoisomers" refer to isomers produced by different spatial arrangements of atoms in molecules, and can be classified into cis-trans isomers and enantiomers, and also into enantiomers and diastereomers. Stereoisomers resulting from rotation of single bonds are referred to as conformational stereo-isomers and sometimes also as rotamers. Stereoisomers resulting from bond lengths, bond angles, intramolecular double bonds, rings and the like are referred to as configuration stereo-isomers, and the configuration stereo-isomers are classified into two categories. Among them, isomers resulting from the fact that a double bond or a single bond of a ring-forming carbon atom cannot rotate freely are referred to as geometric isomers and also as cis-trans isomers, and the isomers are classified into Z, E configurations. For example, cis-2-butene and trans-2-butene are a pair of geometric isomers, and the compounds of the present invention may be understood to comprise the E and/or Z forms if they contain a double bond, as not specifically indicated. Stereoisomers having different optical rotation properties due to the absence of anti-axisymmetry in the molecule are referred to as optical isomers, and are classified into R and S configurations. In the present invention, the term "stereoisomer" may be understood to include one or more of the above enantiomers, configuration isomers and conformational isomers, unless otherwise specified, preferably S configuration.

"Pharmaceutically acceptable salt" as used herein refers to pharmaceutically acceptable acid addition salts or base addition salts, including inorganic and organic acid salts, which may be prepared by methods known in the art.

"Pharmaceutical composition" refers to a mixture containing one or more of the compounds described herein or a physiologically/pharmaceutically acceptable salt or prodrug thereof, and other chemical components, for example physiologically/pharmaceutically acceptable carriers and excipients. The purpose of the pharmaceutical composition is to promote the administration to an organism, which facilitates the absorption of the active ingredient, thereby exerting biological activities.

The present invention is further explained in detail below with reference to examples, which are not intended to limit the present invention, and the present invention is not merely limited to the contents of the examples.

The compound structure of the present invention is determined by nuclear magnetic resonance (NMR) and/or liquid chromatography-mass spectrometry (LC-MS). The NMR chemical shift (δ) is given in parts per million (ppm). The NMR determination is conducted by using a Bruker AVANCE-400/500 nuclear magnetic resonance apparatus, with hexadeuterodimethyl sulfoxide (DMSO-$d_6$), tetradeuteromethanol (MeOH-$d_4$), and deuterated chloroform ($CDCl_3$) as determination solvents, and tetramethylsilane (TMS) as an internal standard.

The LC-MS determination is conducted by using an Agilent 6120 mass spectrometer. The HPLC determination is conducted by using an Agilent 1200 DAD high pressure liquid chromatograph (Sunfire C18 150*4.6 mm chromatographic column) and a Waters 2695-2996 high pressure liquid chromatograph (Gimini C18 150*4.6 mm chromatographic column).

A Yantai Yellow Sea HSGF254 or Qingdao GF254 silica gel plate is adopted as a thin layer chromatography (TLC) silica gel plate. The specification adopted by the TLC is 0.15-0.20 mm, and the specification adopted by the thin layer chromatography for product separation and purification is 0.4-0.5 mm. The Yantai Yellow Sea silica gel of 200-300 mesh is generally utilized as a carrier in column chromatography.

Starting materials in the examples of the present invention are known and commercially available, or may be synthesized by using or according to methods known in the art.

Unless otherwise stated, all reactions of the present invention are carried out under a dry nitrogen or argon atmosphere with continuous magnetic stirring, wherein the solvent is a dry solvent, and the reaction temperature is in degree centigrade (° C.).

I. Preparation of Intermediates

Intermediate 1: Preparation of 2',4'-difluoro-[1,1'-biphenyl]-3-amine

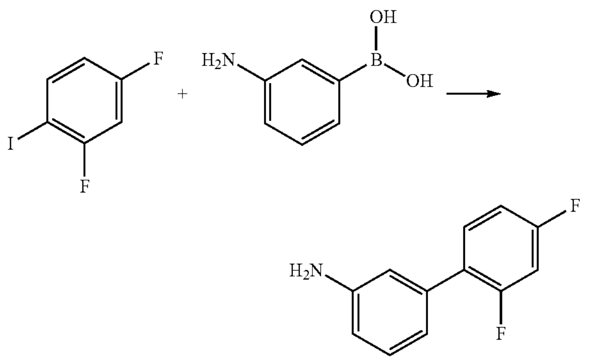

2,4-difluoro-1-iodobenzene (7.96 g, 33.18 mmol), (3-aminophenyl)boronic acid (5.0 g, 36.50 mmol), potassium carbonate (13.74 g, 99.54 mmol) and palladium acetate (372 mg, 1.66 mmol) were added in a mixture of ethanol and water (100 mL, 3:1), and then the mixture was stirred at room temperature under nitrogen protection for 18 hrs. After the reaction was completed, the reaction mixture was diluted with water and extracted with EtOAc. The organic phase was washed with saturated brine, dried over anhydrous sodium sulfate, filtered and concentrated, and the residue was separated by silica gel column chromatography [developing solvent: EtOAc/PE=0-50%] to obtain 2',4'-difluoro-[1,1'-biphenyl]-3-amine (5.67 g, yield: 83%). MS m/z (ESI): 206.2 [M+H]+.

Intermediate 2: Preparation of 2-fluoro-5-(5-fluoropyridin-2-yl)aniline

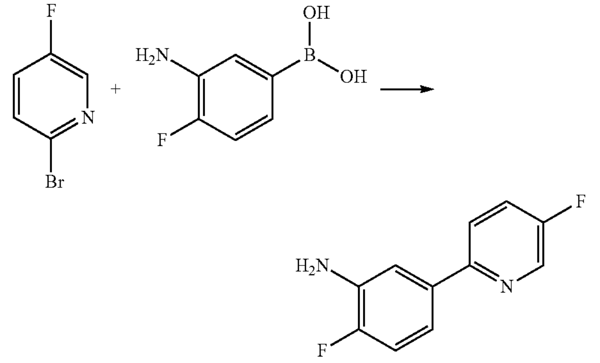

2-bromo-5-fluoropyridine (750 mg, 4.26 mmol), (3-amino-4-fluorophenyl)boronic acid (859 mg, 5.54 mmol), aqueous $Na_2CO_3$ (2N, 8.5 mL, 17.04 mmol) and $Pd(PPh_3)_4$ (246 mg, 0.21 mmol) were added in dioxane (15 mL), the mixture was stirred at 90° C. under nitrogen protection for 18 hrs, and the reaction mixture was diluted with water and extracted with EtOAc. The organic phase was washed with saturated brine, dried over anhydrous sodium sulfate, filtered and concentrated, and the residue was separated by column chromatography [developing solvent: EtOAc/PE=0-50%] to obtain 2-fluoro-5-(5-fluoropyridin-2-yl)aniline (916 mg, yield: >99%). MS m/z (ESI): 207.1 [M+H]+.

Intermediates 3-17 can be Prepared by Referring to the Preparation Method for Intermediate 1 or 2

| Intermediate No. | Structural formula | Chemical name | $[M + H]^+$ |
|---|---|---|---|
| 3 | 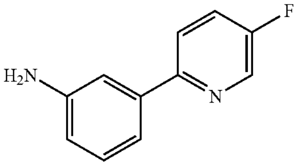 [SMILES: Nc1cccc(-c2ccc(F)cn2)c1] | 3-(5-fluoropyridin-2-yl)aniline | 189.1 |
| 4 | 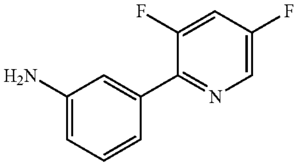 [SMILES: Nc1cccc(-c2ncc(F)cc2F)c1] | 3-(3,5-difluoropyridin-2-yl)aniline | 207.3 |
| 5 | 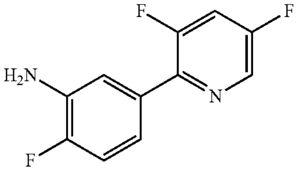 [SMILES: Nc1cc(-c2ncc(F)cc2F)ccc1F] | 5-(3,5-difluoropyridin-2-yl)-2-fluoroaniline | 225.1 |
| 6 | 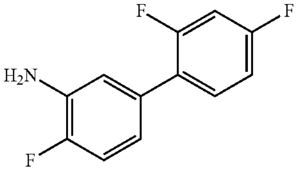 [SMILES: Nc1cc(-c2ccc(F)cc2F)ccc1F] | 2',4,4'-trifluoro-[1,1'-biphenyl]-3-amine | 224.2 |
| 7 | 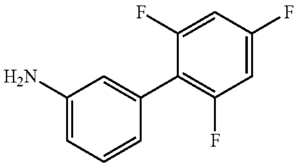 [SMILES: Nc1cccc(-c2c(F)cc(F)cc2F)c1] | 2',4',6'-trifluoro-[1,1'-biphenyl]-3-amine | 224.2 |
| 8 | 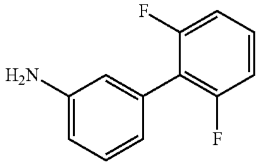 [SMILES: Nc1cccc(-c2c(F)cccc2F)c1] | 2',6'-difluoro-[1,1'-biphenyl]-3-amine | 206.2 |

-continued
| Intermediate No. | Structural formula | Chemical name | [M + H]+ |
|---|---|---|---|
| 9 | 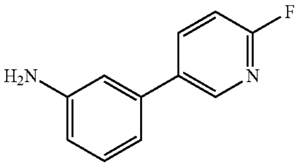 [SMILES: Nc1cccc(-c2ccc(F)nc2)c1] | 3-(6-fluoropyridin-3-yl)aniline | 189.2 |
| 10 | 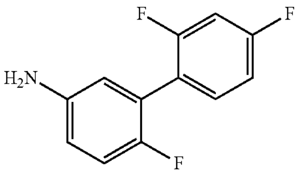 [SMILES: Nc1ccc(F)c(-c2ccc(F)cc2F)c1] | 2',4',6-trifluoro-[1,1'-biphenyl]-3-amine | 224.2 |
| 11 | 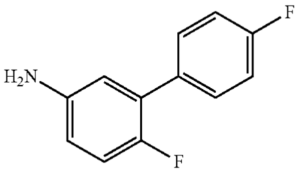 [SMILES: Nc1ccc(F)c(-c2ccc(F)cc2)c1] | 4',6-difluoro-[1,1'-biphenyl]-3-amine | 206.2 |
| 12 | 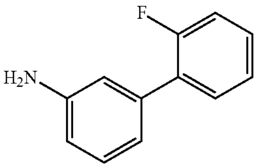 [SMILES: Nc1cccc(-c2ccccc2F)c1] | 2'-fluoro-[1,1'-biphenyl]-3-amine | 188.2 |
| 13 | 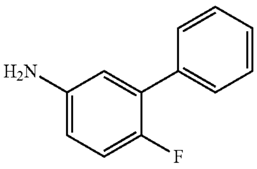 [SMILES: Nc1ccc(F)c(-c2ccccc2)c1] | 6-fluoro-[1,1'-biphenyl]-3-amine | 188.2 |
| 14 | 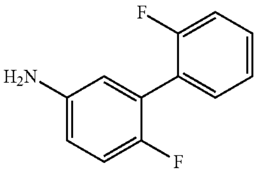 [SMILES: Nc1ccc(F)c(-c2ccccc2F)c1] | 2',6-difluoro-[1,1'-biphenyl]-3-amine | 206.2 |
| 15 | 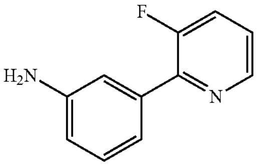 [SMILES: Nc1cccc(-c2ncccc2F)c1] | 3-(3-fluoropyridin-2-yl)aniline | 189.2 |
| 16 | 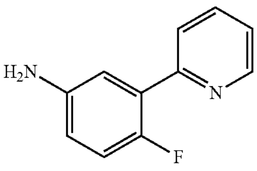 [SMILES: Nc1ccc(F)c(-c2ccccn2)c1] | 4-fluoro-3-(pyridin-2-yl)aniline | 189.2 |

-continued

| Intermediate No. | Structural formula | Chemical name | [M + H]+ |
|---|---|---|---|
| 17 | 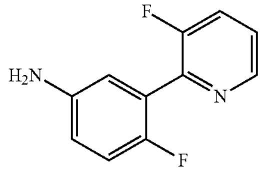 [SMILES: Nc1ccc(F)c(-c2ncccc2F)c1] | 4-fluoro-3-(3-fluoropyridin-2-yl)aniline | 207.1 |

Intermediate 18: Preparation of 2,6,6'-trifluoro-[1,1'-biphenyl]-3-amine

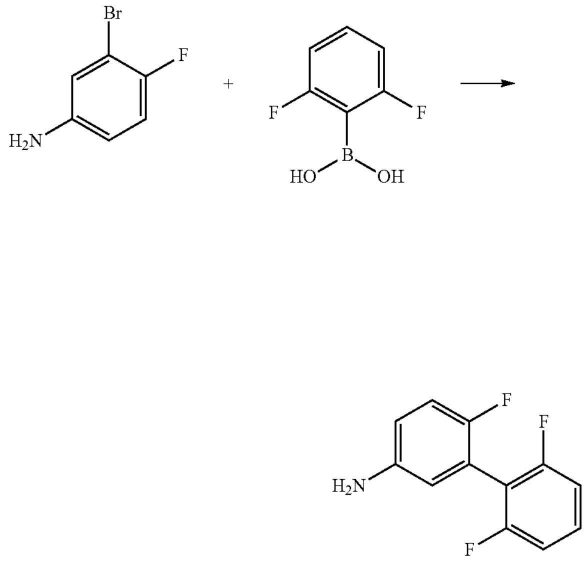

3-bromo-4-fluoroaniline (1.50 g, 7.90 mmol), (2,6-difluorophenyl)boronic acid (1.25 g, 7.90 mmol), potassium carbonate (3.27 g, 23.7 mmol) and SPhos Pd G2 (284 mg, 0.39 mmol) were added in a mixture of dioxane and water (40 mL, 3:1). The mixture was stirred at 60° C. under nitrogen protection for 18 hrs, and then the reaction mixture was diluted with water and extracted with EtOAc. The organic phase was washed with saturated brine, dried over anhydrous sodium sulfate, filtered and concentrated, and the residue was separated by column chromatography [developing solvent: EtOAc/PE=0-20%] to obtain 2',6,6'-trifluoro-[1,1'-biphenyl]-3-amine (183 mg, yield: 10.4%). MS m/z (ESI): 224.2 $[M+H]^+$.

Intermediate 19: Preparation of 2-(2-fluorophenyl)pyridin-4-amine

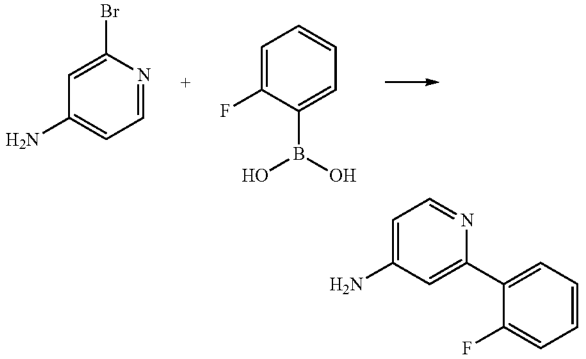

2-bromopyridin-4-amine (10 g, 57.80 mmol) and (2-fluorophenyl)boronic acid (9.70 g, 69.36 mmol) were dissolved in 1,4-dioxane (170 mL), then aqueous $K_2CO_3$ (2M, 86.7 mL, 173.40 mmol) and $Pd(PPh_3)_4$ (1.34 g, 1.16 mmol) were added, and after the nitrogen was replaced for three times, the reaction mixture was heated to 90° C. and stirred for 18 hrs. After the reaction was completed, the reaction mixture was cooled to room temperature, added with saturated brine (600 mL) and extracted with ethyl acetate. The organic phase was washed with saturated brine, dried over anhydrous sodium sulfate, filtered and concentrated, and the crude product was separated by column chromatography [eluent: EtOAc/PE=0-50%] to obtain 2-(2-fluorophenyl)pyridin-4-amine (10.0 g, yield: 92%). MS m/z (ESI): 189.0 $[M+H]^+$.

Intermediates 20-22 can be Prepared by Referring to the Preparation Method for Intermediate 19

| Intermediate No. | Structural formula | Chemical name | [M + H]+ |
|---|---|---|---|
| 20 | 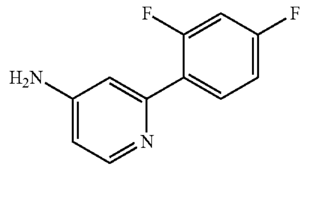 [SMILES: Nc1ccnc(-c2ccc(F)cc2F)c1] | 2-(2,4-difluorophenyl)pyridin-4-amine | 207.0 |

-continued

| Intermediate No. | Structural formula | Chemical name | [M + H]$^+$ |
|---|---|---|---|
| 21 | 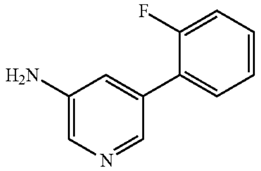 [SMILES: Nc1cncc(-c2ccccc2F)c1] | 5-(2-fluorophenyl) pyridin-3-amine | 189.0 |
| 22 | 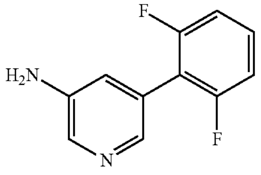 [SMILES: Nc1cncc(-c2c(F)cccc2F)c1] | 5-(2,6-difluorophenyl) pyridin-3-amine | 207.0 |

Intermediate 23: Preparation of 2-(2,6-difluorophenyl)pyridin-4-amine

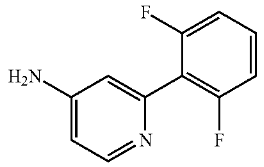 [SMILES: Nc1ccnc(-c2c(F)cccc2F)c1]

Step 1: Synthesis of tert-butyl-(2-(2,6-difluorophenyl)pyridin-4-yl)carbamate

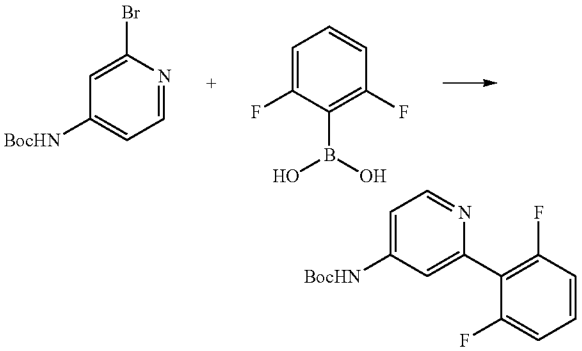

Tert-butyl-(2-bromopyridin-4-yl)carbamate (2.3 g, 8.4 mmol), (2,6-difluorophenyl)boronic acid (1.46 g, 9.3 mmol), $Na_2CO_3$ (2.68 g, 25.3 mmol) and tBuXPhos Pd G3 (methanesulfonato(2-di-tert-butylphosphino-2',4',6'-triisopropyl-1,1'-biphenyl)(2'-amino-1,1'-biphenyl-2-yl)palladium(II) (0.67 g, 0.84 mmol) were added in a mixture of 1,4-dioxane (20 mL) and water (10 mL). The mixture was stirred at 50° C. under nitrogen protection overnight, and the reaction mixture was diluted with water and extracted with EtOAc. The organic phase was washed with saturated brine, dried over anhydrous sodium sulfate, filtered and concentrated, and the residue was separated by column chromatography [developing solvent: MeOH/DCM=0-10%] to obtain tert-butyl-(2-(2,6-difluorophenyl)pyridin-4-yl)carbamate (0.71 g, yield: 26%). MS m/z (ESI): 307.0 [M+H]$^+$.

Step 2: Synthesis of 2-(2,6-difluorophenyl)pyridin-4-amine

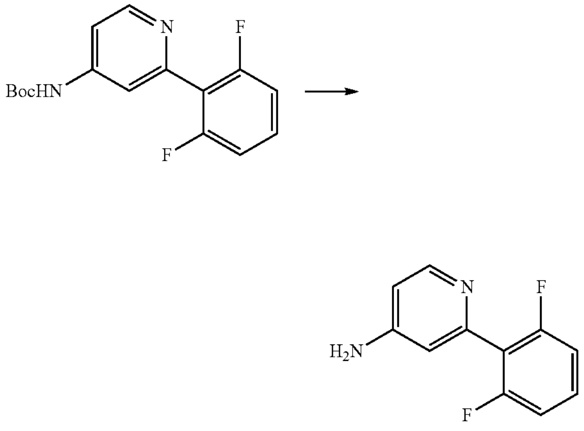

Tert-butyl-(2-(2,6-difluorophenyl)pyridin-4-yl)carbamate (0.71 g, 2.2 mmol) was dissolved in dichloromethane (3 mL), trifluoroacetic acid (0.82 mL, 11.0 mmol) was then added. The reaction mixture was stirred at room temperature for 3 hrs, then concentrated to remove the solvent. The reaction mixture was added with NaOH to adjust pH to 8 and extracted with EtOAc, the organic phase was washed with saturated brine, dried over anhydrous sodium sulfate, filtered and concentrated, and the residue was separated by column chromatography [developing solvent: MeOH/DCM=0-10%] to obtain 2-(2,6-difluorophenyl)pyridin-4-amine (0.40 g, yield: 88%). MS m/z (ESI): 207.0 [M+H]$^+$.

Intermediate 24: Preparation of 7-(3-methyl-3-(4-methylpiperazin-1-yl)but-1-yn-1-yl)-6-nitroquinazolin-4-ol

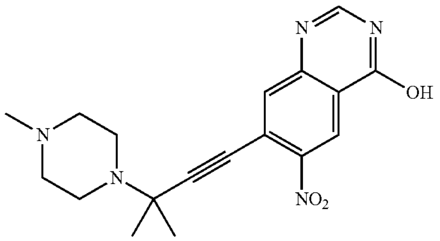 [SMILES: CN1CCN(C(C)(C)C#Cc2cc3ncnc(O)c3cc2[N+](=O)[O-])CC1]

Step 1: Synthesis of 1-methyl-4-(2-methylbut-3-yn-2-yl)piperazine

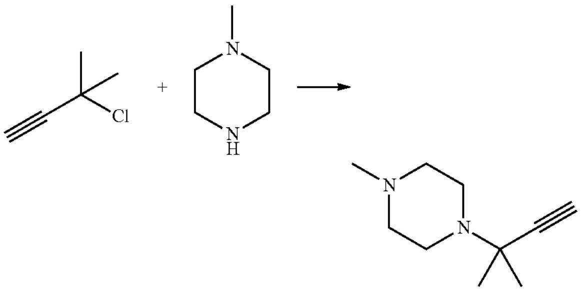

3-chloro-3-methylbut-1-yne (6.14 g, 59.9 mmol), triethylamine (5.05 g, 49.9 mmol) and 1-methylpiperazine (5.0 g, 49.9 mmol) were added in THE (20 mL). The reaction mixture was cooled to 0° C., added with CuCl (0.69 g, 6.96 mmol) under nitrogen protection, and stirred at room temperature. After the reaction was completed as monitored by LCMS, brine was added to quench the reaction. The reaction mixture was extracted with EtOAc 5 times, the organic phases were combined and washed with saturated brine, dried over anhydrous $Na_2SO_4$, filtered and concentrated to obtain the crude product 1-methyl-4-(2-methylbut-3-yn-2-yl)piperazine (5.30 g, yield: 63%).

Step 2: Synthesis of 7-(3-methyl-3-(4-methylpiperazin-1-yl)but-1-yn-1-yl)-6-nitroquinazolin-4-ol

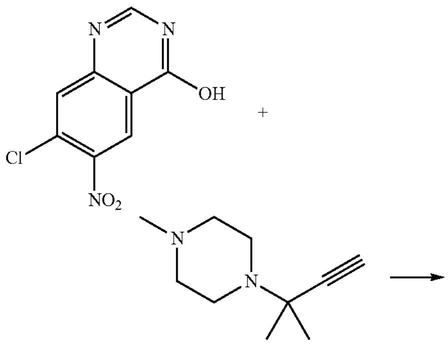

-continued

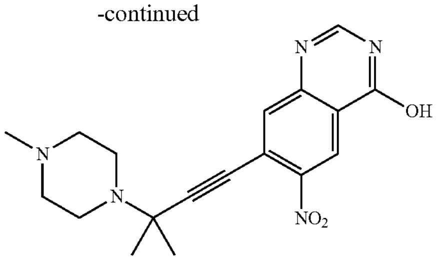

To a solution of 1-methyl-4-(2-methylbut-3-yn-2-yl)piperazine (0.50 g, 3.0 mmol) and 7-chloro-6-nitroquinazolin-4-ol (0.57 g, 2.5 mmol) in DMF (8.0 mL) were added $Pd(PPh_3)_4$ (0.29 g, 0.25 mmol), CuI (95 mg, 0.50 mmol) and triethylamine (3.0 mL). After the nitrogen was replaced, the reaction mixture was heated to 80° C. and stirred for 1.5 hrs. After the reaction was completed as monitored by LCMS, the reaction mixture was cooled and concentrated, and the residue was separated by column chromatography [developing solvent: DCM/MeOH (+1% ammonia liquor)=0-10%] to obtain 7-(3-methyl-3-(4-methylpiperazin-1-yl)but-1-yn-1-yl)-6-nitroquinazolin-4-ol (0.40 g, yield: 35%). MS m/z (ESI): 356.0 $[M+H]^+$.

Intermediate 25: Preparation of 7-(3-(dimethylamino)-3-methylbut-1-yn-1-yl)-6-nitroquinazolin-4-ol

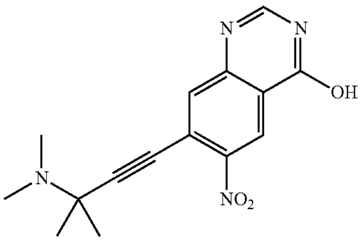 [SMILES: CN(C)C(C)(C)C#Cc1cc2ncnc(O)c2cc1[N+](=O)[O-]]

Intermediate 25 was prepared by synthesis of selecting corresponding starting materials by referring to the preparation method in intermediate 24.

II. Preparation of Specific Examples

Example 1: Preparation of N-(4-((2',4'-difluoro-[1,1'-biphenyl]-3-yl)amino)-7-(3-morpholinopropoxy)quinazolin-6-yl)acrylamide

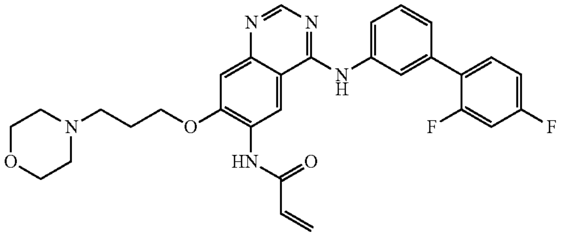 [SMILES: C=CC(=O)Nc1cc2c(Nc3cccc(-c4ccc(F)cc4F)c3)ncnc2cc1OCCCN1CCOCC1]

Step 1: Synthesis of 4-chloro-7-fluoro-6-nitroquinazoline

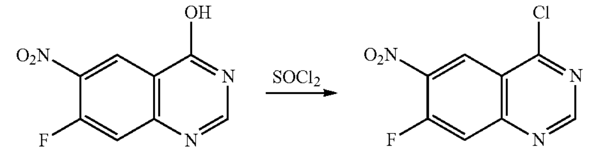

To a solution of 7-fluoro-6-nitroquinazolin-4-ol (5.0 g, 23.92 mmol) in thionyl chloride (15 mL) was added DMF (0.5 mL), and after the nitrogen was replaced several times, the reaction mixture was stirred at 85° C. for 18 hrs, and concentrated to obtain the crude product 4-chloro-7-fluoro-6-nitroquinazoline, which was stored under nitrogen protection.

Step 2: Synthesis of N-(2',4'-difluoro-[1,1'-biphenyl]-3-yl)-7-fluoro-6-nitroquinazolin-4-amine

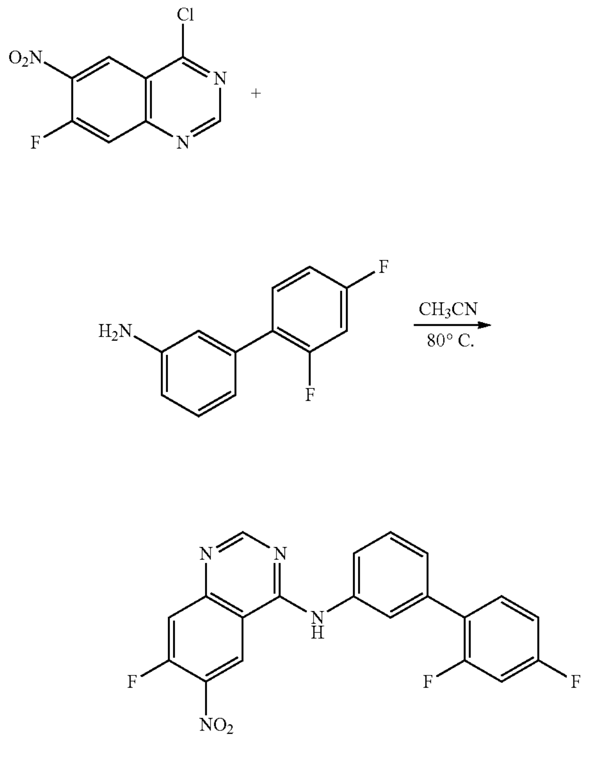

4-chloro-7-fluoro-6-nitroquinazoline (1.0 g, 4.39 mmol) and 2',4'-difluoro-[1,1'-biphenyl]-3-amine (902 mg, 4.39 mmol) were added to anhydrous acetonitrile (20 mL). The reaction mixture was stirred at 80° C. for 1 hr, and filtered. The resulting solid was added with EtOAc (400 mL) to reflux, followed by hot filtration, and the resulting solid was slurried with $CH_2Cl_2$ (20 mL), and filtered to obtain N-(2',4'-difluoro-[1,1'-biphenyl]-3-yl)-7-fluoro-6-nitroquinazolin-4-amine (946 mg, yield: 54%). MS m/z (ESI): 397.0 $[M+H]^+$.

Step 3: Synthesis of N-(2',4'-difluoro-[1,1'-biphenyl]-3-yl)-7-(3-morpholinopropoxy)-6-nitroquinazolin-4-amine

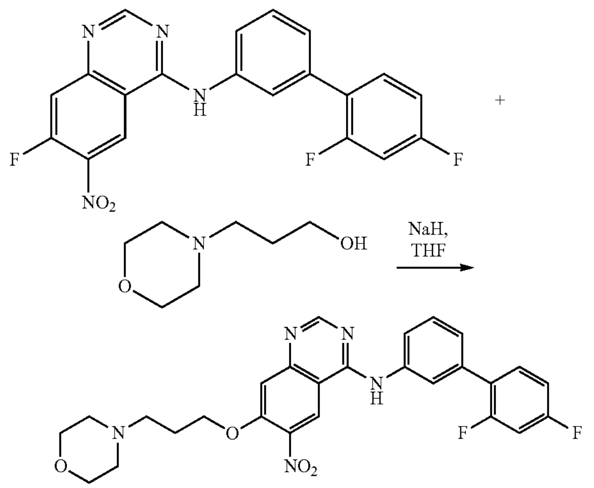

3-morpholinopropan-1-ol (327 mg, 2.26 mmol) was dissolved in anhydrous tetrahydrofuran (10 mL), sodium hydride (90 mg, purity: 60%, 2.26 mmol) was added, and the reaction mixture was stirred at room temperature under nitrogen protection for 10 min. N-(2',4'-difluoro-[1,1'-biphenyl]-3-yl)-7-fluoro-6-nitroquinazolin-4-amine (470 mg, purity: 63%, 0.75 mmol) was then added, the reaction mixture was stirred at 80° C. for 18 hrs, and after the reaction mixture was directly concentrated, the residue was separated by silica gel column chromatography [developing solvent: MeOH/DCM=0-10%] to obtain N-(2',4'-difluoro-[1,1'-biphenyl]-3-yl)-7-(3-morpholinopropoxy)-6-nitroquinazolin-4-amine (550 mg, yield: 90%). MS m/z (ESI): 522.2 $[M+H]^+$.

Step 4: Synthesis of $N^4$-(2',4'-difluoro-[1,1'-biphenyl]-3-yl)-7-(3-morpholinopropoxy)quinazoline-4,6-diamine

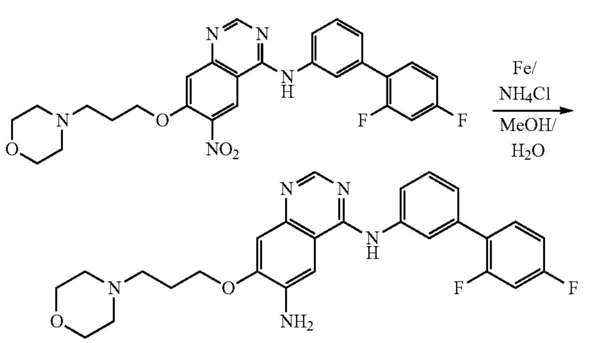

To a solution of N-(2',4'-difluoro-[1,1'-biphenyl]-3-yl)-7-(3-morpholinopropoxy)-6-nitroquinazolin-4-amine (550 mg, 1.05 mmol) in methanol/water (5 mL, 4:1) were added iron powder (472 mg, 8.44 mmol) and ammonium chloride (456 mg, 8.44 mmol), and then the reaction mixture was stirred at 80° C. overnight. If the reaction wasn't completed, iron powder (472 mg, 8.44 mmol) and ammonium chloride (456 mg, 8.44 mmol) were supplemented and then the mixture was heated and stirred overnight. The reaction mixture was filtered, and washed with methanol, and the filtrate was concentrated and then separated with a preparative column to obtain $N_4$-(2',4'-difluoro-[1,1'-biphenyl]-3-yl)-7-(3-morpholinopropoxy)quinazoline-4,6-diamine (100 mg, yield: 27.5%). MS m/z (ESI): 4 92.2 $[M+H]^+$.

Step 5: Synthesis of N-(4-((2',4'-difluoro-[1,1'-biphenyl]-3-yl)amino)-7-(3-morpholinopropoxy)quinazolin-6-yl)acrylamide

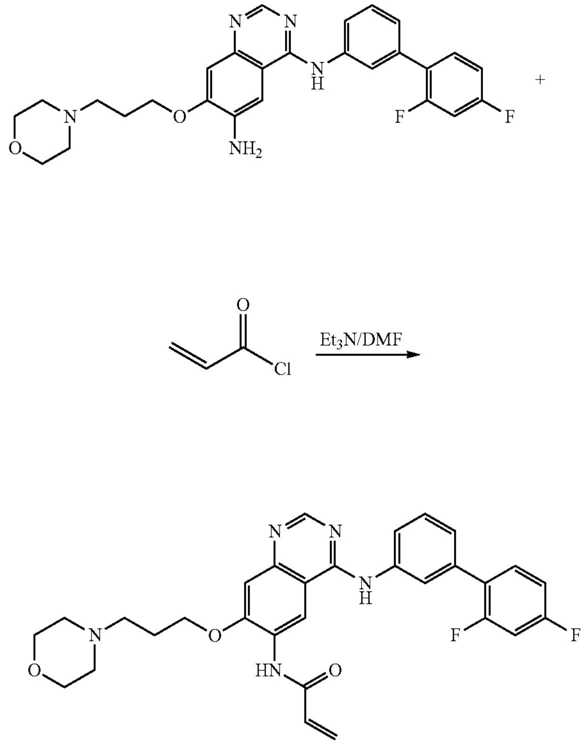

$N^4$-(2',4'-difluoro-[1,1'-biphenyl]-3-yl)-7-(3-morpholinopropoxy)quinazoline-4,6-diamine (100 mg, 0.19 mmol) and triethylamine (187 mg, 1.86 mmol) were added to DMF (3.5 mL), then acryloyl chloride (20 mg, 0.22 mmol) was added, and the reaction mixture was stirred at room temperature for 30 min, then supplemented with acryloyl chloride (20 mg, 0.22 mmol) and triethylamine (187 mg, 1.86 mmol), and stirred for 30 min. After the reaction was completed, the reaction mixture was directly separated by preparative HPLC to obtain N-(4-((2',4'-difluoro-[1,1'-biphenyl]-3-yl)amino)-7-(3-morpholinopropoxy)quinazolin-6-yl)acrylamide (25.5 mg, yield: 25%). MS m/z (ESI): 546.2 $[M+H]^+$.

$^1H$ NMR (400 MHz, MeOH-$d_4$) δ 8.89 (s, 1H), 8.45 (s, 1H), 7.91 (q, J=1.7 Hz, 1H), 7.82-7.76 (m, 1H), 7.61-7.52 (m, 1H), 7.48 (t, J=7.9 Hz, 1H), 7.35-7.30 (m, 1H), 7.24 (s, 1H), 7.10-7.05 (m, 1H), 7.06-7.02 (m, 1H), 6.66 (dd, J=16.9, 10.2 Hz, 1H), 6.47 (dd, J=16.9, 1.7 Hz, 1H), 5.86 (dd, J=10.2, 1.7 Hz, 1H), 4.32 (t, J=6.2 Hz, 2H), 3.71 (t, J=4.7 Hz, 4H), 2.60 (t, J=7.4 Hz, 2H), 2.56-2.47 (m, 4H), 2.14 (p, J=6.6 Hz, 2H).

Example 2: Preparation of N-(4-((5-(3,5-difluoropyridin-2-yl)-2-fluorophenyl)amino)-7-(3-morpholinopropoxy)quinazolin-6-yl)acrylamide

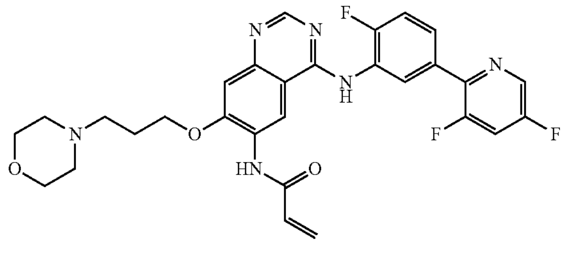 [SMILES: C=CC(=O)Nc1cc2c(Nc3cc(-c4ncc(F)cc4F)ccc3F)ncnc2cc1OCCCN1CCOCC1]

Step 1: Synthesis of 7-(3-morpholinopropoxy)-6-nitroquinazolin-4-ol

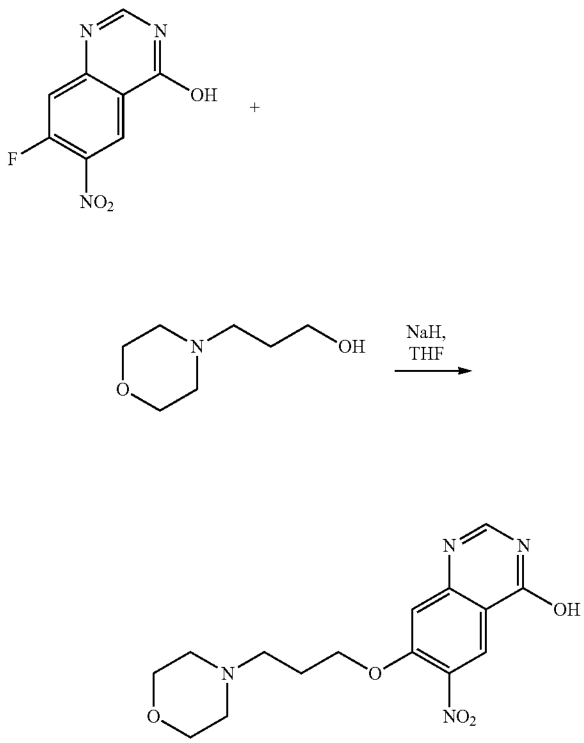

3-morpholinopropan-1-ol (2.78 g, 19.0 mmol) was dissolved in THE (10 mL), NaH (0.80 g, 22.0 mmol, 60% purity) was added portionwise at 0° C. under nitrogen protection, and the reaction mixture was stirred for 0.5 hrs, added with 7-fluoro-6-nitroquinazolin-4-ol (2.0 g, 9.6 mmol), and heated to 75° C. and stirred for 1 hr. After the reaction was completed, the reaction mixture was cooled to room temperature, then poured into ice water, added with 2N hydrochloric acid to adjust pH to 5, stirred for 0.5 hrs, and filtered, and the resulting solid was washed with water, then suspended in water and lyophilized to obtain 7-(3-morpholinopropoxy)-6-nitroquinazolin-4-ol (3.10 g, yield: 88%). MS m/z (ESI): 335.2 $[M+H]^+$.

Step 2: Synthesis of 4-(3-((4-chloro-6-nitroquinazolin-7-yl)oxy)propyl)morpholine

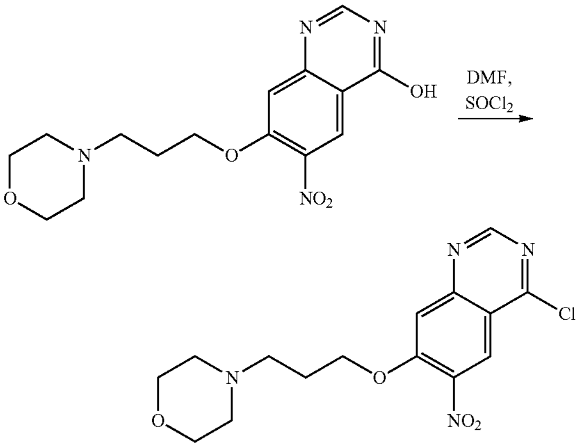

7-(3-morpholinopropoxy)-6-nitroquinazolin-4-ol (1.0 g, 2.7 mmol) and DMF (20 mg, 0.27 mmol) were added to $SOCl_2$ (5 mL), the reaction mixture was heated to 80° C. and stirred for 2.5 hrs. After the reaction was completed, the reaction mixture was cooled to room temperature, and then concentrated to obtain the crude product 4-(3-((4-chloro-6-nitroquinazolin-7-yl)oxy)propyl)morpholine, which was directly used in the next step. MS m/z (ESI): 353.0 $[M+H]^+$.

Step 3: Synthesis of N-(5-(3,5-difluoropyridin-2-yl)-2-fluorophenyl)-7-(3-morpholinopropoxy)-6-nitroquinazolin-4-amine

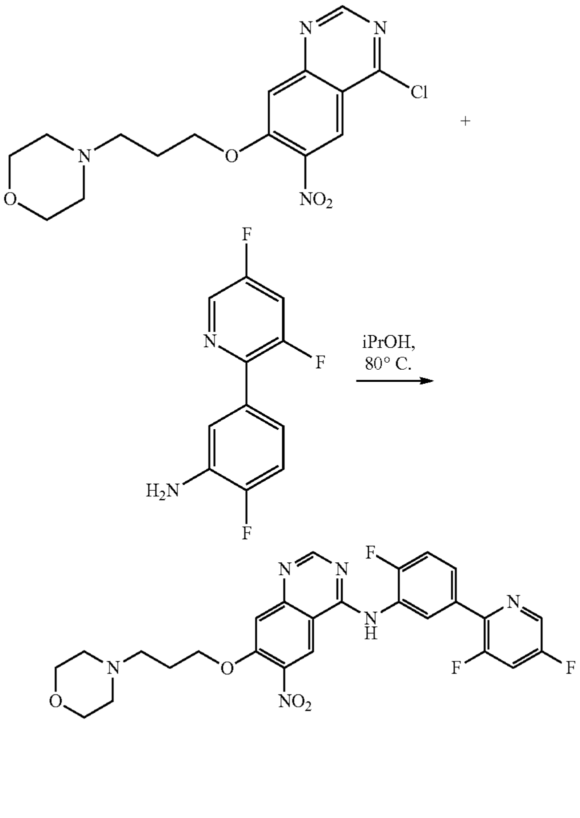

4-(3-((4-chloro-6-nitroquinazolin-7-yl)oxy)propyl)morpholine (0.76 g, 1.6 mmol, 72% purity) and 5-(3,5-difluoropyridin-2-yl)-2-fluoroaniline (0.35 g, 1.6 mmol) were added to isopropanol (5 mL), the reaction mixture was heated to 80° C. and stirred for 15 hrs. After the reaction was completed, the reaction mixture was cooled to room temperature, concentrated to remove the solvent, and the residue was separated by column chromatography [developing solvent: DCM/MeOH=0-10%] to obtain N-(5-(3,5-difluoropyridin-2-yl)-2-fluorophenyl)-7-(3-morpholinopropoxy)-6-nitroquinazolin-4-amine (0.62 g, yield: 69%). MS m/z (ESI): 541.2 $[M+H]^+$.

Step 4: Synthesis of $N^4$-(5-(3,5-difluoropyridin-2-yl)-2-fluorophenyl)-7-(3-morpholinopropoxy)quinazoline-4,6-diamine

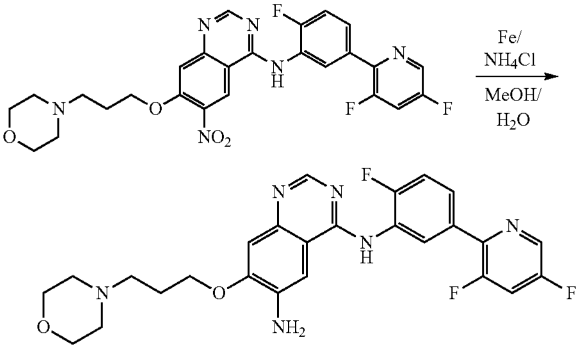

N-(5-(3,5-difluoropyridin-2-yl)-2-fluorophenyl)-7-(3-morpholinopropoxy)-6-nitroquinazolin-4-amine (0.30 g, 0.56 mmol) was dissolved in MeOH/$H_2O$ (8 mL/2 mL), the reaction mixture was added with iron powder (0.15 g, 2.8 mmol) and $NH_4Cl$ solid (0.30 g, 5.6 mmol), heated to 70° C. under nitrogen protection, and stirred for 2 hrs. After the reaction was completed, the reaction mixture was cooled to room temperature, and filtered through celite, and the filtrate was concentrated to obtain the crude product $N^4$-(5-(3,5-difluoropyridin-2-yl)-2-fluorophenyl)-7-(3-morpholinopropoxy)quinazoline-4,6-diamine, which was used directly in the next step. MS m/z (ESI): 511.2 $[M+H]^+$.

Step 5: Synthesis of N-(4-((5-(3,5-difluoropyridin-2-yl)-2-fluorophenyl)amino)-7-(3-morpholinopropoxy)quinazolin-6-yl)acrylamide

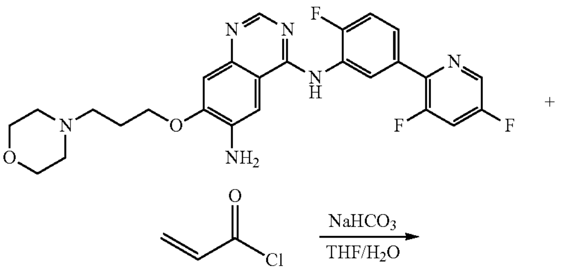

-continued

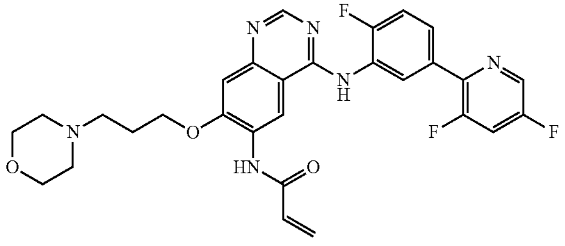

The above crude product N[4]-(5-(3,5-difluoropyridin-2-yl)-2-fluorophenyl)-7-(3-morpholinopropoxy)quinazoline-4,6-diamine was added to THE (2 mL), then saturated aqueous $NaHCO_3$ (2 mL) was added, and acryloyl chloride (61 μL, 0.75 mmol) was added at 0° C. The reaction mixture was stirred for 30 min. After the reaction mixture was concentrated, and the residue was separated by column chromatography [developing solvent: DCM/MeOH (0.1% ammonia liquor)=0-10%] to obtain the crude product, which was further separated by preparative HPLC to obtain N-(4-((5-(3,5-difluoropyridin-2-yl)-2-fluorophenyl)amino)-7-(3-morpholinopropoxy)quinazolin-6-yl)acrylamide (69.4 mg, two-step yield: 22%). MS m/z (ESI): 565.2 $[M+H]^+$.

$^1H$ NMR (400 MHz, DMSO-$d_6$) δ 9.87 (s, 1H), 9.57 (s, 1H), 8.91 (s, 1H), 8.65 (d, J=2.4 Hz, 1H), 8.40 (s, 1H), 8.09 (ddd, J=11.3, 8.8, 2.4 Hz, 1H), 8.06-7.97 (m, 1H), 7.81 (ddt, J=8.7, 4.3, 1.9 Hz, 1H), 7.46 (dd, J=10.2, 8.6 Hz, 1H), 7.29 (s, 1H), 6.73 (dd, J=17.0, 10.2 Hz, 1H), 6.32 (dd, J=17.0, 2.0 Hz, 1H), 5.82 (dd, J=10.2, 2.0 Hz, 1H), 4.29 (t, J=6.4 Hz, 2H), 3.58 (t, J=4.6 Hz, 4H), 2.49-2.46 (m, 2H), 2.39 (t, J=4.7 Hz, 4H), 2.01 (p, J=6.7 Hz, 2H).

Examples 3-64 can be prepared by selecting corresponding starting materials by referring to all or part of the synthesis method in Example 1 or 2.

| Example No. | Structural formula | Chemical name | $[M + H]^+$ |
|---|---|---|---|
| 3 | 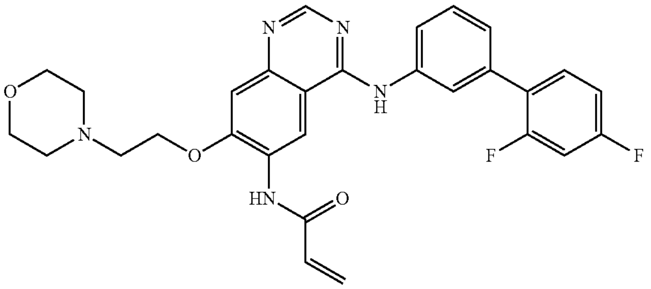 [SMILES: C=CC(=O)Nc1cc2c(Nc3cccc(-c4ccc(F)cc4F)c3)ncnc2cc1OCCN1CCOCC1] | N-(4-((2',4'-difluoro-[1,1'-biphenyl]-3-yl)amino)-7-(2-morpholinoethoxy) quinazolin-6-yl)acrylamide | 532.2 |
| 4 | 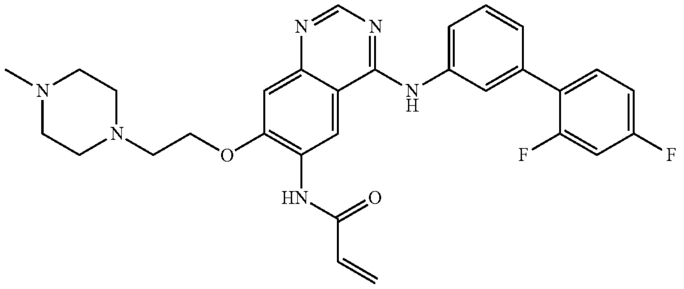 [SMILES: C=CC(=O)Nc1cc2c(Nc3cccc(-c4ccc(F)cc4F)c3)ncnc2cc1OCCN1CCN(C)CC1] | N-(4-((2',4'-difluoro-[1,1'-biphenyl]-3-yl)amino)-7-(2-(4-methylpiperazin-1-yl)ethoxy)quinazolin-6-yl)acrylamide | 545.2 |
| 5 | 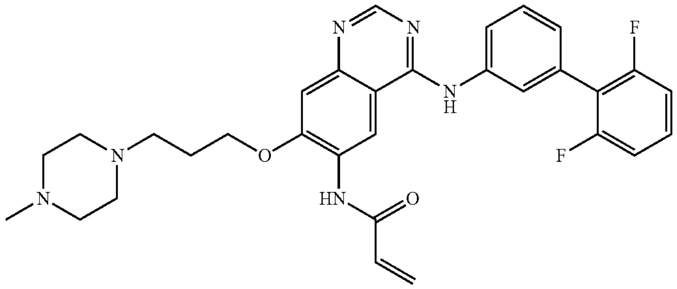 [SMILES: C=CC(=O)Nc1cc2c(Nc3cccc(-c4c(F)cccc4F)c3)ncnc2cc1OCCCN1CCN(C)CC1] | N-(4-((2',6'-difluoro-[1,1'-biphenyl]-3-yl)amino)-7-(3-(4-methylpiperazin-1-yl)propoxy)quinazolin-6-yl)acrylamide | 559.2 |

-continued

| Example No. | Structural formula | Chemical name | [M + H]+ |
|---|---|---|---|
| 6 | 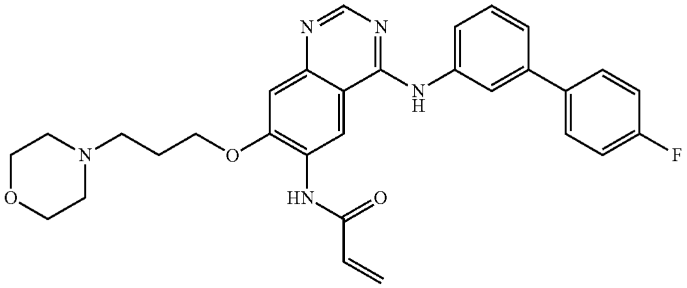 [SMILES: C=CC(=O)Nc1cc2c(Nc3cccc(-c4ccc(F)cc4)c3)ncnc2cc1OCCCN1CCOCC1] | N-(4-((4'-fluoro-[1,1'-biphenyl]-3-yl)amino)-7-(3-morpholinopropoxy)quinazolin-6-yl)acrylamide | 528.2 |
| 7 | 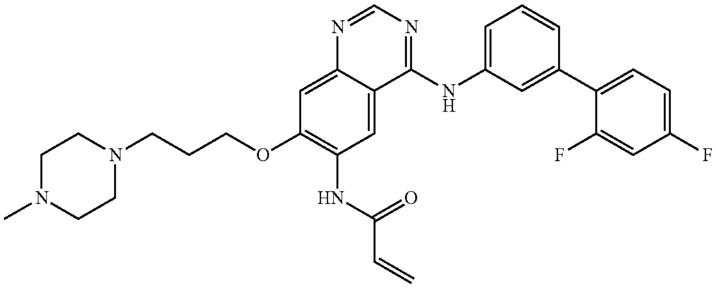 [SMILES: C=CC(=O)Nc1cc2c(Nc3cccc(-c4ccc(F)cc4F)c3)ncnc2cc1OCCCN1CCN(C)CC1] | N-(4-((2',4'-difluoro-[1,1'-biphenyl]-3-yl)amino)-7-(3-(4-methylpiperazin-1-yl)propoxy)quinazolin-6-yl)acrylamide | 559.2 |
| 8 | 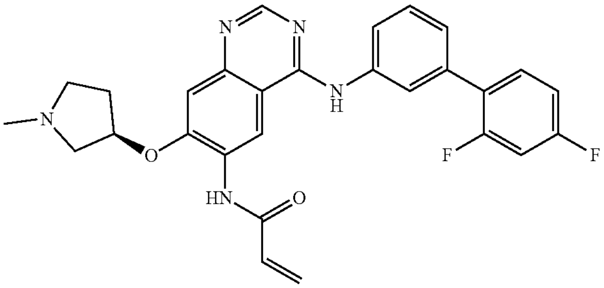 [SMILES: C=CC(=O)Nc1cc2c(Nc3cccc(-c4ccc(F)cc4F)c3)ncnc2cc1O[C@@H]1CCN(C)C1] | (R)-N-(4-((2',4'-difluoro-[1,1'-biphenyl]-3-yl)amino)-7-((1-methylpyrrolidin-3-yl)oxy)quinazolin-6-yl)acrylamide | 502.2 |
| 9 | 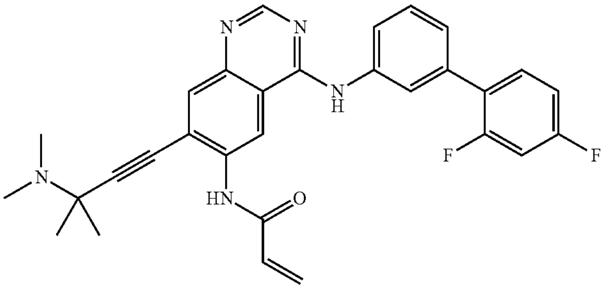 [SMILES: C=CC(=O)Nc1cc2c(Nc3cccc(-c4ccc(F)cc4F)c3)ncnc2cc1C#CC(C)(C)N(C)C] | N-(4-((2',4'-difluoro-[1,1'-biphenyl]-3-yl)amino)-7-(3-(dimethylamino)-3-methylbut-1-yn-1-yl)quinazolin-6-yl)acrylamide | 512.2 |
| 10 | 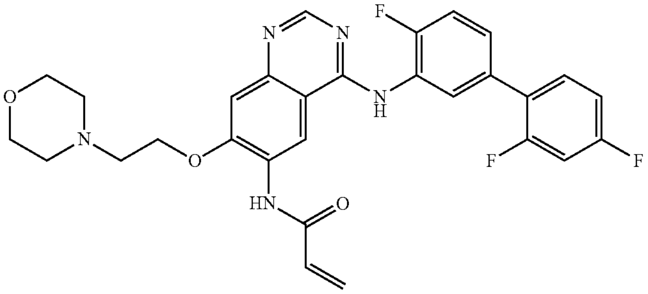 [SMILES: C=CC(=O)Nc1cc2c(Nc3cc(-c4ccc(F)cc4F)ccc3F)ncnc2cc1OCCN1CCOCC1] | N-(7-(2-morpholinoethoxy)-4-((2',4,4'-trifluoro-[1,1'-biphenyl]-3-yl)amino)quinazolin-6-yl)acrylamide | 550.2 |

-continued

| Example No. | Structural formula | Chemical name | [M + H]+ |
|---|---|---|---|
| 11 | 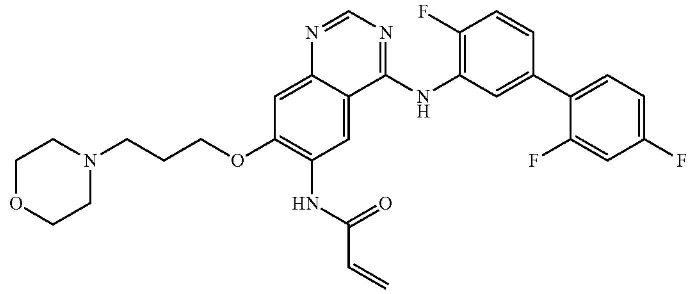 [SMILES: C=CC(=O)Nc1cc2c(Nc3cc(-c4ccc(F)cc4F)ccc3F)ncnc2cc1OCCCN1CCOCC1] | N-(7-(3-morpholinopropoxy)-4-((2',4,4'-trifluoro-[1,1'-biphenyl]-3-yl)amino)quinazolin-6-yl)acrylamide | 563.2 |
| 12 | 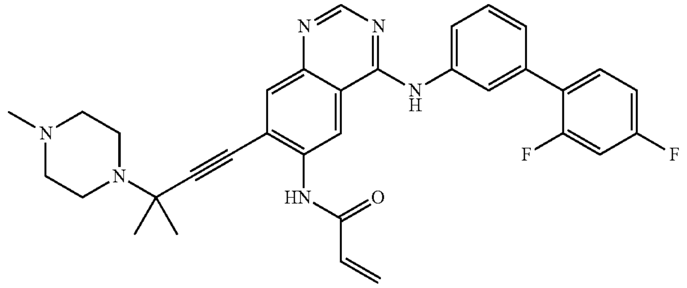 [SMILES: C=CC(=O)Nc1cc2c(Nc3cccc(-c4ccc(F)cc4F)c3)ncnc2cc1C#CC(C)(C)N1CCN(C)CC1] | N-(4-((2',4'-difluoro-[1,1'-biphenyl]-3-yl)amino)-7-(3-methyl-3-(4-methylpiperazin-1-yl)but-1-yn-1-yl)quinazolin-6-yl)acrylamide | 567.2 |
| 13 | 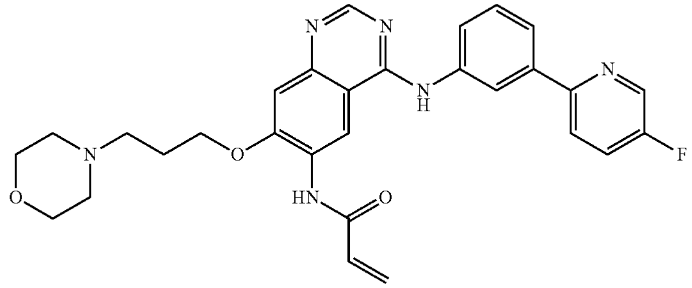 [SMILES: C=CC(=O)Nc1cc2c(Nc3cccc(-c4ccc(F)cn4)c3)ncnc2cc1OCCCN1CCOCC1] | N-(4-((3-(5-fluoropyridin-2-yl)phenyl)amino)-7-(3-morpholinopropoxy) quinazolin-6-yl)acrylamide | 529.2 |
| 14 | 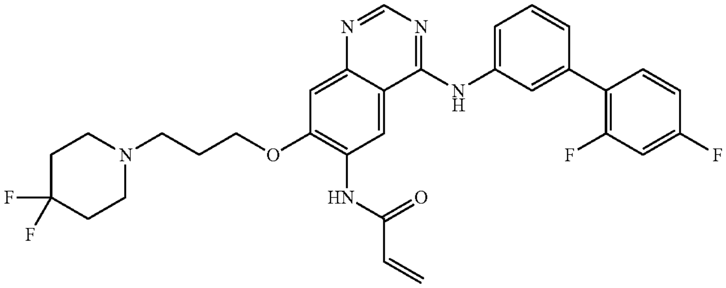 [SMILES: C=CC(=O)Nc1cc2c(Nc3cccc(-c4ccc(F)cc4F)c3)ncnc2cc1OCCCN1CCC(F)(F)CC1] | N-(4-((2',4'-difluoro-[1,1'-biphenyl]-3-yl)amino)-7-(3-(4,4-difluoropiperidin-1-yl)propoxy)quinazolin-6-yl)acrylamide | 580.2 |
| 15 | 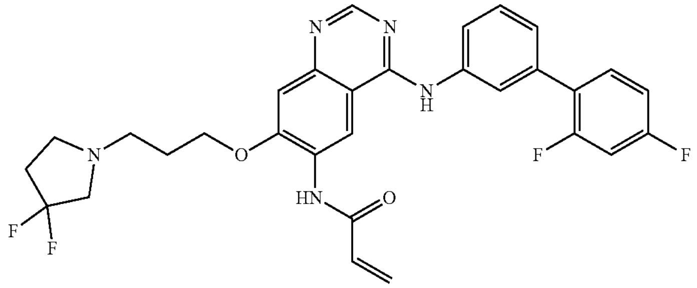 [SMILES: C=CC(=O)Nc1cc2c(Nc3cccc(-c4ccc(F)cc4F)c3)ncnc2cc1OCCCN1CCC(F)(F)C1] | N-(4-((2',4'-difluoro-[1,1'-biphenyl]-3-yl)amino)-7-(3-(3,3-difluoropyrrolidin-1-yl)propoxy)quinazolin-6-yl)acrylamide | 566.2 |

-continued

| Example No. | Structural formula | Chemical name | [M + H]+ |
|---|---|---|---|
| 16 | 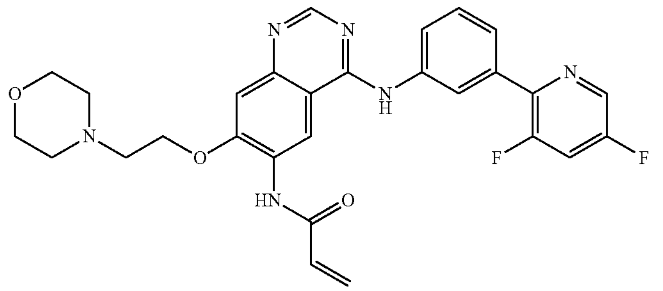 [SMILES: C=CC(=O)Nc1cc2c(Nc3cccc(-c4ncc(F)cc4F)c3)ncnc2cc1OCCN1CCOCC1] | N-(4-((3-(3,5-difluoropyridin-2-yl)phenyl)amino)-7-(2-morpholinoethoxy) quinazolin-6-yl)acrylamide | 533.2 |
| 17 | 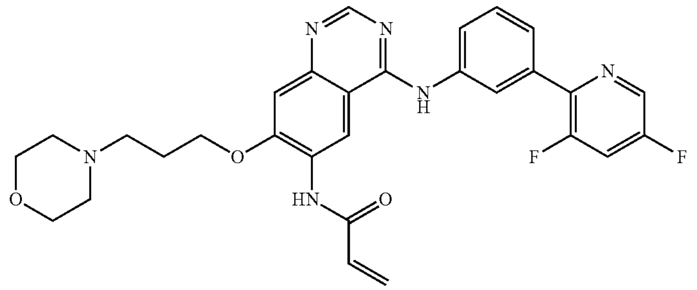 [SMILES: C=CC(=O)Nc1cc2c(Nc3cccc(-c4ncc(F)cc4F)c3)ncnc2cc1OCCCN1CCOCC1] | N-(4-((3-(3,5-difluoropyridin-2-yl)phenyl)amino)-7-(3-morpholinopropoxy) quinazolin-6-yl)acrylamide | 547.2 |
| 18 | 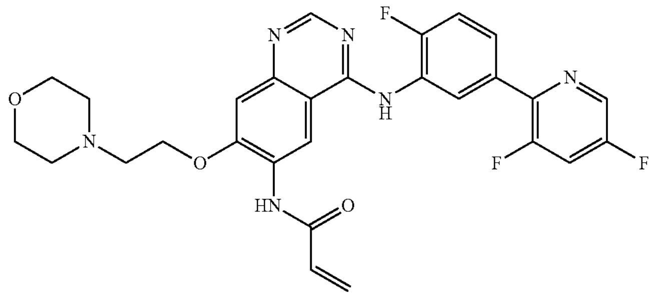 [SMILES: C=CC(=O)Nc1cc2c(Nc3cc(-c4ncc(F)cc4F)ccc3F)ncnc2cc1OCCN1CCOCC1] | N-(4-((5-(3,5-difluoropyridin-2-yl)-2-fluorophenyl)amino)-7-(2-morpholinoethoxy) quinazolin-6-yl)acrylamide | 551.2 |
| 19 | 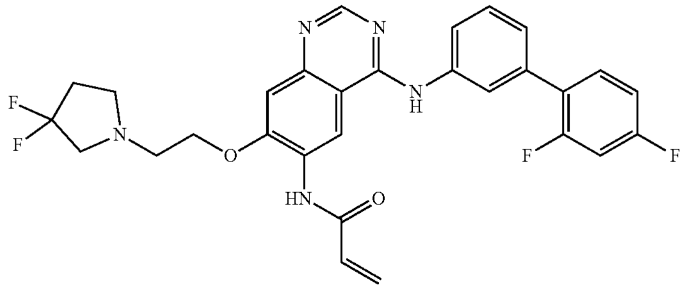 [SMILES: C=CC(=O)Nc1cc2c(Nc3cccc(-c4ccc(F)cc4F)c3)ncnc2cc1OCCN1CCC(F)(F)C1] | N-(4-((2',4'-difluoro-[1,1'-biphenyl]-3-yl)amino)-7-(2-(3,3-difluoropyrrolidin-1-yl)ethoxy)quinazolin-6-yl)acrylamide | 552.2 |
| 20 | 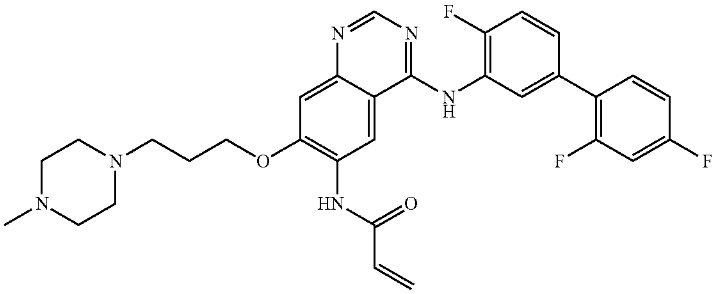 [SMILES: C=CC(=O)Nc1cc2c(Nc3cc(-c4ccc(F)cc4F)ccc3F)ncnc2cc1OCCCN1CCN(C)CC1] | N-(7-(3-(4-methylpiperazin-1-yl)propoxy)-4-((2',4,4'-trifluoro-[1,1'-biphenyl]-3-yl)amino)quinazolin-6-yl)acrylamide | 577.2 |

-continued

| Example No. | Structural formula | Chemical name | [M + H]+ |
|---|---|---|---|
| 21 | 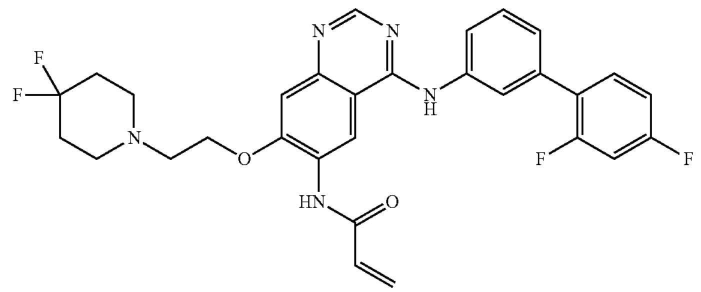 [SMILES: C=CC(=O)Nc1cc2c(Nc3cccc(-c4ccc(F)cc4F)c3)ncnc2cc1OCCN1CCC(F)(F)CC1] | N-(4-((2',4'-difluoro-[1,1'-biphenyl]-3-yl)amino)-7-(2-(4,4-difluoropiperidin-1-yl)ethoxy)quinazolin-6-yl)acrylamide | 566.2 |
| 22 | 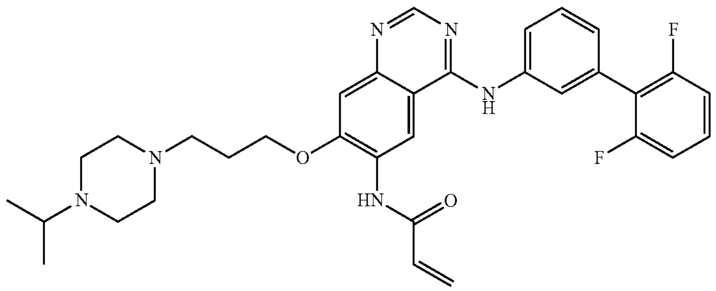 [SMILES: C=CC(=O)Nc1cc2c(Nc3cccc(-c4c(F)cccc4F)c3)ncnc2cc1OCCCN1CCN(C(C)C)CC1] | N-(4-((2',6'-difluoro-[1,1'-biphenyl]-3-yl)amino)-7-(3-(4-isopropylpiperazin-1-yl)propoxy)quinazolin-6-yl)acrylamide | 587.4 |
| 23 | 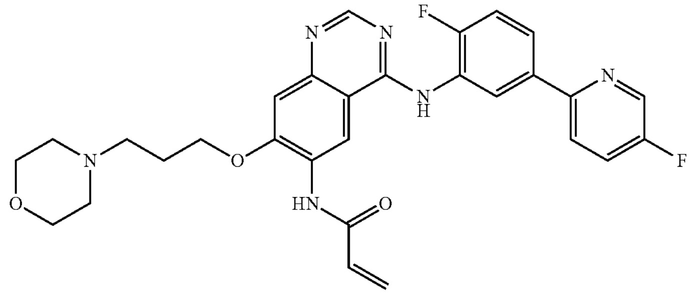 [SMILES: C=CC(=O)Nc1cc2c(Nc3cc(-c4ccc(F)cn4)ccc3F)ncnc2cc1OCCCN1CCOCC1] | N-(4-((2-fluoro-5-(5-fluoropyridin-2-yl)phenyl)amino)-7-(3-morpholinopropoxy) quinazolin-6-yl)acrylamide | 547.2 |
| 24 | 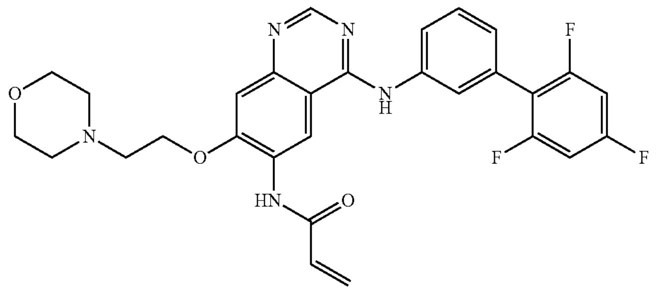 [SMILES: C=CC(=O)Nc1cc2c(Nc3cccc(-c4c(F)cc(F)cc4F)c3)ncnc2cc1OCCN1CCOCC1] | N-(7-(2-morpholinoethoxy)-4-((2',4',6'-trifluoro-[1,1'-biphenyl]-3-yl)amino)quinazolin-6-yl)acrylamide | 550.2 |
| 25 | 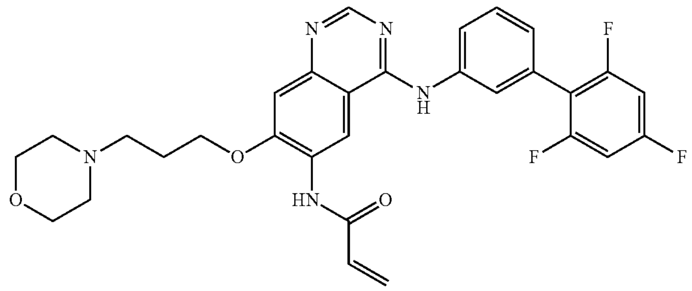 [SMILES: C=CC(=O)Nc1cc2c(Nc3cccc(-c4c(F)cc(F)cc4F)c3)ncnc2cc1OCCCN1CCOCC1] | N-(7-(3-morpholinopropoxy)-4-((2',4',6'-trifluoro-[1,1'-biphenyl]-3-yl)amino)quinazolin-6-yl)acrylamide | 564.2 |

-continued

| Example No. | Structural formula | Chemical name | [M + H]+ |
| --- | --- | --- | --- |
| 26 | 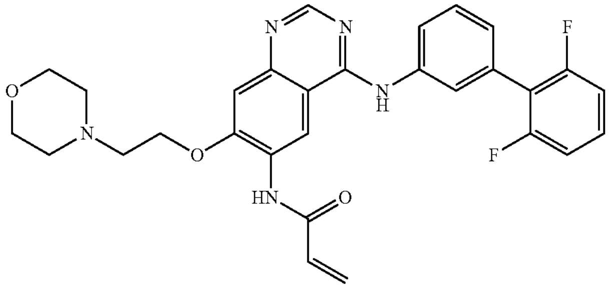 [SMILES: C=CC(=O)Nc1cc2c(Nc3cccc(-c4c(F)cccc4F)c3)ncnc2cc1OCCN1CCOCC1] | N-(4-((2',6'-difluoro-[1,1'-biphenyl]-3-yl)amino)-7-(2-morpholinoethoxy) quinazolin-6-yl)acrylamide | 531.2 |
| 27 | 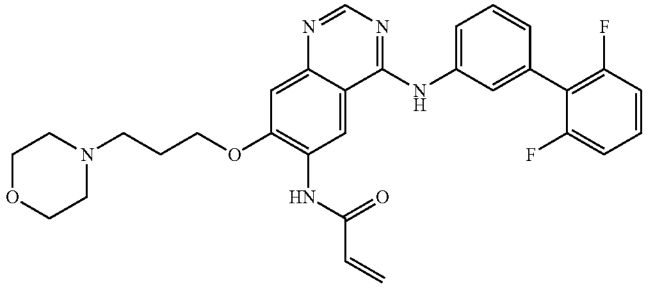 [SMILES: C=CC(=O)Nc1cc2c(Nc3cccc(-c4c(F)cccc4F)c3)ncnc2cc1OCCCN1CCOCC1] | N-(4-((2',6'-difluoro-[1,1'-biphenyl]-3-yl)amino)-7-(3-morpholinopropoxy) quinazolin-6-yl)acrylamide | 545.2 |
| 28 | 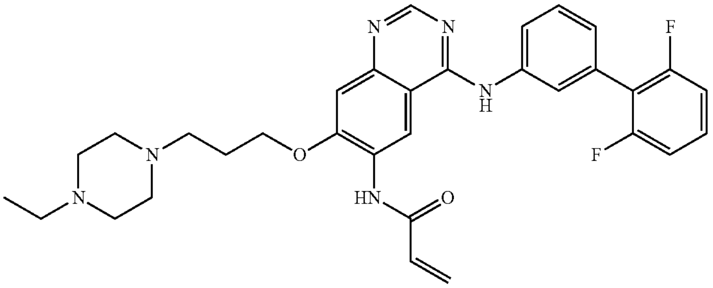 [SMILES: C=CC(=O)Nc1cc2c(Nc3cccc(-c4c(F)cccc4F)c3)ncnc2cc1OCCCN1CCN(CC)CC1] | N-(4-((2',6'-difluoro-[1,1'-biphenyl]-3-yl)amino)-7-(3-(4-ethylpiperazin-1-yl)propoxy)quinazolin-6-yl)acrylamide | 573.3 |
| 29 | 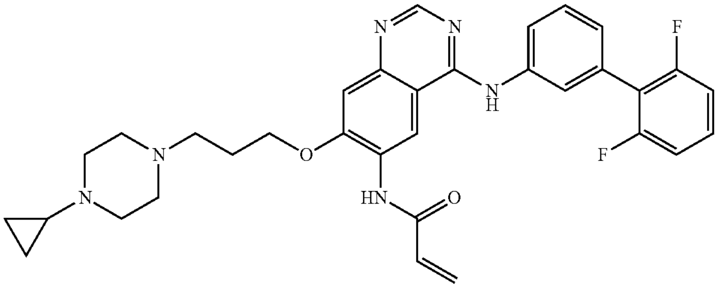 [SMILES: C=CC(=O)Nc1cc2c(Nc3cccc(-c4c(F)cccc4F)c3)ncnc2cc1OCCCN1CCN(C2CC2)CC1] | N-(7-(3-(4-cyclopropylpiperazin-1-yl)propoxy)-4-((2',6'-difluoro-[1,1'-biphenyl]-3-yl)amino)quinazolin-6-yl)acrylamide | 585.3 |
| 30 | 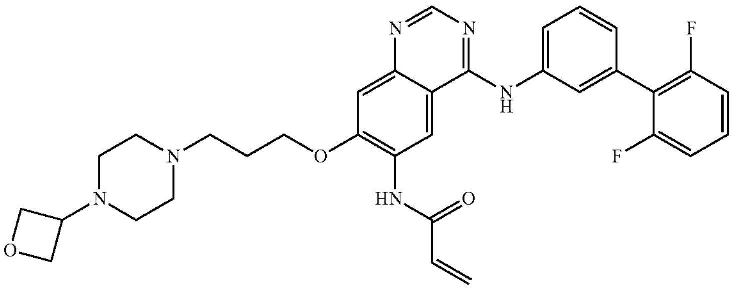 [SMILES: C=CC(=O)Nc1cc2c(Nc3cccc(-c4c(F)cccc4F)c3)ncnc2cc1OCCCN1CCN(C2COC2)CC1] | N-(4-((2',6'-difluoro-[1,1'-biphenyl]-3-yl)amino)-7-(3-(4-(oxetan-3-yl)piperazin-1-yl)propoxy)quinazolin-6-yl)acrylamide | 601.4 |

-continued

| Example No. | Structural formula | Chemical name | [M + H]+ |
|---|---|---|---|
| 31 | 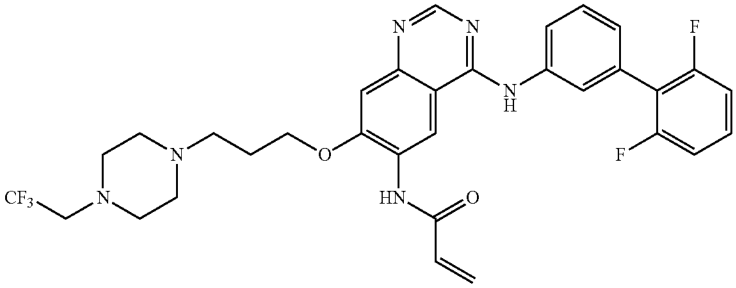 [SMILES: C=CC(=O)Nc1cc2c(Nc3cccc(-c4c(F)cccc4F)c3)ncnc2cc1OCCCN1CCN(CC(F)(F)F)CC1] | N-(4-((2',6'-difluoro-[1,1'-biphenyl]-3-yl)amino)-7-(3-(4-(2,2,2-trifluoroethyl)piperazin-1-yl)propoxy)quinazolin-6-yl)acrylamide | 627.3 |
| 32 | 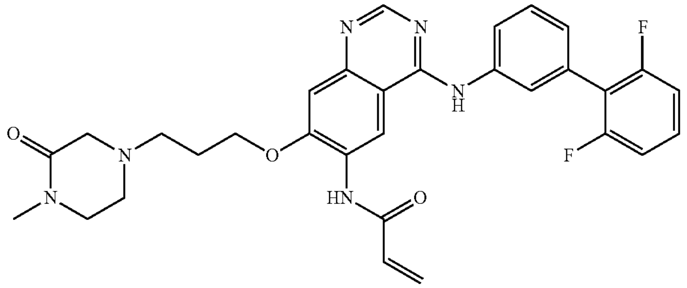 [SMILES: C=CC(=O)Nc1cc2c(Nc3cccc(-c4c(F)cccc4F)c3)ncnc2cc1OCCCN1CCN(C)C(=O)C1] | N-(4-((2',6'-difluoro-[1,1'-biphenyl]-3-yl)amino)-7-(3-(4-methyl-3-oxopiperazin-1-yl)propoxy)quinazolin-6-yl)acrylamide | 573.2 |
| 33 | 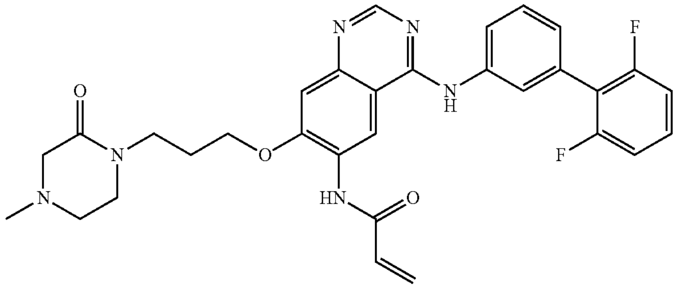 [SMILES: C=CC(=O)Nc1cc2c(Nc3cccc(-c4c(F)cccc4F)c3)ncnc2cc1OCCCN1CCN(C)CC1=O] | N-(4-((2',6'-difluoro-[1,1'-biphenyl]-3-yl)amino)-7-(3-(4-methyl-2-oxopiperazin-1-yl)propoxy)quinazolin-6-yl)acrylamide | 573.2 |
| 34 | 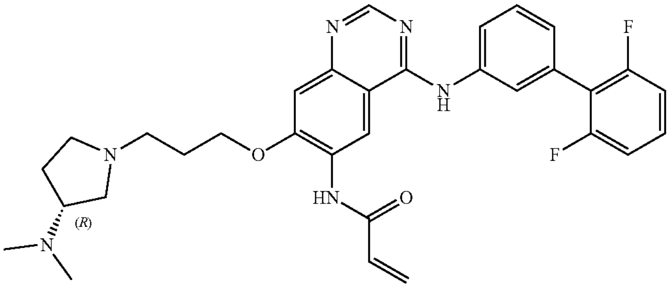 | (R)-N-(4-((2',6'-difluoro-[1,1'-biphenyl]-3-yl)amino)-7-(3-(3-(dimethylamino)pyrrolidin-1-yl)propoxy)quinazolin-6-yl)acrylamide | 573.3 |
| 35 | 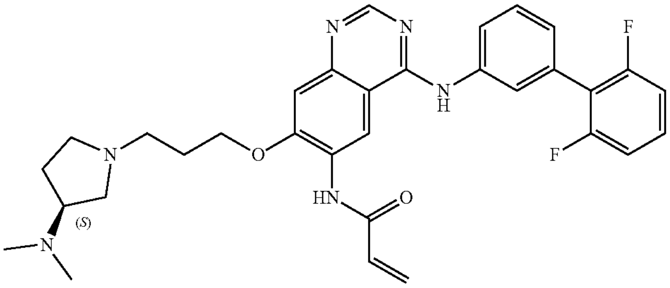 | (S)-N-(4-((2',6'-difluoro-[1,1'-biphenyl]-3-yl)amino)-7-(3-(3-(dimethylamino)pyrrolidin-1-yl)propoxy)quinazolin-6-yl)acrylamide | 573.3 |

-continued

| Example No. | Structural formula | Chemical name | [M + H]+ |
| --- | --- | --- | --- |
| 36 | 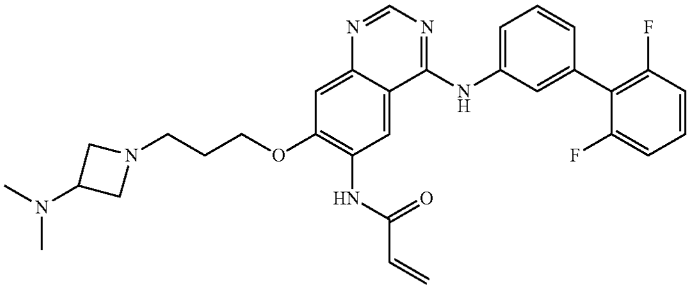 [SMILES: C=CC(=O)Nc1cc2c(Nc3cccc(-c4c(F)cccc4F)c3)ncnc2cc1OCCCN1CC(N(C)C)C1] | N-(4-((2',6'-difluoro-[1,1'-biphenyl]-3-yl)amino)-7-(3-(3-(dimethylamino)azetidin-1-yl)propoxy)quinazolin-6-yl)acrylamide | 559.3 |
| 37 | 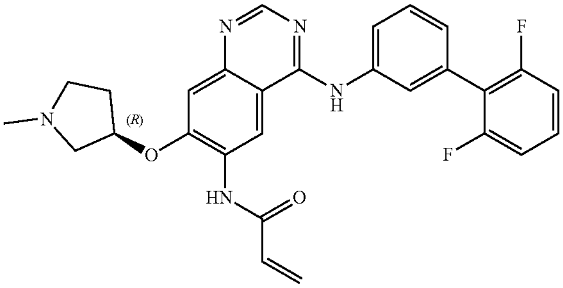 | (R)-N-(4-((2',6'-difluoro-[1,1'-biphenyl]-3-yl)amino)-7-((1-methylpyrrolidin-3-yl)oxy)quinazolin-6-yl)acrylamide | 502.2 |
| 38 | 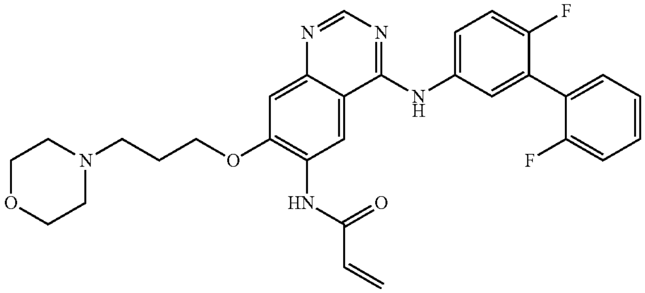 [SMILES: C=CC(=O)Nc1cc2c(Nc3ccc(F)c(-c4ccccc4F)c3)ncnc2cc1OCCCN1CCOCC1] | N-(4-((2',6-difluoro-[1,1'-biphenyl]-3-yl)amino)-7-(3-morpholinopropoxy) quinazolin-6-yl)acrylamide | 546.2 |
| 39 | 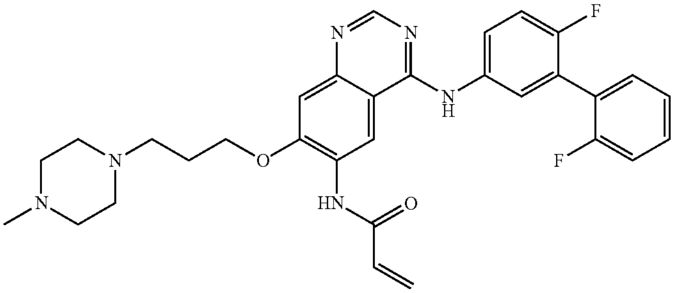 | N-(4-((2',6-difluoro-[1,1'-biphenyl]-3-yl)amino)-7-(3-(4-methylpiperazin-1-yl)propoxy)quinazolin-6-yl)acrylamide | 559.2 |
| 40 | 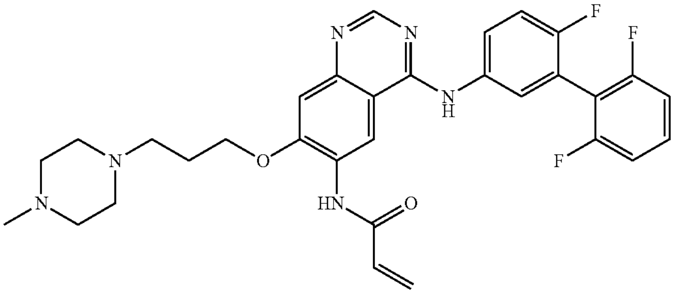 [SMILES: C=CC(=O)Nc1cc2c(Nc3ccc(F)c(-c4c(F)cccc4F)c3)ncnc2cc1OCCCN1CCN(C)CC1] | N-(7-(3-(4-methylpiperazin-1-yl)propoxy)-4-((2',6,6'-trifluoro-[1,1'-biphenyl]-3-yl)amino)quinazolin-6-yl)acrylamide | 577.2 |

-continued

| Example No. | Structural formula | Chemical name | [M + H]+ |
|---|---|---|---|
| 41 | 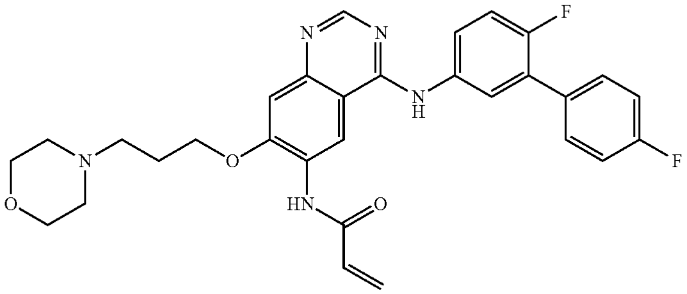 [SMILES: C=CC(=O)Nc1cc2c(Nc3ccc(F)c(-c4ccc(F)cc4)c3)ncnc2cc1OCCCN1CCOCC1] | N-(4-((4',6-difluoro-[1,1'-biphenyl]-3-yl)amino)-7-(3-morpholinopropoxy) quinazolin-6-yl)acrylamide | 546.2 |
| 42 | 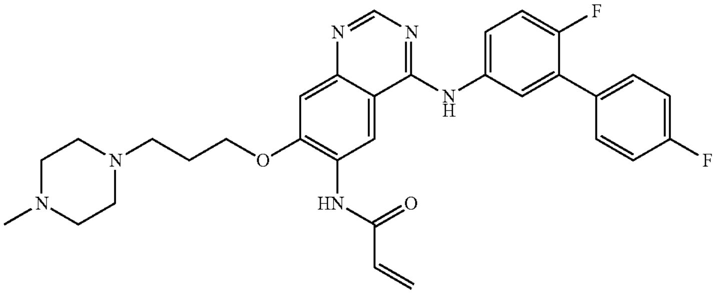 [SMILES: C=CC(=O)Nc1cc2c(Nc3ccc(F)c(-c4ccc(F)cc4)c3)ncnc2cc1OCCCN1CCN(C)CC1] | N-(4-((4',6-difluoro-[1,1'-biphenyl]-3-yl)amino)-7-(3-(4-methylpiperazin-1-yl)propoxy)quinazolin-6-yl)acrylamide | 559.2 |
| 43 | 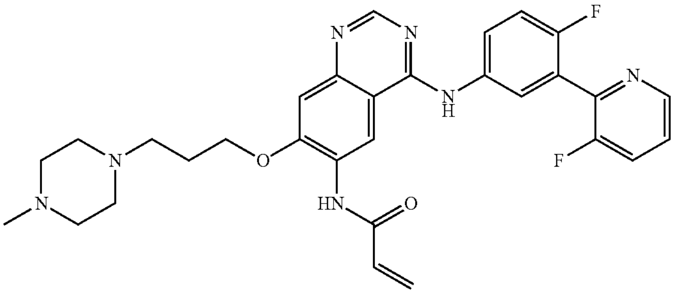 [SMILES: C=CC(=O)Nc1cc2c(Nc3ccc(F)c(-c4ncccc4F)c3)ncnc2cc1OCCCN1CCN(C)CC1] | N-(4-((4-fluoro-3-(3-fluoropyridin-2-yl)phenyl)amino)-7-(3-(4-methylpiperazin-1-yl)propoxy)quinazolin-6-yl)acrylamide | 560.2 |
| 44 | 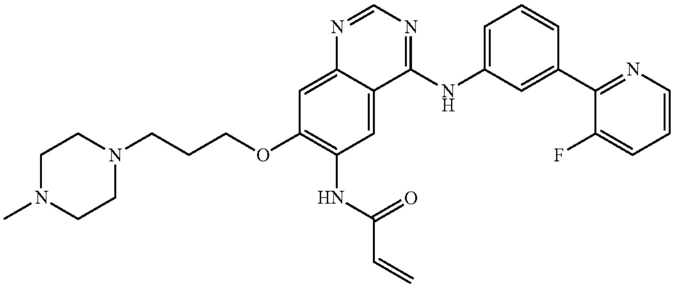 [SMILES: C=CC(=O)Nc1cc2c(Nc3cccc(-c4ncccc4F)c3)ncnc2cc1OCCCN1CCN(C)CC1] | N-(4-((3-(3-fluoropyridin-2-yl)phenyl)amino)-7-(3-(4-methylpiperazin-1-yl)propoxy)quinazolin-6-yl)acrylamide | 542.2 |
| 45 | 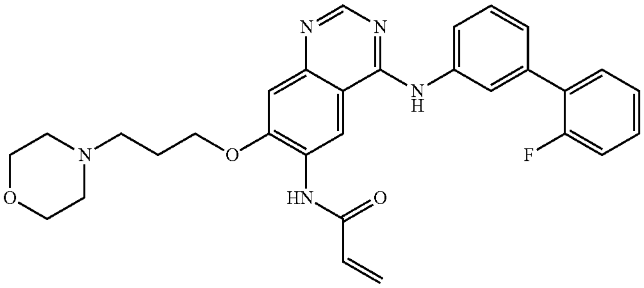 [SMILES: C=CC(=O)Nc1cc2c(Nc3cccc(-c4ccccc4F)c3)ncnc2cc1OCCCN1CCOCC1] | N-(4-((2'-fluoro-[1,1'-biphenyl]-3-yl)amino)-7-(3-morpholinopropoxy) quinazolin-6-yl)acrylamide | 528.2 |

-continued

| Example No. | Structural formula | Chemical name | [M + H]+ |
|---|---|---|---|
| 46 | 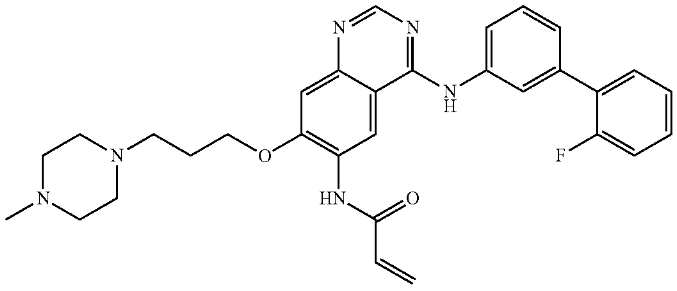 [SMILES: C=CC(=O)Nc1cc2c(Nc3cccc(-c4ccccc4F)c3)ncnc2cc1OCCCN1CCN(C)CC1] | N-(4-((2'-fluoro-[1,1'-biphenyl]-3-yl)amino)-7-(3-(4-methylpiperazin-1-yl)propoxy)quinazolin-6-yl)acrylamide | 541.2 |
| 47 | 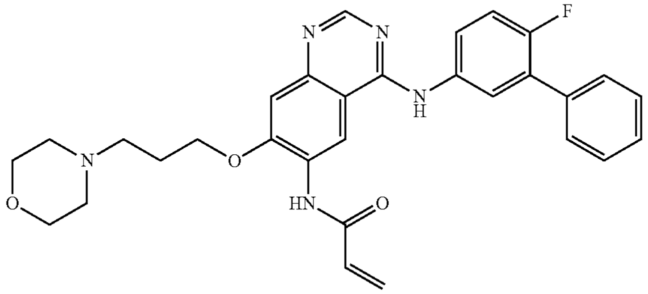 [SMILES: C=CC(=O)Nc1cc2c(Nc3ccc(F)c(-c4ccccc4)c3)ncnc2cc1OCCCN1CCOCC1] | N-(4-((6-fluoro-[1,1'-biphenyl]-3-yl)amino)-7-(3-morpholinopropoxy) quinazolin-6-yl)acrylamide | 528.2 |
| 48 | 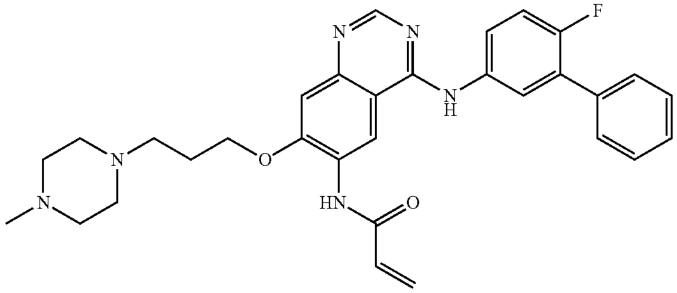 [SMILES: C=CC(=O)Nc1cc2c(Nc3ccc(F)c(-c4ccccc4)c3)ncnc2cc1OCCCN1CCN(C)CC1] | N-(4-((6-fluoro-[1,1'-biphenyl]-3-yl)amino)-7-(3-(4-methylpiperazin-1-yl)propoxy)quinazolin-6-yl)acrylamide | 541.2 |
| 49 | 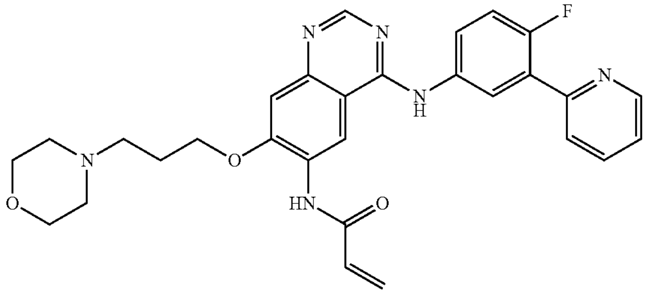 [SMILES: C=CC(=O)Nc1cc2c(Nc3ccc(F)c(-c4ccccn4)c3)ncnc2cc1OCCCN1CCOCC1] | N-(4-((4-fluoro-3-(pyridin-2-yl)phenyl)amino)-7-(3-morpholinopropoxy) quinazolin-6-yl)acrylamide | 529.2 |
| 50 | 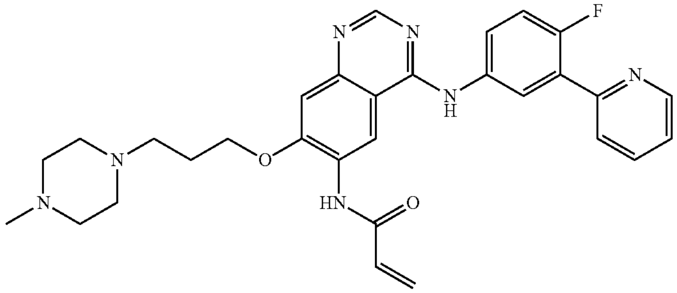 [SMILES: C=CC(=O)Nc1cc2c(Nc3ccc(F)c(-c4ccccn4)c3)ncnc2cc1OCCCN1CCN(C)CC1] | N-(4-((4-fluoro-3-(pyridin-2-yl)phenyl)amino)-7-(3-(4-methylpiperazin-1-yl)propoxy)quinazolin-6-yl)acrylamide | 542.2 |

-continued

| Example No. | Structural formula | Chemical name | [M + H]+ |
|---|---|---|---|
| 51 | 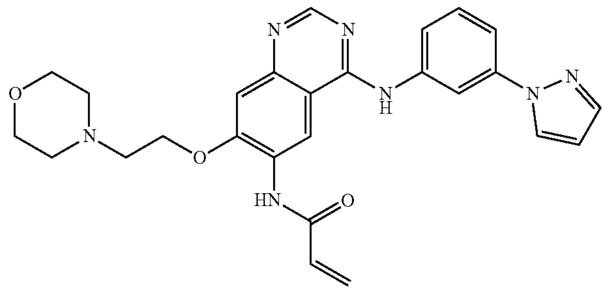 [SMILES: C=CC(=O)Nc1cc2c(Nc3cccc(-n4cccn4)c3)ncnc2cc1OCCN1CCOCC1] | N-(4-((3-(1H-pyrazol-1-yl)phenyl)amino)-7-(2-morpholinoethoxy) quinazolin-6-yl)acrylamide | 486.2 |
| 52 | 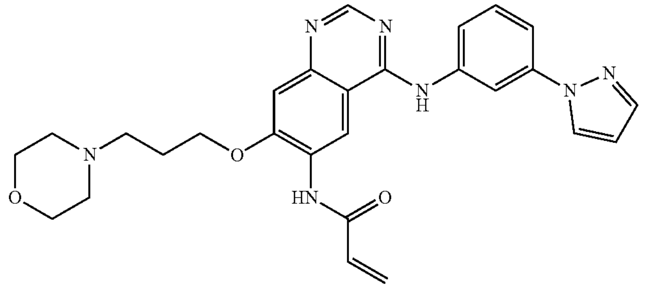 [SMILES: C=CC(=O)Nc1cc2c(Nc3cccc(-n4cccn4)c3)ncnc2cc1OCCCN1CCOCC1] | N-(4-((3-(1H-pyrazol-1-yl)phenyl)amino)-7-(3-morpholinopropoxy) quinazolin-6-yl)acrylamide | 500.2 |
| 53 | 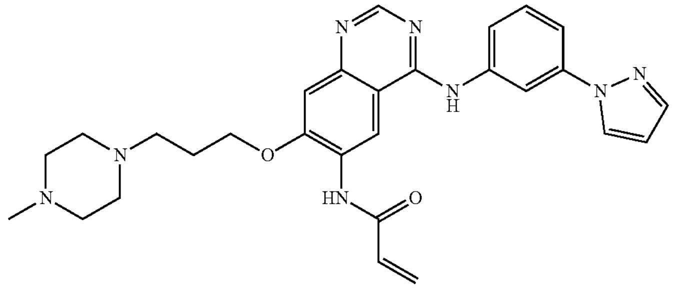 [SMILES: C=CC(=O)Nc1cc2c(Nc3cccc(-n4cccn4)c3)ncnc2cc1OCCCN1CCN(C)CC1] | N-(4-((3-(1H-pyrazol-1-yl)phenyl)amino)-7-(3-(4-methylpiperazin-1-yl)propoxy)quinazolin-6-yl)acrylamide | 513.2 |
| 54 | 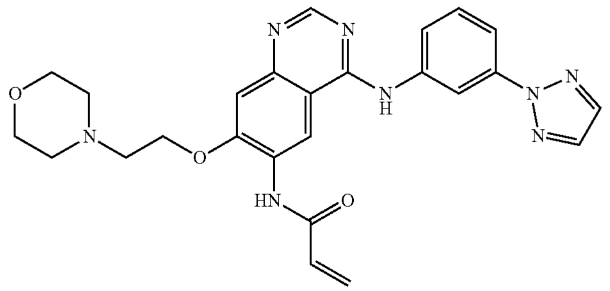 [SMILES: C=CC(=O)Nc1cc2c(Nc3cccc(-n4nccn4)c3)ncnc2cc1OCCN1CCOCC1] | N-(4-((3-(2H-1,2,3-triazol-2-yl)phenyl)amino)-7-(2-morpholinoethoxy) quinazolin-6-yl)acrylamide | 487.2 |
| 55 | 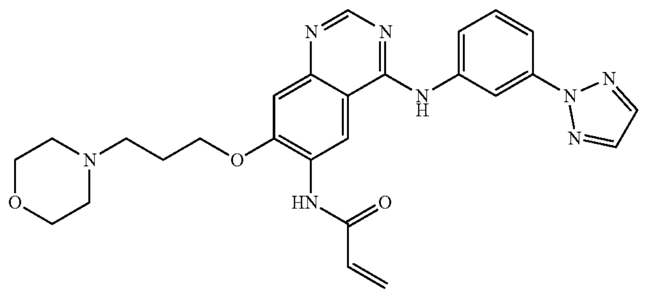 [SMILES: C=CC(=O)Nc1cc2c(Nc3cccc(-n4nccn4)c3)ncnc2cc1OCCCN1CCOCC1] | N-(4-((3-(2H-1,2,3-triazol-2-yl)phenyl)amino)-7-(3-morpholinopropoxy) quinazolin-6-yl)acrylamide | 501.2 |

-continued

| Example No. | Structural formula | Chemical name | [M + H]+ |
|---|---|---|---|
| 56 | 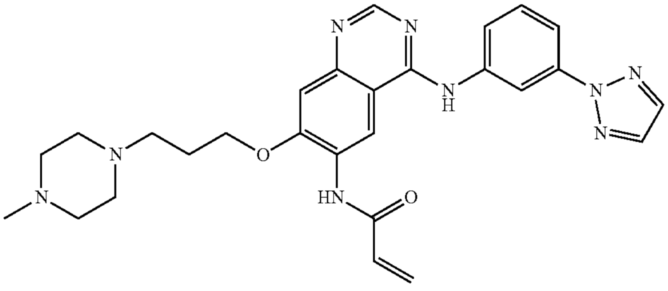 | N-(4-((3-(2H-1,2,3-triazol-2-yl)phenyl)amino)-7-(3-(4-methylpiperazin-1-yl)propoxy)quinazolin-6-yl)acrylamide | 514.2 |
| 57 | 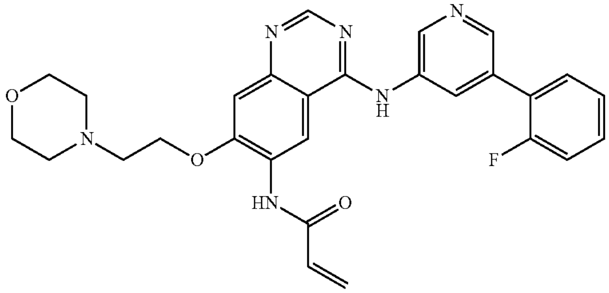 [SMILES: C=CC(=O)Nc1cc2c(Nc3cncc(-c4ccccc4F)c3)ncnc2cc1OCCN1CCOCC1] | N-(4-((5-(2-fluorophenyl)pyridin-3-yl)amino)-7-(2-morpholinoethoxy) quinazolin-6-yl)acrylamide | 515.2 |
| 58 | 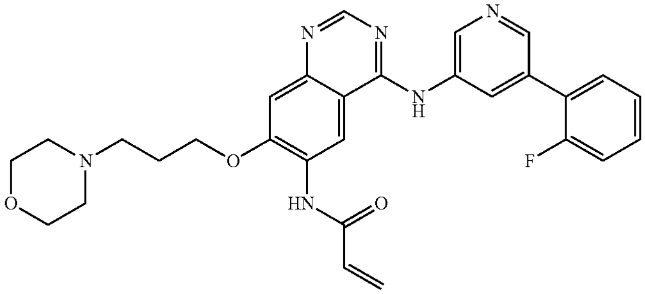 [SMILES: C=CC(=O)Nc1cc2c(Nc3cncc(-c4ccccc4F)c3)ncnc2cc1OCCCN1CCOCC1] | N-(4-((5-(2-fluorophenyl)pyridin-3-yl)amino)-7-(3-morpholinopropoxy) quinazolin-6-yl)acrylamide | 529.2 |
| 59 | 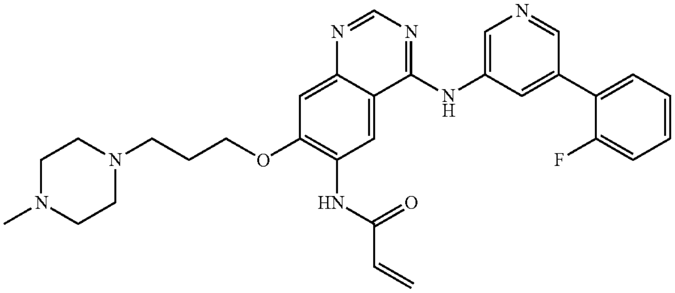 [SMILES: C=CC(=O)Nc1cc2c(Nc3cncc(-c4ccccc4F)c3)ncnc2cc1OCCCN1CCN(C)CC1] | N-(4-((5-(2-fluorophenyl)pyridin-3-yl)amino)-7-(3-(4-methylpiperazin-1-yl)propoxy)quinazolin-6-yl)acrylamide | 542.2 |
| 60 | 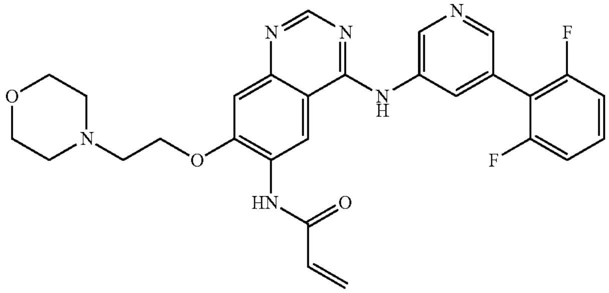 [SMILES: C=CC(=O)Nc1cc2c(Nc3cncc(-c4c(F)cccc4F)c3)ncnc2cc1OCCN1CCOCC1] | N-(4-((5-(2,6-difluorophenyl)pyridin-3-yl)amino)-7-(2-morpholinoethoxy) quinazolin-6-yl)acrylamide | 533.2 |

-continued

| Example No. | Structural formula | Chemical name | [M + H]+ |
|---|---|---|---|
| 61 | 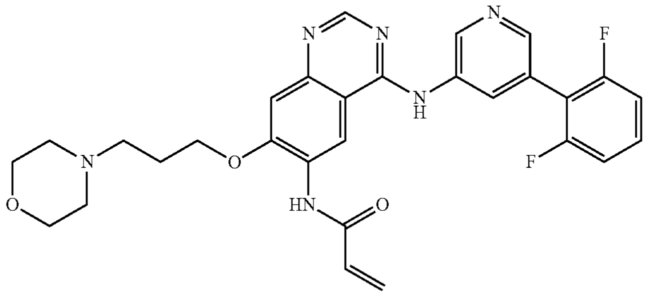 [SMILES: C=CC(=O)Nc1cc2c(Nc3cncc(-c4c(F)cccc4F)c3)ncnc2cc1OCCCN1CCOCC1] | N-(4-((5-(2,6-difluorophenyl)pyridin-3-yl)amino)-7-(3-morpholinopropoxy) quinazolin-6-yl)acrylamide | 547.2 |
| 62 | 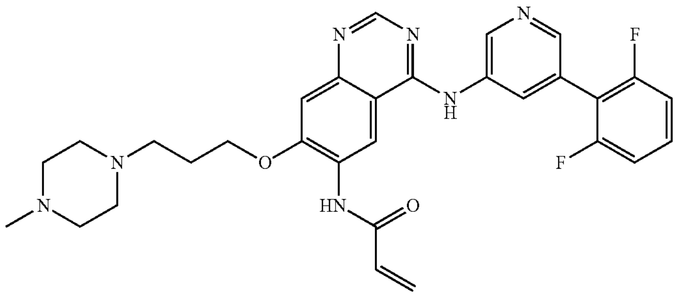 [SMILES: C=CC(=O)Nc1cc2c(Nc3cncc(-c4c(F)cccc4F)c3)ncnc2cc1OCCCN1CCN(C)CC1] | N-(4-((5-(2,6-difluorophenyl)pyridin-3-yl)amino)-7-(3-(4-methylpiperazin-1-yl)propoxy)quinazolin-6-yl)acrylamide | 560.2 |
| 63 | 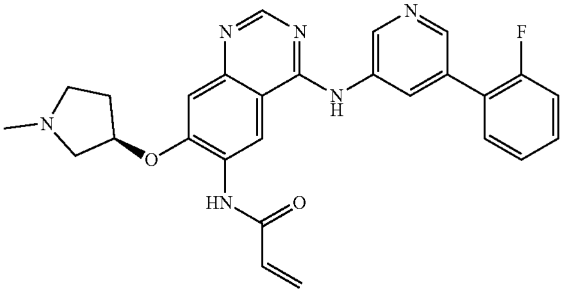 [SMILES: C=CC(=O)Nc1cc2c(Nc3cncc(-c4ccccc4F)c3)ncnc2cc1O[C@@H]1CCN(C)C1] | (R)-N-(4-((5-(2-fluorophenyl)pyridin-3-yl)amino)-7-((1-methylpyrrolidin-3-yl)oxy)quinazolin-6-yl)acrylamide | 485.2 |
| 64 | 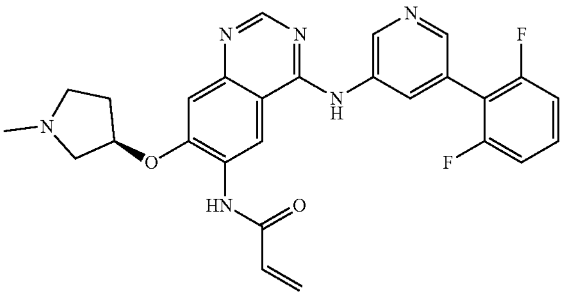 [SMILES: C=CC(=O)Nc1cc2c(Nc3cncc(-c4c(F)cccc4F)c3)ncnc2cc1O[C@@H]1CCN(C)C1] | (R)-N-(4-((5-(2,6-difluorophenyl)pyridin-3-yl)amino)-7-((1-methylpyrrolidin-3-yl)oxy)quinazolin-6-yl)acrylamide | 503.2 |

Example 65: Preparation of (R)—N-(4-((2-(2-fluorophenyl)pyridin-4-yl)amino)-7-((1-methylpyrrolidin-3-yl)oxy)quinazolin-6-yl)acrylamide

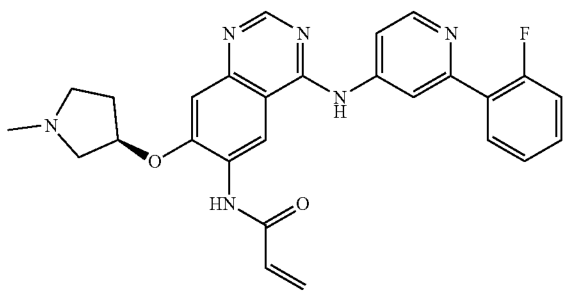 [SMILES: C=CC(=O)Nc1cc2c(Nc3ccnc(-c4ccccc4F)c3)ncnc2cc1O[C@@H]1CCN(C)C1]

Step 1: Synthesis of 7-fluoro-N-(2-(2-fluorophenyl)pyridin-4-yl)-6-nitroquinazolin-4-amine

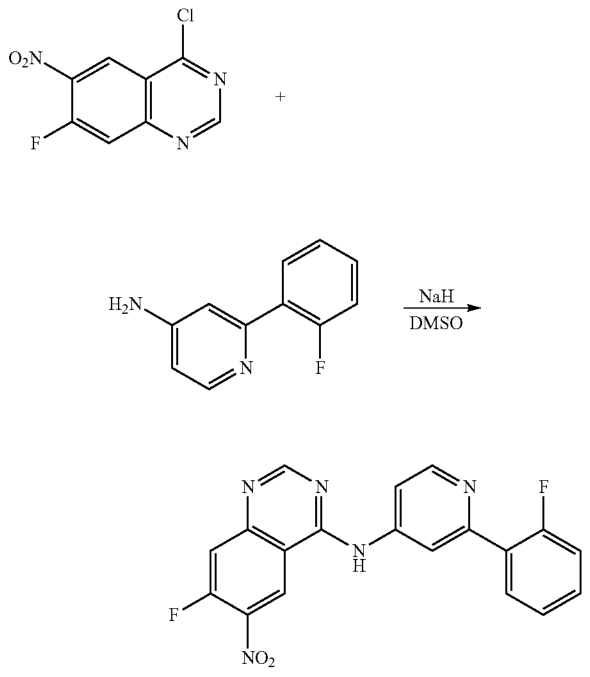

4-chloro-7-fluoro-6-nitroquinazoline (12.0 g, 52.73 mmol) and 5-(2-fluorophenyl)pyridin-3-amine (11.1 g, 59.06 mmol) were dissolved in DMSO (40 mL). The reaction mixture was cooled to 0° C., then added portionwise with sodium hydride (60% wt, 4.22 g, 105.46 mmol), then heated to room temperature and stirred overnight. After the reaction was completed, the reaction mixture was poured into saturated brine (300 mL) and extracted with ethyl acetate. The organic phases were combined, washed with saturated brine, and concentrated, and the crude product was separated by column chromatography [eluent: EtOAc/PE=0-50%] to obtain 7-fluoro-N-(2-(2-fluorophenyl)pyridin-4-yl)-6-nitroquinazolin-4-amine (4.9 g, yield: 25%). MS m/z (ESI): 380.0 $[M+H]^+$.

Step 2: Synthesis of (R)—N-(2-(2-fluorophenyl)pyridin-4-yl)-7-((1-methylpyrrolidin-3-yl)oxy)-6-nitroquinazolin-4-amine

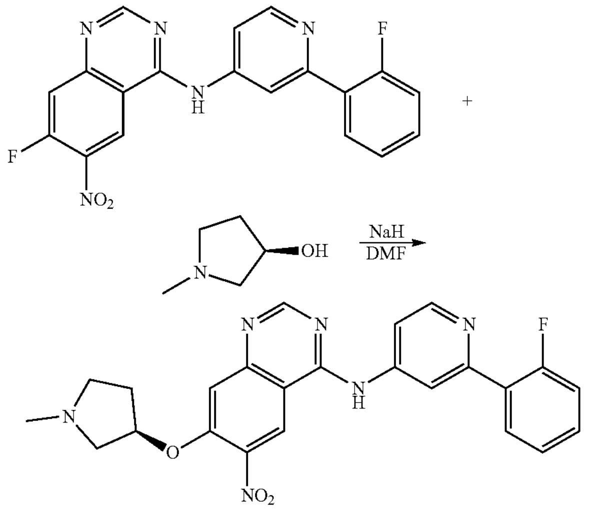

(R)-1-methylpyrrolidin-3-ol (0.32 mL, 2.90 mmol) was dissolved in anhydrous THF (40 mL), sodium hydride (60% wt, 105.45 mg, 2.64 mmol) was added portionwise, and then the reaction mixture was stirred at room temperature for 30 min, added with 7-fluoro-N-(2-(2-fluorophenyl)pyridin-4-yl)-6-nitroquinazolin-4-amine (500 mg, 1.32 mmol) and stirred for 1 hr. After the reaction was completed, EtOH (1 mL) was added to quench the reaction, the reaction mixture was concentrated, and the crude product was separated by column chromatography [eluent: DCM/MeOH=89/11] to obtain (R)—N-(2-(2-fluorophenyl)pyridin-4-yl)-7-((1-methylpyrrolidin-3-yl)oxy)-6-nitroquinazolin-4-amine (420 mg, yield: 69%). MS m/z (ESI): 461.2 $[M+H]^+$.

Step 3: Synthesis of (R)—$N^4$-(2-(2-fluorophenyl)pyridin-4-yl)-7-((1-methylpyrrolidin-3-yl)oxy)quinazoline-4,6-diamine

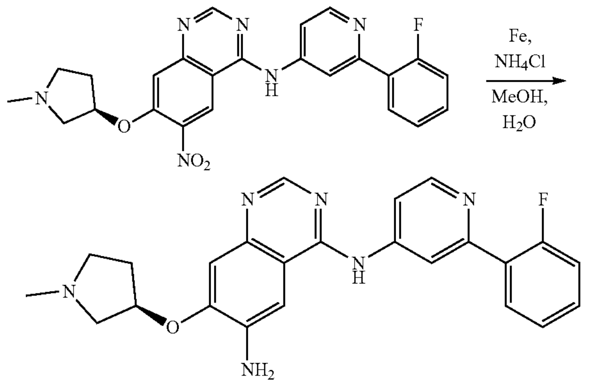

(R)—N-(2-(2-fluorophenyl)pyridin-4-yl)-7-((1-methylpyrrolidin-3-yl)oxy)-6-nitroquinazolin-4-amine (1.6 g, 3.5 mmol) was dissolved in methanol/water (40 mL/10 mL), then iron powder (1.55 g, 27.8 mmol) and ammonium chloride (1.86 g, 34.7 mmol) were added, and the reaction mixture was heated to 80° C. to reflux and reacted for 1 hr. After the reaction was completed, the reaction mixture was cooled to room temperature, and filtered through celite, the filter residue was washed with methanol. The filtrate was concentrated, then added with saturated aqueous sodium bicarbonate (30 mL), and extracted with DCM/MeOH (v:v=10/1). The organic phases were combined, washed with saturated sodium bicarbonate solution, dried over anhydrous sodium sulfate, filtered and concentrated to obtain (R)—$N^4$-(2-(2-fluorophenyl)pyridin-4-yl)-7-((1-methylpyrrolidin-3-yl)oxy)quinazoline-4,6-diamine (1.4 g, yield: 93%). MS m/z (ESI): 431.2 $[M+H]^+$.

Step 4: Synthesis of (R)—N-(4-((2-(2-fluorophenyl)pyridin-4-yl)amino)-7-((1-methylpyrrolidin-3-yl)oxy)quinazolin-6-yl)acrylamide

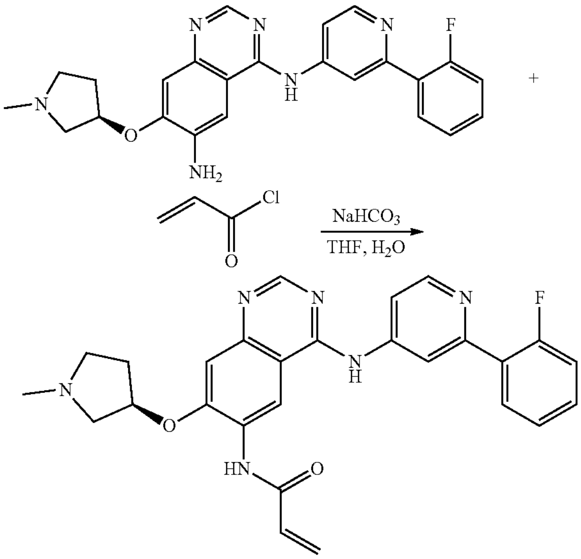

(R)—N-(2-(2-fluorophenyl)pyridin-4-yl)-7-((1-methylpyrrolidin-3-yl)oxy)-6-nitroquinazolin-4-amine (600 mg, 1.39 mmol) was dissolved in THF/$H_2O$ (12 mL/3 mL), then sodium bicarbonate (585 mg, 6.97 mmol) was added, and the reaction mixture was cooled to 0° C. and added slowly and dropwise with a solution of acryloyl chloride (151 mg, 1.67 mmol) in anhydrous THF (2 mL). After the dropwise addition was completed, the reaction mixture was stirred at 0° C. for 10 min. After the reaction was completed, ammonia liquor was added to quench the reaction, and then was added with saturated sodium bicarbonate solution (20 mL) and extracted with DCM/MeOH (v:v=10/1). The organic phases were combined and concentrated, and the crude product was separated by column chromatography [eluent: DCM/MeOH=93/7] to obtain (R)—N-(4-((2-(2-fluorophenyl)pyridin-4-yl)amino)-7-((1-methylpyrrolidin-3-yl)oxy)quinazolin-6-yl)acrylamide (375 mg, yield: 56%). MS m/z (ESI): 485.2 $[M+H]^+$.

$^1H$ NMR (400 MHz, MeOH-$d_4$) δ 8.95 (s, 1H), 8.56 (s, 1H), 8.44 (d, J=5.8 Hz, 1H), 8.24 (t, J=2.0 Hz, 1H), 8.03 (dd, J=5.8, 2.2 Hz, 1H), 7.70 (td, J=7.7, 1.8 Hz, 1H), 7.39 (tdd, J=7.3, 5.0, 1.8 Hz, 1H), 7.23 (td, J=7.6, 1.1 Hz, 1H), 7.20-7.13 (m, 1H), 7.10 (s, 1H), 6.56 (dd, J=17.0, 10.1 Hz, 1H), 6.41 (dd, J=16.9, 1.9 Hz, 1H), 5.78 (dd, J=10.1, 1.8 Hz, 1H), 5.14 (t, J=5.7 Hz, 1H), 3.18 (s, 1H), 3.10 (dd, J=9.2, 3.1 Hz, 1H), 2.50 (dd, J=11.3, 4.6 Hz, 2H), 2.42 (s, 3H), 2.27 (q, J=9.0 Hz, 1H), 1.96 (dd, J=14.7, 7.9 Hz, 1H).

Example 66: Preparation of (R)-2-fluoro-N-(4-((2-(2-fluorophenyl)pyridin-4-yl)amino)-7-((1-methylpyrrolidin-3-yl)oxy)quinazolin-6-yl)acrylamide

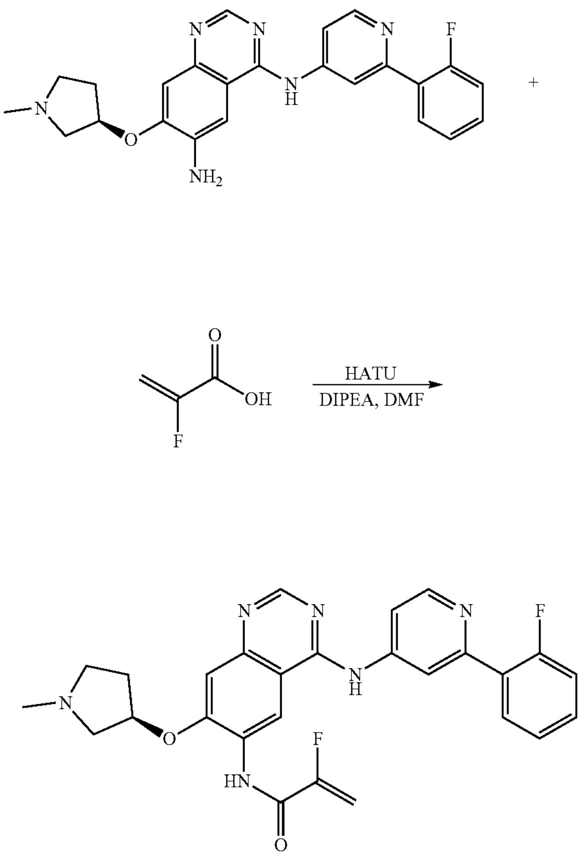

(R)—N-(2-(2-fluorophenyl)pyridin-4-yl)-7-((1-methylpyrrolidin-3-yl)oxy)-6-nitroquinazolin-4-amine (50 mg, 0.12 mmol), 2-fluoroacrylic acid (13 mg, 0.14 mmol) and HATU (66 mg, 0.17 mmol) were dissolved in DMF (3.0 mL). The reaction mixture was stirred at room temperature for 10 min, then added with N,N-diisopropylethylamine (45 mg, 0.35 mmol), and stirred for 10 min. After the reaction was completed, the reaction mixture was separated by reversed-phase column chromatography to obtain (R)-2-fluoro-N-(4-((2-(2-fluorophenyl)pyridin-4-yl)amino)-7-((1-methylpyrrolidin-3-yl)oxy)quinazolin-6-yl)acrylamide (15 mg, yield: 25%). MS m/z (ESI): 503.2 $[M+H]^+$.

$^1H$ NMR (400 MHz, MeOH-$d_4$) δ 8.99 (s, 1H), 8.69 (s, 1H), 8.55 (d, J=5.8 Hz, 1H), 8.34 (t, J=2.0 Hz, 1H), 8.13 (dd, J=5.8, 2.2 Hz, 1H), 7.82 (td, J=7.8, 1.8 Hz, 1H), 7.56-7.45 (m, 1H), 7.35 (td, J=7.6, 1.2 Hz, 1H), 7.28 (ddd, J=11.1, 8.3, 1.2 Hz, 1H), 7.21 (s, 1H), 5.87 (dd, J=46.8, 3.6 Hz, 1H), 5.44 (dd, J=15.1, 3.6 Hz, 1H), 5.21 (t, J=6.0 Hz, 1H), 3.15 (d, J=11.5 Hz, 1H), 3.09 (dd, J=8.9, 3.8 Hz, 1H), 2.74 (dd, J=11.3, 5.2 Hz, 1H), 2.69-2.52 (m, 1H), 2.48 (s, 3H), 2.43 (q, J=8.5 Hz, 1H), 2.11 (dt, J=16.2, 8.8 Hz, 1H).

Example 67: Preparation of (R,E)-4-(dimethylamino)-N-(4-((2-(2-fluorophenyl)pyridin-4-yl)amino)-7-((1-methylpyrrolidin-3-yl)oxy)quinazolin-6-yl)but-2-enamide

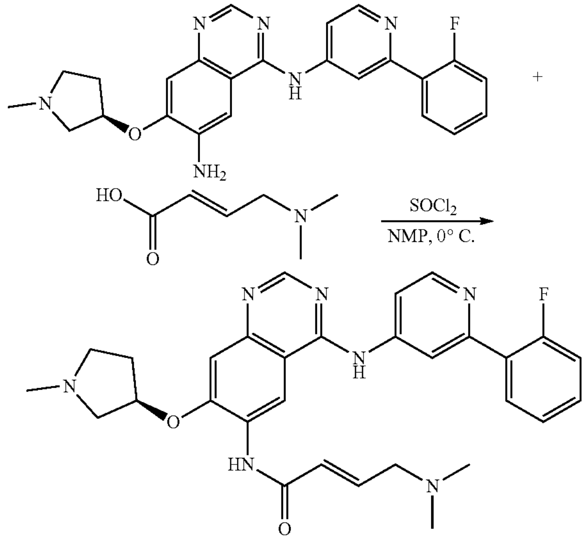

(E)-4-(dimethylamino)but-2-enoic acid hydrochloride (77 mg, 0.47 mmol) was placed in NMP (4 mL), thionyl chloride (50 mg, 0.42 mmol) was added under an ice-water bath, and the reaction mixture was stirred at room temperature for 30 min. A solution of (R)—$N^4$-(2-(2-fluorophenyl)pyridin-4-yl)-7-((1-methylpyrrolidin-3-yl)oxy)quinazoline-4,6-diamine (100 mg, 0.23 mmol) in NMP (1.5 mL) was added dropwise under an ice-water bath, the reaction mixture was stirred under an ice bath for 15 m. After the reaction was completed, the reaction mixture was directly separated by reversed-phase column chromatography [developing solvent: $CH_3CN/H_2O$=0-100%] to obtain (R,E)-4-(dimethylamino)-N-(4-((2-(2-fluorophenyl)pyridin-4-yl)amino)-7-((1-methylpyrrolidin-3-yl)oxy)quinazolin-6-yl)but-2-enamide (62.5 mg, yield: 497%). MS m/z (ESI): 542.2 $[M+H]^+$.

$^1$H NMR (400 MHz, DMSO-$d_6$) δ 10.06 (s, 1H), 9.53 (s, 1H), 9.04 (s, 1H), 8.65 (s, 1H), 8.60 (d, J=5.7 Hz, 1H), 8.37 (s, 1H), 8.07 (dd, J=5.7, 2.1 Hz, 1H), 7.97 (td, J=7.8, 1.9 Hz, 1H), 7.49 (tdd, J=7.4, 5.1, 1.9 Hz, 1H), 7.39-7.31 (m, 2H), 7.22 (s, 1H), 6.82 (dt, J=15.4, 6.0 Hz, 1H), 6.61 (d, J=15.4 Hz, 1H), 5.13 (tt, J=7.1, 2.8 Hz, 1H), 3.09 (dd, J=6.0, 1.5 Hz, 2H), 2.90-2.81 (m, 2H), 2.77 (td, J=8.5, 7.1, 3.5 Hz, 1H), 2.46-2.33 (m, 2H), 2.29 (s, 3H), 2.19 (s, 6H), 2.03 (ddd, J=14.4, 7.1, 3.1 Hz, 1H).

Examples 68-91 can be prepared by selecting corresponding starting materials by referring to all or part of the synthesis method in Example 65.

| Example No. | Structural formula | Chemical name | $[M + H]^+$ |
|---|---|---|---|
| 68 | 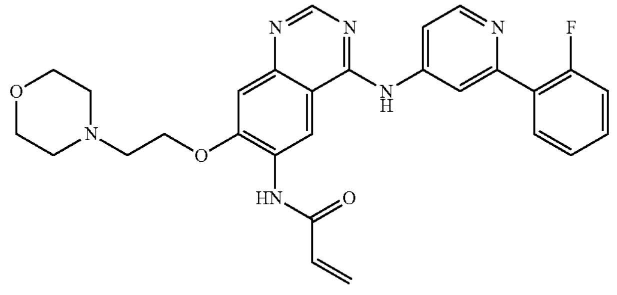 [SMILES: C=CC(=O)Nc1cc2c(Nc3ccnc(-c4ccccc4F)c3)ncnc2cc1OCCN1CCOCC1] | N-(4-((2-(2-fluorophenyl)pyridin-4-yl)amino)-7-(2-morpholinoethoxy) quinazolin-6-yl)acrylamide | 515.2 |
| 69 | 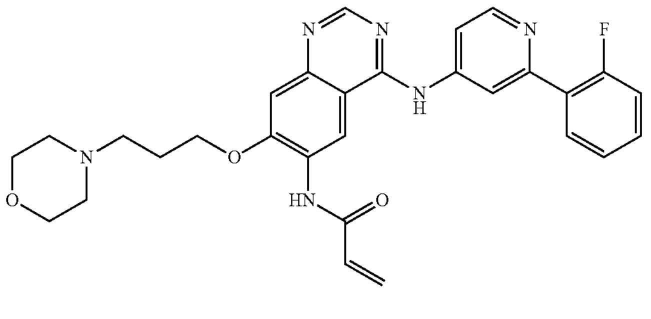 [SMILES: C=CC(=O)Nc1cc2c(Nc3ccnc(-c4ccccc4F)c3)ncnc2cc1OCCCN1CCOCC1] | N-(4-((2-(2-fluorophenyl)pyridin-4-yl)amino)-7-(3-morpholinopropoxy) quinazolin-6-yl)acrylamide | 529.2 |

-continued

| Example No. | Structural formula | Chemical name | [M + H]$^+$ |
|---|---|---|---|
| 70 | 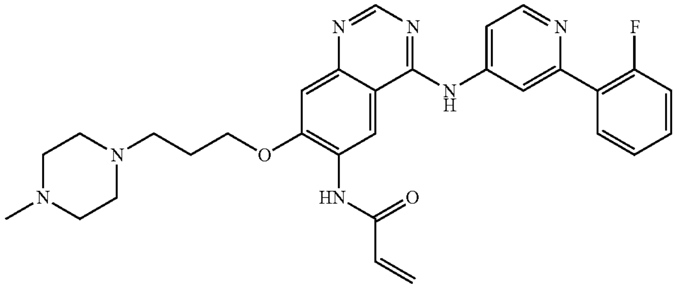 [SMILES: C=CC(=O)Nc1cc2c(Nc3ccnc(-c4ccccc4F)c3)ncnc2cc1OCCCN1CCN(C)CC1] | N-(4-((2-(2-fluorophenyl)pyridin-4-yl)amino)-7-(3-(4-methylpiperazin-1-yl)propoxy)quinazolin-6-yl)acrylamide | 542.2 |
| 71 | 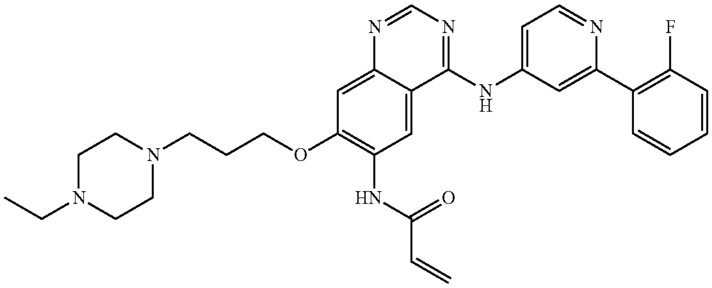 [SMILES: C=CC(=O)Nc1cc2c(Nc3ccnc(-c4ccccc4F)c3)ncnc2cc1OCCCN1CCN(CC)CC1] | N-(7-(3-(4-ethylpiperazin-1-yl)propoxy)-4-((2-(2-fluorophenyl)pyridin-4-yl)amino)quinazolin-6-yl)acrylamide | 556.2 |
| 72 | 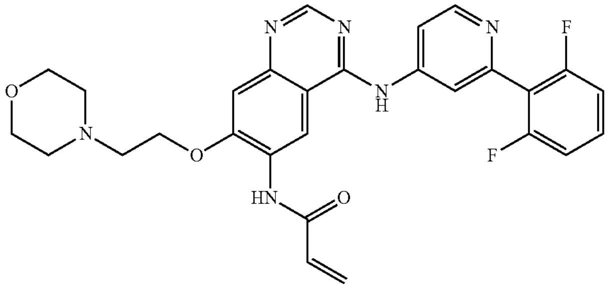 [SMILES: C=CC(=O)Nc1cc2c(Nc3ccnc(-c4c(F)cccc4F)c3)ncnc2cc1OCCN1CCOCC1] | N-(4-((2-(2,6-difluorophenyl)pyridin-4-yl)amino)-7-(2-morpholinoethoxy) quinazolin-6-yl)acrylamide | 533.2 |
| 73 | 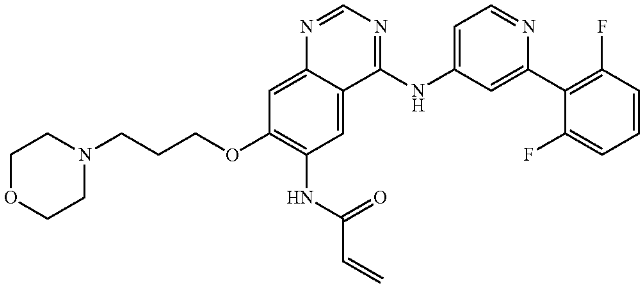 [SMILES: C=CC(=O)Nc1cc2c(Nc3ccnc(-c4c(F)cccc4F)c3)ncnc2cc1OCCCN1CCOCC1] | N-(4-((2-(2,6-difluorophenyl)pyridin-4-yl)amino)-7-(3-morpholinopropoxy) quinazolin-6-yl)acrylamide | 547.2 |
| 74 | 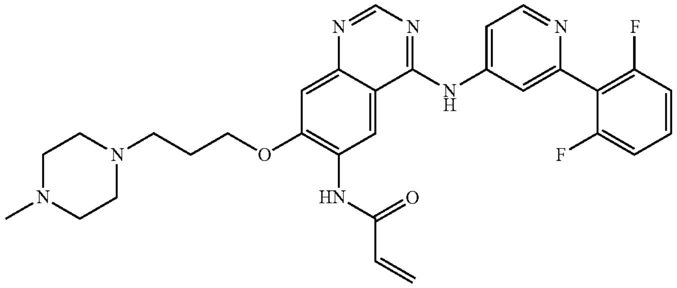 [SMILES: C=CC(=O)Nc1cc2c(Nc3ccnc(-c4c(F)cccc4F)c3)ncnc2cc1OCCCN1CCN(C)CC1] | N-(4-((2-(2,6-difluorophenyl)pyridin-4-yl)amino)-7-(3-(4-methylpiperazin-1-yl)propoxy)quinazolin-6-yl)acrylamide | 560.2 |

-continued

| Example No. | Structural formula | Chemical name | [M + H]+ |
| --- | --- | --- | --- |
| 75 | 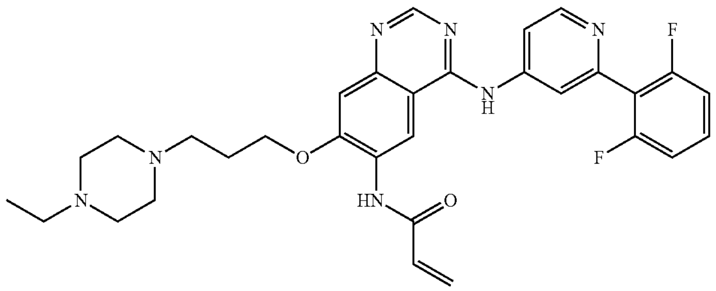 [SMILES: C=CC(=O)Nc1cc2c(Nc3ccnc(-c4c(F)cccc4F)c3)ncnc2cc1OCCCN1CCN(CC)CC1] | N-(4-((2-(2,6-difluorophenyl)pyridin-4-yl)amino)-7-(3-(4-ethylpiperazin-1-yl)propoxy)quinazolin-6-yl)acrylamide | 574.2 |
| 76 | 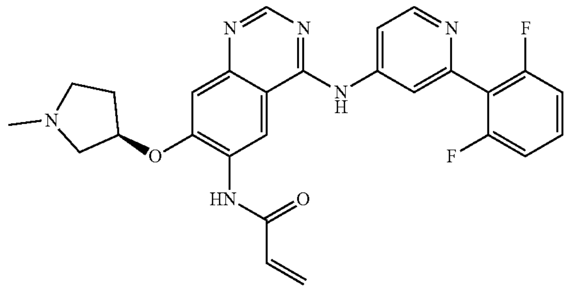 [SMILES: C=CC(=O)Nc1cc2c(Nc3ccnc(-c4c(F)cccc4F)c3)ncnc2cc1O[C@@H]1CCN(C)C1] | (R)-N-(4-((2-(2,6-difluorophenyl)pyridin-4-yl)amino)-7-((1-methylpyrrolidin-3-yl)oxy)quinazolin-6-yl)acrylamide | 503.2 |
| 77 | 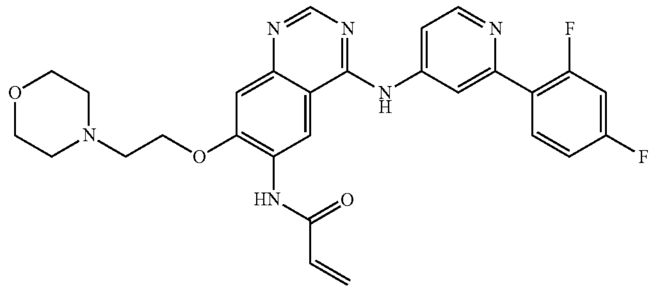 [SMILES: C=CC(=O)Nc1cc2c(Nc3ccnc(-c4ccc(F)cc4F)c3)ncnc2cc1OCCN1CCOCC1] | N-(4-((2-(2,4-difluorophenyl)pyridin-4-yl)amino)-7-(2-morpholinoethoxy) quinazolin-6-yl)acrylamide | 533.2 |
| 78 | 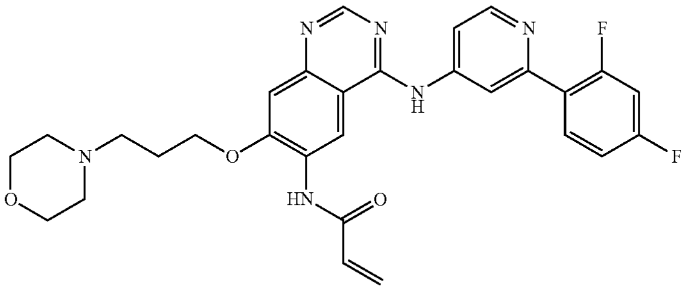 [SMILES: C=CC(=O)Nc1cc2c(Nc3ccnc(-c4ccc(F)cc4F)c3)ncnc2cc1OCCCN1CCOCC1] | N-(4-((2-(2,4-difluorophenyl)pyridin-4-yl)amino)-7-(3-morpholinopropoxy) quinazolin-6-yl)acrylamide | 547.2 |
| 79 | 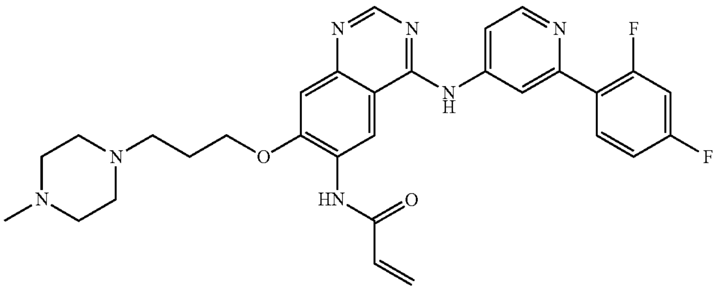 [SMILES: C=CC(=O)Nc1cc2c(Nc3ccnc(-c4ccc(F)cc4F)c3)ncnc2cc1OCCCN1CCN(C)CC1] | N-(4-((2-(2,4-difluorophenyl)pyridin-4-yl)amino)-7-(3-(4-methylpiperazin-1-yl)propoxy)quinazolin-6-yl)acrylamide | 560.2 |

-continued

| Example No. | Structural formula | Chemical name | [M + H]+ |
|---|---|---|---|
| 80 | 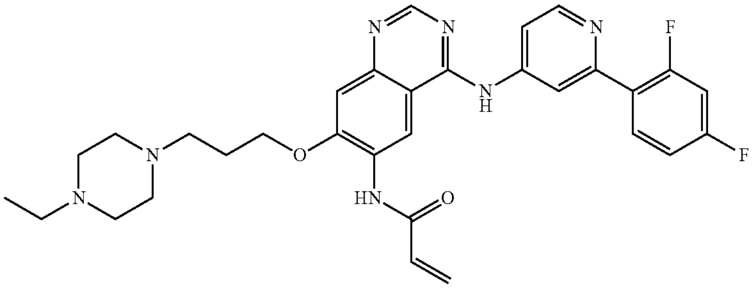 [SMILES: C=CC(=O)Nc1cc2c(Nc3ccnc(-c4ccc(F)cc4F)c3)ncnc2cc1OCCCN1CCN(CC)CC1] | N-(4-((2-(2,4-difluorophenyl)pyridin-4-yl)amino)-7-(3-(4-ethylpiperazin-1-yl)propoxy)quinazolin-6-yl)acrylamide | 574.2 |
| 81 | 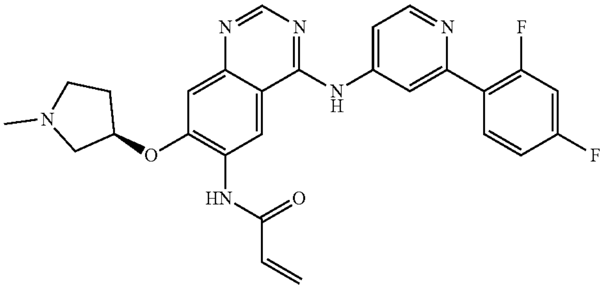 [SMILES: C=CC(=O)Nc1cc2c(Nc3ccnc(-c4ccc(F)cc4F)c3)ncnc2cc1O[C@@H]1CCN(C)C1] | (R)-N-(4-((2-(2,4-difluorophenyl)pyridin-4-yl)amino)-7-((1-methylpyrrolidin-3-yl)oxy)quinazolin-6-yl)acrylamide | 503.2 |
| 82 | 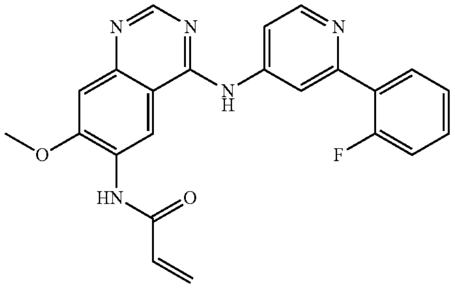 [SMILES: C=CC(=O)Nc1cc2c(Nc3ccnc(-c4ccccc4F)c3)ncnc2cc1OC] | N-(4-((2-(2-fluorophenyl)pyridin-4-yl)amino)-7-methoxyquinazolin-6-yl)acrylamide | 416.2 |
| 83 | 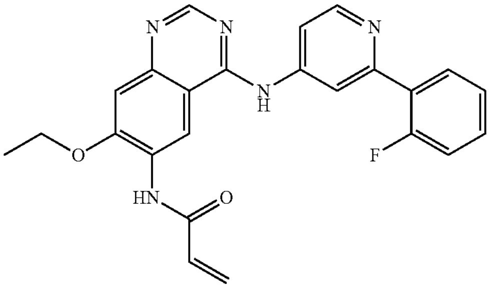 [SMILES: C=CC(=O)Nc1cc2c(Nc3ccnc(-c4ccccc4F)c3)ncnc2cc1OCC] | N-(4-((2-(2-fluorophenyl)pyridin-4-yl)amino)-7-ethoxyquinazolin-6-yl)acrylamide | 430.2 |
| 84 | 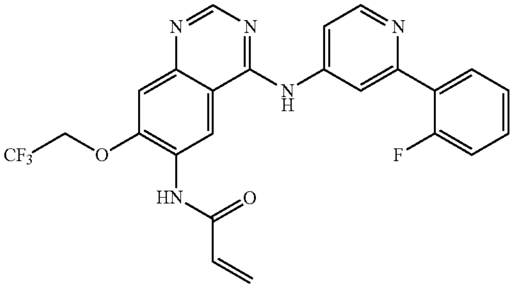 [SMILES: C=CC(=O)Nc1cc2c(Nc3ccnc(-c4ccccc4F)c3)ncnc2cc1OCC(F)(F)F] | N-(4-((2-(2-fluorophenyl)pyridin-4-yl)amino)-7-(2,2,2-trifluoroethoxy) quinazolin-6-yl)acrylamide | 484.2 |

-continued

| Example No. | Structural formula | Chemical name | [M + H]+ |
|---|---|---|---|
| 85 | 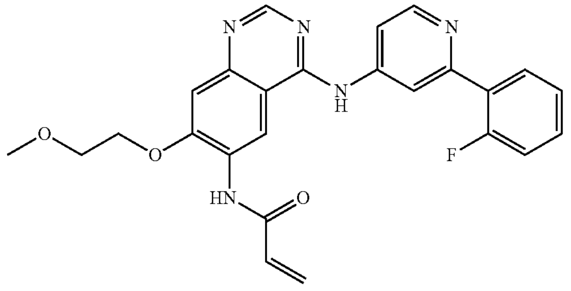 [SMILES: C=CC(=O)Nc1cc2c(Nc3ccnc(-c4ccccc4F)c3)ncnc2cc1OCCOC] | N-(4-((2-(2-fluorophenyl)pyridin-4-yl)amino)-7-(2-methoxyethoxy)quinazolin-6-yl)acrylamide | 460.2 |
| 86 | 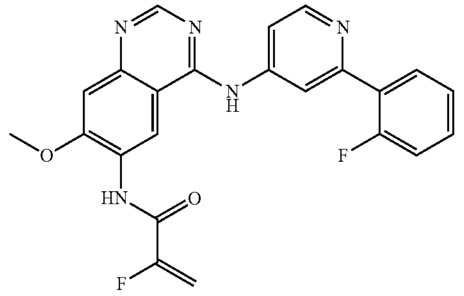 [SMILES: C=C(F)C(=O)Nc1cc2c(Nc3ccnc(-c4ccccc4F)c3)ncnc2cc1OC] | 2-fluoro-N-(4-((2-(2-fluorophenyl)pyridin-4-yl)amino)-7-methoxyquinazolin-6-yl)acrylamide | 434.2 |
| 87 | 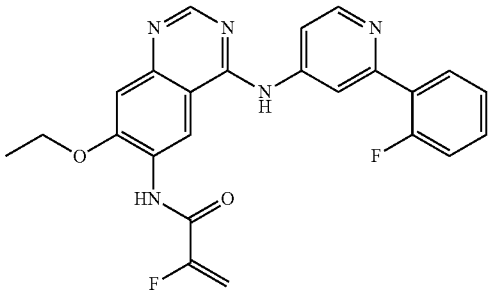 [SMILES: C=C(F)C(=O)Nc1cc2c(Nc3ccnc(-c4ccccc4F)c3)ncnc2cc1OCC] | 2-fluoro-N-(4-((2-(2-fluorophenyl)pyridin-4-yl)amino)-7-ethoxyquinazolin-6-yl)acrylamide | 448.2 |
| 88 | 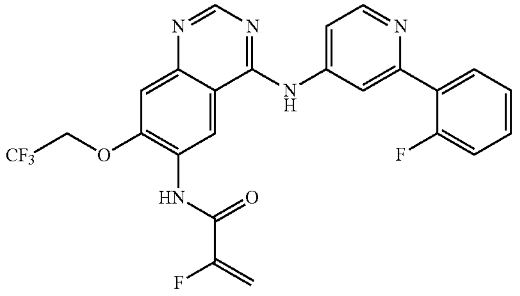 [SMILES: C=C(F)C(=O)Nc1cc2c(Nc3ccnc(-c4ccccc4F)c3)ncnc2cc1OCC(F)(F)F] | 2-fluoro-N-(4-((2-(2-fluorophenyl)pyridin-4-yl)amino)-7-(2,2,2-trifluoroethoxy)quinazolin-6-yl)acrylamide | 502.2 |
| 89 | 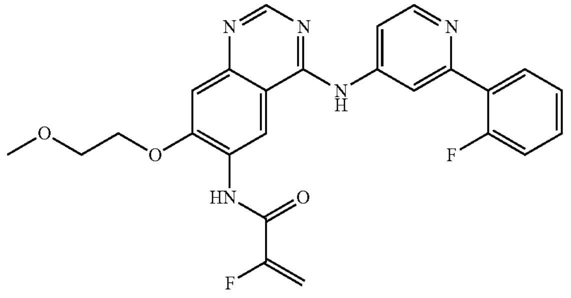 [SMILES: C=C(F)C(=O)Nc1cc2c(Nc3ccnc(-c4ccccc4F)c3)ncnc2cc1OCCOC] | 2-fluoro-N-(4-((2-(2-fluorophenyl)pyridin-4-yl)amino)-7-(2-methoxyethoxy)quinazolin-6-yl)acrylamide | 478.2 |

-continued

| Example No. | Structural formula | Chemical name | $[M + H]^+$ |
| --- | --- | --- | --- |
| 90 | 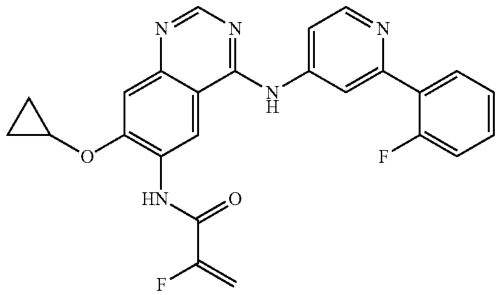 [SMILES: C=C(F)C(=O)Nc1cc2c(Nc3ccnc(-c4ccccc4F)c3)ncnc2cc1OC1CC1] | N-(7-cyclopropoxy-4-((2-(2-fluorophenyl)pyridin-4-yl)amino)quinazolin-6-yl)-2-fluoroacrylamide | 460.2 |
| 91 | 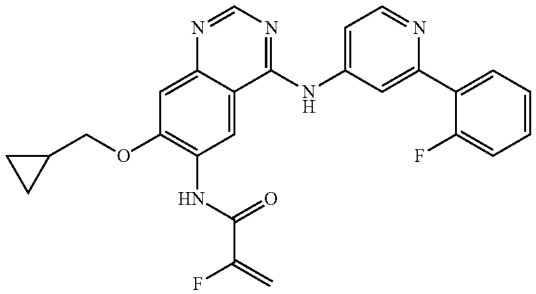 [SMILES: C=C(F)C(=O)Nc1cc2c(Nc3ccnc(-c4ccccc4F)c3)ncnc2cc1OCC1CC1] | N-(7-(cyclopropylmethoxy)-4-((2-(2-fluorophenyl)pyridin-4-yl)amino)quinazolin-6-yl)-2-fluoroacrylamide | 474.2 |

Example 92: Preparation of N-(7-fluoro-4-((2-(2-fluorophenyl)pyridin-4-yl)amino)quinazolin-6-yl)acrylamide

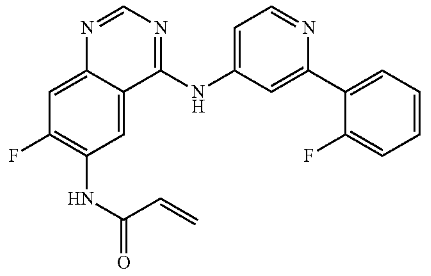 [SMILES: C=CC(=O)Nc1cc2c(Nc3ccnc(-c4ccccc4F)c3)ncnc2cc1F]

Step 1: Synthesis of 7-fluoro-$N^4$-(2-(2-fluorophenyl)pyridin-4-yl)quinazoline-4,6-diamine

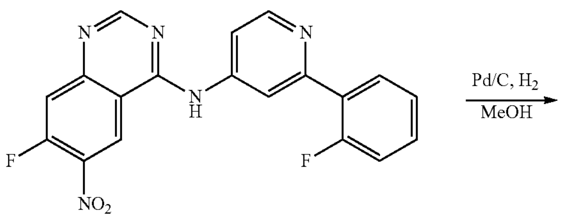

-continued

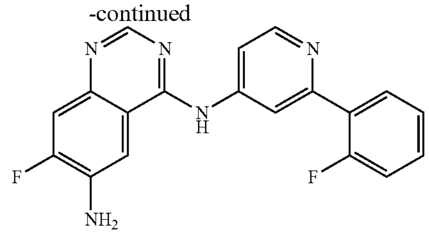

To a solution of 7-fluoro-N-(2-(2-fluorophenyl)pyridin-4-yl)-6-nitroquinazolin-4-amine (130 mg, 0.34 mmol) in methanol (10 mL) was added wet Pd/C (36 mg), and then the reaction mixture was stirred under an atmospheric hydrogen atmosphere overnight. After the reaction was completed, the reaction mixture was filtered and concentrated to obtain 7-fluoro-$N^4$-(2-(2-fluorophenyl)pyridin-4-yl)quinazoline-4,6-diamine (121 mg), which was used directly in the next step. MS m/z (ESI): 350.2 $[M+H]^+$.

Step 2: Synthesis of N-(7-fluoro-4-((2-(2-fluorophenyl)pyridin-4-yl)amino)quinazolin-6-yl)acrylamide

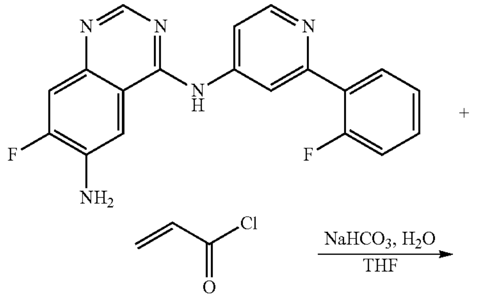

-continued

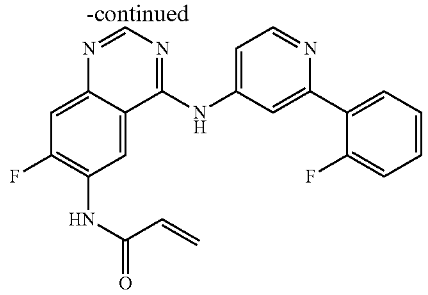

To a mixed solution of 7-fluoro-$N^4$-(2-(2-fluorophenyl)pyridin-4-yl)quinazoline-4,6-diamine (60 mg, 0.17 mmol) and sodium bicarbonate (71.8 mg, 0.86 mmol) in tetrahydrofuran (6 mL) and water (1.5 mL) was added acryloyl chloride (23 mg, 0.26 mmol) under an ice-water bath, after stirring for 15 min, the reaction mixture was then added with acryloyl chloride (23 mg, 0.26 mmol), stirred for 15 min, and then added with acryloyl chloride (46 mg, 0.51 mmol). Then ammonia liquor (5 mL) was added and stirred for 5 min, and the reaction mixture was extracted with DCM twice. The organic phase was dried over anhydrous sodium sulfate, filtered and concentrated, and the residue was separated by column chromatography [developing solvent: EtOAc/PE=0-50%] to obtain the crude product which was then stirred with methanol (5 mL) and filtered to obtain N-(7-fluoro-4-((2-(2-fluorophenyl)pyridin-4-yl)amino)quinazolin-6-yl)acrylamide (6.4 mg, yield: 8.9%). MS m/z (ESI): 404.0 $[M+H]^+$.

$^1H$ NMR (400 MHz, $CDCl_3$) δ 9.24 (d, J=8.0 Hz, 1H), 8.84 (s, 1H), 8.70 (d, J=5.7 Hz, 1H), 8.22 (s, 1H), 8.06 (br s, 1H), 8.04-7.98 (m, 2H), 7.80 (s, 1H), 7.67 (d, J=11.9 Hz, 1H), 7.43-7.37 (m, 1H), 7.29 (td, J=7.5, 1.1 Hz, 1H), 7.23-7.15 (m, 1H), 6.56 (dd, J=16.8, 1.0 Hz, 1H), 6.37 (dd, J=16.8, 10.2 Hz, 1H), 5.95 (dd, J=10.1, 1.1 Hz, 1H).

Example 93: Preparation of 2-fluoro-N-(7-fluoro-4-((2-(2-fluorophenyl)pyridin-4-yl)amino)quinazolin-6-yl)acrylamide

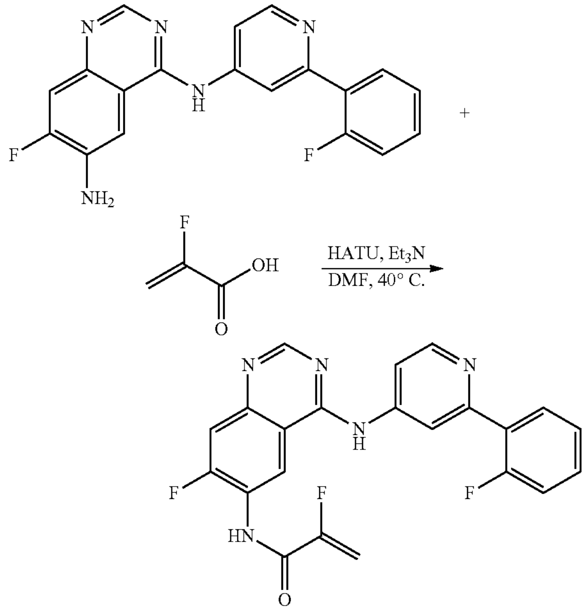

2-fluoroacrylic acid (46 mg, 0.51 mmol) and HATU (195 mg, 0.51 mmol) were dissolved in DMF (5 mL), then triethylamine (86 mg, 0.86 mmol) was added, and the reaction mixture was stirred at room temperature for 2 min, then added with 7-fluoro-N-(2-(2-fluorophenyl)pyridin-4-yl)quinazoline-4,6-diamine (60 mg, 0.17 mmol), and heated to 40° C. and stirred for 5 hrs. If the reaction wasn't completed, the reaction mixture was supplemented with 2-fluoroacrylic acid (46 mg, 0.51 mmol), HATU (195 mg, 0.51 mmol) and a solution of triethylamine (86 mg, 0.86 mmol) in DMF (5 mL). Then the mixture was stirred at 50° C. overnight, diluted with water, and extracted with EA twice, the organic phases were combined, dried over anhydrous sodium sulfate, and concentrated, and the residue was separated with a preparative column to obtain 2-fluoro-N-(7-fluoro-4-((2-(2-fluorophenyl)pyridin-4-yl)amino)quinazolin-6-yl)acrylamide (13.0 mg, yield: 18.5%). MS m/z (ESI): 422.0 $[M+H]^+$.

$^1H$ NMR (400 MHz, $CDCl_3$) δ 9.13 (d, J=7.9 Hz, 1H), 8.82 (s, 1H), 8.66 (d, J=5.6 Hz, 1H), 8.51 (s, 1H), 8.39 (s, 1H), 8.17 (s, 1H), 8.00 (ddd, J=12.2, 6.7, 2.1 Hz, 2H), 7.67 (d, J=11.6 Hz, 1H), 7.42-7.34 (m, 1H), 7.28 (d, J=7.1 Hz, 1H), 7.16 (dd, J=11.5, 8.2 Hz, 1H), 5.91 (dd, J=47.0, 3.7 Hz, 1H), 5.40 (dd, J=14.9, 3.7 Hz, 1H).

Example 94: Preparation of N-(4-((2-(2-fluorophenyl)pyridin-4-yl)amino)-7-morpholinoquinazolin-6-yl)acrylamide

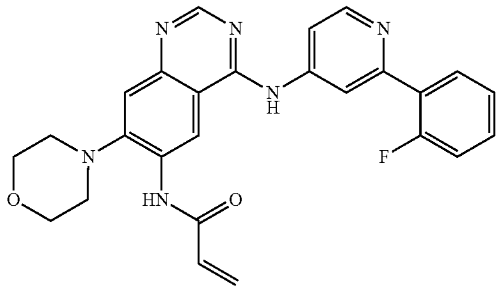 [SMILES: C=CC(=O)Nc1cc2c(Nc3ccnc(-c4ccccc4F)c3)ncnc2cc1N1CCOCC1]

Step 1: Synthesis of N-(2-(2-fluorophenyl)pyridin-4-yl)-7-morpholino-6-nitroquinazolin-4-amine

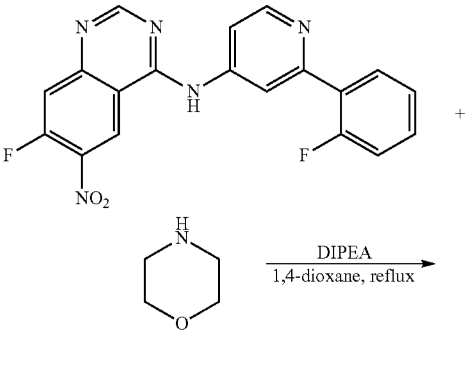

-continued

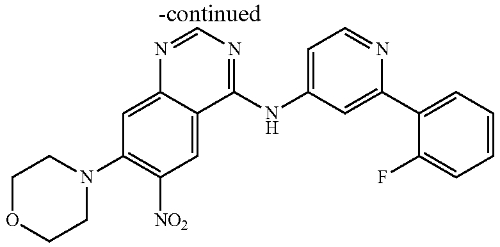

To a solution of 7-fluoro-N-(2-(2-fluorophenyl)pyridin-4-yl)-6-nitroquinazolin-4-amine (0.36 g, 0.95 mmol) in 1,4-dioxane (10 mL) were added morpholine (0.10 mL, 1.14 mmol) and DIPEA (0.47 mL, 2.85 mmol), the reaction mixture was heated to 110° C. for 2 hrs. After the reaction was completed, the reaction mixture was concentrated, and the crude product was separated by column chromatography [developing solvent: DCM/MeOH (1% ammonia liquor)=0-10%] to obtain N-(2-(2-fluorophenyl)pyridin-4-yl)-7-morpholino-6-nitroquinazolin-4-amine (0.47 g, yield: 94%). MS m/z (ESI): 447.3 $[M+H]^+$.

Step 2: Synthesis of $N^4$-(2-(2-fluorophenyl)pyridin-4-yl)-7-morpholinoquinazoline-4,6-diamine

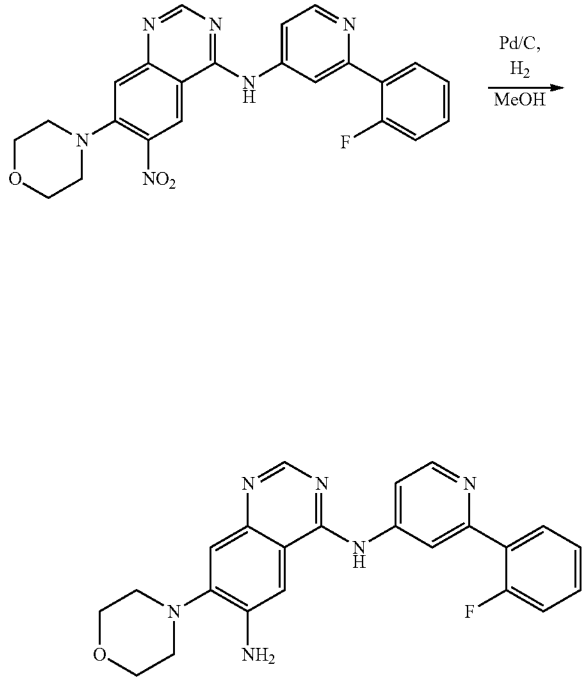

N-(2-(2-fluorophenyl)pyridin-4-yl)-7-morpholino-6-nitroquinazolin-4-amine (0.47 g, 0.89 mmol) was dissolved in methanol (30 mL), then Pd/C (0.10 g) was added in one portion, and the reaction mixture was replaced with hydrogen for three times and then heated to 40° C. under the hydrogen atmosphere and reacted overnight, then cooled to room temperature, and filtered through celite, and the filtrate was concentrated to obtain the crude product $N_4$-(2-(2-fluorophenyl)pyridin-4-yl)-7-morpholinoquinazoline-4,6-diamine (0.33 g, yield: 78%). MS m/z (ESI): 417.2 $[M+H]^+$.

Step 3: Synthesis of N-(4-((2-(2-fluorophenyl)pyridin-4-yl)amino)-7-morpholinoquinazolin-6-yl)acrylamide

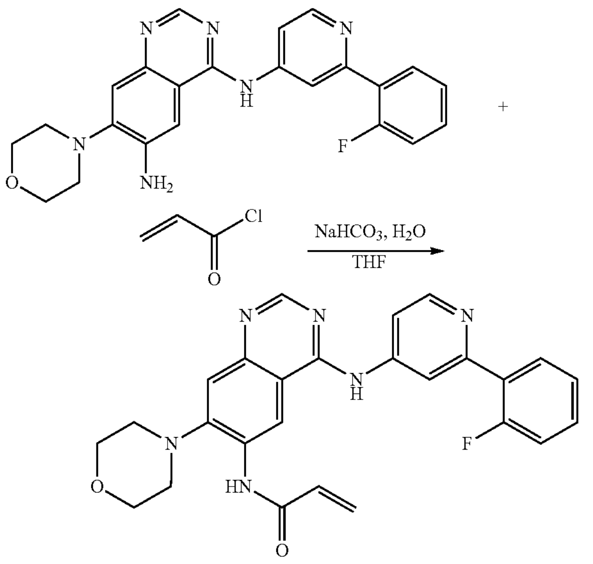

The above obtained crude product $N^4$-(2-(2-fluorophenyl)pyridin-4-yl)-7-morpholinoquinazoline-4,6-diamine (0.20 g, 0.43 mmol) was added to a mixture of THF (4 mL) and saturated aqueous $NaHCO_3$ (2 mL), acryloyl chloride (52 μL, 0.64 mmol) was added at 0° C., and the reaction mixture was stirred for 1 hr at 0° C. After the reaction was completed as monitored by LCMS, MeOH was added to quench the reaction, and the reaction mixture was directly separated with a reverse preparative column to obtain N-(4-((2-(2-fluorophenyl)pyridin-4-yl)amino)-7-morpholinoquinazolin-6-yl)acrylamide (26.3 mg, yield: 13%). MS m/z (ESI): 471.2 $[M+H]^+$.

$^1H$ NMR (400 MHz, DMSO-$d_6$) δ 10.08 (s, 1H), 9.66 (s, 1H), 8.83 (s, 1H), 8.68 (s, 1H), 8.61 (d, J=5.7 Hz, 1H), 8.39 (t, J=2.0 Hz, 1H), 8.10 (dd, J=5.7, 2.1 Hz, 1H), 7.97 (td, J=7.9, 1.7 Hz, 1H), 7.50 (tdd, J=7.3, 5.0, 1.9 Hz, 1H), 7.42-7.30 (m, 3H), 6.72 (dd, J=16.9, 10.2 Hz, 1H), 6.35 (dd, J=17.0, 2.0 Hz, 1H), 5.85 (dd, J=10.1, 2.0 Hz, 1H), 3.83 (t, J=4.4 Hz, 4H), 3.03 (t, J=4.5 Hz, 4H).

Example 95: Preparation of 2-fluoro-N-(4-((2-(2-fluorophenyl)pyridin-4-yl)amino)-7-morpholinoquinazolin-6-yl)acrylamide

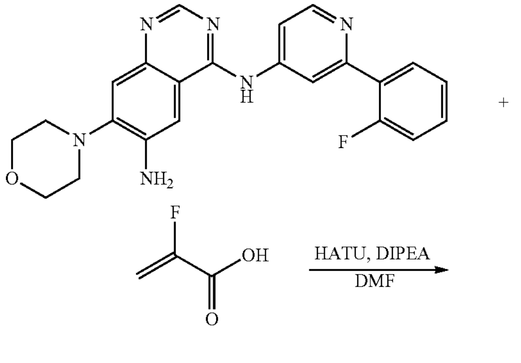

-continued

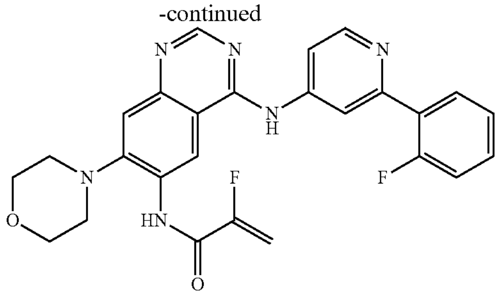

$N^4$-(2-(2-fluorophenyl)pyridin-4-yl)-7-morpholinoquinazoline-4,6-diamine (0.13 g, 0.28 mmol) was dissolved in DMF (4 mL), then 2-fluoroacrylic acid (50 dg, 0.55 mmol), HATU (0.21 g, 0.55 mmol) and DIPEA (0.14 mL, 0.83 mmol) were added, and the reaction mixture was heated to 40° C. and stirred for 1 hr. After the reaction was completed as monitored by LCMS, the reaction mixture was concentrated, and the residue was directly separated by reversed-phase chromatography to obtain 2-fluoro-N-(4-((2-(2-fluorophenyl)pyridin-4-yl)amino)-7-morpholinoquinazolin-6-yl)acrylamide (50.5 mg, yield: 36%). MS m/z (ESI): 489.2 $[M+H]^+$.

$^1H$ NMR (400 MHz, DMSO-$d_6$) δ 10.14 (s, 1H), 9.87 (d, J=2.6 Hz, 1H), 8.88 (s, 1H), 8.71 (s, 1H), 8.61 (d, J=5.6 Hz, 1H), 8.38 (d, J=2.0 Hz, 1H), 8.10 (dd, J=5.7, 2.1 Hz, 1H), 7.97 (td, J=7.9, 1.7 Hz, 1H), 7.55-7.47 (m, 2H), 7.41-7.31 (m, 2H), 5.81 (dd, J=48.3, 3.8 Hz, 1H), 5.54 (dd, J=15.8, 3.8 Hz, 1H), 3.79 (dd, J=5.8, 3.3 Hz, 4H), 3.05 (t, J=4.6 Hz, 4H).

Examples 96-110 can be prepared by selecting corresponding starting materials by referring to all or part of the synthesis method in Example 94 or 95.

| Example No. | Structural formula | Chemical name | $[M + H]^+$ |
|---|---|---|---|
| 96 | 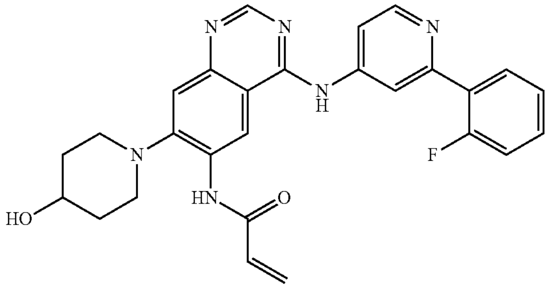 [SMILES: C=CC(=O)Nc1cc2c(Nc3ccnc(-c4ccccc4F)c3)ncnc2cc1N1CCC(O)CC1] | N-(4-((2-(2-fluorophenyl)pyridin-4-yl)amino)-7-(4-hydroxypiperidin-1-yl)quinazolin-6-yl)acrylamide | 485.2 |
| 97 | 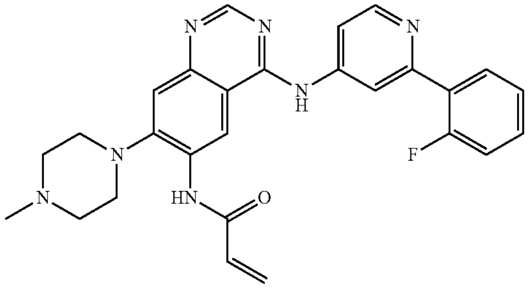 [SMILES: C=CC(=O)Nc1cc2c(Nc3ccnc(-c4ccccc4F)c3)ncnc2cc1N1CCN(C)CC1] | N-(4-((2-(2-fluorophenyl)pyridin-4-yl)amino)-7-(4-methylpiperazin-1-yl)quinazolin-6-yl)acrylamide | 484.2 |
| 98 | 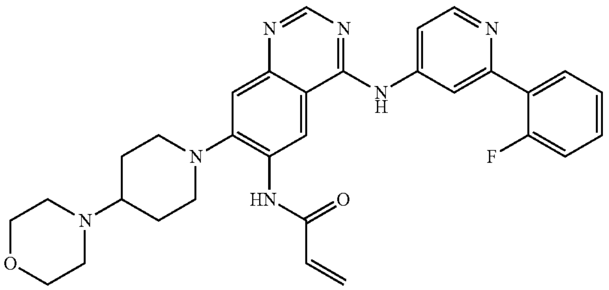 [SMILES: C=CC(=O)Nc1cc2c(Nc3ccnc(-c4ccccc4F)c3)ncnc2cc1N1CCC(N2CCOCC2)CC1] | N-(4-((2-(2-fluorophenyl)pyridin-4-yl)amino)-7-(4-morpholinopiperidin-1-yl)quinazolin-6-yl)acrylamide | 554.2 |

-continued

| Example No. | Structural formula | Chemical name | [M + H]+ |
|---|---|---|---|
| 99 | 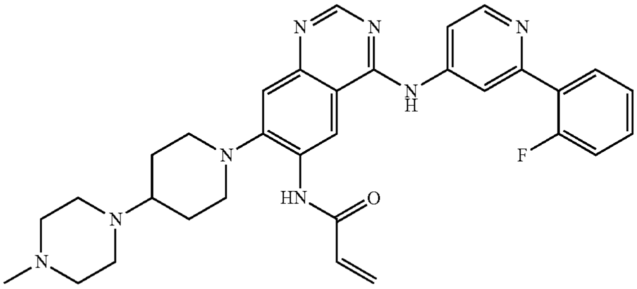 [SMILES: C=CC(=O)Nc1cc2c(Nc3ccnc(-c4ccccc4F)c3)ncnc2cc1N1CCC(N2CCN(C)CC2)CC1] | N-(4-((2-(2-fluorophenyl)pyridin-4-yl)amino)-7-(4-(4-methylpiperazin-1-yl)piperidin-1-yl)quinazolin-6-yl)acrylamide | 567.2 |
| 100 | 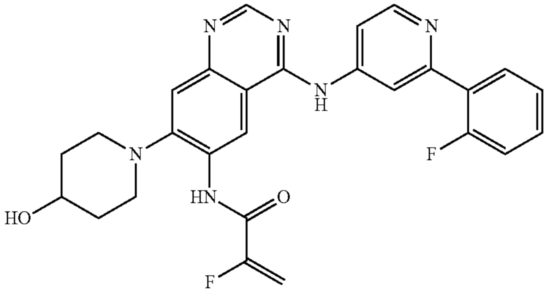 [SMILES: C=C(F)C(=O)Nc1cc2c(Nc3ccnc(-c4ccccc4F)c3)ncnc2cc1N1CCC(O)CC1] | 2-fluoro-N-(4-((2-(2-fluorophenyl)pyridin-4-yl)amino)-7-(4-hydroxypiperidin-1-yl)quinazolin-6-yl)acrylamide | 503.2 |
| 101 | 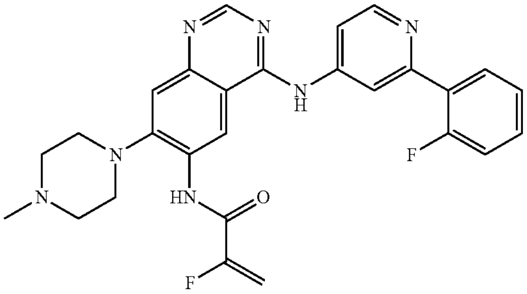 [SMILES: C=C(F)C(=O)Nc1cc2c(Nc3ccnc(-c4ccccc4F)c3)ncnc2cc1N1CCN(C)CC1] | 2-fluoro-N-(4-((2-(2-fluorophenyl)pyridin-4-yl)amino)-7-(4-methylpiperazin-1-yl)quinazolin-6-yl)acrylamide | 502.2 |
| 102 | 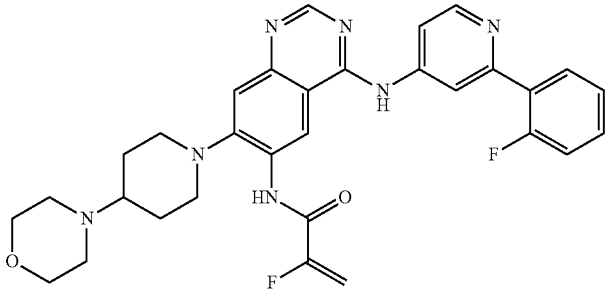 [SMILES: C=C(F)C(=O)Nc1cc2c(Nc3ccnc(-c4ccccc4F)c3)ncnc2cc1N1CCC(N2CCOCC2)CC1] | 2-fluoro-N-(4-((2-(2-fluorophenyl)pyridin-4-yl)amino)-7-(4-morpholinopiperidin-1-yl)quinazolin-6-yl)acrylamide | 572.2 |
| 103 | 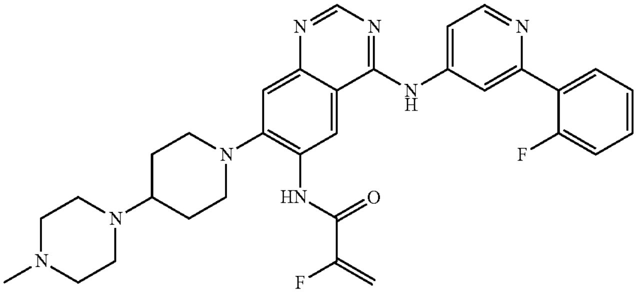 [SMILES: C=C(F)C(=O)Nc1cc2c(Nc3ccnc(-c4ccccc4F)c3)ncnc2cc1N1CCC(N2CCN(C)CC2)CC1] | 2-fluoro-N-(4-((2-(2-fluorophenyl)pyridin-4-yl)amino)-7-(4-(4-methylpiperazin-1-yl) piperidin-1-yl)quinazolin-6-yl)acrylamide | 585.3 |

-continued

| Example No. | Structural formula | Chemical name | [M + H]$^+$ |
|---|---|---|---|
| 104 | 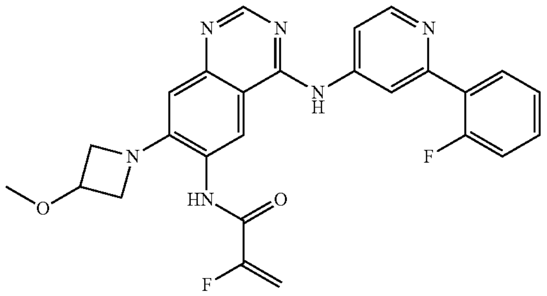 [SMILES: C=C(F)C(=O)Nc1cc2c(Nc3ccnc(-c4ccccc4F)c3)ncnc2cc1N1CC(OC)C1] | 2-fluoro-N-(4-((2-(2-fluorophenyl)pyridin-4-yl)amino)-7-(3-methoxyazetidin-1-yl)quinazolin-6-yl)acrylamide | 489.2 |
| 105 | 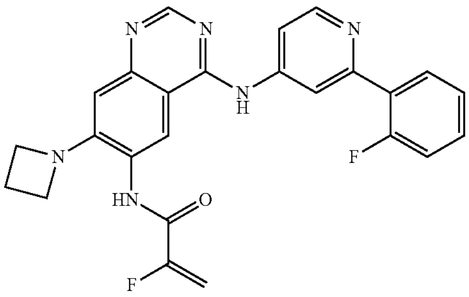 [SMILES: C=C(F)C(=O)Nc1cc2c(Nc3ccnc(-c4ccccc4F)c3)ncnc2cc1N1CCC1] | N-(7-(azetidin-1-yl)-4-((2-(2-fluorophenyl)pyridin-4-yl)amino)quinazolin-6-yl)-2-fluoroacrylamide | 459.2 |
| 106 | 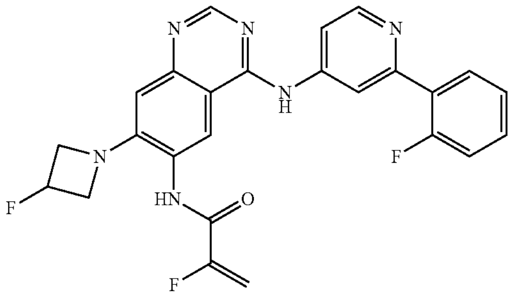 [SMILES: C=C(F)C(=O)Nc1cc2c(Nc3ccnc(-c4ccccc4F)c3)ncnc2cc1N1CC(F)C1] | 2-fluoro-N-(7-(3-fluoroazetidin-1-yl)-4-((2-(2-fluorophenyl)pyridin-4-yl)amino)quinazolin-6-yl)acrylamide | 477.0 |
| 107 | 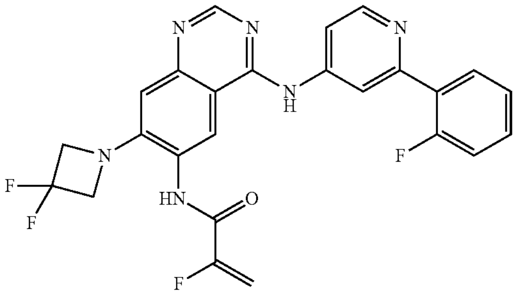 [SMILES: C=C(F)C(=O)Nc1cc2c(Nc3ccnc(-c4ccccc4F)c3)ncnc2cc1N1CC(F)(F)C1] | N-(7-(3,3-difluoroazetidin-1-yl)-4-((2-(2-fluorophenyl)pyridin-4-yl)amino)quinazolin-6-yl)-2-fluoroacrylamide | 495.2 |
| 108 | 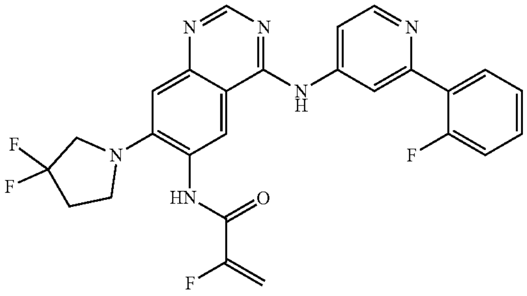 [SMILES: C=C(F)C(=O)Nc1cc2c(Nc3ccnc(-c4ccccc4F)c3)ncnc2cc1N1CCC(F)(F)C1] | N-(7-(3,3-difluoropyrrolidin-1-yl)-4-((2-(2-fluorophenyl)pyridin-4-yl)amino)quinazolin-6-yl)-2-fluoroacrylamide | 509.2 |

-continued

| Example No. | Structural formula | Chemical name | $[M + H]^+$ |
| --- | --- | --- | --- |
| 109 | 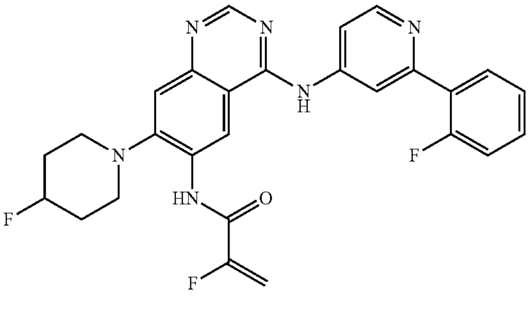 [SMILES: C=C(F)C(=O)Nc1cc2c(Nc3ccnc(-c4ccccc4F)c3)ncnc2cc1N1CCC(F)CC1] | 2-fluoro-N-(4-((2-(2-fluorophenyl)pyridin-4-yl)amino)-7-(4-fluoropiperidin-1-yl)quinazolin-6-yl)acrylamide | 505.2 |
| 110 | 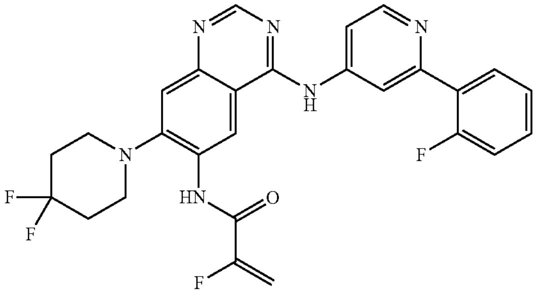 [SMILES: C=C(F)C(=O)Nc1cc2c(Nc3ccnc(-c4ccccc4F)c3)ncnc2cc1N1CCC(F)(F)CC1] | N-(7-(4,4-difluoropiperidin-1-yl)-4-((2-(2-fluorophenyl)pyridin-4-yl)amino)quinazolin-6-yl)-2-fluoroacrylamide | 523.2 |

Example 111: preparation of (R)—N-(4-((2-(2-fluorophenyl)pyridin-4-yl)amino)-7-((1-(2-methoxyethyl)pyrrolidin-3-yl)oxy)quinazolin-6-yl)acrylamide

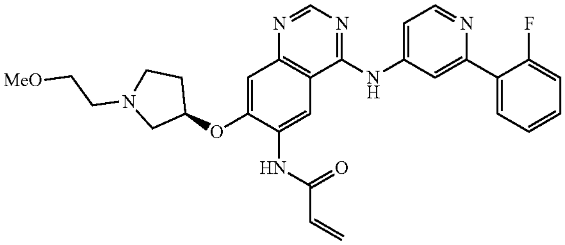 [SMILES: C=CC(=O)Nc1cc2c(Nc3ccnc(-c4ccccc4F)c3)ncnc2cc1O[C@@H]1CCN(CCOC)C1]

Step 1: Synthesis of tert-butyl (R)-3-((4-((2-(2-fluorophenyl)pyridin-4-yl)amino)-6-nitroquinazolin-7-yl)oxy)pyrrolidine-1-carboxylate

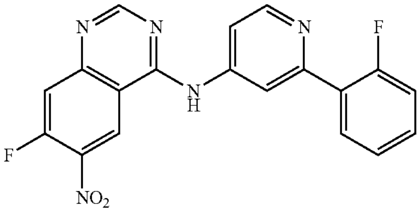

+

-continued

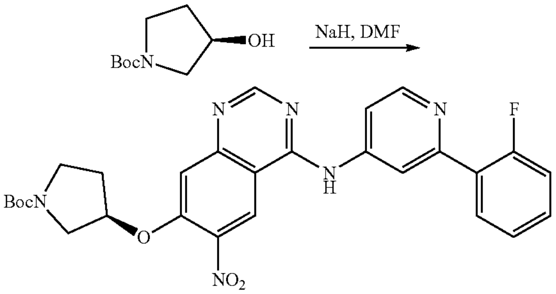

Tert-butyl (R)-3-hydroxypyrrolidine-1-carboxylate (2.96 g, 15.82 mmol) was added in DMF (40 mL), NaH (60%, 0.63 g, 15.82 mmol) was then added under an ice-water bath. The reaction mixture was stirred at 0° C. for 15 min, then added with 7-fluoro-N-(2-(2-fluorophenyl)pyridin-4-yl)-6-nitroquinazolin-4-amine (1.26 g, 3.16 mmol) and stirred at 0° C. for 1 hr. After the reaction was completed, the reaction mixture was diluted with water and extracted with EtOAc, the organic phase was washed with saturated brine, dried over anhydrous sodium sulfate, filtered and concentrated, and the residue was separated by column chromatography [developing solvent: MeOH/DCM=0-8%] to obtain tert-butyl (R)-3-((4-((2-(2-fluorophenyl)pyridin-4-yl)amino)-6-nitroquinazolin-7-yl)oxy)pyrrolidine-1-carboxylate (1.73 g, yield: 100%). MS m/z (ESI): 547.2 $[M+H]^+$.

Step 2: Synthesis of tert-butyl (R)-3-((6-amino-4-((2-(2-fluorophenyl)pyridin-4-yl)amino)quinazolin-7-yl)oxy)pyrrolidine-1-carboxylate

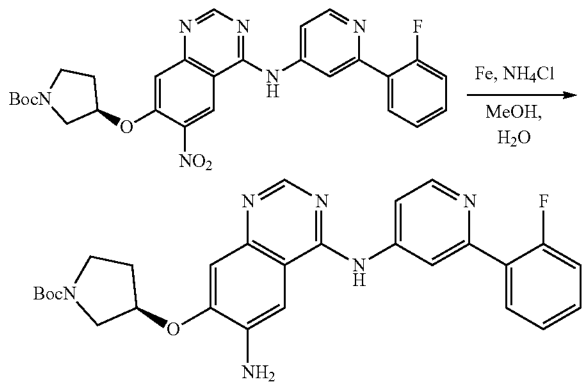

Tert-butyl (R)-3-((4-((2-(2-fluorophenyl)pyridin-4-yl)amino)-6-nitroquinazolin-7-yl)oxy) pyrrolidine-1-carboxylate (1.73 g, 3.16 mmol) was added to methanol (40 mL) an d saturated aqueous ammonium chloride (15 mL), then iron powder (3.53 g, 63.3 mmol) was added, and the reaction mixture was stirred at 70° C. for 1 hr. After the reaction was completed, the mixture was filtered, then diluted with saturated aqueous sodium bicarbonate and extracted with DCM. The organic phase was washed with saturated brine, dried over anhydrous sodium sulfate, filtered and concentrated, and the residue was separated by column chromatography [developing solvent: MeOH/DCM=0-15%] to obtain tert-butyl (R)-3-((6-amino-4-((2-(2-fluorophenyl)pyridin-4-yl)amino)quinazolin-7-yl)oxy)pyrrolidine-1-carboxylate (580 mg, yield: 35.4%). MS m/z (ESI): 517.2 $[M+H]^+$.

Step 3: Synthesis of tert-butyl (R)-3-((6-acrylamido-4-((2-(2-fluorophenyl)pyridin-4-yl)amino) quinazolin-7-yl)oxy) pyrrolidine-1-carboxylate

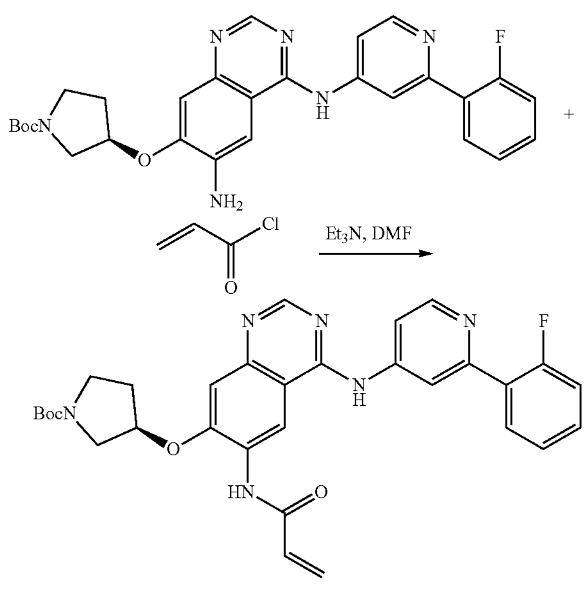

Tert-butyl (R)-3-((6-amino-4-((2-(2-fluorophenyl)pyridin-4-yl)amino)quinazolin-7-yl)oxy) pyrrolidine-1-carboxylate (580 mg, 1.12 mmol) was dissolved in DMF (15 mL), triethylamine (340 mg, 3.36 mmol) and acryloyl chloride (91 mg, 1.01 mmol) were added sequentially at 0° C., the reaction mixture was stirred for 1 hr. After the reaction was completed, the reaction mixture was diluted with water and extracted with DCM, the organic phase was washed with saturated brine, dried over anhydrous sodium sulfate, filtered and concentrated, and the residue was separated by column chromatography [developing solvent: MeOH/DCM=0-15%] to obtain tert-butyl (R)-3-((6-acrylamido-4-((2-(2-fluorophenyl)pyridin-4-yl)amino)quinazolin-7-yl)oxy)pyrrolidine-1-carboxylate (340 mg, yield: 48.3%). MS m/z (ESI): 571.2 $[M+H]^+$.

Step 4: Synthesis of (R)—N-(4-((2-(2-fluorophenyl)pyridin-4-yl)amino)-7-(pyrrolidin-3-oxy)quinazolin-6-yl)acrylamide trifluoroacetate

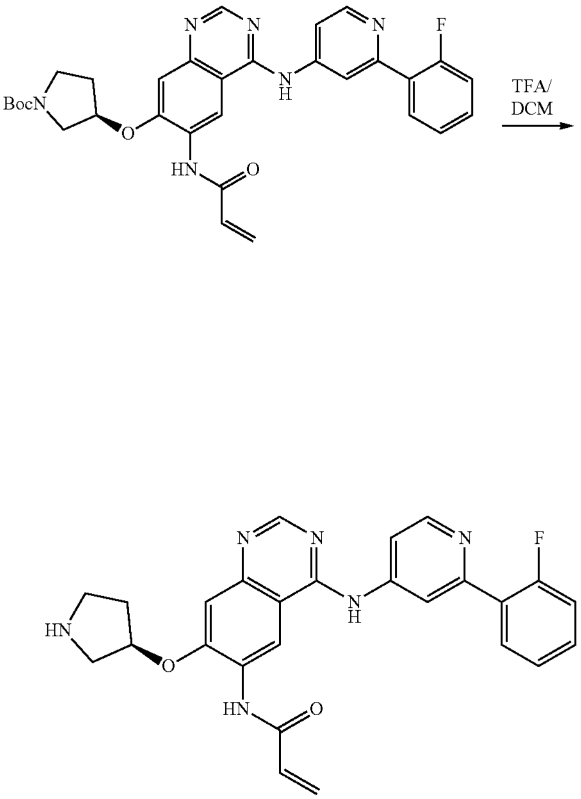

Tert-butyl (R)-3-((6-acrylamido-4-((2-(2-fluorophenyl)pyridin-4-yl)amino)quinazol in-7-yl)oxy) pyrrolidine-1-carboxylate (340 mg, 0.60 mmol) was dissolved in DCM (25 mL), TFA (5 mL) was added at 0° C., and the reaction mixture was reacted at room temperature for 1 hr. After the reaction was completed, the reaction mixture was directly concentrated to obtain (R)—N-(4-((2-(2-fluorophenyl)pyridin-4-yl)amino)-7-(pyrrolidin-3-oxy)quinazolin-6-yl)acrylamide trifluoroacetate, and the crude product was used directly in the next step (550 mg, yield: 100%). MS m/z (ESI): 471.2 $[M+H]^+$.

Step 5: Synthesis of (R)—N-(4-((2-(2-fluorophenyl)pyridin-4-yl)amino)-7-((1-(2-methoxyethyl)pyrrolidin-3-yl)oxy)quinazolin-6-yl)acrylamide

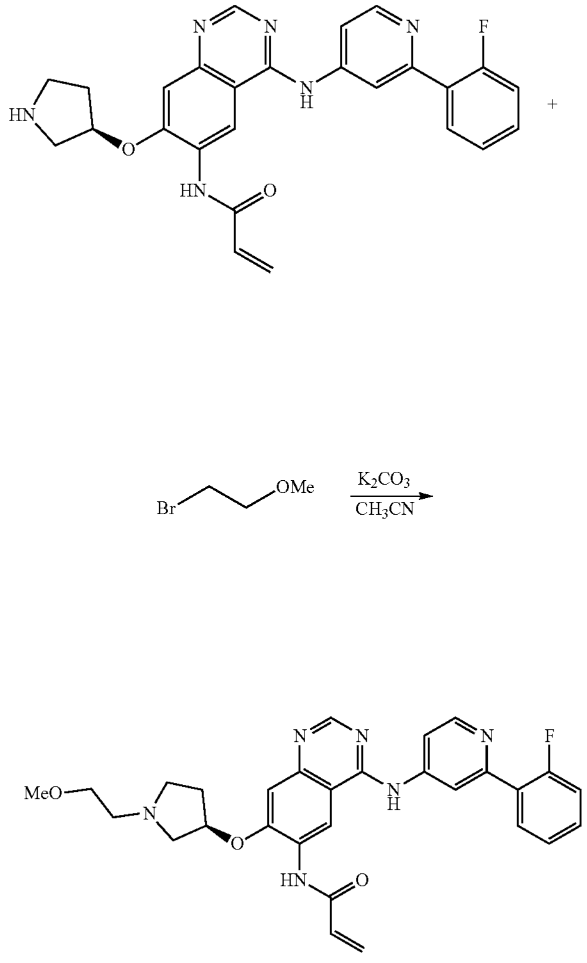

(R)—N-(4-((2-(2-fluorophenyl)pyridin-4-yl)amino)-7-(pyrrolidin-3-oxy)quinazolin-6-yl)acrylamide trifluoroacetate (60 mg, 0.13 mmol) was placed in acetonitrile (5 mL), $K_2CO_3$ (180 mg, 1.3 mmol) and 1-bromo-2-methoxyethane (181 mg, 1.3 mmol) were added, and the reaction mixture was stirred at room temperature for 18 hrs. After the reaction was completed, the reaction mixture was directly concentrated, and the crude product was separated by preparative HPLC to obtain (R)—N-(4-((2-(2-fluorophenyl)pyridin-4-yl)amino)-7-((1-(2-methoxyethyl)pyrrolidin-3-yl)oxy)quinazolin-6-yl)acrylamide (25.2 mg, yield: 37.3%). MS m/z (ESI): 529.2 $[M+H]^+$.

$^1H$ NMR (400 MHz, DMSO-$d_6$) δ 10.07 (s, 1H), 9.62 (s, 1H), 9.02 (s, 1H), 8.66 (s, 1H), 8.60 (d, J=5.7 Hz, 1H), 8.37 (s, 1H), 8.16-8.02 (m, 1H), 7.97 (td, J=7.8, 2.0 Hz, 1H), 7.57-7.45 (m, 1H), 7.40-7.30 (m, 2H), 7.23 (s, 1H), 6.77 (dd, J=17.0, 10.2 Hz, 1H), 6.34 (dd, J=16.9, 2.0 Hz, 1H), 5.83 (dd, J=10.1, 2.1 Hz, 1H), 5.22-5.05 (m, 1H), 3.44 (t, J=5.9 Hz, 3H), 3.23 (s, 3H), 2.96 (dd, J=10.7, 6.1 Hz, 1H), 2.89 (dd, J=10.7, 2.8 Hz, 1H), 2.83 (td, J=8.2, 5.4 Hz, 1H), 2.66-2.60 (m, 2H), 2.41-2.31 (m, 1H), 2.02 (ddd, J=13.1, 6.7, 3.0 Hz, 1H).

Example 112: Preparation of (R)—N-(4-((2-(2-fluorophenyl)pyridin-4-yl)amino)-7-((1-(2-hydroxyethyl)pyrrolidin-3-yl)oxy)quinazolin-6-yl)acrylamide

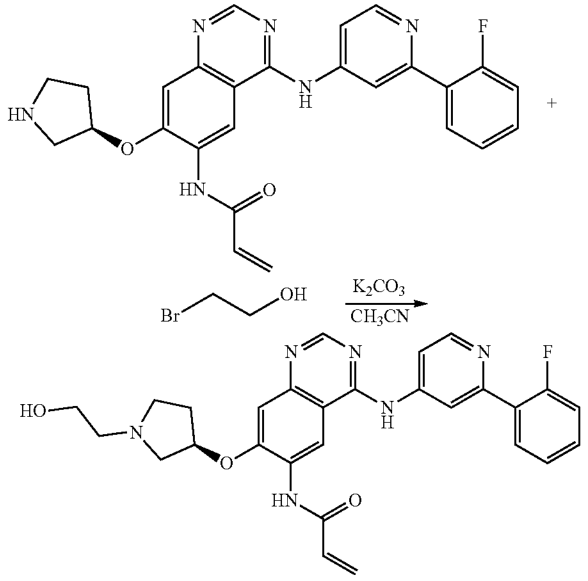

It was prepared by referring to the step 5 of the synthesis method in Example 111. MS m/z (ESI): 515.2 $[M+H]^+$.

Example 113: Preparation of (R)—N-(7-((1-cyclopropylpyrrolidin-3-yl)oxy)-4-((2-(2-fluorophenyl)pyridin-4-yl)amino)quinazolin-6-yl)acrylamide

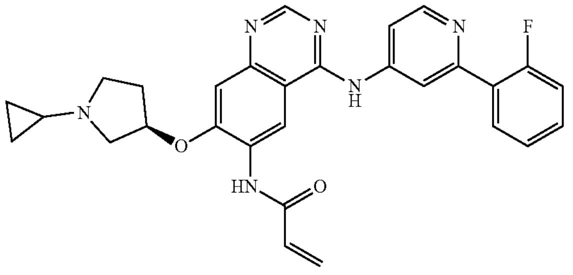 [SMILES: C=CC(=O)Nc1cc2c(Nc3ccnc(-c4ccccc4F)c3)ncnc2cc1O[C@@H]1CCN(C2CC2)C1]

Step 1: Synthesis of (R)—N-(2-(2-fluorophenyl)pyridin-4-yl)-6-nitro-7-(pyrrolidin-3-oxy)quinazolin-4-amine

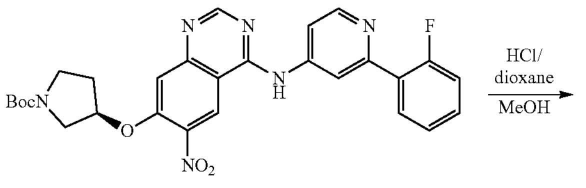

-continued

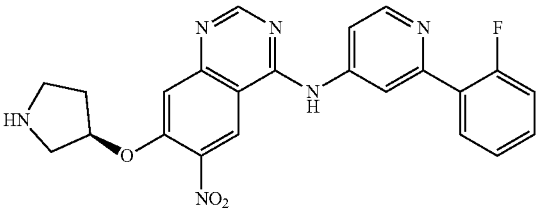

Tert-butyl (R)-3-((4-((2-(2-fluorophenyl)pyridin-4-yl)amino)-6-nitroquinazolin-7-yl)oxy)pyrrolidine-1-carboxylate (1.73 g, 3.165 mmol) was dissolved in methanol (20 m L), 4M HCl/dioxane solution (10 mL) was added, and then the reaction mixture was stir red at room temperature under nitrogen protection for 1 hr. After the reaction was completed, the reaction mixture was diluted with dichloromethane, and washed sequentially with saturated sodium carbonate solution and saturated brine, the organic phase was concentrated, and the residue was separated by column chromatography [developing solvent: MeOH/DCM=0-1%] to obtain (R)—N-(2-(2-fluorophenyl)pyridin-4-yl)-6-nitro-7-(pyrrolidin-3-oxy)quinazolin-4-amine (1.01 g, yield: 71%). MS m/z (ESI): 447.2 $[M+H]^+$.

Step 2: Synthesis of (R)-7-((1-cyclopropylpyrrolidin-3-yl)oxy)-N-(2-(2-fluorophenyl)pyridin-4-yl)-6-nitroquinazolin-4-amine

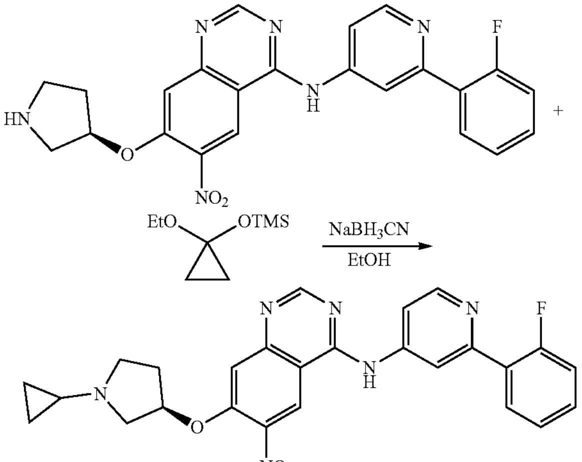

(R)—N-(2-(2-fluorophenyl)pyridin-4-yl)-6-nitro-7-(pyrrolidin-3-oxy)quinazolin-4-amine (400 mg, 0.896 mmol), (1-ethoxycyclopropoxy)trimethylsilane (0.90 mL, 4.48 mmol) and sodium cyanoborohydride (219.56 mg, 4.48 mmol) were placed in ethanol (15 mL), the mixture was stirred at 60° C. under nitrogen protection for 18 hrs. After the reaction was completed, the reaction mixture was directly concentrated, and the residue was separated by column chromatography [developing solvent: MeOH/DCM=0-10%] to obtain (R)-7-((1-cyclopropylpyrrolidin-3-yl)oxy)-N-(2-(2-fluorophenyl)pyridin-4-yl)-6-nitroquinazolin-4-amine (200 mg, yield: 37%). MS m/z (ESI): 487.2 $[M+H]^+$.

Step 3: Synthesis of (R)-7-((1-cyclopropylpyrrolidin-3-yl)oxy)-$N^4$-(2-(2-fluorophenyl)pyridin-4-yl)quinazoline-4,6-diamine

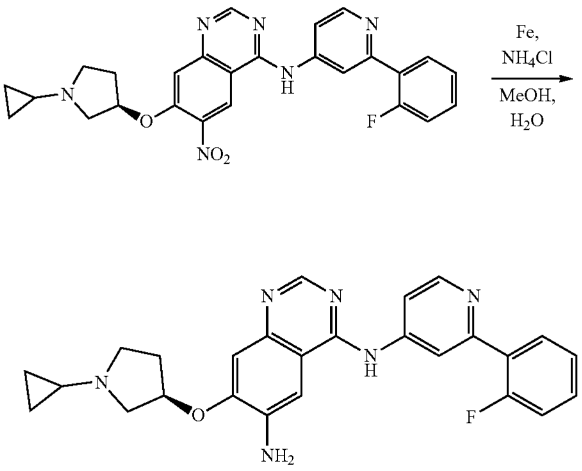

(R)-7-((1-cyclopropylpyrrolidin-3-yl)oxy)-N-(2-(2-fluorophenyl)pyridin-4-yl)-6-nitroquinazolin-4-amine (200 mg, 0.41 mmol), iron powder (114.8 mg, 2.05 mmol), and ammonium chloride (219.9 mg, 4.11 mmol) were placed in a mixed solution of methanol (30 mL) and water (10 mL). The mixture was stirred at 70° C. under nitrogen protection for 1 hr, filtered, concentrated, and separated by column chromatography [developing solvent: MeOH/DCM=0-15%] to obtain (R)-7-((1-cyclopropylpyrrolidin-3-yl)oxy)-$N^4$-(2-(2-fluorophenyl)pyridin-4-yl)quinazoline-4,6-diamine (110 mg, yield: 53%). MS m/z (ESI): 457.2 $[M+H]^+$.

Step 4: Synthesis of (R)—N-(7-((1-cyclopropylpyrrolidin-3-yl)oxy)-4-((2-(2-fluorophenyl)pyridin-4-yl)amino)quinazolin-6-yl)acrylamide

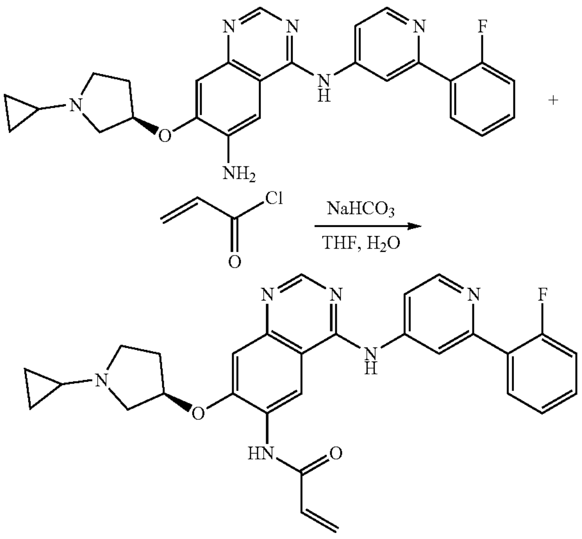

(R)-7-((1-cyclopropylpyrrolidin-3-yl)oxy)-$N^4$-(2-(2-fluorophenyl)pyridin-4-yl)quinazoline-4,6-diamine (110 mg, 0.24 mmol) and sodium bicarbonate (40.48 mg, 0.48 mmol) were added in a mixed solution of THF (4 mL) and water (1 mL), acryloyl chloride (26.17 mg, 0.28 mmol) was added at 0° C. and stirred for 0.5 hrs. After the reaction was completed, the reaction mixture was directly separated by column chromatography [developing solvent: MeOH/DCM=0-10%] to obtain (R)—N-(7-((1-cyclopropylpyrrolidin-3-yl)oxy)-4-((2-(2-fluorophenyl)pyridin-4-yl)amino)quinazolin-6-yl)acrylamide (55 mg, yield: 43%). MS m/z (ESI): 511.2 $[M+H]^+$.

$^1$H NMR (400 MHz, MeOH-$d_4$) δ 9.04 (s, 1H), 8.67 (s, 1H), 8.54 (d, J=5.8 Hz, 1H), 8.34 (s, 1H), 8.13 (dd, J=5.9, 2.2 Hz, 1H), 7.80 (td, J=7.8, 1.8 Hz, 1H), 7.48 (tdd, J=7.3, 5.0, 1.9 Hz, 1H), 7.33 (td, J=7.6, 1.2 Hz, 1H), 7.31-7.23 (m, 1H), 7.26-7.15 (m, 2H), 6.63 (dd, J=16.9, 10.1 Hz, 1H), 6.50 (dd, J=17.0, 1.8 Hz, 1H), 5.88 (dd, J=10.0, 1.9 Hz, 1H), 5.23 (brs, 1H), 2.92 (dd, J=11.6, 5.2 Hz, 2H), 2.66 (q, J=8.8 Hz, 1H), 2.63-2.50 (m, 1H), 2.04 (dt, J=15.4, 8.2 Hz, 1H), 1.84 (dt, J=8.0, 4.7 Hz, 1H), 1.33-1.23 (m, 1H), 0.62-0.52 (m, 4H).

Example 114: Preparation of (R)—N-(4-((2-(2-fluorophenyl)pyridin-4-yl)amino)-7-((1-(oxetan-3-yl)pyrrolidin-3-yl oxy)quinazolin-6-yl acrylamide

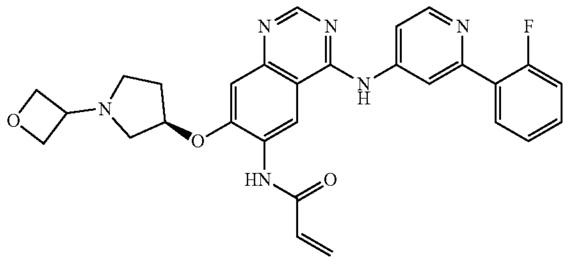 [SMILES: C=CC(=O)Nc1cc2c(Nc3ccnc(-c4ccccc4F)c3)ncnc2cc1O[C@@H]1CCN(C2COC2)C1]

(R)—N-(4-((2-(2-fluorophenyl)pyridin-4-yl)amino)-7-((1-(oxetan-3-yl)pyrrolidin-3-yl)oxy)quinazolin-6-yl)acrylamide was prepared by replacing (1-ethoxycyclopropoxy)trimethylsilane with 3-oxetanone and by referring to the steps 2 to 4 of the preparation method in Example 113. MS m/z (ESI): 527.2 $[M+H]^+$.

Examples 115-121 can be prepared by selecting corresponding starting materials by referring to all or part of the synthesis method in Example 95, 113 or 114.

| Example No. | Structural formula | Chemical name | $[M + H]^+$ |
| --- | --- | --- | --- |
| 115 | 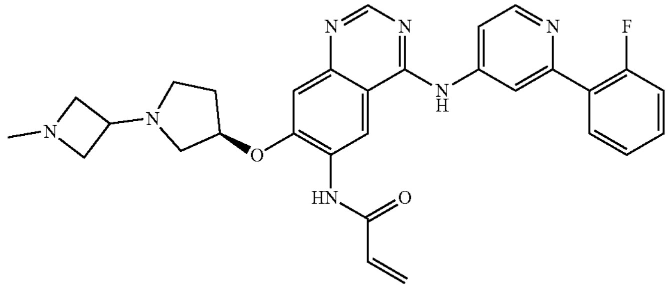 [SMILES: C=CC(=O)Nc1cc2c(Nc3ccnc(-c4ccccc4F)c3)ncnc2cc1O[C@@H]1CCN(C2CN(C)C2)C1] | (R)-N-(4-((2-(2-fluorophenyl)pyridin-4-yl)amino)-7-((1-(1-methylazetidin-3-yl)pyrrolidin-3-yl)oxy)quinazolin-6-yl)acrylamide | 540.2 |
| 116 | 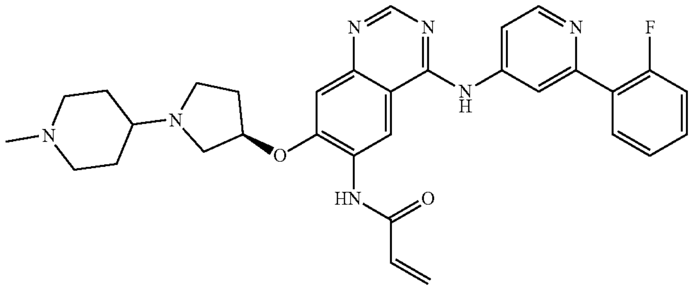 [SMILES: C=CC(=O)Nc1cc2c(Nc3ccnc(-c4ccccc4F)c3)ncnc2cc1O[C@@H]1CCN(C2CCN(C)CC2)C1] | (R)-N-(4-((2-(2-fluorophenyl)pyridin-4-yl)amino)-7-((1-(1-methylpiperidin-4-yl)pyrrolidin-3-yl)oxy)quinazolin-6-yl)acrylamide | 568.2 |
| 117 | 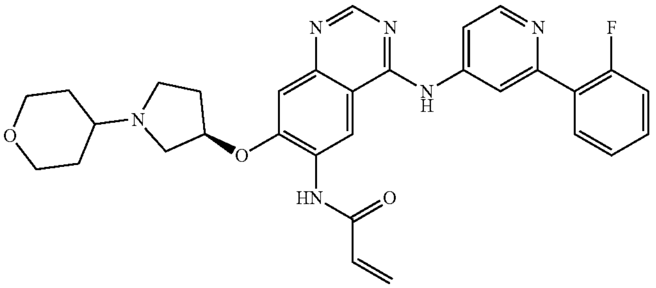 [SMILES: C=CC(=O)Nc1cc2c(Nc3ccnc(-c4ccccc4F)c3)ncnc2cc1O[C@@H]1CCN(C2CCOCC2)C1] | (R)-N-(4-((2-(2-fluorophenyl)pyridin-4-yl)amino)-7-((1-(tetrahydro-2H-pyran-4-yl)pyrrolidin-3-yl)oxy)quinazolin-6-yl)acrylamide | 555.2 |

-continued

| Example No. | Structural formula | Chemical name | [M + H]+ |
|---|---|---|---|
| 118 | 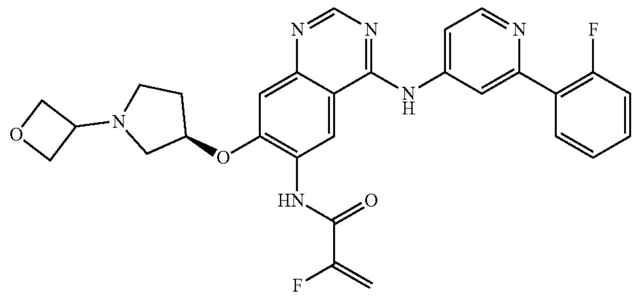 [SMILES: C=C(F)C(=O)Nc1cc2c(Nc3ccnc(-c4ccccc4F)c3)ncnc2cc1O[C@@H]1CCN(C2COC2)C1] | (R)-2-fluoro-N-(4-((2-(2-fluorophenyl)pyridin-4-yl)amino)-7-((1-(oxetan-3-yl)pyrrolidin-3-yl)oxy)quinazolin-6-yl)acrylamide | 545.2 |
| 119 | 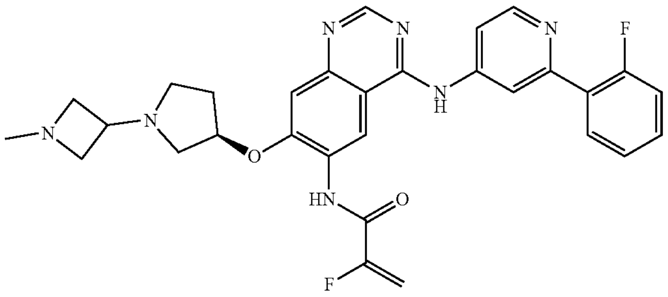 [SMILES: C=C(F)C(=O)Nc1cc2c(Nc3ccnc(-c4ccccc4F)c3)ncnc2cc1O[C@@H]1CCN(C2CN(C)C2)C1] | (R)-2-fluoro-N-(4-((2-(2-fluorophenyl)pyridin-4-yl)amino)-7-((1-(1-methylazetidin-3-yl)pyrrolidin-3-yl)oxy)quinazolin-6-yl)acrylamide | 558.2 |
| 120 | 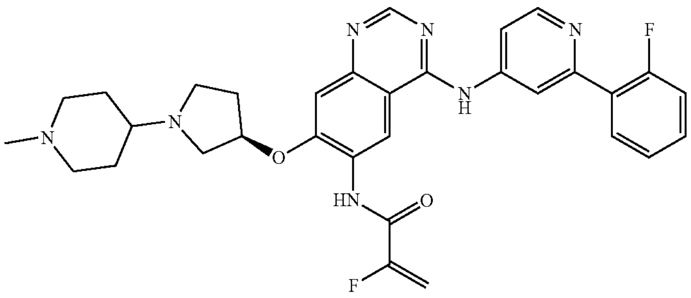 [SMILES: C=C(F)C(=O)Nc1cc2c(Nc3ccnc(-c4ccccc4F)c3)ncnc2cc1O[C@@H]1CCN(C2CCN(C)CC2)C1] | (R)-2-fluoro-N-(4-((2-(2-fluorophenyl)pyridin-4-yl)amino)-7-((1-(1-methylpiperidin-4-yl)pyrrolidin-3-yl)oxy)quinazolin-6-yl)acrylamide | 586.2 |
| 121 | 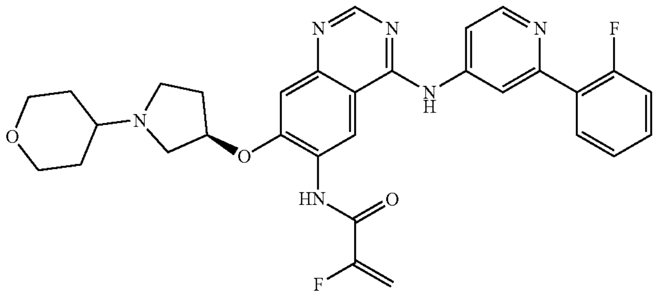 [SMILES: C=C(F)C(=O)Nc1cc2c(Nc3ccnc(-c4ccccc4F)c3)ncnc2cc1O[C@@H]1CCN(C2CCOCC2)C1] | (R)-2-fluoro-N-(4-((2-(2-fluorophenyl)pyridin-4-yl)amino)-7-((1-(tetrahydro-2H-pyran-4-yl)pyrrolidin-3-yl)oxy)quinazolin-6-yl)acrylamide | 573.2 |

Example 122: Preparation of N-(4-((2-(2-fluorophenyl)pyridin-4-yl)amino)-7-(3-(4-(2-hydroxyethyl) piperazin-1-yl)propoxy)quinazolin-6-yl)acrylamide

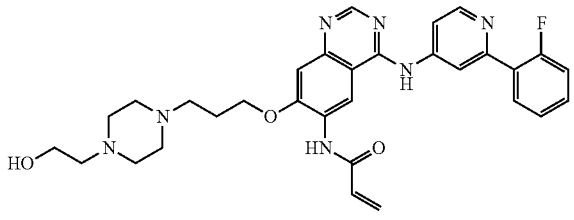 [SMILES: C=CC(=O)Nc1cc2c(Nc3ccnc(-c4ccccc4F)c3)ncnc2cc1OCCCN1CCN(CCO)CC1]

Step 1: Synthesis of tert-butyl 4-(3-((4-((2-(2-fluorophenyl)pyridin-4-yl)amino)-6-nitroquinazolin-7-yl)oxy)propyl)piperazine-1-carboxylate

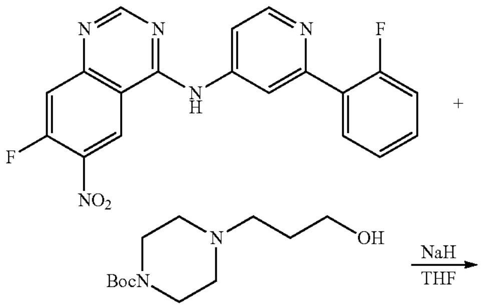

-continued

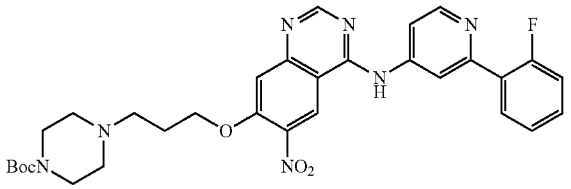

Tert-butyl 4-(3-hydroxypropyl)piperazine-1-carboxylate (1.50 g, 6.1 mmol) was dissolved in THE (20 mL), sodium hydride (0.38 g, 60% in oil, 9.4 mmol) was added portion-wise at room temperature, and after stirring for 30 min 7-fluoro-N-(2-(2-fluorophenyl)pyridin-4-yl)-6-nitroquinazolin-4-amine (1.19 g, 3.1 mmol) was added, and the reaction mixture was reacted at room temperature for 1.5 hrs. After the reaction was completed, saturated ammonium chloride aqueous solution was added to quench the reaction, the reaction mixture was extracted with EtOAc twice. The organic phase was washed with saturated brine, dried over anhydrous sodium sulfate, filtered and concentrated, and the residue was separated by column chromatography [developing solvent: DCM/MeOH (1% ammonia liquor)=0-8%] to obtain tert-butyl 4-(3-((4-((2-(2-fluorophenyl)pyridin-4-yl) amino)-6-nitroquinazolin-7-yl)oxy)propyl)piperazine-1-carboxylate (2.04 g, yield: 100%). MS m/z (ESI): 604.2 $[M+H]^+$.

Step 2: Synthesis of N-(2-(2-fluorophenyl)pyridin-4-yl)-6-nitro-7-(3-(piperazin-1-yl)propoxy)quinazolin-4-amine

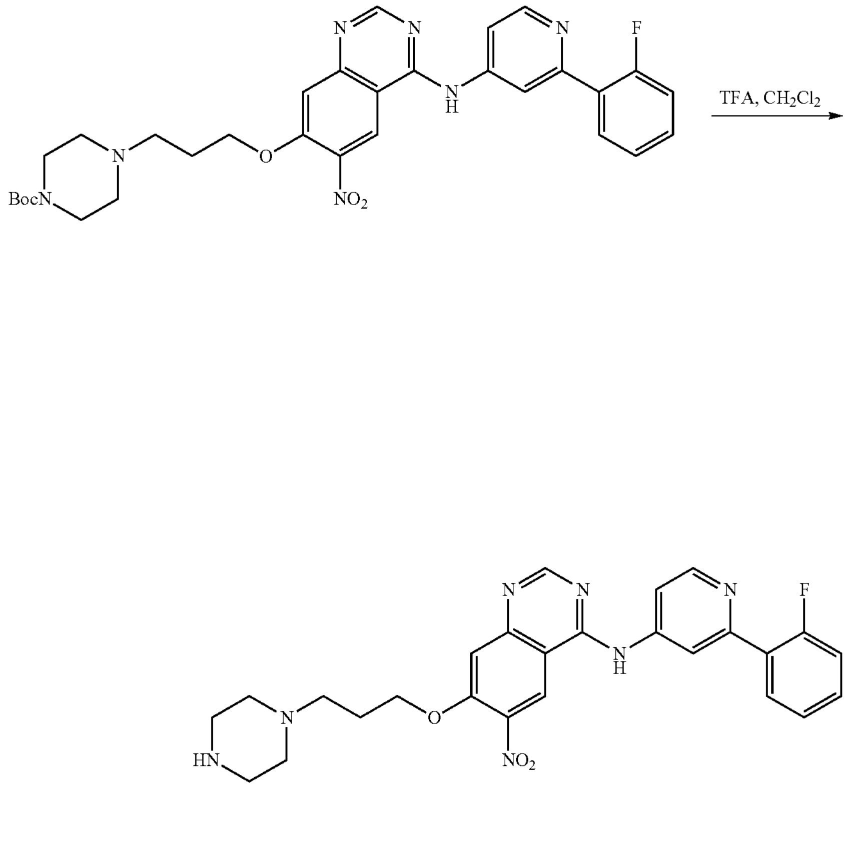

To a solution of 4-(3-((4-((2-(2-fluorophenyl)pyridin-4-yl)amino)-6-nitroquinazolin-7-yl)oxy)propyl)piperazine-1-carboxylate (2.04 g, 3.1 mmol) in dichloromethane (5 m L) was added trifluoroacetic acid (2.33 mL, 31.4 mmol) at room temperature. The reaction mixture was stirred at room temperature for 2 hrs until the reaction was completed, then concentrated to remove the solvent, and the residue was added with saturated sodium hydroxide solution to adjust pH to 8, then extracted with EtOAc twice, washed with saturated brine, dried and concentrated, and the residue was separated by column chromatography [developing solvent: DCM/MeOH (1% ammonia liquor)=0-8%] to obtain N-(2-(2-fluorophenyl)pyridin-4-yl)-6-nitro-7-(3-(piperazin-1-yl)propoxy)quinazolin-4-amine (1.59 g, yield: 100%). MS m/z (ESI): 504.2 $[M+H]^+$.

Step 3: Synthesis of N-(2-(2-fluorophenyl)pyridin-4-yl)-6-nitro-7-(3-(4-(2-((tetrahydro-2H-pyran-2-yl)oxy)ethyl)piperazin-1-yl)propoxy)quinazolin-4-amine

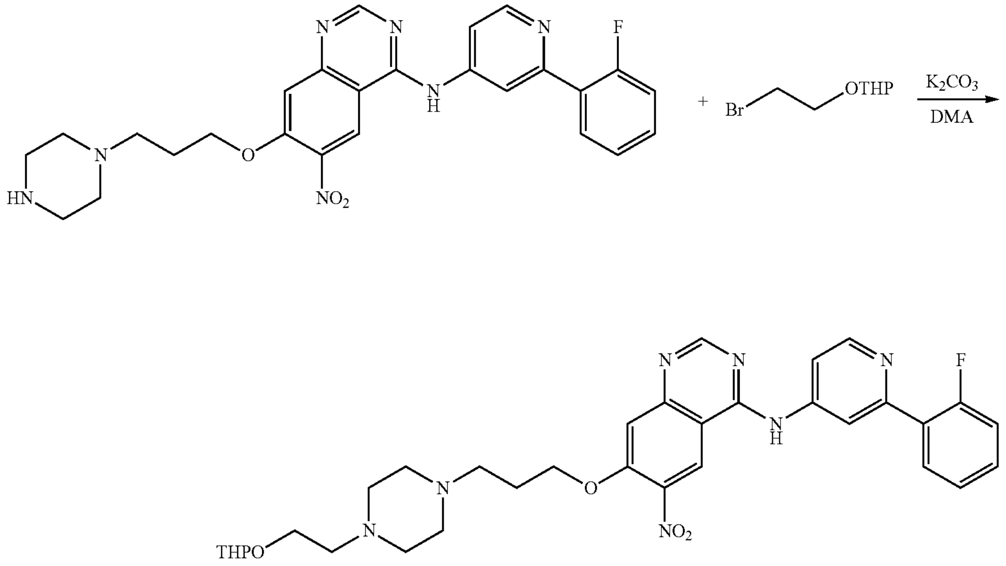

To a solution of N-(2-(2-fluorophenyl)pyridin-4-yl)-6-nitro-7-(3-(piperazin-1-yl)propoxy)quinazolin-4-amine (0.50 g, 0.99 mmol) in N,N-dimethylacetamide (10 mL) were added 2-(2-bromoethoxy)tetrahydro-2H-pyran (0.15 mL, 0.99 mmol), potassium carbonate (0.41 g, 2.96 mmol) and potassium iodide (0.16 g, 0.99 mmol). The reaction mixture was stirred at room temperature under nitrogen protection for 1.5 hrs. After the reaction was completed, acetonitrile (20 mL) was added, the solid was filtered through celite, the filtrate was concentrated, and the residue was separated by column chromatography [developing solvent: DCM/MeOH (1% ammonia liquor)=0-8%] to obtain N-(2-(2-fluorophenyl)pyridin-4-yl)-6-nitro-7-(3-(4-(2-((tetrahydro-2H-pyran-2-yl)oxy)ethyl)piperazin-1-yl)propoxy)quinazolin-4-amine (0.50 g, yield: 74%). MS m/z (ESI): 623.2 $[M+H]^+$.

Step 4: Synthesis of $N^4$-(2-(2-fluorophenyl)pyridin-4-yl)-7-(3-(4-(2-((tetrahydro-2H-pyran-2-yl)oxy)ethyl)piperazin-1-yl)propoxy)quinazoline-4,6-diamine

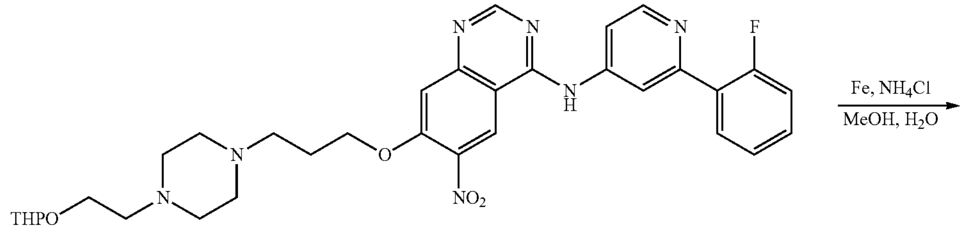

-continued

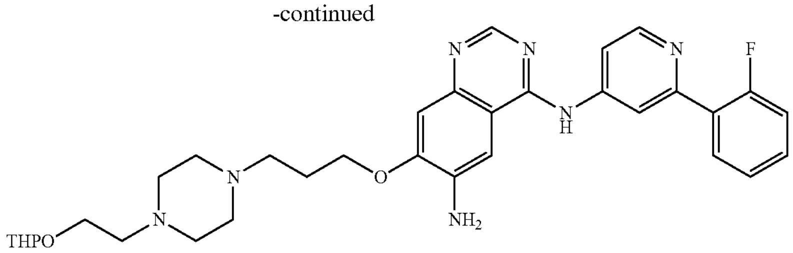

Iron powder (0.20 g, 3.66 mmol) and ammonium chloride solid (0.39 g, 7.3 mmol) were added in one portion to N-(2-(2-fluorophenyl)pyridin-4-yl)-6-nitro-7-(3-(4-(2-((tetrahydro-2H-pyran-2-yl)oxy)ethyl)piperazin-1-yl)propoxy) quinazolin-4-amine (0.50 g, 0.73 mmol) in methanol/water (8 mL/2 mL). After the nitrogen was replaced for three time s for three times, the reaction mixture was heated to 70° C. and stirred for 1 hr until the reaction was completed. The reaction mixture was cooled to room temperature, and filtered through celite, and the filtrate was concentrated to obtain the crude product $N^4$-(2-(2-fluorophenyl)pyridin-4-yl)-7-(3-(4-(2-((tetrahydro-2H-pyran-2-yl)oxy)ethyl)piperazin-1-yl)propoxy)quinazoline-4,6-diamine, which was directly used in the next step. MS m/z (ESI): 602.2 $[M+H]^+$.

Step 5: Synthesis of N-(4-((2-(2-fluorophenyl)pyridin-4-yl)amino)-7-(3-(4-(2-((tetrahydro-2H-pyran-2-yl)oxy)ethyl)piperazin-1-yl)propoxy)quinazolin-6-yl)acrylamide

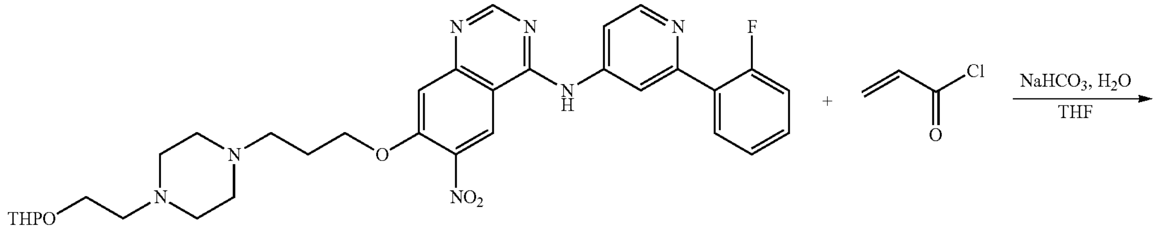

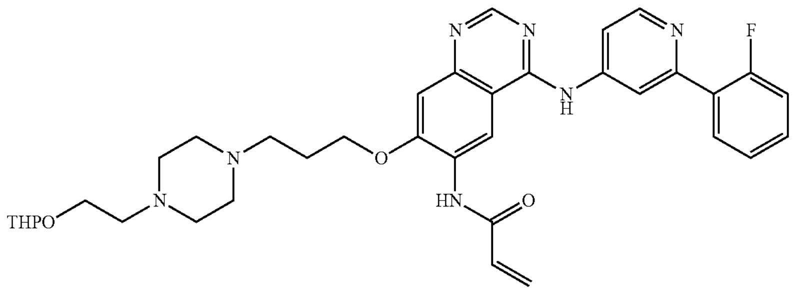

The above crude product $N^4$-(2-(2-fluorophenyl)pyridin-4-yl)-7-(3-(4-(2-((tetrahydro-2H-pyran-2-yl)oxy)ethyl)piperazin-1-yl)propoxy)quinazoline-4,6-diamine was added to THE (3 mL) and saturated aqueous $NaHCO_3$ (3 mL), acryloyl chloride (58 μL, 0.72 mmol) was added at 0° C., and the reaction mixture was stirred at 0° C. for 20 min. After the reaction was completed as monitored by LCMS, methanol was added to quench the reaction, the reaction mixture was extracted with dichloromethane twice, and the organic phase was washed with saturated brine, dried over anhydrous sodium sulfate, filtered and concentrated, and the residue was separated by column chromatography [developing solvent: DCM/MeOH (1% ammonia liquor)=0-8%] to obtain N-(4-((2-(2-fluorophenyl)pyri din-4-yl)amino)-7-(3-(4-(2-((tetrahydro-2H-pyran-2-yl)oxy)ethyl)piperazin-1-yl) propoxy)quinazolin-6-yl)acrylamide (0.22 g, yield: 44.5%). MS m/z (ESI): 656.4 $[M+H]^+$.

Step 6: Synthesis of N-(4-((2-(2-fluorophenyl)pyridin-4-yl)amino)-7-(3-(4-(2-hydroxyethyl)piperazin-1-yl)propoxy)quinazolin-6-yl)acrylamide

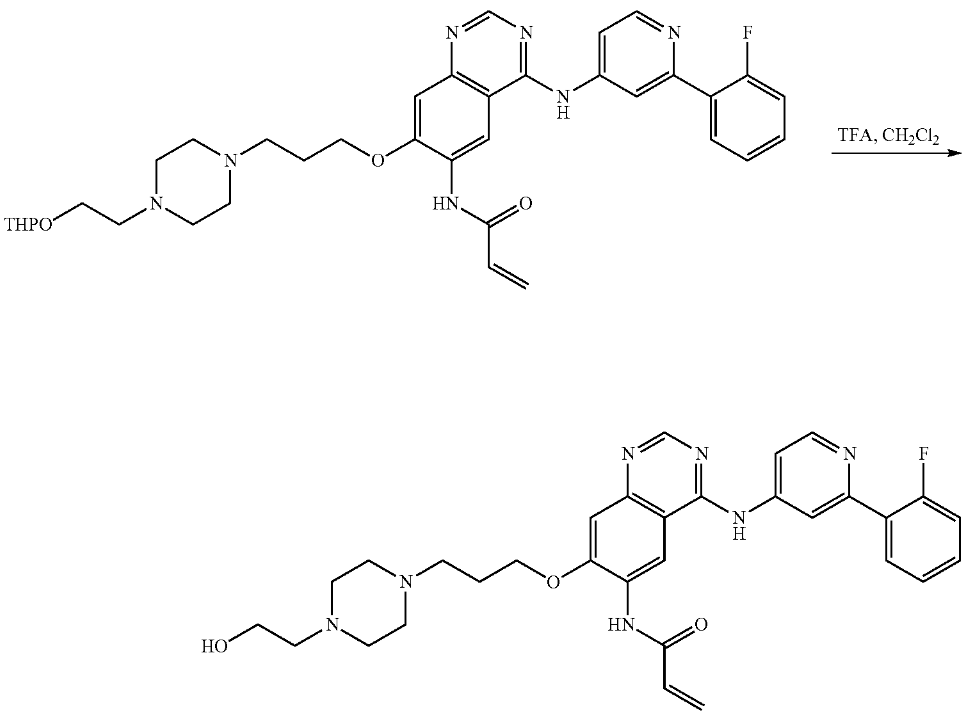

N-(4-((2-(2-fluorophenyl)pyridin-4-yl)amino)-7-(3-(4-(2-((tetrahydro-2H-pyran-2-yl)oxy)ethyl)piperazin-1-yl)propoxy)quinazolin-6-yl)acrylamide (0.22 g, 0.32 mmol) was dissolved in dichloromethane (3 mL), trifluoroacetic acid (1.08 mL, 14.5 mmol) was added, and the reaction mixture was reacted at room temperature for 1.5 hrs. After the reaction was completed as monitored by LCMS, the reaction mixture was concentrated to remove the solvent, the residue was added with ammonia liquor to adjust pH to 8, and the crude product was separated by preparative HPLC to obtain N-(4-((2-(2-fluorophenyl)pyridin-4-yl)amino)-7-(3-(4-(2-hydroxyethyl)piperazin-1-yl)propoxy)quinazolin-6-yl)acrylamide (36.6 mg, yield: 20%). MS m/z (ESI): 572.2 $[M+H]^+$.

$^1$H NMR (400 MHz, DMSO-$d_6$) δ 10.06 (s, 1H), 9.64 (s, 1H), 8.97 (s, 1H), 8.67 (s, 1H), 8.60 (d, J=5.6 Hz, 1H), 8.37 (s, 1H), 8.20-8.05 (m, 1H), 7.97 (td, J=7.9, 1.8 Hz, 1H), 7.50 (tdd, J=7.3, 6.0, 1.9 Hz, 1H), 7.43-7.26 (m, 3H), 6.73 (dd, J=17.0, 10.2 Hz, 1H), 6.33 (dd, J=17.0, 2.0 Hz, 1H), 5.83 (dd, J=10.2, 2.0 Hz, 1H), 4.34 (t, J=5.4 Hz, 1H), 4.27 (t, J=6.3 Hz, 2H), 3.47 (q, J=6.0 Hz, 2H), 2.48-2.20 (m, 12H), 1.99 (p, J=6.6 Hz, 2H).

Examples 123-125 can be prepared by selecting corresponding starting materials by referring to all or part of the synthesis method in Example 122.

| Example No. | Structural formula | Chemical name | $[M + H]^+$ |
| --- | --- | --- | --- |
| 123 | 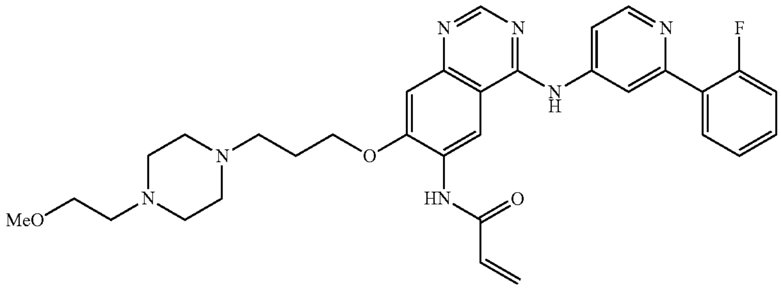 [SMILES: C=CC(=O)Nc1cc2c(Nc3ccnc(-c4ccccc4F)c3)ncnc2cc1OCCCN1CCN(CCOC)CC1] | N-(4-((2-(2-fluorophenyl)pyridin-4-yl)amino)-7-(3-(4-(2-methoxyethyl)piperazin-1-yl)propoxy)quinazolin-6-yl)acrylamide | 586.3 |

-continued

| Example No. | Structural formula | Chemical name | [M + H]$^+$ |
|---|---|---|---|
| 124 | 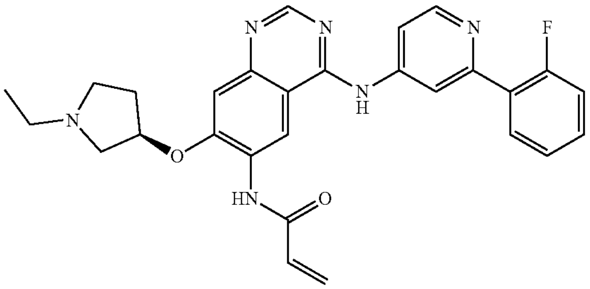 [SMILES: C=CC(=O)Nc1cc2c(Nc3ccnc(-c4ccccc4F)c3)ncnc2cc1O[C@@H]1CCN(CC)C1] | (R)-N-(7-((1-ethylpyrrolidin-3-yl)oxy)-4-((2-(2-fluorophenyl)pyridin-4-yl)amino)quinazolin-6-yl)acrylamide | 499.2 |
| 125 | 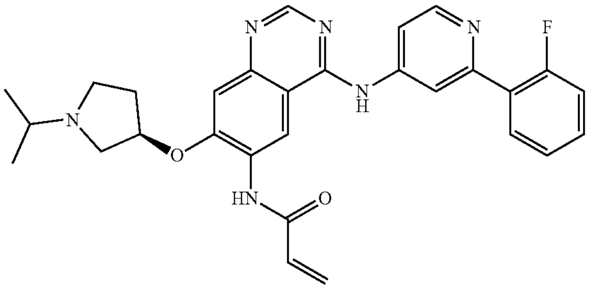 [SMILES: C=CC(=O)Nc1cc2c(Nc3ccnc(-c4ccccc4F)c3)ncnc2cc1O[C@@H]1CCN(C(C)C)C1] | (R)-N-(4-((2-(2-fluorophenyl)pyridin-4-yl)amino)-7-((1-isopropylpyrrolidin-3-yl)oxy)quinazolin-6-yl)acrylamide | 513.2 |

$^1$H NMR data of the compound prepared in the above example are as follows:

| Example No. | $^1$H NMR |
|---|---|
| 3 | $^1$H NMR (400 MHz, MeOH-$d_4$) δ 8.96 (s, 1H), 8.49 (s, 1H), 7.80 (q, J = 1.8 Hz, 1H), 7.67 (ddd, J = 8.1, 2.2, 1.1 Hz, 1H), 7.51-7.39 (m, 2H), 7.32 (dq, J = 7.7, 1.5 Hz, 1H), 7.22 (s, 1H), 7.04-6.92 (m, 2H), 6.75 (dd, J = 16.9, 10.2 Hz, 1H), 6.40 (dd, J = 16.9, 1.6 Hz, 1H), 5.79 (dd, J = 10.2, 1.6 Hz, 1H), 4.51 (t, J = 4.9 Hz, 2H), 3.85 (t, J = 4.8 Hz, 4H), 3.41 (brs, 2H), 3.09 (brs, 4H). |
| 4 | $^1$H NMR (400 MHz, MeOH-$d_4$) δ 9.15 (s, 1H), 8.63 (s, 1H), 7.78 (t, J = 1.8 Hz, 1H), 7.71-7.62 (m, 1H), 7.52-7.46 (m, 2H), 7.46-7.39 (m, 2H), 7.28 (s, 1H), 7.03-6.94 (m, 2H), 6.88 (dd, J = 16.8, 10.5 Hz, 1H), 6.41 (dd, J = 16.9, 1.7 Hz, 1H), 5.79 (dd, J = 10.3, 1.6 Hz, 1H), 4.68-4.64 (m, 2H), 4.62-4.54 (m, 2H), 3.56 (brs, 8H), 3.25 (s, 1H), 2.90 (s, 3H). |
| 5 | $^1$H NMR (400 MHz, DMSO-$d_6$) δ 9.76 (s, 1H), 9.58 (s, 1H), 8.89 (s, 1H), 8.50 (s, 1H), 7.97 (dd, J = 8.8, 2.3 Hz, 1H), 7.91 (s, 1H), 7.56-7.44 (m, 2H), 7.29-7.20 (m, 3H), 7.17 (d, J = 7.7 Hz, 1H), 6.70 (dd, J = 17.0, 10.2 Hz, 1H), 6.31 (dd, J = 17.0, 2.0 Hz, 1H), 5.81 (dd, J = 10.0, 2.0 Hz, 1H), 4.25 (t, J = 6.3 Hz, 2H), 2.47 (t, J = 7.0 Hz, 2H), 2.43-2.21 (m, 8H), 2.14 (s, 3H), 1.99 (dt, J = 13.4, 7.1 Hz, 2H). |
| 6 | $^1$H NMR (400 MHz, $CDCl_3$) δ 8.80 (s, 1H), 8.37 (s, 1H), 7.89 (t, J = 2.0 Hz, 1H), 7.64 (dt, J = 8.1, 1.6 Hz, 1H), 7.61-7.54 (m, 2H), 7.38 (t, J = 7.8 Hz, 1H), 7.31 (dt, J = 7.8, 1.5 Hz, 1H), 7.14 (s, 1H), 7.12-7.04 (m, 2H), 6.57 (dd, J = 17.0, 10.2 Hz, 1H), 6.38 (dd, J = 16.9, 1.7 Hz, 1H), 5.77 (dd, J = 10.2, 1.7 Hz, 1H), 4.23 (t, J = 6.2 Hz, 2H), 3.62 (t, J = 4.7 Hz, 4H), 2.52 (t, J = 7.4 Hz, 2H), 2.43 (t, J = 4.7 Hz, 4H), 2.05 (p, J = 6.5 Hz, 2H). |
| 7 | $^1$H NMR (400 MHz, MeOH-$d_4$) δ 8.78 (s, 1H), 8.36 (s, 1H), 7.81 (q, J = 1.8 Hz, 1H), 7.72-7.65 (m, 1H), 7.47 (td, J = 8.6, 6.4 Hz, 1H), 7.39 (t, J = 7.9 Hz, 1H), 7.26-7.21 (m, 1H), 7.14 (s, 1H), 7.00-6.93 (m, 2H), 6.56 (dd, J = 16.9, 10.2 Hz, 1H), 6.37 (dd, J = 16.9, 1.7 Hz, 1H), 5.77 (dd, J = 10.2, 1.7 Hz, 1H), 4.23 (t, J = 6.2 Hz, 2H), 2.76-2.54 (m, 8H), 2.60-2.54 (t, J = 7.2 Hz, 2H), 2.36 (s, 3H), 2.05 (p, J = 6.5 Hz, 2H). |
| 8 | $^1$H NMR (400 MHz, MeOH-$d_4$) δ 8.89 (s, 1H), 8.35 (s, 1H), 7.82 (q, J = 1.7 Hz, 1H), 7.69 (ddd, J = 8.1, 2.2, 1.1 Hz, 1H), 7.53-7.42 (m, 1H), 7.39 (t, J = 7.9 Hz, 1H), 7.27-7.20 (m, 1H), 7.05 (s, 1H), 7.02-6.92 (m, 2H), 6.56 (dd, J = 16.9, 10.1 Hz, 1H), 6.39 (dd, J = 16.9, 1.8 Hz, 1H), 5.77 (dd, J = 10.1, 1.8 Hz, 1H), 5.14 (t, J = 5.7 Hz, 1H), 3.15 (td, J = 9.2, 3.4 Hz, 1H), 2.60 (dd, J = 11.4, 4.7 Hz, 1H), 2.52-2.42 (m, 4H), 2.36 (q, J = 8.8 Hz, 1H), 1.99 (dt, J = 15.2, 8.2 Hz, 1H), 1.25-1.20 (m, 1H). |

-continued

| Example No. | $^{1}H$ NMR |
|---|---|
| 9 | $^{1}H$ NMR (400 MHz, DMSO-$d_6$) δ 9.96 (s, 1H), 9.88 (s, 1H), 8.71 (s, 1H), 8.59 (s, 1H), 8.01 (s, 1H), 7.96 (dd, J = 8.1, 2.1 Hz, 1H), 7.84 (s, 1H), 7.62 (td, J = 9.0, 6.7 Hz, 1H), 7.51 (t, J = 7.9 Hz, 1H), 7.38 (ddd, J = 11.4, 9.3, 2.6 Hz, 1H), 7.29 (d, J = 7.4 Hz, 1H), 7.22 (td, J = 8.5, 2.6 Hz, 1H), 6.55 (dd, J = 17.0, 10.2 Hz, 1H), 6.32 (dd, J = 17.0, 2.0 Hz, 1H), 5.83 (dd, J = 10.2, 2.0 Hz, 1H), 2.25 (s, 6H), 1.42 (s, 6H). |
| 10 | $^{1}H$ NMR (400 MHz, DMSO-$d_6$) δ 9.81 (s, 1H), 9.63 (s, 1H), 8.91 (s, 1H), 8.40 (s, 1H), 7.67 (d, J = 7.2 Hz, 1H), 7.62 (td, J = 8.9, 6.7 Hz, 1H), 7.48-7.35 (m, 3H), 7.33 (s, 1H), 7.21 (td, J = 8.3, 2.2 Hz, 1H), 6.71 (dd, J = 16.9, 10.2 Hz, 1H), 6.32 (dd, J = 17.0, 1.9 Hz, 1H), 5.82 (dd, J = 10.2, 1.9 Hz, 1H), 4.36 (t, J = 5.7 Hz, 2H), 3.58 (t, J = 4.7 Hz, 4H), 2.84 (t, J = 5.7 Hz, 2H), 2.55-2.50 (m, 4H). |
| 11 | $^{1}H$ NMR (400 MHz, DMSO-$d_6$) δ 9.80 (s, 1H), 9.58 (s, 1H), 8.90 (s, 1H), 8.40 (s, 1H), 7.67 (d, J = 7.2 Hz, 1H), 7.62 (q, J = 9.0 Hz, 1H), 7.50-7.33 (m, 3H), 7.29 (s, 1H), 7.21 (td, J = 8.5, 2.5 Hz, 1H), 6.73 (dd, J = 17.0, 10.2 Hz, 1H), 5.82 (dd, J = 10.2, 2.1 Hz, 1H), 4.28 (t, J = 6.4 Hz, 2H), 3.58 (t, J = 4.5 Hz, 4H), 2.50-2.45 (m, 2H), 2.39 (t, J = 4.5 Hz, 4H), 2.02 (q, J = 6.8 Hz, 2H). |
| 12 | $^{1}H$ NMR (400 MHz, DMSO-$d_6$) δ 9.96 (s, 1H), 9.84 (s, 1H), 8.72 (s, 1H), 8.59 (s, 1H), 8.01 (q, J = 1.8 Hz, 1H), 7.96 (dd, J = 8.2, 2.1 Hz, 1H), 7.82 (s, 1H), 7.62 (td, J = 8.9, 6.6 Hz, 1H), 7.50 (t, J = 7.9 Hz, 1H), 7.39 (ddd, J = 11.5, 9.3, 2.6 Hz, 1H), 7.35-7.27 (m, 1H), 7.22 (td, J = 8.5, 2.6 Hz, 1H), 6.57 (dd, J = 17.0, 10.2 Hz, 1H), 6.32 (dd, J = 17.0, 1.9 Hz, 1H), 5.83 (dd, J = 10.2, 1.9 Hz, 1H), 2.63 (brs, 4H), 2.34 (brs, 4H), 2.14 (s, 3H), 1.43 (s, 6H). |
| 13 | $^{1}H$ NMR (400 MHz, DMSO-$d_6$) δ 9.82 (s, 1H), 9.60 (s, 1H), 8.93 (s, 1H), 8.68 (d, J = 2.8 Hz, 1H), 8.52 (s, 1H), 8.46 (s, 1H), 8.09-7.98 (m, 2H), 7.84 (td, J = 8.7, 3.0 Hz, 1H), 7.76 (d, J = 7.8 Hz, 1H), 7.49 (t, J = 7.9 Hz, 1H), 7.29 (s, 1H), 6.72 (dd, J = 17.0, 10.1 Hz, 1H), 6.32 (d, J = 17.0 Hz, 1H), 5.82 (d, J = 10.3 Hz, 1H), 4.27 (t, J = 6.4 Hz, 2H), 3.58 (t, J = 4.6 Hz, 4H), 2.50-2.45 (m, 2H), 2.38 (t, J = 4.5 Hz, 4H), 2.00 (dt, J = 13.0, 6.3 Hz, 2H). |
| 14 | $^{1}H$ NMR (400 MHz, DMSO-$d_6$) δ 9.76 (s, 1H), 9.59 (s, 1H), 8.89 (s, 1H), 8.50 (s, 1H), 7.98 (q, J = 1.8 Hz, 1H), 7.93 (dt, J = 7.8, 1.3 Hz, 1H), 7.62 (td, J = 8.9, 6.6 Hz, 1H), 7.48 (t, J = 7.9 Hz, 1H), 7.38 (ddd, J = 11.5, 9.3, 2.6 Hz, 1H), 7.29 (s, 1H), 7.27-7.23 (m, 1H), 7.21 (dd, J = 8.9, 2.4 Hz, 1H), 6.71 (dd, J = 17.0, 10.2 Hz, 1H), 6.32 (dd, J = 17.0, 2.0 Hz, 1H), 5.82 (dd, J = 10.2, 2.0 Hz, 1H), 4.27 (t, J = 6.3 Hz, 2H), 2.60-2.52 (m, 6H), 2.06-1.88 (m, 6H). |
| 15 | $^{1}H$ NMR (400 MHz, DMSO-$d_6$) δ 9.76 (s, 1H), 9.59 (s, 1H), 8.90 (s, 1H), 8.50 (d, J = 1.3 Hz, 1H), 7.98 (d, J = 2.2 Hz, 1H), 7.96-7.88 (m, 1H), 7.62 (td, J = 8.8, 6.6 Hz, 1H), 7.48 (t, J = 7.9 Hz, 1H), 7.38 (ddd, J = 11.4, 9.2, 2.5 Hz, 1H), 7.27 (s, 1H), 7.25 (d, J = 7.5 Hz, 1H), 7.21 (dd, J = 8.5, 2.6 Hz, 1H), 6.71 (dd, J = 17.0, 10.2 Hz, 1H), 6.32 (dd, J = 17.0, 2.0 Hz, 1H), 5.82 (dd, J = 10.2, 2.0 Hz, 1H), 4.26 (t, J = 6.2 Hz, 2H), 2.91 (t, J = 13.5 Hz, 2H), 2.71 (t, J = 6.9 Hz, 2H), 2.63 (t, J = 7.1 Hz, 2H), 2.24 (tt, J = 14.9, 6.9 Hz, 2H), 2.00 (p, J = 6.8 Hz, 2H). |
| 16 | $^{1}H$ NMR (400 MHz, MeOH-$d_4$) δ 8.91 (s, 1H), 8.39 (d, J = 2.4 Hz, 1H), 8.35 (s, 1H), 8.20 (q, J = 1.8 Hz, 1H), 7.79 (ddd, J = 8.1, 2.2, 1.0 Hz, 1H), 7.65-7.52 (m, 2H), 7.43 (t, J = 7.9 Hz, 1H), 7.15 (s, 1H), 6.60 (dd, J = 17.0, 10.2 Hz, 1H), 6.39 (dd, J = 17.0, 1.7 Hz, 1H), 5.77 (dd, J = 10.2, 1.7 Hz, 1H), 4.29 (t, J = 5.1 Hz, 2H), 3.68 (t, J = 4.7 Hz, 4H), 2.86 (t, J = 5.1 Hz, 2H), 2.54 (t, J = 4.7 Hz, 4H). |
| 17 | $^{1}H$ NMR (400 MHz, MeOH-$d_4$) δ 8.79 (s, 1H), 8.39 (d, J = 2.4 Hz, 1H), 8.36 (s, 1H), 8.19 (q, J = 1.7 Hz, 1H), 7.78 (ddd, J = 8.1, 2.2, 1.1 Hz, 1H), 7.66-7.54 (m, 2H), 7.43 (t, J = 7.9 Hz, 1H), 7.14 (s, 1H), 6.56 (dd, J = 16.9, 10.2 Hz, 1H), 6.38 (dd, J = 16.9, 1.7 Hz, 1H), 5.77 (dd, J = 10.2, 1.7 Hz, 1H), 4.23 (t, J = 6.2 Hz, 2H), 3.64 (t, J = 4.7 Hz, 4H), 2.60 (t, J = 6.2 Hz, 2H), 2.54-2.48 (m, 4H), 2.14-2.01 (m, 2H). |
| 18 | $^{1}H$ NMR (400 MHz, DMSO-$d_6$) δ 9.87 (s, 1H), 9.56 (s, 1H), 8.91 (s, 1H), 8.65 (d, J = 2.4 Hz, 1H), 8.40 (s, 1H), 8.09 (ddd, J = 11.2, 8.7, 2.4 Hz, 1H), 8.06-8.00 (m, 1H), 7.81 (ddt, J = 8.6, 4.2, 1.9 Hz, 1H), 7.46 (dd, J = 10.2, 8.7 Hz, 1H), 7.34 (s, 1H), 6.70 (dd, J = 17.0, 10.2 Hz, 1H), 6.31 (dd, J = 17.0, 2.0 Hz, 1H), 5.82 (dd, J = 10.2, 1.9 Hz, 1H), 4.36 (t, J = 5.8 Hz, 2H), 3.58 (t, J = 4.6 Hz, 4H), 2.84 (t, J = 5.8 Hz, 2H), 2.55-2.50 (m, 4H). |
| 19 | $^{1}H$ NMR (400 MHz, DMSO-$d_6$) δ 9.77 (s, 1H), 9.62 (s, 1H), 8.87 (s, 1H), 8.51 (s, 1H), 7.98 (q, J = 1.8 Hz, 1H), 7.93 (dt, J = 8.1, 1.5 Hz, 1H), 7.62 (td, J = 8.8, 6.6 Hz, 1H), 7.48 (t, J = 7.9 Hz, 1H), 7.38 (ddd, J = 11.5, 9.3, 2.6 Hz, 1H), 7.32 (s, 1H), 7.25 (dd, J = 8.5, 1.8 Hz, 1H), 7.21 (dd, J = 8.4, 2.4 Hz, 1H), 6.67 (dd, J = 17.0, 10.2 Hz, 1H), 6.31 (dd, J = 17.0, 2.0 Hz, 1H), 5.81 (dd, J = 10.2, 2.0 Hz, 1H), 4.34 (t, J = 5.6 Hz, 2H), 3.04 (t, J = 13.6 Hz, 2H), 2.97 (t, J = 5.5 Hz, 2H), 2.84 (t, J = 7.0 Hz, 2H), 2.22 (tt, J = 15.0, 7.0 Hz, 2H). |

-continued

| Example No. | $^1$H NMR |
|---|---|
| 20 | $^1$H NMR (400 MHz, DMSO-$d_6$) δ 9.79 (s, 1H), 9.56 (s, 1H), 8.90 (s, 1H), 7.67 (d, J = 7.3 Hz, 1H), 7.65-7.55 (m, 1H), 7.50-7.34 (m, 3H), 7.27 (s, 1H), 7.21 (td, J = 8.8, 1.8 Hz, 1H), 6.73 (dd, J = 17.0, 10.2 Hz, 1H), 6.32 (dd, J = 17.1, 1.9 Hz, 1H), 5.82 (dt, J = 10.2, 1.7 Hz, 1H), 4.26 (t, J = 6.3 Hz, 2H), 2.50-2.45 (m, 2H), 2.42-2.25 (m, 8H), 2.14 (s, 3H), 1.98 (q, J = 6.7 Hz, 2H). |
| 21 | $^1$H NMR (400 MHz, DMSO-$d_6$) δ 9.77 (s, 1H), 9.59 (s, 1H), 8.89 (s, 1H), 8.51 (s, 1H), 7.98 (q, J = 1.8 Hz, 1H), 7.93 (dd, J = 7.8, 2.1 Hz, 1H), 7.62 (td, J = 8.8, 6.6 Hz, 1H), 7.48 (t, J = 7.9 Hz, 1H), 7.38 (ddd, J = 11.5, 9.3, 2.6 Hz, 1H), 7.33 (s, 1H), 7.28-7.24 (m, 1H), 7.21 (dd, J = 8.5, 2.7 Hz, 1H), 6.68 (dd, J = 17.0, 10.2 Hz, 1H), 6.31 (dd, J = 17.0, 2.0 Hz, 1H), 5.82 (dd, J = 10.2, 2.0 Hz, 1H), 4.35 (t, J = 5.7 Hz, 2H), 2.93 (brs, 2H), 2.67 (brs, 4H), 2.03-1.84 (m, 4H). |
| 22 | $^1$H NMR (400 MHz, DMSO-$d_6$) δ 9.77 (s, 1H), 9.59 (s, 1H), 8.90 (s, 1H), 8.50 (s, 1H), 7.97 (d, J = 8.0, 1H), 7.91 (s, 1H), 7.52-7.48 (m, 2H), 7.27-7.21 (m, 3H), 7.18-7.16 (m, 1H,), 6.74-6.67 (m, 1H), 6.34-6.29 (m, 1H), 5.83-5.80 (m, 1H), 4.25 (t, 2H, J = 6.0), 2.61-2.57 (m, 2H), 2.46 (t, J = 6.8, 2H), 2.44-2.30 (m, 8H), 2.01-1.96 (m, 2H), 1.95 (d, J = 6.46, 6H). |
| 23 | $^1$H NMR (400 MHz, DMSO-$d_6$) δ 9.85 (s, 1H), 9.57 (s, 1H), 8.91 (s, 1H), 8.65 (d, J = 3.0 Hz, 1H), 8.40 (s, 1H), 8.21 (dd, J = 7.5, 2.4 Hz, 1H), 8.06 (dd, J = 8.9, 4.3 Hz, 1H), 7.97 (ddd, J = 8.6, 4.6, 2.4 Hz, 1H), 7.83 (td, J = 8.7, 3.0 Hz, 1H), 7.41 (dd, J = 10.1, 8.6 Hz, 1H), 7.29 (s, 1H), 6.73 (dd, J = 17.0, 10.2 Hz, 1H), 6.32 (dd, J = 17.0, 2.0 Hz, 1H), 5.82 (dd, J = 10.2, 2.0 Hz, 1H), 4.28 (t, J = 6.4 Hz, 2H), 3.59 (t, J = 4.6 Hz, 4H), 2.49-2.46 (m, 2H), 2.39 (d, J = 4.7 Hz, 4H), 2.01 (p, J = 6.8 Hz, 2H). |
| 24 | $^1$H NMR (400 MHz, DMSO-$d_6$) δ 9.77 (s, 1H), 9.59 (s, 1H), 8.89 (s, 1H), 8.50 (s, 1H), 7.97 (d, J = 8.3 Hz, 1H), 7.89 (s, 1H), 7.50 (t, J = 7.9 Hz, 1H), 7.42-7.28 (m, 3H), 7.16 (d, J = 7.8 Hz, 1H), 6.68 (dd, J = 17.1, 10.4 Hz, 1H), 6.31 (dd, J = 17.1, 2.0 Hz, 1H), 5.82 (dd, J = 10.2, 2.0 Hz, 1H), 4.35 (t, J = 5.8 Hz, 2H), 3.57 (t, J = 4.6 Hz, 4H), 2.83 (t, J = 5.7 Hz, 2H), 2.55-2.50 (m, 4H). |
| 25 | $^1$H NMR (400 MHz, DMSO-$d_6$) δ 9.77 (s, 1H), 9.59 (s, 1H), 8.89 (s, 1H), 8.50 (s, 1H), 7.97 (ddd, J = 8.2, 2.2, 1.1 Hz, 2H), 7.89 (s, 1H), 7.50 (t, J = 7.9 Hz, 1H), 7.34 (t, J = 8.6 Hz, 2H), 7.28 (s, 1H), 7.15 (d, J = 7.6 Hz, 1H), 6.70 (dd, J = 17.0, 10.2 Hz, 1H), 6.31 (dd, J = 17.0, 2.0 Hz, 1H), 5.81 (dd, J = 10.1, 2.0 Hz, 1H), 4.27 (t, J = 6.3 Hz, 2H), 3.58 (t, J = 4.6 Hz, 4H), 2.50-2.45 (m, 4H), 2.38 (brs, 4H), 1.99 (p, J = 6.9 Hz, 2H). |
| 26 | $^1$H NMR (400 MHz, DMSO-$d_6$) δ 9.77 (s, 1H), 9.67 (s, 1H), 8.90 (s, 1H), 8.50 (s, 1H), 7.96 (d, J = 8.1 Hz, 1H), 7.90 (s, 1H), 7.50 (t, J = 7.9 Hz, 2H), 7.32 (s, 1H), 7.24 (t, J = 7.8 Hz, 2H), 7.17 (d, J = 7.6 Hz, 1H), 6.68 (dd, J = 17.0, 10.2 Hz, 1H), 6.31 (dd, J = 17.0, 2.0 Hz, 1H), 5.81 (dd, J = 10.0, 2.0 Hz, 1H), 4.34 (t, J = 5.7 Hz, 2H), 3.57 (t, J = 4.7 Hz, 4H), 3.42-3.36 (m, 4H), 2.82 (t, J = 5.7 Hz, 2H). |
| 27 | $^1$H NMR (400 MHz, DMSO-$d_6$) δ 9.76 (s, 1H), 9.59 (s, 1H), 8.89 (s, 1H), 8.50 (s, 1H), 7.97 (d, J = 8.7 Hz, 1H), 7.91 (s, 1H), 7.50 (t, J = 7.8 Hz, 2H), 7.28 (s, 1H), 7.24 (t, J = 7.9 Hz, 2H), 7.17 (d, J = 7.5 Hz, 1H), 6.70 (dd, J = 16.9, 10.2 Hz, 1H), 6.31 (d, J = 17.2 Hz, 1H), 5.81 (d, J = 10.1 Hz, 1H), 4.27 (t, J = 6.3 Hz, 2H), 3.58 (t, J = 4.7 Hz, 4H), 2.50-2.45 (m, 2H), 2.38 (brs, 4H), 2.05-1.95 (m, 2H). |
| 28 | $^1$H NMR (400 MHz, DMSO-$d_6$) δ 9.76 (s, 1H), 9.59 (s, 1H), 8.89 (s, 1H), 8.50 (d, J = 1.3 Hz, 1H), 7.97 (dd, J = 8.5, 1.9 Hz, 1H), 7.91 (s, 1H), 7.54-7.45 (m, 2H), 7.30-7.21 (m, 3H), 7.17 (d, J = 7.7 Hz, 1H), 6.70 (dd, J = 17.0, 10.2 Hz, 1H), 6.31 (dd, J = 17.0, 1.9 Hz, 1H), 5.81 (dd, J = 10.2, 1.9 Hz, 1H), 4.25 (t, J = 6.3 Hz, 2H), 2.46 (d, J = 7.0 Hz, 2H), 2.45-2.14 (m, 10H), 2.02-1.94 (m, 2H), 0.97 (t, J = 7.2 Hz, 3H). |
| 29 | $^1$H NMR (400 MHz, DMSO-$d_6$) δ 9.77 (s, 1H), 9.59 (s, 1H), 8.90 (s, 1H), 8.51 (s, 1H), 7.97 (d, J = 8.4 Hz, 1H), 7.91 (s, 1H), 7.50 (t, J = 7.8 Hz, 2H), 7.29-7.21 (m, 3H), 7.18 (d, J = 7.7 Hz, 1H), 6.71 (dd, J = 17.0, 10.1 Hz, 1H), 6.32 (dd, J = 17.0, 2.2 Hz, 1H), 5.82 (d, J = 9.9 Hz, 1H), 4.26 (t, J = 6.4 Hz, 2H), 2.54 (s, 2H), 2.48-2.44 (m, 4H), 2.40-2.32 (m, 4H), 1.98 (t, J = 6.8 Hz, 2H), 1.60-1.55 (m, 1H), 0.45-0.34 (m, 2H), 0.31-0.19 (m, 2H). |
| 30 | $^1$H NMR (400 MHz, DMSO-$d_6$) δ 9.76 (s, 1H), 9.58 (s, 1H), 8.89 (s, 1H), 8.50 (s, 1H), 7.97 (d, J = 8.4 Hz, 1H), 7.91 (s, 1H), 7.50 (t, J = 7.8 Hz, 2H), 7.27-7.22 (m, 3H), 7.17 (d, J = 7.9 Hz, 1H), 6.73-6.64 (m, 1H), 6.31 (d, J = 17.0 Hz, 1H), 5.81 (d, J = 10.4 Hz, 1H), 4.51 (t, J = 8.0 Hz, 2H), 4.41 (t, J = 6.0 Hz, 2H), 4.25 (t, J = 6.0 Hz, 2H), 2.47-2.45 (m, 1H), 2.44-2.39 (m, 4H), 2.30-2.21 (m, 4H), 2.01-1.96 (m, 4H). |
| 31 | $^1$H NMR (400 MHz, DMSO-$d_6$) δ 9.76 (s, 1H), 9.58 (s, 1H), 8.89 (s, 1H), 8.50 (s, 1H), 7.97 (dd, J = 8.2, 2.1 Hz, 1H), 7.91 (s, 1H), 7.54-7.45 (m, 2H), 7.29-7.20 (m, 3H), 7.17 (d, J = 7.7 Hz, 1H), 6.70 (dd, J = 16.9, 10.2 Hz, 1H), 6.31 (dd, J = 16.9, 2.0 Hz, 1H), 5.81 (dd, J = 10.1, 2.0 Hz, 1H), 4.25 (t, J = 6.3 Hz, 2H), 3.13 (q, J = 10.3 Hz, 2H), 2.61 (d, J = 4.9 Hz, 4H), 2.48-2.44 (m, 2H), 2.41 (s, 4H), 2.00-1.95 (m, 2H). |

-continued

| Example No. | $^1$H NMR |
|---|---|
| 32 | $^1$H NMR (400 MHz, DMSO-$d_6$) δ 9.77 (s, 1H), 9.59 (s, 1H), 8.89 (s, 1H), 8.50 (s, 1H), 7.97 (d, J = 8.4, 1H), 7.91 (s, 1H), 7.52-7.48 (m, 2H), 7.27-7.23 (m, 3H), 7.18-7.16 (m, 1H), 6.74-6.67 (m, 1H), 6.34-6.30 (m, 1H), 5.83-5.80 (m, 1H), 4.26 (t, J = 6.0, 2H), 3.27 (t, J = 6.4, 2H), 3.30 (s, 2H), 2.91 (s, 3H), 2.66 (t, J = 5.2, 2H), 2.55 (t, J = 6.4, 2H), 2.02-2.00 (m, 2H). |
| 33 | $^1$H NMR (400 MHz, DMSO-$d_6$) δ 9.77 (s, 1H), 9.62 (s, 1H), 8.96 (s, 1H), 8.49 (s, 1H), 7.97 (d, J = 8.4, 1H), 7.90 (s, 1H), 7.51-7.47 (m, 2H), 7.26-7.22 (m, 3H), 7.17 (d, J = 7.2, 1H), 6.76-6.70 (m, 1H), 6.35-6.31 (m, 1H), 5.84-5.81 (m, 1H), 4.22 (t, J = 6.0, 2H), 3.53 (t, J = 6.4, 2H), 3.32 (t, J = 5.6, 2H), 2.93 (s, 2H), 2.58 (t, J = 5.6, 2H), 2.20 (s, 3H), 2.08-2.03 (m, 2H). |
| 34 | $^1$H NMR (400 MHz, MeOH-$d_4$) δ 8.84 (s, 1H), 8.46 (s, 1H), 7.88-7.82 (m, 2H), 7.51 (t, J = 8.3 Hz, 1H), 7.41 (ddd, J = 14.8, 8.4, 6.4 Hz, 1H), 7.30-7.21 (m, 2H), 7.13-7.04 (m, 2H), 6.65 (dd, J = 16.9, 10.2 Hz, 1H), 6.47 (dd, J = 16.9, 1.7 Hz, 1H), 5.87 (dd, J = 10.2, 1.7 Hz, 1H), 4.35 (t, J = 6.1 Hz, 2H), 3.61 (dd, J = 13.1, 6.9 Hz, 1H), 3.12-3.00 (m, 2H), 2.98-2.92 (m, 1H), 2.89 (t, J = 7.3 Hz, 2H), 2.76-2.71 (m, 1H), 2.69 (s, 6H), 2.33-2.23 (m, 1H), 2.18 (q, J = 6.6 Hz, 2H), 2.06-1.96 (m, 1H). |
| 35 | $^1$H NMR (400 MHz, MeOH-$d_4$) δ 8.86 (s, 1H), 8.46 (s, 1H), 7.89-7.82 (m, 2H), 7.55-7.46 (m, 1H), 7.41 (tt, J = 8.4, 6.3 Hz, 1H), 7.28-7.22 (m, 2H), 7.13-7.04 (m, 2H), 6.65 (dd, J = 16.9, 10.2 Hz, 1H), 6.47 (dd, J = 16.9, 1.7 Hz, 1H), 5.86 (dd, J = 10.1, 1.7 Hz, 1H), 4.34 (t, J = 6.2 Hz, 2H), 3.41-3.33 (m, 1H), 2.97-2.88 (m, 2H), 2.87-2.75 (m, 4H), 2.54 (s, 6H), 2.25-2.19 (m, 1H), 2.19-2.12 (m, 2H), 1.91 (dq, J = 14.1, 7.0 Hz, 1H). |
| 36 | $^1$H NMR (400 MHz, DMSO-$d_6$) δ 9.77 (s, 1H), 9.59 (s, 1H), 8.90 (s, 1H), 8.49 (s, 1H), 7.96 (d, J = 8.0, 1H), 7.90 (s, 1H), 7.51-7.47 (m, 2H), 7.26-7.22 (m, 3H), 7.18-7.16 (m, 1H), 6.72-6.67 (m, 1H), 6.33-6.29 (m, 1H), 5.82-5.80 (m, 1H), 4.22 (t, J = 6.4, 2H), 3.37 (t, J = 4.8, 2H), 2.74-2.66 (m, 3H), 2.56-2.53 (m, 2H), 1.99 (s, 6H), 1.86-1.81 (m, 1H). |
| 37 | $^1$H NMR (400 MHz, DMSO-$d_6$) δ 9.71 (s, 1H), 9.53 (s, 1H), 8.89 (s, 1H), 8.42 (s, 1H), 7.89 (d, J = 8.3 Hz, 1H), 7.83 (s, 1H), 7.43 (t, J = 7.8 Hz, 2H), 7.17 (t, J = 7.9 Hz, 2H), 7.10 (d, J = 6.9 Hz, 2H), 6.68 (dd, J = 16.9, 10.3 Hz, 1H), 6.25 (dd, J = 17.0, 2.3 Hz, 1H), 5.75 (d, J = 9.9 Hz, 1H), 5.05 (s, 1H), 2.79-2.68 (m, 3H), 2.35-2.26 (m, 2H), 2.22 (s, 3H), 1.95-1.88 (m, 1H). |
| 38 | $^1$H NMR (400 MHz, DMSO-$d_6$) δ 9.77 (s, 1H), 9.58 (s, 1H), 8.87 (s, 1H), 8.49 (s, 1H), 7.95 (ddd, J = 9.0, 4.6, 2.7 Hz, 1H), 7.88 (dd, J = 6.7, 2.7 Hz, 1H), 7.56-7.46 (m, 2H), 7.41-7.30 (m, 3H), 7.28 (s, 1H), 6.70 (dd, J = 17.0, 10.2 Hz, 1H), 6.31 (dd, J = 17.0, 2.0 Hz, 1H), 5.81 (dd, J = 10.2, 2.0 Hz, 1H), 4.27 (t, J = 6.3 Hz, 2H), 3.58 (t, J = 4.6 Hz, 4H), 2.48 (t, J = 7.1 Hz, 2H), 2.38 (t, J = 4.5 Hz, 4H), 1.99 (p, J = 6.6 Hz, 2H). |
| 39 | $^1$H NMR (400 MHz, DMSO-$d_6$) δ 9.78 (s, 1H), 9.59 (s, 1H), 8.88 (s, 1H), 8.49 (s, 1H), 7.97-7.93 (m, 1H), 7.89 (dd, J = 6.7, 2.6 Hz, 1H), 7.55-7.49 (m, 2H), 7.39-7.33 (m, 3H), 7.27 (s, 1H), 6.71 (dd, J = 17.0, 10.2 Hz, 1H), 6.32 (dd, J = 17.0, 1.9 Hz, 1H), 5.82 (dd, J = 10.2, 1.9 Hz, 1H), 4.25 (t, J = 6.4 Hz, 2H), 2.47 (t, J = 7.0 Hz, 2H), 2.45-2.31 (m, 8H), 2.15 (s, 3H), 1.98 (t, J = 6.8 Hz, 2H). |
| 40 | $^1$H NMR (400 MHz, MeOH-$d_4$) δ 8.76 (d, J = 2.1 Hz, 1H), 8.34 (s, 1H), 7.79 (ddd, J = 9.0, 4.5, 2.8 Hz, 1H), 7.69 (dd, J = 6.3, 2.7 Hz, 1H), 7.38 (tt, J = 8.3, 6.3 Hz, 1H), 7.18 (t, J = 9.1 Hz, 1H), 7.11 (d, J = 2.8 Hz, 1H), 7.01 (t, J = 7.9 Hz, 2H), 6.55 (dd, J = 16.9, 10.2 Hz, 1H), 6.36 (dd, J = 17.0, 1.7 Hz, 1H), 5.75 (dd, J = 10.1, 1.7 Hz, 1H), 4.84-4.76 (m, 2H), 4.46 (s, 2H), 4.20 (td, J = 6.2, 2.1 Hz, 2H), 2.52 (d, J = 7.4 Hz, 2H), 2.45 (br s, 4H), 2.20 (s, 3H), 2.03 (p, J = 6.6 Hz, 2H). |
| 41 | $^1$H NMR (400 MHz, MeOH-$d_4$) δ 8.78 (s, 1H), 8.34 (s, 1H), 7.73 (dd, J = 7.1, 2.7 Hz, 1H), 7.62 (ddd, J = 8.8, 4.3, 2.8 Hz, 1H), 7.52 (ddd, J = 9.0, 5.3, 1.7 Hz, 2H), 7.16-7.06 (m, 4H), 6.56 (dd, J = 17.0, 10.2 Hz, 1H), 6.37 (dd, J = 17.0, 1.7 Hz, 1H), 5.77 (dd, J = 10.2, 1.7 Hz, 1H), 4.22 (t, J = 6.3 Hz, 2H), 3.62 (t, J = 4.7 Hz, 4H), 2.51 (t, J = 7.4 Hz, 2H), 2.42 (t, J = 4.7 Hz, 4H), 2.04 (p, J = 6.5 Hz, 2H). |
| 42 | $^1$H NMR (400 MHz, MeOH-$d_4$) δ 8.76 (s, 1H), 8.40 (brs, 1H), 8.35 (s, 1H), 7.72 (dd, J = 7.1, 2.8 Hz, 1H), 7.61 (dt, J = 9.0, 3.4 Hz, 1H), 7.55-7.47 (m, 2H), 7.16-7.12 (m, 2H), 7.12-7.06 (m, 2H), 6.56 (dd, J = 17.0, 10.2 Hz, 1H), 6.37 (dd, J = 16.9, 1.7 Hz, 1H), 5.77 (dd, J = 10.2, 1.7 Hz, 1H), 4.23 (t, J = 6.2 Hz, 2H), 2.91 (s, 4H), 2.72-2.64 (br s, 4H), 2.62 (t, J = 7.1 Hz, 2H), 2.56 (s, 3H), 2.05 (p, J = 6.6 Hz, 2H). |
| 43 | $^1$H NMR (400 MHz, DMSO-$d_6$) δ 9.83 (s, 1H), 9.58 (s, 1H), 8.89 (s, 1H), 8.60 (dt, J = 4.6, 1.5 Hz, 1H), 8.49 (s, 1H), 8.08-8.00 (m, 2H), 7.89 (t, J = 9.0 Hz, 1H), 7.60 (dt, J = 8.4, 4.1 Hz, 1H), 7.37 (t, J = 9.4 Hz, 1H), 7.26 (s, 1H), 6.71 (dd, J = 17.0, 10.2 Hz, 1H), 6.31 (dd, J = 17.0, 2.0 Hz, 1H), 5.81 (dd, J = 10.1, 2.0 Hz, 1H), 4.25 (t, J = 6.3 Hz, 2H), 2.49-2.42 (m, 4H), 2.44-2.18 (m, 8H), 2.14 (s, 3H), 1.98 (q, J = 6.8 Hz, 2H). |
| 44 | $^1$H NMR (400 MHz, DMSO-$d_6$) δ 9.85 (s, 1H), 9.60 (s, 1H), 8.94 (s, 1H), 8.58 (dd, J = 4.4, 1.8 Hz, 1H), 8.51 (s, 1H), 8.37 (s, 1H), 8.04 (d, J = 8.2 Hz, 1H), 7.86 (dd, J = 11.7, 8.4 Hz, 1H), 7.66 (d, J = 7.8 Hz, 1H), 7.54-7.48 (m, 2H), 7.27 (s, 1H), 6.72 (dd, J = 17.0, 10.2 Hz, 1H), 6.32 (dd, J = |

-continued

| Example No. | $^1$H NMR |
|---|---|
| | 16.9, 1.9 Hz, 1H), 5.82 (dd, J = 10.2, 1.8 Hz, 1H), 4.26 (t, J = 6.2 Hz, 2H), 2.47 (t, J = 8.0 Hz, 2H), 2.44-2.25 (m, 8H), 2.15 (s, 3H), 2.02-1.95 (m, 2H). |
| 45 | $^1$H NMR (400 MHz, MeOH-$d_4$) δ 9.19 (s, 1H), 8.73 (s, 1H), 7.95 (q, J = 1.7 Hz, 1H), 7.78 (dt, J = 7.8, 1.7 Hz, 1H), 7.65-7.59 (m, 1H), 7.57 (ddd, J = 9.4, 5.0, 3.1 Hz, 2H), 7.44 (dtd, J = 7.2, 5.4, 2.5 Hz, 1H), 7.41 (s, 1H), 7.32 (td, J = 7.6, 1.3 Hz, 1H), 7.29-7.22 (m, 1H), 6.77 (dd, J = 16.9, 10.2 Hz, 1H), 6.55 (dd, J = 16.9, 1.6 Hz, 1H), 5.94 (dd, J = 10.2, 1.7 Hz, 1H), 4.48 (t, J = 5.8 Hz, 2H), 4.00 (br s, 4H), 3.55-3.46 (m, 2H), 3.42 (br s, 4H), 2.48 (dq, J = 11.6, 5.9 Hz, 2H). |
| 46 | $^1$H NMR (400 MHz, MeOH-$d_4$) δ 8.89 (s, 1H), 8.45 (s, 1H), 7.97-7.90 (m, 1H), 7.84-7.75 (m, 1H), 7.53 (dd, J = 7.8, 1.8 Hz, 1H), 7.48 (t, J = 7.9 Hz, 1H), 7.38 (ddt, J = 9.8, 7.5, 1.9 Hz, 2H), 7.27 (dd, J = 8.1, 6.9 Hz, 1H), 7.23 (s, 1H), 7.23-7.17 (m, 1H), 6.66 (dd, J = 16.9, 10.2 Hz, 1H), 6.47 (dd, J = 17.0, 1.7 Hz, 1H), 5.86 (dd, J = 10.2, 1.7 Hz, 1H), 4.31 (t, J = 6.2 Hz, 2H), 2.63 (d, J = 7.4 Hz, 2H), 2.55 (br s, 8H), 2.30 (s, 3H), 2.14 (p, J = 6.5 Hz, 2H). |
| 47 | $^1$H NMR (400 MHz, DMSO-$d_6$) δ 9.75 (s, 1H), 9.58 (s, 1H), 8.87 (s, 1H), 8.49 (s, 1H), 7.95-7.90 (m, 1H), 7.89-7.86 (m, 1H), 7.60-7.58 (m, 2H), 7.52-7.48 (m, 2H), 7.44-7.40 (m, 2H), 7.34-7.29 (m, 1H), 7.27 (s, 1H), 6.74-6.67 (m, 1H), 6.33-6.28 (m, 1H), 5.83-5.80 (m, 1H), 4.26 (t, J = 6.4, 2H), 3.58 (t, J = 4.8, 4H), 2.49 (t, J = 6.4, 2H), 2.38 (t, J = 4.8, 4H), 2.02-1.90 (m, 2H). |
| 48 | $^1$H NMR (400 MHz, DMSO-$d_6$) δ 9.87 (s, 1H), 9.49 (s, 1H), 8.79 (s, 1H), 8.40 (s, 1H), 7.865-7.84 (m, 1H), 7.82-7.78 (m, 1H), 7.51-7.49 (m, 2H), 7.44-7.40 (m, 2H), 7.35-7.32 (m, 2H), 7.26-7.21 (m, 1H), 7.17 (s, 1H), 6.65-6.59 (m, 1H), 6.25-6.20 (m, 1H), 5.74-5.71 (m, 1H), 4.16 (t, J = 6.0, 2H), 2.38 (t, J = 6.8, 2H), 2.36-2.23 (m, 8H), 2.05 (s, 3H), 1.92-1.86 (m, 2H). |
| 49 | $^1$H NMR (400 MHz, DMSO-$d_6$) δ 9.85 (s, 1H), 9.58 (s, 1H), 8.91 (s, 1H), 8.74 (dd, J = 4.7, 1.4 Hz, 1H), 8.49 (s, 1H), 8.32 (dd, J = 7.1, 2.8 Hz, 1H), 8.03 (ddd, J = 8.9, 4.4, 2.8 Hz, 1H), 7.93 (td, J = 7.7, 1.9 Hz, 1H), 7.84 (d, J = 8.0 Hz, 1H), 7.43 (ddd, J = 7.4, 4.8, 1.1 Hz, 1H), 7.35 (dd, J = 11.0, 8.9 Hz, 1H), 7.28 (s, 1H), 6.71 (dd, J = 17.0, 10.2 Hz, 1H), 6.32 (dd, J = 17.0, 2.0 Hz, 1H), 5.82 (dd, J = 10.1, 2.0 Hz, 1H), 4.27 (t, J = 6.3 Hz, 2H), 3.58 (t, J = 4.6 Hz, 4H), 2.49-2.44 (m, 2H), 2.38 (t, J = 4.6 Hz, 4H), 1.99 (p, J = 6.8 Hz, 2H). |
| 50 | $^1$H NMR (400 MHz, DMSO-$d_6$) δ 9.85 (s, 1H), 9.57 (s, 1H), 8.91 (s, 1H), 8.74 (d, J = 4.6 Hz, 1H), 8.49 (s, 1H), 8.32 (dd, J = 7.2, 2.8 Hz, 1H), 8.03 (dt, J = 8.2, 3.6 Hz, 1H), 7.93 (td, J = 7.7, 1.8 Hz, 1H), 7.84 (d, J = 7.7 Hz, 1H), 7.47-7.40 (m, 1H), 7.35 (dd, J = 11.1, 9.0 Hz, 1H), 7.26 (s, 1H), 6.71 (dd, J = 16.9, 10.2 Hz, 1H), 6.32 (dd, J = 17.0, 1.9 Hz, 1H), 5.81 (dd, J = 10.1, 1.9 Hz, 1H), 4.25 (t, J = 6.3 Hz, 2H), 2.49-2.42 (m, 4H), 2.45-2.18 (m, 8H), 2.14 (s, 3H), 1.98 (p, J = 6.6 Hz, 2H). |
| 51 | $^1$H NMR (400 MHz, $CDCl_3$) δ 9.15 (s, 1H), 8.73 (s, 1H), 8.69 (s, 1H), 8.28 (s, 1H), 7.99 (d, J = 2.5 Hz, 1H), 7.86 (s, 1H), 7.78-7.72 (m, 1H), 7.68 (d, J = 6.6 Hz, 1H), 7.52-7.42 (m, 2H), 6.56-6.39 (m, 3H), 5.91-5.81 (m, 1H), 4.34 (t, J = 5.5 Hz, 2H), 3.78 (t, J = 4.6 Hz, 4H), 2.92 (t, J = 5.4 Hz, 2H), 2.62 (t, J = 4.6 Hz, 4H). |
| 52 | $^1$H NMR (400 MHz, $CDCl_3$) δ 9.17 (s, 1H), 8.71 (s, 1H), 8.30 (d, J = 2.2 Hz, 1H), 8.23 (br s, 1H), 8.00 (d, J = 2.5 Hz, 1H), 7.74 (d, J = 1.8 Hz, 1H), 7.68 (dd, J = 6.8, 2.4 Hz, 1H), 7.62 (s, 1H), 7.49 (d, J = 1.8 Hz, 1H), 7.48 (d, J = 4.7 Hz, 1H), 7.30 (s, 1H), 6.54-6.48 (m, 2H), 6.44 (br s, 1H), 5.88 (d, J = 11.1 Hz, 1H), 4.33 (t, J = 6.4 Hz, 2H), 3.77 (t, J = 5.0 Hz,, 4H), 2.62 (s, 2H), 2.54 (s, 4H), 2.24-2.12 (m, 2H). |
| 53 | $^1$H NMR (400 MHz, MeOH-$d_4$) δ 8.88 (s, 1H), 8.53 (s, 1H), 8.50 (brs, 1H), 8.31 (d, J = 2.2 Hz, 1H), 8.25 (d, J = 2.5 Hz, 1H), 7.76 (d, J = 1.8 Hz, 1H), 7.74 (dd, J = 7.1, 2.2 Hz, 1H), 7.59-7.48 (m, 2H), 7.26 (s, 1H), 6.69 (dd, J = 16.9, 10.2 Hz, 1H), 6.57 (t, J = 2.2 Hz, 1H), 6.50 (dd, J = 17.0, 1.7 Hz, 1H), 5.89 (dd, J = 10.1, 1.6 Hz, 1H), 4.34 (t, J = 6.1 Hz, 2H), 2.94 (s, 4H), 2.77 (br s, 4H), 2.72 (t, J = 7.1 Hz, 2H), 2.61 (s, 3H), 2.17 (p, J = 6.5 Hz, 2H). |
| 54 | $^1$H NMR (400 MHz, $CDCl_3$) δ 9.16 (s, 1H), 8.73 (s, 1H), 8.61 (t, J = 2.1 Hz, 1H), 8.52 (s, 1H), 7.86 (ddd, J = 8.1, 2.1, 1.0 Hz, 1H), 7.83 (s, 2H), 7.78 (ddd, J = 8.1, 2.2, 1.0 Hz, 1H), 7.73 (s, 1H), 7.50 (t, J = 8.1 Hz, 1H), 7.28 (s, 1H), 6.50 (dd, J = 16.9, 1.4 Hz, 1H), 6.37 (dd, J = 16.9, 10.1 Hz, 1H), 5.86 (dd, J = 10.0, 1.3 Hz, 1H), 4.35 (t, J = 5.6 Hz, 2H), 3.76 (t, J = 4.7 Hz, 4H), 2.90 (t, J = 5.5 Hz, 2H), 2.68-2.56 (m, 4H). |
| 55 | $^1$H NMR (400 MHz, $CDCl_3$) δ 9.20 (s, 1H), 8.73 (s, 1H), 8.62 (t, J = 2.1 Hz, 1H), 8.33 (br s, 1H), 7.92-7.86 (m, 1H), 7.83 (s, 2H), 7.78 (ddd, J = 8.1, 2.2, 1.0 Hz, 1H), 7.64 (s, 1H), 7.51 (t, J = 8.2 Hz, 1H), 7.30 (s, 1H), 6.50 (d, J = 9.6 Hz, 2H), 5.91-5.84 (m, 1H), 4.33 (t, J = 6.3 Hz, 2H), 3.82 (s, 4H), 2.68 (s, 2H), 2.63 (s, 4H), 2.23 (s, 2H). |
| 56 | $^1$H NMR (400 MHz, $CDCl_3$) δ 9.18 (s, 1H), 8.73 (s, 1H), 8.62 (t, J = 2.1 Hz, 1H), 8.21 (br s, 1H), 7.90-7.85 (m, 1H), 7.83 (s, 2H), 7.79 (ddd, J = 8.2, 2.4, 1.0 Hz, 1H), 7.62 (s, 1H), 7.51 (t, J = 8.1 Hz, 1H), 7.30 (s, 1H), 6.51 (dd, J = 16.9, 1.3 Hz, 1H), 6.38 (t, J = 13.3 Hz, 1H), 5.93-5.84 (m, |

-continued

| Example No. | $^1$H NMR |
|---|---|
| | 1H), 4.32 (t, J = 6.4 Hz, 2H), 2.64-2.58 (m, 4H), 2.55 (br s, 6H), 2.34 (s, 3H), 2.15 (p, J = 6.5 Hz, 2H). |
| 57 | $^1$H NMR (400 MHz, MeOH-$d_4$) δ 9.10 (s, 2H), 9.08 (d, J = 2.5 Hz, 2H), 8.60-8.55 (m, 2H), 8.51 (t, J = 1.9 Hz, 1H), 7.63 (td, J = 7.8, 1.8 Hz, 1H), 7.55-7.45 (m, 1H), 7.37 (td, J = 7.6, 1.2 Hz, 1H), 7.35-7.26 (m, 2H), 6.73 (dd, J = 16.9, 10.2 Hz, 1H), 6.52 (dd, J = 17.0, 1.8 Hz, 1H), 5.90 (dd, J = 10.1, 1.8 Hz, 1H), 4.43 (t, J = 5.1 Hz, 2H), 3.81 (t, J = 4.7 Hz, 4H), 2.99 (t, J = 5.1 Hz, 2H), 2.67 (t, J = 4.7 Hz, 4H). |
| 58 | $^1$H NMR (400 MHz, MeOH-$d_4$) δ 8.96 (d, J = 2.5 Hz, 1H), 8.85 (s, 1H), 8.46 (d, J = 4.0 Hz, 2H), 8.39 (d, J = 2.0 Hz, 1H), 7.51 (t, J = 7.8 Hz, 1H), 7.45-7.34 (m, 1H), 7.31-7.15 (m, 3H), 6.64-6.51 (m, 1H), 6.39 (d, J = 17.0 Hz, 1H), 5.78 (dd, J = 10.1, 2.3 Hz, 1H), 4.24 (t, J = 6.3 Hz, 2H), 3.63 (q, J = 4.7, 3.5 Hz, 4H), 2.53 (t, J = 7.3 Hz, 2H), 2.50-2.39 (m, 4H), 2.06 (p, J = 6.6 Hz, 2H). |
| 59 | $^1$H NMR (400 MHz, DMSO-$d_6$) δ 9.94 (s, 1H), 9.61 (s, 1H), 9.07 (d, J = 2.3 Hz, 1H), 8.93 (s, 1H), 8.54 (s, 1H), 8.47 (dt, J = 8.4, 1.9 Hz, 2H), 7.65 (td, J = 7.8, 1.6 Hz, 1H), 7.51 (tdd, J = 7.1, 5.2, 1.8 Hz, 1H), 7.44-7.33 (m, 2H), 7.30 (s, 1H), 6.73 (dd, J = 17.0, 10.2 Hz, 1H), 6.33 (dd, J = 17.0, 2.0 Hz, 1H), 5.83 (dd, J = 10.2, 2.0 Hz, 1H), 4.27 (t, J = 6.3 Hz, 2H), 2.49-2.21 (m, 10H), 2.14 (s, 3H), 1.99 (p, J = 6.6 Hz, 2H). |
| 62 | $^1$H NMR (400 MHz, $CDCl_3$) δ 9.18 (s, 1H), 9.00 (t, J = 1.7 Hz, 1H), 8.68 (d, J = 1.2 Hz, 1H), 8.48 (d, J = 9.1 Hz, 2H), 8.28 (s, 1H), 7.87 (s, 1H), 7.36 (p, J = 7.6 Hz, 1H), 7.30 (s, 1H), 7.05 (t, J = 7.8 Hz, 2H), 6.50 (d, J = 16.6 Hz, 1H), 6.42 (t, J = 13.2 Hz, 1H), 5.88 (d, J = 10.0 Hz, 1H), 4.31 (t, J = 6.4 Hz, 2H), 2.67-2.62 (m, 2H), 2.60 (s, 8H), 2.37 (s, 3H), 2.16 (dt, J = 11.1, 5.4 Hz, 2H). |
| 63 | $^1$H NMR (400 MHz, DMSO-$d_6$) δ 9.96 (s, 1H), 9.59 (s, 1H), 9.07 (d, J = 2.4 Hz, 1H), 8.98 (s, 1H), 8.53 (s, 1H), 8.48 (d, J = 1.9 Hz, 1H), 8.45 (q, J = 1.9 Hz, 1H), 7.69-7.60 (m, 1H), 7.56-7.46 (m, 1H), 7.44-7.33 (m, 2H), 7.20 (s, 1H), 6.77 (dd, J = 17.0, 10.2 Hz, 1H), 6.33 (dd, J = 17.0, 1.9 Hz, 1H), 5.83 (dd, J = 10.2, 1.9 Hz, 1H), 5.13 (dt, J = 8.1, 4.0 Hz, 1H), 2.88-2.80 (m, 2H), 2.82-2.73 (m, 1H), 2.43-2.36 (m, 2H), 2.31 (s, 3H), 2.05-1.98 (m, 1H). |
| 64 | $^1$H NMR (400 MHz, DMSO-$d_6$) δ 9.99 (s, 1H), 9.64 (d, J = 5.0 Hz, 1H), 9.10 (s, 1H), 8.99 (s, 1H), 8.53 (s, 1H), 8.39 (s, 2H), 7.57 (tt, J = 8.4, 6.5 Hz, 1H), 7.41-7.24 (m, 2H), 7.20 (s, 1H), 6.77 (dd, J = 17.0, 10.2 Hz, 1H), 6.34 (dd, J = 17.0, 2.0 Hz, 1H), 5.84 (dd, J = 10.2, 2.0 Hz, 1H), 5.13 (brs, 1H), 2.91-2.71 (m, 3H), 2.46-2.31 (m, 2H), 2.30 (s, 3H), 2.07-1.93 (m, 1H). |
| 68 | $^1$H NMR (400 MHz, DMSO-$d_6$) δ 10.01 (s, 1H), 9.62 (s, 1H), 8.90 (s, 1H), 8.61 (s, 1H), 8.54 (d, J = 5.6 Hz, 1H), 8.31 (t, J = 1.9 Hz, 1H), 8.02 (dd, J = 5.7, 2.1 Hz, 1H), 7.90 (td, J = 7.8, 1.8 Hz, 1H), 7.43 (td, J = 7.8, 5.3 Hz, 1H), 7.35-7.26 (m, 3H), 6.64 (dd, J = 17.0, 10.2 Hz, 1H), 6.26 (dd, J = 16.9, 1.9 Hz, 1H), 5.77 (dd, J = 10.1, 1.9 Hz, 1H), 4.31 (t, J = 5.7 Hz, 2H), 3.51 (t, J = 4.6 Hz, 4H), 2.77 (t, J = 5.7 Hz, 2H), 2.48-2.45 (m, 4H). |
| 69 | $^1$H NMR (400 MHz, DMSO-$d_6$) δ 10.00 (s, 1H), 9.59 (s, 1H), 8.90 (s, 1H), 8.61 (s, 1H), 8.53 (d, J = 5.7 Hz, 1H), 8.31 (s, 1H), 8.02 (s, 1H), 7.90 (t, J = 8.0 Hz, 1H), 7.42 (t, J = 6.7 Hz, 1H), 7.31-7.26 (m, 3H), 6.66 (dd, J = 17.0, 10.1 Hz, 1H), 6.26 (dd, J = 17.1, 1.9 Hz, 1H), 5.77 (d, J = 10.3 Hz, 1H), 4.23 (t, J = 6.4 Hz, 2H), 3.51 (t, J = 4.5 Hz, 4H), 2.51-2.47 (m, 2H), 2.34-2.89 (m, 4H), 1.94 (t, J = 6.8 Hz, 2H). |
| 70 | $^1$H NMR (400 MHz, MeOH-$d_4$) δ 8.84 (s, 1H), 8.58 (s, 1H), 8.45 (d, J = 5.8 Hz, 1H), 8.24 (s, 1H), 8.06-7.96 (m, 1H), 7.71 (t, J = 7.8 Hz, 1H), 7.43-7.33 (m, 1H), 7.29-7.20 (m, 2H), 7.20-7.12 (m, 1H), 6.57 (dd, J = 17.0, 10.1 Hz, 1H), 6.39 (d, J = 16.9 Hz, 1H), 5.78 (d, J = 10.2 Hz, 1H), 4.26 (t, J = 6.3 Hz, 2H), 2.89 (s, 4H), 2.68 (br s, 4H), 2.62 (t, J = 7.1 Hz, 2H), 2.54 (s, 3H), 2.07 (dt, J = 13.1, 6.1 Hz, 2H). |
| 71 | $^1$H NMR (400 MHz, $CDCl_3$) δ 9.18 (s, 1H), 8.78 (s, 1H), 8.67 (d, J = 5.6 Hz, 1H), 8.22 (s, 1H), 8.20 (t, J = 1.9 Hz, 1H), 8.03-7.95 (m, 2H), 7.80 (s, 1H), 7.39 (tdd, J = 7.5, 4.9, 1.8 Hz, 1H), 7.33 (s, 1H), 7.29 (dd, J = 7.6, 1.3 Hz, 1H), 7.22-7.15 (m, 1H), 6.51 (dd, J = 16.8, 1.2 Hz, 1H), 6.38 (dd, J = 18.7, 10.3 Hz, 1H), 5.89 (dd, J = 10.0, 1.3 Hz, 1H), 4.32 (t, J = 6.4 Hz, 2H), 2.80-2.53 (m, 8H), 2.50 (br s, 4H), 2.16 (dt, J = 13.4, 6.4 Hz, 2H), 1.13 (t, J = 7.1 Hz, 3H). |
| 74 | $^1$H NMR (400 MHz, DMSO-$d_6$) δ 10.08 (s, 1H), 9.64 (s, 1H), 8.96 (s, 1H), 8.67 (s, 1H), 8.59 (d, J = 5.7 Hz, 1H), 8.14 (s, 1H), 8.08 (dd, J = 5.8, 2.1 Hz, 1H), 7.55 (tt, J = 8.4, 6.5 Hz, 1H), 7.34 (s, 1H), 7.25 (t, J = 7.9 Hz, 2H), 6.72 (dd, J = 17.0, 10.2 Hz, 1H), 6.33 (dd, J = 17.0, 2.0 Hz, 1H), 5.83 (dd, J = 10.2, 2.0 Hz, 1H), 4.27 (t, J = 6.3 Hz, 2H), 2.48-2.24 (m, 10H), 2.14 (s, 3H), 1.98 (p, J = 6.8 Hz, 2H). |
| 76 | $^1$H NMR (400 MHz, DMSO-$d_6$) δ 10.08 (s, 1H), 9.61 (s, 1H), 9.01 (s, 1H), 8.66 (s, 1H), 8.59 (d, J = 5.8 Hz, 1H), 8.16-8.00 (m, 2H), 7.62-7.50 (m, 1H), 7.30-7.22 (m, 3H), 6.77 (dd, J = 16.9, 10.1 Hz, 1H), 6.33 (dd, J = 17.0, 2.0 Hz, 1H), 5.83 (dd, J = 10.2, 2.0 Hz, 1H), 5.13 (dt, J = 7.7, 4.0 Hz, 1H), 2.86-2.81 (m, 2H), 2.76 (dt, J = 8.7, 4.1 Hz, 1H), 2.38 (dd, J = 11.2, 7.7 Hz, 2H), 2.29 (s, 3H), 1.99 (dd, J = 12.2, 5.9 Hz, 1H). |

-continued

| Example No. | $^1$H NMR |
|---|---|
| 77 | $^1$H NMR (400 MHz, DMSO-$d_6$) δ 10.08 (s, 1H), 9.63 (s, 1H), 8.97 (s, 1H), 8.69 (s, 1H), 8.60 (d, J = 5.7 Hz, 1H), 8.44-8.35 (m, 1H), 8.17-7.96 (m, 2H), 7.52-7.35 (m, 2H), 7.25 (td, J = 8.3, 2.5 Hz, 1H), 6.71 (dd, J = 17.0, 10.3 Hz, 1H), 6.33 (dd, J = 16.9, 2.0 Hz, 1H), 5.84 (dd, J = 10.2, 2.0 Hz, 1H), 4.38 (t, J = 5.8 Hz, 2H), 3.72-3.52 (m, 4H), 2.85 (t, J = 5.7 Hz, 2H), 2.54-2.50 (m, 4H). |
| 78 | $^1$H NMR (400 MHz, MeOH-$d_4$) δ 8.85 (s, 1H), 8.57 (s, 1H), 8.44-8.42 (m, 1H), 8.23 (s, 1H), 8.02-8.00 (m, 1H), 7.76-7.75 (m, 1H), 7.20 (s, 1H), 7.05-7.02 (m, 2H), 6.61-6.54 (m, 1H), 6.41-6.36 (m, 1H), 5.79-5.76 (m, 1H), 4.24 (t, J = 6.4, 2H), 3.62 (t, J = 4.8, 4H), 2.52 (t, J = 7.2, 2H), 2.45-2.41 (m, 4H), 2.07-2.04 (m, 2H). |
| 79 | $^1$H NMR (400 MHz, MeOH-$d_4$) δ 8.83 (s, 1H), 8.55 (s, 1H), 8.43-8.38 (m, 1H), 8.21 (s, 1H), 8.00-7.96 (m, 1H), 7.76-7.72 (m, 1H), 7.17 (s, 1H), 7.04-6.99 (m, 2H), 6.60-6.53 (m, 1H), 6.40-6.36 (m, 1H), 5.78-5.76 (m, 1H), 4.23-4.17 (m, 2H), 2.52-2.43 (m, 10H), 2.20 (s, 3H), 2.04-2.03 (m, 2H). |
| 81 | $^1$H NMR (400 MHz, MeOH-$d_4$) δ 8.96 (s, 1H), 8.56 (s, 1H), 8.44-8.43 (m, 1H), 8.23 (s, 1H), 8.02-8.01 (m, 1H), 7.79-7.73 (m, 1H), 7.11 (s, 1H), 7.05-7.00 (m, 2H), 6.60-6.53 (m, 1H), 6.43-6.38 (m, 1H), 5.15-5.13 (m, 1H), 3.15-3.03 (m, 2H), 2.51-2.43 (m, 2H), 2.41 (s, 3H), 2.29-2.22 (m, 1H), 1.99-1.93 (m, 1H). |
| 82 | $^1$H NMR (400 MHz, DMSO-$d_6$) δ 10.08 (s, 1H), 9.83 (s, 1H), 9.04 (s, 1H), 8.68 (s, 1H), 8.60 (d, J = 5.6 Hz, 1H), 8.37 (s, 1H), 8.08 (dd, J = 5.6, 2.0 Hz, 1H), 7.97 (td, J = 7.8, 1.8 Hz, 1H), 7.54-7.45 (m, 1H), 7.39-7.31 (m, 3H), 6.77 (dd, J = 17.0, 10.2 Hz, 1H), 6.34 (dd, J = 17.0, 2.0 Hz, 1H), 5.82 (dd, J = 10.1, 2.0 Hz, 1H), 4.05 (s, 3H). |
| 83 | $^1$H NMR (400 MHz, DMSO-$d_6$) δ 10.07 (s, 1H), 9.67 (s, 1H), 9.02 (s, 1H), 8.67 (s, 1H), 8.61 (d, J = 5.6 Hz, 1H), 8.38 (s, 1H), 8.15-8.05 (m, 1H), 7.97 (t, J = 8.0 Hz, 1H), 7.53-7.48 (m, 1H), 7.38-7.33 (m, 3H), 6.77 (dd, J = 17.0, 10.2 Hz, 1H), 6.34 (d, J = 17.0 Hz, 1H), 5.84 (d, J = 17.0 Hz, 1H), 4.33 (q, J = 7.0 Hz, 2H), 1.47 (t, J = 6.9 Hz, 3H). |
| 84 | 1H NMR (400 MHz, DMSO-$d_6$) δ 10.11 (s, 1H), 9.80 (s, 1H), 8.91 (s, 1H), 8.72 (s, 1H), 8.62 (d, J = 5.6 Hz, 1H), 8.38 (s, 1H), 8.11-8.09 (m, 2H), 7.99-7.95 (m, 1H), 7.57 (s, 1H), 7.51-7.47 (m, 1H), 7.38-7.33 (m, 2H), 6.71-6.64 (m, 1H), 6.34-6.30 (m, 1H), 5.84-5.81 (m, 1H), 5.10-5.04 (m, 2H). |
| 85 | $^1$H NMR (400 MHz, DMSO-$d_6$) δ 10.07 (s, 1H), 9.67 (s, 1H), 8.99 (s, 1H), 8.67 (s, 1H), 8.60 (d, J = 5.2 Hz, 1H), 8.37 (s, 1H), 8.09-8.07 (m, 2H), 7.99-7.94 (m, 1H), 7.52-7.47 (m, 1H), 7.39-7.33 (m, 3H), 6.77-6.70 (m, 1H), 6.35-6.31 (m, 1H), 5.85-5.82 (m, 1H), 4.40 (t, J = 4.8 Hz, 4H), 3.81 (t, J = 4.8 Hz, 4H), 3.35 (s, 3H). |
| 86 | $^1$H NMR (400 MHz, DMSO-$d_6$) δ 10.07 (s, 1H), 9.88 (s, 1H), 8.80 (s, 1H), 8.72 (s, 1H), 8.61 (d, J = 5.6 Hz, 1H), 8.39 (s, 1H), 8.11 (dd, J = 5.7, 2.0 Hz, 1H), 8.00-7.95 (m, 1H), 7.49 (ddd, J = 7.6, 5.4, 1.9 Hz, 1H), 7.40-7.33 (m, 3H), 5.84 (d, J = 3.8 Hz, 1H), 5.72 (d, J = 3.8 Hz, 1H), 5.51 (dd, J = 15.7, 3.8 Hz, 1H), 4.02 (s, 3H). |
| 87 | $^1$H NMR (400 MHz, DMSO-$d_6$) δ 8.84 (s, 1H), 8.70 (s, 1H), 8.61 (d, J = 5.7 Hz, 1H), 8.38 (s, 1H), 8.10 (dd, J = 5.6, 2.1 Hz, 1H), 7.97 (td, J = 7.9, 1.7 Hz, 1H), 7.55-7.45 (m, 1H), 7.40-7.32 (m, 3H), 5.85 (d, J = 3.8 Hz, 0H), 5.73 (d, J = 3.8 Hz, 1H), 5.52 (dd, J = 15.7, 3.8 Hz, 1H), 4.30 (q, J = 6.9 Hz, 2H), 1.43 (t, J = 6.9 Hz, 3H). |
| 88 | $^1$H NMR (400 MHz, DMSO-$d_6$) δ 10.13 (s, 1H), 10.01 (s, 1H), 8.78 (s, 1H), 8.76 (s, 1H), 8.63 (d, J = 5.6 Hz, 1H), 8.40 (s, 1H), 8.14-8.12 (m, 1H), 8.00-7.95 (m, 1H), 7.59 (s, 1H), 7.52-7.48 (m, 1H), 7.39-7.37 (m, 1H), 7.36-7.34 (m, 1H), 5.82-5.69 (m, 1H), 5.53-5.48 (m, 1H), 5.10-5.04 (m, 2H). |
| 89 | $^1$H NMR (400 MHz, MeOH-$d_4$) δ 8.88 (s, 1H), 8.56 (s, 1H), 8.43 (d, J = 5.6 Hz, 1H), 8.22 (s, 1H), 8.01-8.00 (m, 1H), 7.71-7.67 (m, 1H), 7.39-7.37 (m, 1H), 7.39-7.37 (m, 1H), 7.24-7.13 (m, 3H), 5.82-5.69 (m, 1H), 5.38-5.29 (m, 1H), 4.31 (t, J = 8.0 Hz, 2H), 3.79 (t, J = 8.0 Hz, 2H), 3.38 (s, 3H). |
| 90 | $^1$H NMR (400 MHz, MeOH-$d_4$) δ 8.98 (s, 1H), 8.70 (s, 1H), 8.55 (d, J = 5.8 Hz, 1H), 8.35 (s, 1H), 8.12 (d, J = 6.1 Hz, 1H), 7.80 (t, J = 7.9 Hz, 1H), 7.70 (s, 1H), 7.51-7.45 (m, 1H), 7.33 (t, J = 7.6 Hz, 1H), 7.26 (t, J = 9.8 Hz, 1H), 5.84 (dd, J = 46.7, 2.2 Hz, 1H), 5.41 (dd, J = 15.6, 2.5 Hz, 1H), 4.17-4.09 (m, 1H), 1.04-0.95 (m, 2H), 0.95-0.86 (m, 2H). |
| 91 | $^1$H NMR (400 MHz, DMSO-$d_6$) δ 10.08 (s, 1H), 9.76 (s, 1H), 8.84 (s, 1H), 8.70 (s, 1H), 8.61 (d, J = 5.6 Hz, 1H), 8.38 (t, J = 1.9 Hz, 1H), 8.10 (dd, J = 5.7, 2.1 Hz, 1H), 7.97 (td, J = 7.9, 1.7 Hz, 1H), 7.55-7.46 (m, 1H), 7.40-7.32 (m, 3H), 5.79 (dd, J = 48.2, 3.8 Hz, 1H), 5.52 (dd, J = 15.7, 3.8 Hz, 1H), 4.13 (d, J = 6.8 Hz, 2H), 1.37-1.26 (m, 1H), 0.65-0.57 (m, 2H), 0.47-0.39 (m, 2H). |
| 98 | $^1$H NMR (400 MHz, MeOH-$d_4$) δ 8.63 (s, 1H), 8.53 (s, 1H), 8.43 (s, 1H), 8.20 (s, 1H), 8.02 (s, 1H), 7.71-7.68 (m, 1H), 7.40-7.29 (m, 2H), 7.24-7.12 (m, 2H), 6.55-6.50 (m, 1H), 6.42-6.38 (m, 1H), 5.81-5.78 (m, 1H), |

-continued

| Example No. | $^1$H NMR |
|---|---|
| | 3.66-3.62 (m, 4H), 3.28-3.20 (m, 2H), 2.72-2.65 (m, 3H), 2.57-2.53 (m, 4H), 2.32-2.28 (m, 1H), 1.99-1.93 (m, 2H), 1.69-1.65 (m, 2H). |
| 99 | $^1$H NMR (400 MHz, $CDCl_3$) δ 9.11 (s, 1H), 8.79 (s, 1H), 8.67 (d, J = 6.1 Hz, 1H), 8.66 (s, 1H), 8.21 (d, J = 1.8 Hz, 1H), 8.04-7.88 (m, 3H), 7.61 (s, 1H), 7.42-7.34 (m, 1H), 7.28 (d, J = 7.1 Hz, 1H), 7.17 (dd, J = 11.4, 8.2 Hz, 1H), 6.49 (d, J = 16.9 Hz, 1H), 6.33 (dd, J = 16.9, 10.2 Hz, 1H), 5.88 (d, J = 10.2 Hz, 1H), 3.24 (d, J = 11.8 Hz, 2H), 2.87-2.79 (m, 2H), 2.71 (s, 4H), 2.56 (s, 4H), 2.44-2.38 (m, 1H), 2.35 (s, 3H), 2.15 (d, J = 12.7 Hz, 2H), 1.73 (qd, J = 11.9, 3.7 Hz, 2H). |
| 100 | $^1$H NMR (400 MHz, DMSO-$d_6$) δ 10.13 (s, 1H), 9.75 (d, J = 2.9 Hz, 1H), 8.90 (s, 1H), 8.69 (s, 1H), 8.61 (d, J = 5.6 Hz, 1H), 8.38 (t, J = 2.0 Hz, 1H), 8.10-8.08 (m, 1H), 8.00-7.94 (m, 1H), 7.52-7.47 (m, 1H), 7.45 (s, 1H), 7.39-7.33 (m, 2H), 5.88 (d, J = 3.8 Hz, 1H), 5.76 (d, J = 3.8 Hz, OH), 5.58-5.53 (m, 1H), 4.78 (d, J = 4.0 Hz, 1H), 3.72-3.67 (m1H), 3.26-3.18 (m, 2H), 2.88-2.81 (m, 2H), 1.94-1.88 (m, 2H), 1.60-1.56 (m, 2H). |
| 101 | $^1$H NMR (400 MHz, DMSO-$d_6$) δ 10.14 (s, 1H), 9.76 (s, 1H), 8.89 (s, 1H), 8.70 (s, 1H), 8.61 (d, J = 5.6 Hz, 1H), 8.38 (d, J = 1.9 Hz, 1H), 8.09 (dd, J = 5.7, 2.1 Hz, 1H), 7.97 (td, J = 7.9, 1.8 Hz, 1H), 7.54-7.48 (m, 1H), 7.47 (s, 1H), 7.39-7.36 (m, 1H), 7.34 (d, J = 7.8 Hz, 1H), 5.81 (dd, J = 48.4, 3.8 Hz, 1H), 5.55 (dd, J = 15.8, 3.9 Hz, 1H), 3.04 (t, J = 4.8 Hz, 4H), 2.52 (d, J = 9.3 Hz, 4H), 2.26 (s, 3H). |
| 102 | $^1$H NMR (400 MHz, DMSO-$d_6$) δ 10.13 (s, 1H), 9.73 (d, J = 2.8 Hz, 1H), 8.89 (s, 1H), 8.69 (s, 1H), 8.61 (d, J = 5.6 Hz, 1H), 8.38 (d, J = 1.9 Hz, 1H), 8.09 (dd, J = 5.6, 2.1 Hz, 1H), 7.97 (td, J = 7.8, 1.7 Hz, 1H), 7.49 (ddd, J = 7.4, 5.3, 1.8 Hz, 2H), 7.45 (s, 1H), 7.41-7.30 (m, 2H), 5.82 (dd, J = 48.5, 3.8 Hz, 1H), 5.55 (dd, J = 15.8, 3.8 Hz, 1H), 3.60 (t, J = 4.6 Hz, 4H), 2.84-2.73 (m, 2H), 2.32 (td, J = 11.0, 5.4 Hz, 1H), 1.95 (d, J = 12.3 Hz, 2H), 1.58 (tt, J = 13.4, 6.8 Hz, 2H). |
| 103 | $^1$H NMR (400 MHz, $CDCl_3$) δ 9.46 (d, J = 3.7 Hz, 1H), 9.06 (s, 1H), 8.81 (s, 1H), 8.68 (d, J = 5.6 Hz, 1H), 8.19 (d, J = 1.9 Hz, 1H), 8.00 (td, J = 5.5, 2.3 Hz, 2H), 7.85 (s, 1H), 7.63 (s, 1H), 7.43-7.35 (m, 1H), 7.29 (d, J = 7.4 Hz, 1H), 7.18 (dd, J = 11.4, 8.1 Hz, 1H), 5.90 (dd, J = 47.5, 3.6 Hz, 1H), 5.36 (dd, J = 15.1, 3.6 Hz, 1H), 3.25 (d, J = 11.8 Hz, 2H), 2.83 (t, J = 11.7 Hz, 2H), 2.71 (s, 4H), 2.57 (s, 4H), 2.44 (d, J = 11.8 Hz, 1H), 2.36 (s, 3H), 2.10 (d, J = 12.7 Hz, 2H), 1.78 (d, J = 12.2 Hz, 2H). |
| 104 | $^1$H NMR (400 MHz, DMSO-$d_6$) δ 10.28 (s, 1H), 9.84 (s, 1H), 8.64-8.56 (m, 2H), 8.38 (brs, 1H), 8.33 (s, 1H), 8.13 (dd, J = 5.7, 2.1 Hz, 1H), 7.95 (td, J = 7.8, 1.7 Hz, 1H), 7.54-7.44 (m, 1H), 7.39-7.35 (m, 1H), 7.33 (d, J = 7.8 Hz, 1H), 6.66 (s, 1H), 5.75 (dd, J = 47.8, 3.8 Hz, 1H), 5.49 (dd, J = 15.6, 3.7 Hz, 1H), 4.35-4.22 (m, 3H), 3.89 (dd, J = 8.9, 3.1 Hz, 2H), 3.25 (s, 3H). |
| 105 | $^1$H NMR (400 MHz, $CDCl_3$) δ 8.69 (s, 1H), 8.64 (d, J = 5.6 Hz, 1H), 8.51 (s, 1H), 8.23 (s, 1H), 8.14 (s, 1H), 8.06-7.95 (m, 2H), 7.38 (td, J = 8.1, 4.0 Hz, 1H), 7.30-7.26 (m, 1H), 7.20-7.13 (m, 1H), 6.88 (s, 1H), 5.92 (dd, J = 47.7, 3.6 Hz, 1H), 5.37 (dd, J = 15.2, 3.6 Hz, 1H), 4.00 (t, J = 7.3 Hz, 4H), 2.33 (p, J = 7.4 Hz, 2H). |
| 106 | $^1$H NMR (400 MHz, DMSO-$d_6$) δ 10.30 (s, 1H), 9.87 (s, 1H), 8.62 (s, 1H), 8.59 (d, J = 5.7 Hz, 2H), 8.38 (d, J = 1.9 Hz, 2H), 8.37 (s, 2H), 8.14 (dd, J = 5.7, 2.1 Hz, 1H), 7.96 (td, J = 7.8, 1.7 Hz, 1H), 7.49 (tdd, J = 7.4, 6.1, 1.9 Hz, 1H), 7.42-7.30 (m, 2H), 6.73 (s, 1H), 5.76 (dd, J = 47.8, 3.8 Hz, 1H), 5.57-5.42 (m, 1H), 5.50 (dd, J = 15.7, 3.7 Hz, 1H), 4.40 (dddd, J = 22.1, 10.1, 5.8, 1.3 Hz, 2H), 4.21-4.07 (m, 2H). |
| 107 | $^1$H NMR (400 MHz, MeOH-$d_4$) δ 8.53 (s, 1H), 8.43 (d, J = 5.8 Hz, 1H), 8.27-8.21 (m, 2H), 8.03 (dd, J = 5.9, 2.2 Hz, 1H), 7.70 (td, J = 7.8, 1.9 Hz, 1H), 7.40 (tdd, J = 7.5, 5.0, 1.8 Hz, 1H), 7.24 (td, J = 7.6, 1.1 Hz, 1H), 7.20-7.13 (m, 1H), 6.70 (s, 1H), 5.75 (dd, J = 46.7, 3.5 Hz, 1H), 5.34 (dd, J = 15.0, 3.5 Hz, 1H), 4.34 (t, J = 11.9 Hz, 4H). |
| 108 | $^1$H NMR (400 MHz, DMSO-$d_6$) δ 10.43 (s, 1H), 9.92 (s, 1H), 8.65 (s, 1H), 8.60 (d, J = 5.6 Hz, 1H), 8.42 (s, 1H), 8.39 (t, J = 1.9 Hz, 1H), 8.15 (dd, J = 5.7, 2.1 Hz, 1H), 7.96 (td, J = 7.9, 1.7 Hz, 1H), 7.55-7.45 (m, 1H), 7.39-7.32 (m, 2H), 7.03 (s, 1H), 5.77 (dd, J = 47.9, 3.8 Hz, 1H), 5.52 (dd, J = 15.6, 3.8 Hz, 1H), 3.87 (t, J = 13.2 Hz, 2H), 3.68 (t, J = 7.2 Hz, 2H), 2.61-2.51 (m, 2H). |
| 109 | $^1$H NMR (400 MHz, DMSO-$d_6$) δ 10.13 (s, 1H), 9.80 (s, 1H), 8.88 (s, 1H), 8.70 (s, 1H), 8.61 (d, J = 5.6 Hz, 1H), 8.38 (t, J = 1.9 Hz, 1H), 8.09 (dd, J = 5.7, 2.1 Hz, 1H), 7.97 (td, J = 7.8, 1.7 Hz, 1H), 7.50 (dt, J = 7.4, 2.0 Hz, 1H), 7.47 (s, 1H), 7.40-7.31 (m, 2H), 5.82 (dd, J = 48.4, 3.8 Hz, 1H), 5.55 (dd, J = 15.8, 3.8 Hz, 1H), 4.90 (ddd, J = 48.4, 7.0, 3.5 Hz, 1H), 3.17 (t, J = 9.8 Hz, 2H), 3.00 (ddd, J = 11.4, 6.8, 3.7 Hz, 2H), 2.15-2.00 (m, 2H), 1.99-1.87 (m, 2H) |
| 110 | $^1$H NMR (400 MHz, DMSO-$d_6$) δ 10.12 (s, 1H), 9.87 (s, 1H), 8.86 (s, 1H), 8.70 (s, 1H), 8.61 (d, J = 5.7 Hz, 1H), 8.38 (s, 1H), 8.10 (dd, J = 5.7, 2.0 Hz, 1H), 7.97 (td, J = 7.9, 1.7 Hz, 1H), 7.55-7.45 (m, 2H), 7.41-7.31 (m, 2H), 5.82 (dd, J = 48.3, 3.8 Hz, 1H), 5.55 (dd, J = 15.8, 3.8 Hz, 1H), 3.17 (t, J = 5.7 Hz, 4H), 2.16 (td, J = 14.3, 13.3, 6.9 Hz, 4H). |

-continued

| Example No. | $^1$H NMR |
|---|---|
| 112 | $^1$H NMR (400 MHz, MeOH-$d_4$) δ 9.03 (s, 1H), 8.65 (s, 1H), 8.53 (d, J = 5.9 Hz, 1H), 8.33 (s, 1H), 8.18-8.08 (m, 1H), 7.79 (td, J = 7.8, 1.9 Hz, 1H), 7.56-7.44 (m, 1H), 7.33 (td, J = 7.5, 1.2 Hz, 1H), 7.26 (ddd, J = 11.2, 8.3, 1.2 Hz, 1H), 7.23-7.18 (m, 1H), 6.66 (dd, J = 16.9, 10.2 Hz, 1H), 6.50 (dd, J = 17.0, 1.8 Hz, 1H), 5.87 (dd, J = 10.1, 1.8 Hz, 1H), 5.22 (brs, 1H), 3.77 (t, J = 6.0 Hz, 2H), 3.38-3.32 (m, 1H), 3.25 (dd, J = 9.2, 3.3 Hz, 1H), 2.76 (t, J = 6.0 Hz, 2H), 2.68 (dd, J = 11.3, 4.9 Hz, 1H), 2.64-2.50 (m, 1H), 2.43 (q, J = 8.8 Hz, 1H), 2.04 (dt, J = 15.1, 8.4 Hz, 1H). |
| 114 | $^1$H NMR (400 MHz, MeOH-$d_4$) δ 9.05 (s, 1H), 8.67 (s, 1H), 8.54 (d, J = 5.8 Hz, 1H), 8.34 (d, J = 2.1 Hz, 1H), 8.13 (dd, J = 5.8, 2.2 Hz, 1H), 7.80 (t, J = 7.8 Hz, 1H), 7.55-7.42 (m, 1H), 7.33 (t, J = 7.6 Hz, 1H), 7.31-7.20 (m, 2H), 6.68 (dd, J = 16.9, 10.2 Hz, 1H), 6.52 (dd, J = 16.9, 1.9 Hz, 1H), 5.89 (dd, J = 10.0, 2.0 Hz, 1H), 5.26 (t, J = 5.7 Hz, 1H), 4.75-4.63 (m, 2H), 3.83-3.72 (m, 1H), 3.24 (d, J = 11.1 Hz, 1H), 3.23-3.10 (m, 1H), 2.65 (dd, J = 10.8, 5.0 Hz, 1H), 2.62-2.51 (m, 1H), 2.39 (q, J = 8.6 Hz, 1H), 2.10 (dt, J = 15.4, 8.2 Hz, 1H). |
| 115 | $^1$H NMR (400 MHz, MeOH-$d_4$) δ 8.96 (s, 1H), 8.59 (d, J = 5.7 Hz, 1H), 8.45 (d, J = 5.8 Hz, 1H), 8.25 (s, 1H), 8.04 (d, J = 5.7 Hz, 1H), 7.70 (d, J = 7.7 Hz, 1H), 7.40 (d, J = 6.9 Hz, 1H), 7.25 (d, J = 7.8 Hz, 1H), 7.19-7.16 (m, 2H), 6.61-6.58 (m, 1H), 6.44-6.40 (m, 1H), 5.80 (d, J = 10.2 Hz, 1H), 5.14 (s, 1H), 3.50 (d, J = 6.7 Hz, 2H), 3.08-3.04 (m, 4H), 2.90 (d, J = 10.3 Hz, 2H), 2.62-2.57 (m, 1H), 2.49-2.41 (m, 2H), 2.31 (s, 3H). |
| 116 | $^1$H NMR (400 MHz, DMSO-$d_6$) δ 10.07 (s, 1H), 9.59 (s, 1H), 9.02 (s, 1H), 8.66 (s, 1H), 8.60 (d, J = 5.7 Hz, 1H), 8.37 (s, 1H), 8.08 (dd, J = 5.7, 2.0 Hz, 1H), 7.97 (t, J = 8.1 Hz, 1H), 7.50 (q, J = 6.7 Hz, 1H), 7.40-7.30 (m, 2H), 7.24 (s, 1H), 6.76 (dd, J = 17.0, 10.2 Hz, 1H), 6.34 (dd, J = 17.0, 1.9 Hz, 1H), 5.87-5.79 (m, 1H), 5.12 (d, J = 5.9 Hz, 1H), 3.00 (dd, J = 10.5, 6.3 Hz, 1H), 2.91-2.81 (m, 2H), 2.76-2.66 (m, 2H), 2.36 (dd, J = 13.8, 7.1 Hz, 2H), 2.13 (s, 3H), 1.99 (dd, J = 9.6, 5.2 Hz, 2H), 1.85 (dd, J = 26.5, 14.6 Hz, 4H), 1.48-1.37 (m, 2H). |
| 117 | $^1$H NMR (400 MHz, MeOH-$d_4$) δ 8.94 (d, J = 2.5 Hz, 1H), 8.56 (d, J = 2.5 Hz, 1H), 8.44 (d, J = 5.9 Hz, 1H), 8.23 (s, 1H), 8.04-8.01 (m, 1H), 7.72-7.68 (m, 1H), 7.41-7.37 (m, 1H), 7.23 (t, J = 7.6 Hz, 1H), 7.18-7.14 (m, 1H), 7.11 (d, J = 2.6 Hz, 1H), 6.61-6.52 (m, 1H), 6.43-6.39 (m, 1H), 5.81-5.78 (m, 1H), 5.14 (s, 1H), 3.91-3.88 (m, 2H), 3.40-3.25 (m, 4H), 2.64-2.60 (m, 1H), 2.48-2.32 (m, 3H), 1.98-1.79 (m, 3H), 1.57-1.47 (m, 2H). |
| 118 | $^1$H NMR (400 MHz, DMSO-$d_6$) δ 10.03 (s, 1H), 9.74 (s, 1H), 8.78 (s, 1H), 8.64 (s, 1H), 8.55 (d, J = 5.6 Hz, 1H), 8.32 (s, 1H), 8.06-8.02 (m, 1H), 7.92-7.88 (m, 1H), 7.47-7.40 (m, 1H), 7.33-7.24 (m, 3H), 5.48-5.44 (m, 1H), 5.13 (t, J = 6.4 Hz, 1H), 4.51 (t, J = 6.5 Hz, 2H), 4.42-4.38 (m, 2H), 3.61 (m, 1H), 2.95-2.91 (m, 1H), 2.72-2.56 (m, 3H), 2.32-2.28 (m, 1H), 1.88-1.84 (m, 1H). |
| 119 | $^1$H NMR (400 MHz, MeOH-$d_4$) δ 8.98 (s, 1H), 8.68 (s, 1H), 8.55 (d, J = 5.9 Hz, 1H), 8.34 (s, 1H), 8.14-8.10 (m, 1H), 7.84-7.80 (m, 1H), 7.49 (s, 1H), 7.35 (t, J = 7.5 Hz, 1H), 7.30-7.26 (m, 1H), 7.21 (s, 1H), 5.47-5.43 (m, 1H), 5.19 (d, J = 6.6 Hz, 1H), 3.60-3.56 (m, 2H), 3.28 (s, 1H), 3.16-3.08 (m, 2H), 3.04-2.95 (m, 2H), 2.84-2.80 (m, 1H), 2.56-2.45 (m, 2H), 2.40 (s, 3H), 2.10 (s, 1H). |
| 120 | $^1$H NMR (400 MHz, DMSO-$d_6$) δ 10.08 (s, 1H), 9.73 (s, 1H), 8.85 (s, 1H), 8.69 (s, 1H), 8.61 (d, J = 5.6 Hz, 1H), 8.37 (s, 1H), 8.09 (d, J = 5.5 Hz, 1H), 7.97 (t, J = 8.1 Hz, 1H), 7.50 (d, J = 7.2 Hz, 1H), 7.34 (dd, J = 17.3, 9.2 Hz, 3H), 5.78 (dd, J = 48.4, 3.6 Hz, 1H), 5.52 (dd, J = 15.9, 3.7 Hz, 1H), 5.15 (s, 1H), 2.97 (dd, J = 10.9, 6.0 Hz, 1H), 2.79 (d, J = 9.7 Hz, 2H), 2.70 (d, J = 11.8 Hz, 2H), 2.34 (q, J = 6.9 Hz, 2H), 2.12 (s, 3H), 2.00 (q, J = 8.0 Hz, 2H), 1.89-1.76 (m, 4H), 1.40 (q, J = 12.0, 11.3 Hz, 2H). |
| 123 | $^1$H NMR (400 MHz, DMSO-$d_6$) δ 10.06 (s, 1H), 9.64 (s, 1H), 8.97 (s, 1H), 8.67 (s, 1H), 8.60 (d, J = 5.7 Hz, 1H), 8.37 (d, J = 1.9 Hz, 1H), 8.09 (dd, J = 5.7, 2.1 Hz, 1H), 7.97 (td, J = 7.9, 1.8 Hz, 1H), 7.50 (tdd, J = 7.3, 6.0, 1.9 Hz, 1H), 7.40-7.30 (m, 3H), 6.73 (dd, J = 17.0, 10.2 Hz, 1H), 6.33 (dd, J = 17.0, 2.0 Hz, 1H), 5.83 (dd, J = 10.2, 2.0 Hz, 1H), 4.27 (t, J = 6.3 Hz, 2H), 3.41 (t, J = 5.9 Hz, 2H), 3.22 (s, 3H), 2.49-2.31 (m, 12H), 1.98 (p, J = 6.5 Hz, 2H). |
| 124 | $^1$H NMR (400 MHz, DMSO-$d_6$) δ 10.09 (s, 1H), 9.63 (s, 1H), 9.03 (s, 1H), 8.67 (s, 1H), 8.60 (d, J = 5.6 Hz, 1H), 8.37 (d, J = 1.9 Hz, 1H), 8.08 (dd, J = 5.6, 2.1 Hz, 1H), 7.97 (td, J = 7.9, 1.7 Hz, 1H), 7.55-7.45 (m, 1H), 7.41-7.31 (m, 2H), 7.24 (s, 1H), 6.78 (dd, J = 17.0, 10.2 Hz, 1H), 6.34 (dd, J = 16.9, 2.0 Hz, 1H), 5.84 (dd, J = 10.1, 2.0 Hz, 1H), 5.14 (s, 1H), 3.00-2.78 (m, 3H), 2.48-2.27 (m, 4H), 2.10-1.98 (m, 1H), 1.05 (t, J = 7.2 Hz, 3H). |
| 125 | $^1$H NMR (400 MHz, DMSO-$d_6$) δ 10.07 (s, 1H), 9.59 (s, 1H), 9.02 (s, 1H), 8.65 (s, 1H), 8.59 (d, J = 5.5 Hz, 1H), 8.36 (s, 1H), 8.07 (s, 1H), 8.01-7.92 (m, 1H), 7.55-7.45 (m, 1H), 7.40-7.30 (m, 2H), 7.23 (s, 1H), 6.76 |

-continued

| Example No. | $^1H$ NMR |
|---|---|
| | (dd, J = 17.0, 10.2 Hz, 1H), 6.33 (dd, J = 17.0, 2.1 Hz, 1H), 5.83 (dd, J = 10.1, 2.1 Hz, 1H), 5.12 (s, 1H), 2.99 (dd, J = 10.7, 6.4 Hz, 1H), 2.92-2.79 (m, 2H), 2.38 (dq, J = 19.6, 5.9, 5.5 Hz, 2H), 2.01 (dt, J = 15.1, 6.8 Hz, 2H), 1.05 (t, J = 6.1 Hz, 6H). |

Biological Test Evaluation

Proliferation Experiment of Ba/F3 Cell Line (I) Reagents and Materials

Fetal bovine serum FBS (GBICO, Cat #10099-141);

CellTiter-Glo® luminescent cell viability assay kit (Promega, Cat #G7572);

Black transparent flat-bottom 96 well plate (Corning®, Cat #3603).

(II) Instruments

SpectraMax multi-label microplate reader MD, 2104-0010A;

Carbon dioxide incubator, Thermo Scientific 3100 series;

Biological safety cabinet, Thermo Scientific, 1300 series model A2;

Inverted microscope, Olympus, CKX41SF;

Siemens refrigerator KK25E76TI.

(III) Cell Lines and Culture Conditions

| No. | Cell lines | Cell culture medium | Cell density |
|---|---|---|---|
| 1 | A431 | DMEM + 15% FBS | 5000 |
| 2 | Ba/F3 EGFR-D770-N771ins_SVD | RPMI1640 + 10% FBS | 3000 |
| 3 | Ba/F3 EGFR-V769_D770insASV | RPMI1640 + 10% FBS | 3000 |

(IV) Experimental Procedures

1. Cell Culture and Inoculation:

(1) Cells in the logarithmic growth phase were harvested and counted using a platelet counter. Cell viability was detected by Trypan Blue Dye Exclusion Method to ensure cell viability above 90%.

(2) The cell concentration was adjusted to reach a desired final density; 90 μL of cell suspension was added to the 96-well plate.

(3) The cells were incubated overnight in the 96-well plate at 37° C., 5% $CO_2$ and at 95% humidity.

2. T0 Reference Data:

(1) 10 μL PBS was added to each well of the TO plate containing the cells.

(2) The CTG reagent was thawed and the cell plate was equilibrated to room temperature for 30 min.

(3) An equal volume of CTG solution was added to each well.

(4) The cells were lysed by shaking on an orbital shaker for 5 min.

(5) The cell plate was left at room temperature for 20 min to stabilize the luminescence signal.

(6) The fluorescence signal values of TO were read.

3. Dilution and Addition of Compounds (1) According to the compound information table, a corresponding volume of DMSO was added to the corresponding compound powder to prepare a 10 mM stock solution.

(2) A 1000-fold, 3.16-fold-diluted compound solution was prepared.

(3) The 1000× diluted compound solution was diluted 100-fold with PBS to prepare a 10-fold compound solution with a maximum concentration of 10 PM, including 9 concentrations, with 3.16-fold dilution, and 10 μL of the medicament solution was added to each well of the 96-well plate to seed the cells. Triplicate wells were set for each compound concentration, with a final concentration of DMSO being 0.1%.

(4) The cells were placed in the 96-well plate filled with the medicament at 37° C., 5% $CO_2$ and at 95% humidity, and cultured for 72 hrs before CTG analysis.

4. Fluorescence Signal Reading (1) The CTG reagent was thawed and the cell plate was equilibrated to room temperature for 30 min.

(2) An equal volume of CTG solution was added to each well.

(3) The cells were lysed by shaking on an orbital shaker for 5 min.

(4) The cell plate was left at room temperature for 20 min to stabilize the fluorescence signal.

(5) The fluorescence values were read.

5. Data Processing

Data were analyzed using GraphPad Prism 7.0 software and fitted data were regressed using non-linear S-curves to obtain dose-response curves from which $IC_{50}$ values (in nM) were calculated. The specific experimental results are shown in Table 1:

$$\text{Cell viablity (\%)} = (\text{Lum test medicament} - \text{Lum medium control})/(\text{Lum cell control} - \text{Lum medium control}) \times 100\%.$$

TABLE 1

Biological Test Results

| Example No. | A431 (EGFR-WT) | Ba/F3 EGFR-D770-N771ins_SVD | Ba/F3 EGFR-V769_D770insASV |
|---|---|---|---|
| 1 | 215 | 11.8 | 42.4 |
| 2 | NT | 120.7 | NT |
| 3 | 343 | 38.5 | 117.5 |
| 4 | NT | 52.5 | 174.8 |
| 5 | 223 | 13.0 | 20.3 |
| 6 | 61.4 | 37.5 | 89.0 |
| 7 | 238 | 25.2 | 28.4 |
| 8 | 343 | 88.8 | 178 |
| 9 | 625 | 40.1 | NT |
| 10 | 625 | 28.7 | NT |
| 11 | 479 | 29.3 | 119 |
| 12 | 624 | 32.3 | NT |
| 13 | 625 | 105 | NT |
| 14 | 365 | 34.4 | 221 |
| 15 | 498 | 56.1 | 137 |
| 16 | 372 | 34.0 | NT |

TABLE 1-continued

Biological Test Results

| Example No. | A431 (EGFR-WT) | Ba/F3 EGFR-D770-N771ins_SVD | Ba/F3 EGFR-V769_D770insASV |
|---|---|---|---|
| 17 | 518 | 26.1 | 90.9 |
| 18 | NT | 129 | NT |
| 19 | 597 | 70.5 | 177 |
| 20 | 252 | 36.5 | 53.9 |
| 21 | 966 | 103.9 | 240 |
| 22 | 270 | 13.7 | 30.6 |
| 23 | NT | 260.5 | NT |
| 24 | 378 | 46.2 | NT |
| 25 | 352 | 33.9 | 106 |
| 26 | 33.4 | 52.1 | 97.4 |
| 27 | 204 | 15.2 | 44.3 |
| 28 | 362 | 22.6 | 21.0 |
| 29 | 51.8 | 37.0 | 44.6 |
| 30 | 68.1 | 25.3 | 54.1 |
| 31 | 225 | 68.2 | 111 |
| 32 | 205 | 35.9 | 86.3 |
| 33 | 458 | 38.3 | 68.3 |
| 34 | 260 | 21.5 | 33.1 |
| 35 | 193 | 26.8 | 35.6 |
| 36 | 235 | 32.3 | 68.6 |
| 37 | 302 | 31.6 | 47.5 |
| 38 | 431 | 23.6 | 31.5 |
| 39 | 271 | 18.0 | 25.6 |
| 40 | 372 | 15.0 | 25.4 |
| 41 | 927 | 19.2 | 36.5 |
| 42 | 287 | 31.8 | 55.6 |
| 43 | 284 | 27.8 | 49.3 |
| 44 | 83 | 13.9 | 29.3 |
| 45 | 66 | 17.0 | 27.0 |
| 46 | 120 | 11.9 | 15.8 |
| 47 | 190 | 29.5 | 41.4 |
| 48 | 26 | 14.5 | 41.4 |
| 49 | 377 | 28.6 | 59.1 |
| 50 | 48 | 23.3 | 37.9 |
| 51 | NT | 40.6 | 89.9 |
| 52 | NT | 10.4 | 17.9 |
| 53 | 341 | 11.4 | 22.3 |
| 54 | NT | 67.9 | 107 |
| 55 | NT | 15.0 | 34.6 |
| 56 | 357 | 11.4 | 22.6 |
| 57 | 1068 | 10.8 | 28.7 |
| 58 | 840 | 5.1 | 13.6 |
| 59 | 226 | 4.2 | 11.2 |
| 60 | NT | NT | NT |
| 61 | NT | NT | NT |
| 62 | 348 | 11.0 | 23.6 |
| 63 | 972 | 14.1 | 38.1 |
| 64 | 1005 | 34.5 | 63.6 |
| 65 | 289 | 4.1 | 7.9 |
| 66 | 10.2 | 5.9 | 6.5 |
| 67 | 21.1 | 9.5 | 11.5 |
| 68 | 19.3 | 1.3 | 2.5 |
| 69 | 38.1 | 3.4 | 5.0 |
| 70 | 81 | 3.1 | 5.0 |
| 71 | 9.3 | 1.9 | 3.1 |
| 72 | NT | NT | NT |
| 73 | NT | NT | NT |
| 74 | 136 | 3.5 | 4.4 |
| 75 | NT | NT | NT |
| 76 | 73.2 | 2.9 | 6.4 |
| 77 | 317 | 1.6 | 4.4 |
| 78 | 41.0 | 3.2 | 3.8 |
| 79 | 32.1 | 4.2 | 6.8 |
| 80 | NT | NT | NT |
| 81 | 122 | 3.1 | 5.2 |
| 82 | 624 | 1.7 | 2.6 |
| 83 | 820 | 3.3 | 7.5 |
| 84 | 1779 | NT | 3.2 |
| 85 | 1533 | NT | 3.0 |
| 86 | 316 | 3.3 | 5.1 |
| 87 | 487 | 4.1 | 10.7 |
| 88 | 687 | 10.1 | 25.5 |
| 89 | 112 | NT | 12.8 |
| 90 | 461 | 11.9 | 35.8 |

TABLE 1-continued

Biological Test Results

| Example No. | A431 (EGFR-WT) | Ba/F3 EGFR-D770-N771ins_SVD | Ba/F3 EGFR-V769_D770insASV |
|---|---|---|---|
| 91 | 655 | 12.7 | 32.7 |
| 92 | 355 | 30.5 | 16.7 |
| 93 | 877 | 14.5 | 51.1 |
| 94 | 2330 | 1.4 | 1.9 |
| 95 | 1816 | 3.3 | 8.3 |
| 96 | NT | NT | NT |
| 97 | NT | NT | NT |
| 98 | 1531 | 2.0 | 6.3 |
| 99 | 315 | 2.8 | 6.1 |
| 100 | 225 | 4.4 | 14.8 |
| 101 | 240 | NT | 20.8 |
| 102 | 733 | 6.1 | 17.0 |
| 103 | 15.0 | 30.0 | 6.1 |
| 104 | 1186 | NT | 30.0 |
| 105 | 2500 | 12.7 | 35.0 |
| 106 | 1644 | NT | 40.9 |
| 107 | 2500 | 18.3 | NT |
| 108 | NT | NT | 29.9 |
| 109 | 159 | NT | 25.8 |
| 110 | 703 | NT | 52.6 |
| 111 | 84.6 | 1.8 | 3.4 |
| 112 | 89.3 | 1.4 | 3.6 |
| 113 | 173 | 3.9 | 11.6 |
| 114 | 26.3 | 1.1 | 3.3 |
| 115 | 23.2 | NT | 7.6 |
| 116 | 142 | 3.0 | 3.4 |
| 117 | 988 | NT | 2.9 |
| 118 | 19.1 | 2.6 | 9.8 |
| 119 | 10.2 | NT | 3.4 |
| 120 | 6.0 | NT | 7.1 |
| 121 | 44.1 | 6.5 | 16.5 |
| 122 | 63.9 | 3.8 | 6.8 |
| 123 | 20.5 | 1.6 | 2.4 |
| 124 | 104 | 2.9 | 9.1 |
| 125 | 86.5 | 2.4 | 7.8 |

Notes

"NT" is an abbreviation of "Not Tested", and means that an object has not been detected yet.

From the biological activity data of the compounds of the specific examples, the series of compounds of the present invention have a strong inhibition effect on insertion, deletion or other mutations of EGFR Exon 20 at cellular level and have high selectivity for EGFR WT.

All documents mentioned in the present invention are incorporated as references, just as each document is individually cited as a reference. In addition, it should be understood that various modifications or changes may be made by those skilled in the art after reading the above disclosure of the present invention, and these equivalent forms also fall within the scope defined by the claims appended hereto.

The invention claimed is:

1. A compound of formula (IIb) or formula (IIc), a stereoisomer or pharmaceutically acceptable salt thereof:

(IIb)

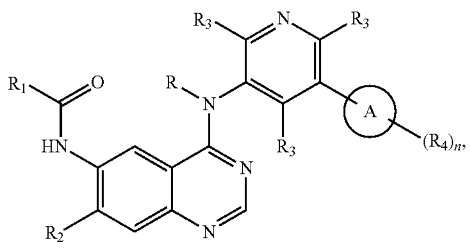

or

-continued (IIc)

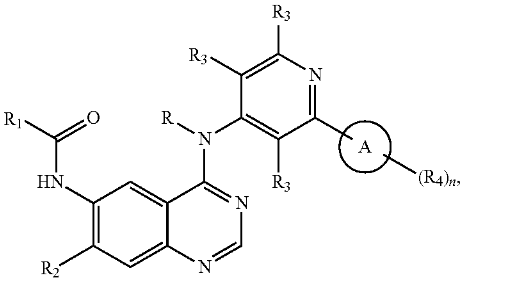

wherein ring A, together with $-(R_4)_n$, forms the following structure:

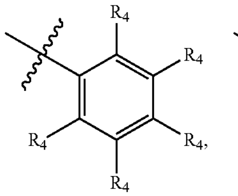

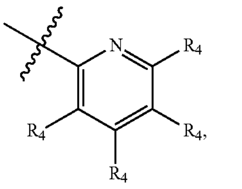

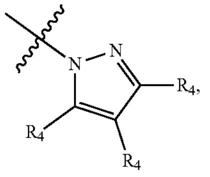

or

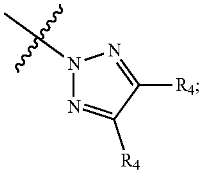

wherein each R is independently hydrogen;

each $R_1$ s independently vinyl optionally further substituted with one or more $R_1$ substituents selected from the group consisting of deuterium, fluoro, cyano, methyl, and dimethylaminomethyl;

each $R_2$ is independently selected from the group consisting of hydrogen, deuterium, fluoro, chloro, bromo, $C_{1-4}$ alkyl, $C_{2-4}$ alkynyl, 3-6 membered heterocyclyl, $-O-R_9$, and $-NR_{12}R_{13}$, the above $R_2$ groups independently optionally further substituted with one or more $R_2$ substituents selected from the group consisting of deuterium, fluoro, chloro, bromo, cyano, $C_{1-4}$ alkyl, $C_{3-6}$ cycloalkyl, 3-6 membered heterocyclyl, =O, $-O-R_9$, and $-NR_{12}R_{13}$, the above one or more $R_2$ substituent groups independently optionally further substituted with one or more $R_2$ further substituents selected from the group consisting of deuterium, fluoro, chloro, bromo, cyano, $C_{1-4}$ alkyl, $C_{1-4}$ haloalkyl, $C_{1-4}$ deuterioalkyl, $C_{3-6}$ cycloalkyl, 3-6 membered heterocyclyl, =O, $-O-R_9$, and $-NR_{12}R_{13}$;

each $R_3$ is independently selected from the group consisting of hydrogen;

each $R_4$ is independently selected from the group consisting of hydrogen, fluoro, chloro and bromo;

each $R_9$ is independently selected from the group consisting of hydrogen, deuterium, $C_{1-4}$ alkyl, $C_{2-4}$ alkenyl, $C_{3-6}$ cycloalkyl, 3-6 membered heterocyclyl, $C_{6-8}$ aryl, and 5-8 membered heteroaryl, the above $R_9$ groups independently optionally further substituted with one or more $R_9$ substituents selected from the group consisting of deuterium, halogen, hydroxy, oxo, cyano, $C_{1-4}$ alkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, and $-NR_{12}R_{13}$;

each of $R_{12}$ and $R_{13}$ is independently selected from the group consisting of hydrogen, deuterium, hydroxy, $C_{1-4}$ alkyl, $C_{2-4}$ alkenyl, $C_{2-4}$ alkynyl, $C_{3-6}$ cycloalkyl, 3-6 membered heterocyclyl, $C_{6-8}$ aryl, 5-8 membered heteroaryl, sulfinyl, sulfonyl, methylsulfonyl, isopropylsulfonyl, cyclopropylsulfonyl, p-toluenesulfonyl, aminosulfonyl, dimethylaminosulfonyl, amino, mono$C_{1-4}$ alkylamino, di$C_{1-4}$ alkylamino, and $C_{1-4}$ alkanoyl, each of the above $R_{12}/R_{13}$ groups independently optionally further substituted with one or more $R_{12}/R_{13}$ substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino, and $C_{1-4}$ alkanoyl, or, $R_{12}$ and $R_{13}$, together with the nitrogen atom to which they are directly attached, form a 4-8 membered heterocyclyl, or 5-8 membered heteroaryl, the 4-8 membered heterocyclyl or 5-8 membered heteroaryl optionally further substituted with one or more $R_{12}/R_{13}$ substituents selected from the group consisting of deuterium, halogen, hydroxy, $C_{1-4}$ alkyl, $C_{2-4}$ alkenyl, $C_{2-4}$ alkynyl, $C_{1-4}$ haloalkyl, $C_{1-4}$ deuterioalkyl, $C_{1-4}$ alkoxy, $C_{3-6}$ cycloalkyl, $C_{3-6}$ cycloalkyloxy, 3-6 membered heterocyclyl, 3-6 membered heterocyclyloxy, $C_{6-8}$ aryl, $C_{6-8}$ aryloxy, 5-8 membered heteroaryl, 5-8 membered heteroaryloxy, amino, mono$C_{1-4}$ alkylamino, di$C_{1-4}$ alkylamino, and $C_{1-4}$ alkanoyl.

2. The compound of formula (IIb) or formula (IIc), the stereoisomer or pharmaceutically acceptable salt thereof of claim 1, wherein the compound is selected from the group consisting of the following compounds:

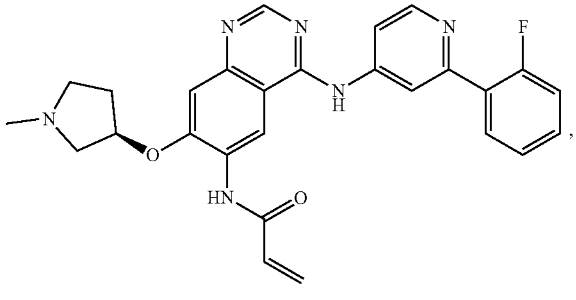
,

-continued
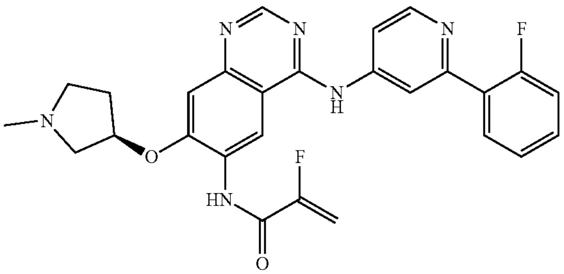
,
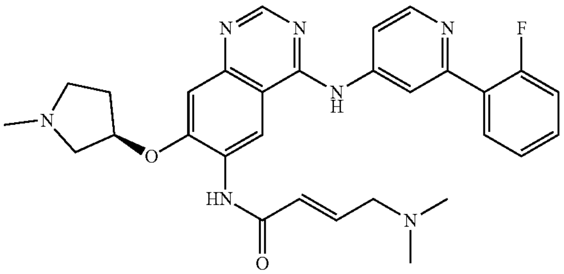
,
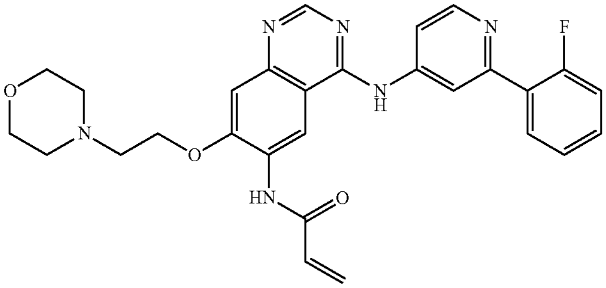
,
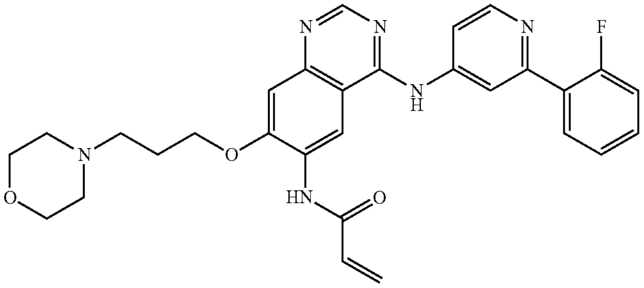
,
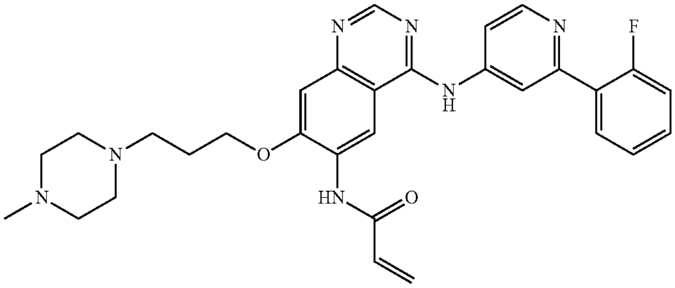
,
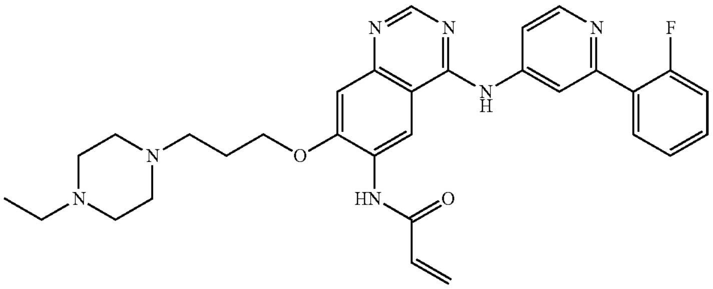
, -continued
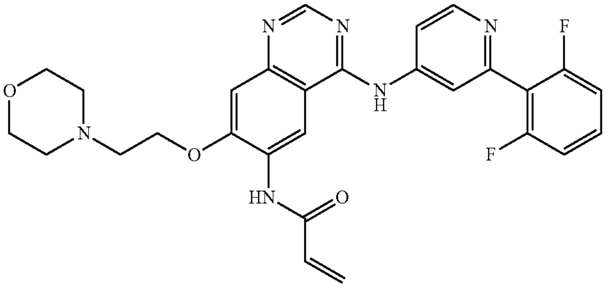
,
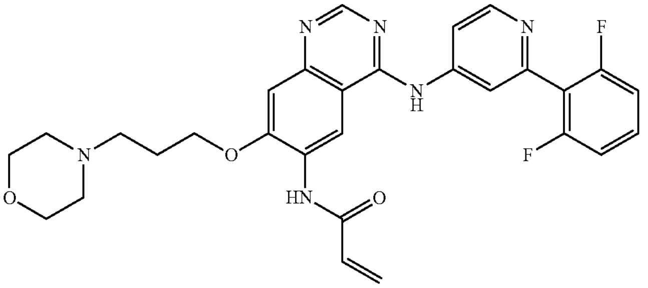
,
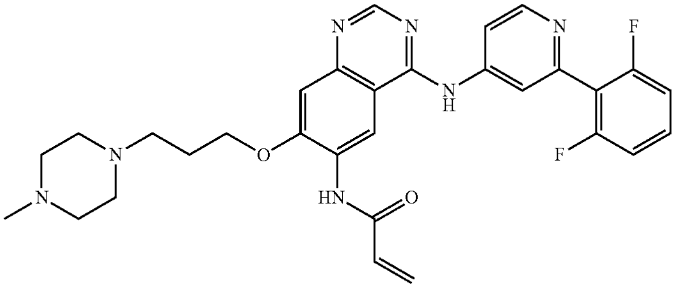
,
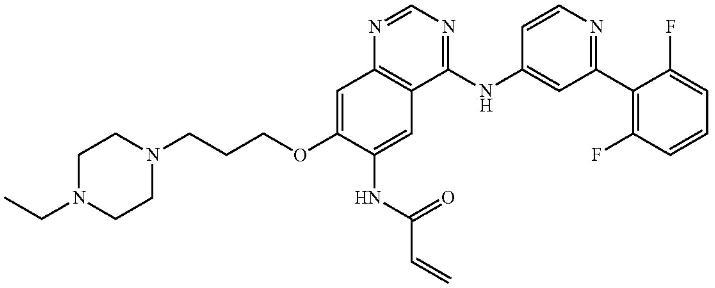
,
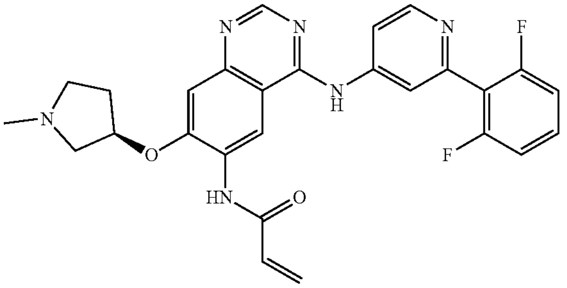
,
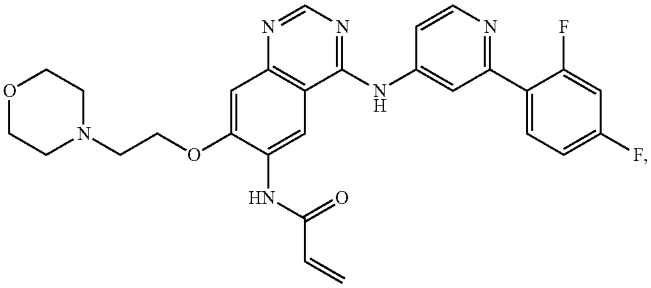
, -continued
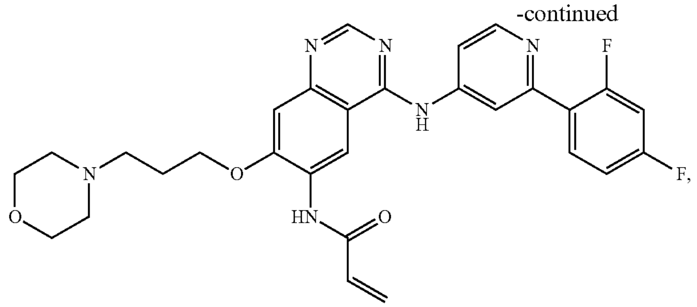
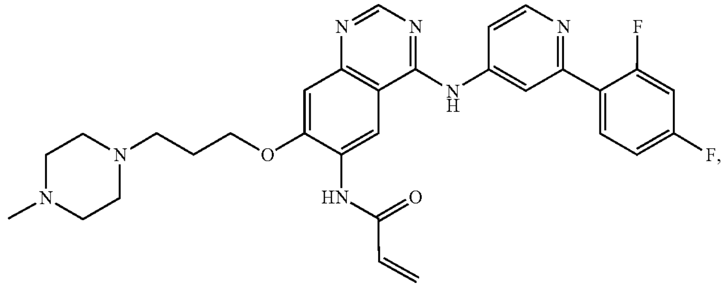
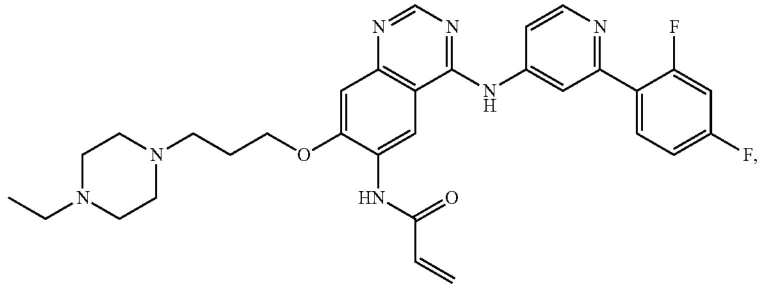
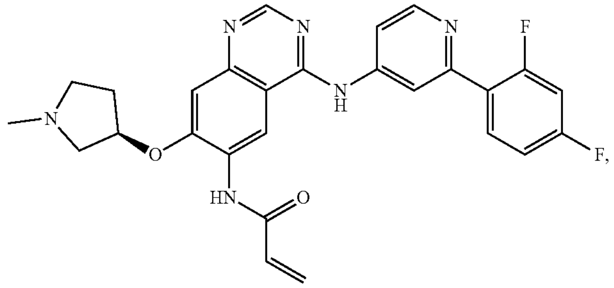
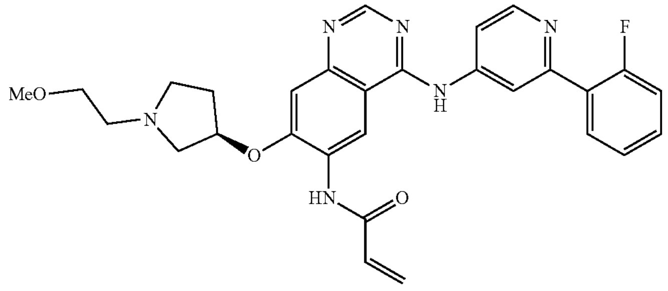
,
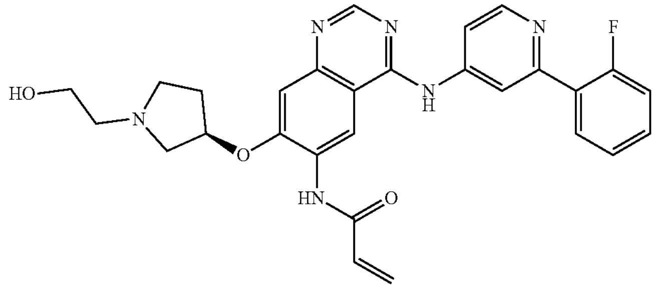
, -continued
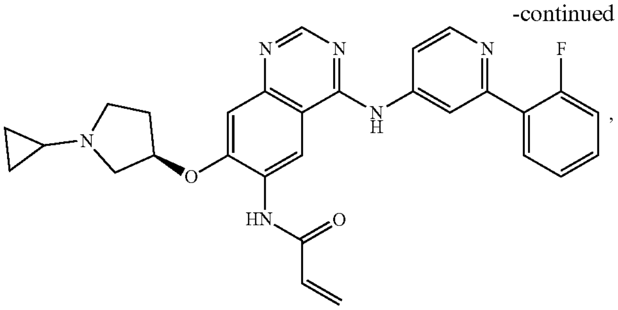
,
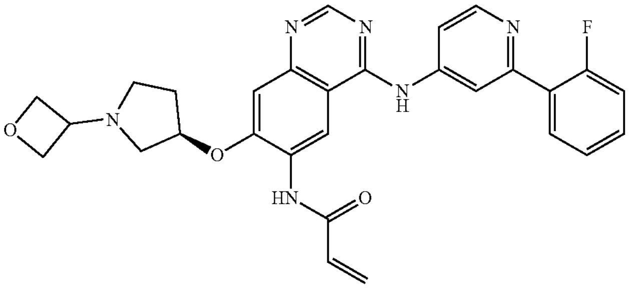
,
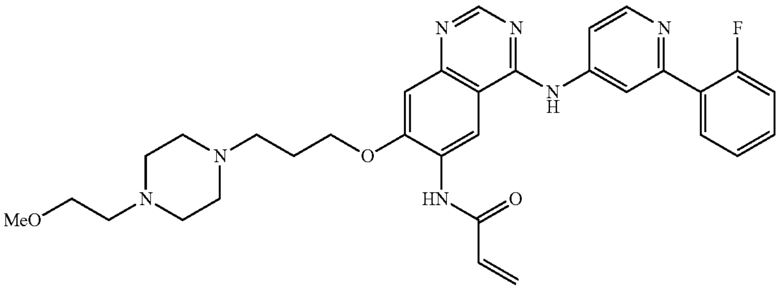
,
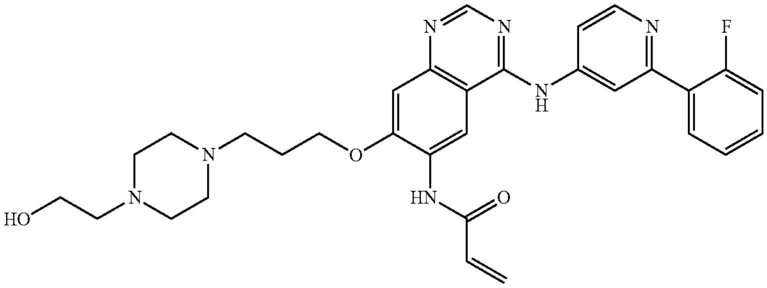
,
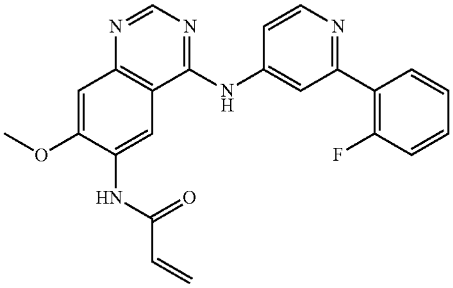
,
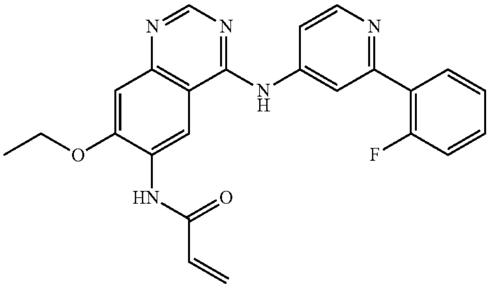
,
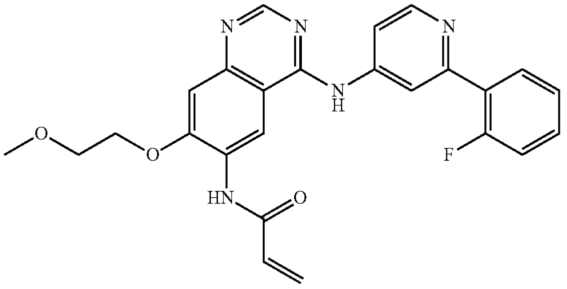
, -continued
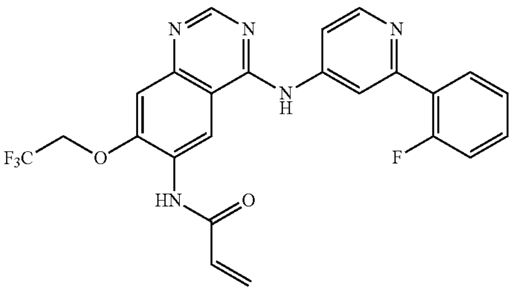
,
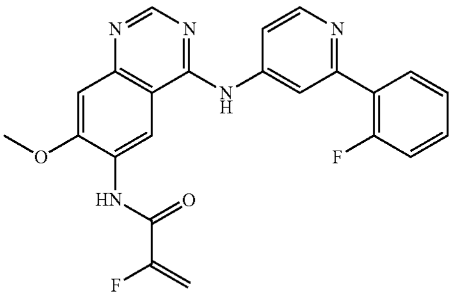
,
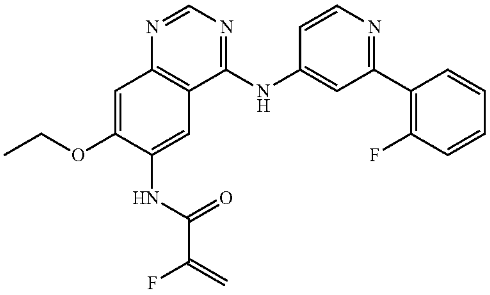
,
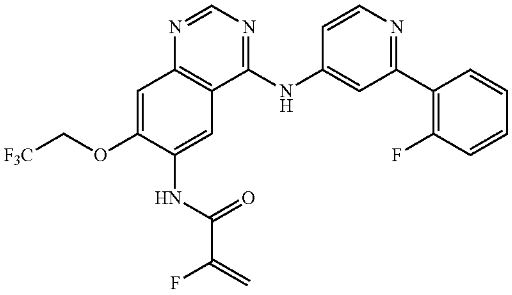
,
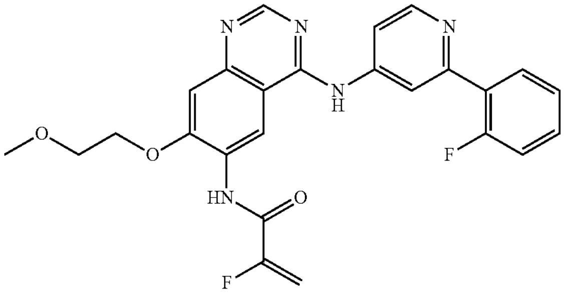
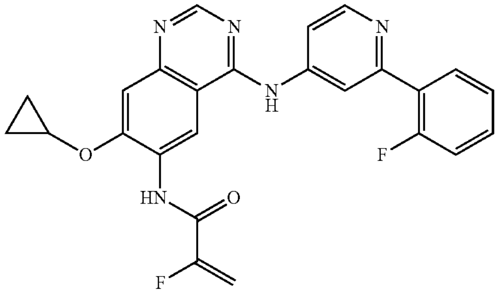
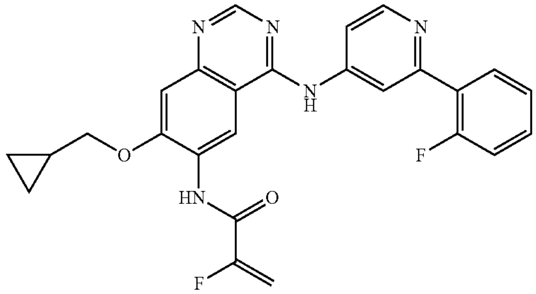
, -continued
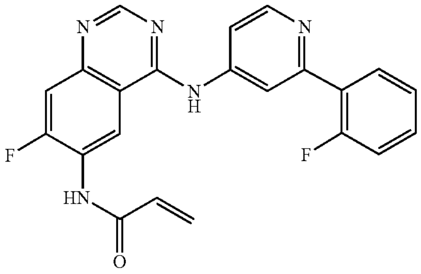
,
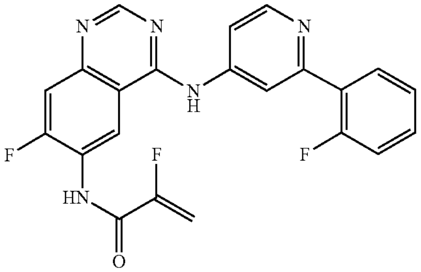
,
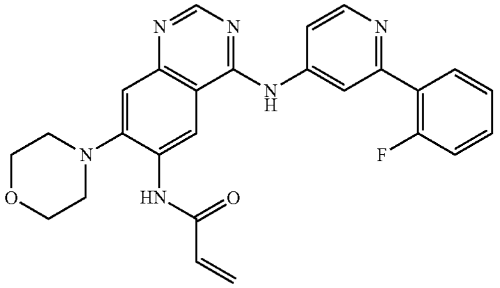
,
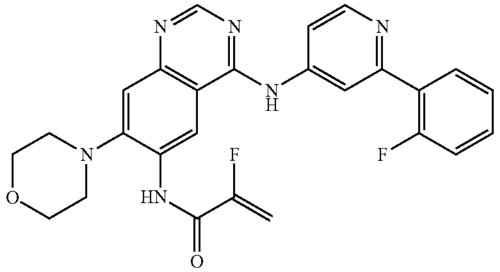
,
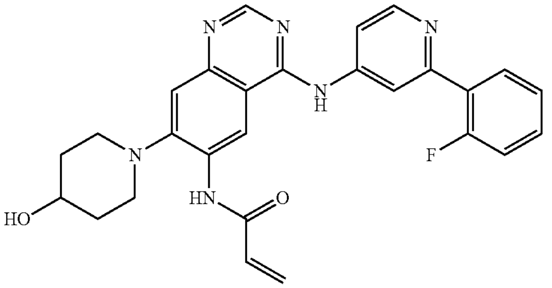
,
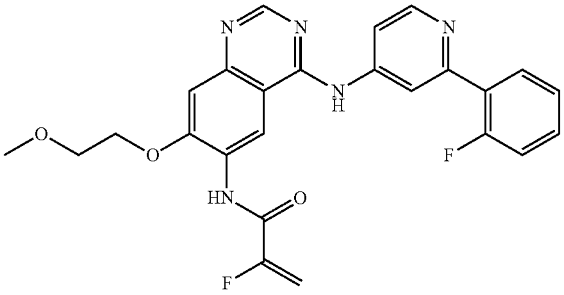
,
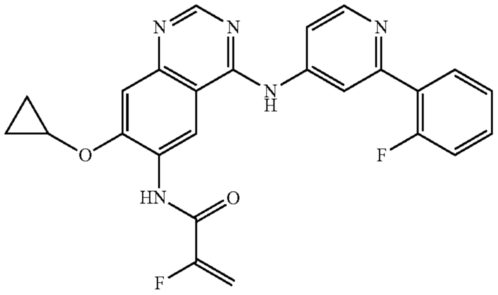
, -continued
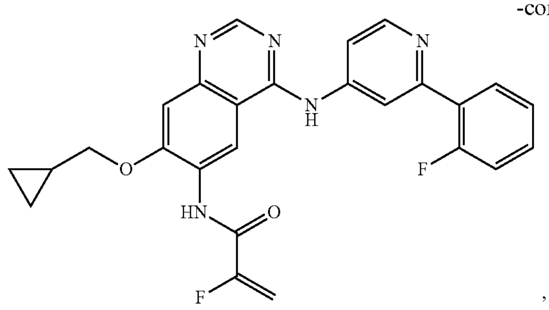
,
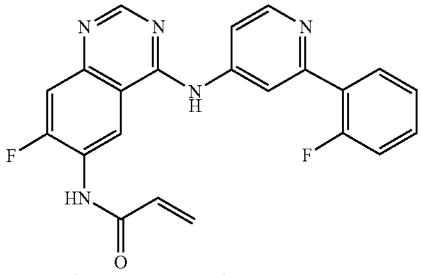
,
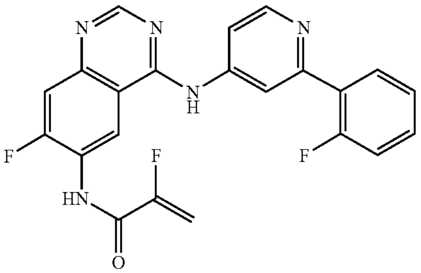
,
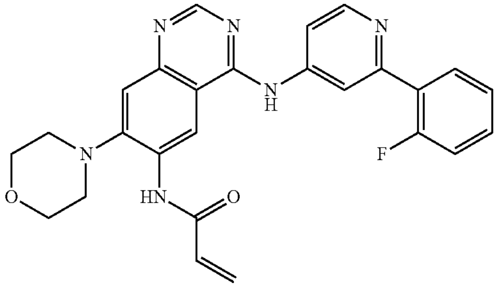
,
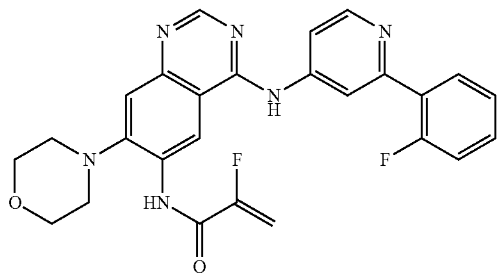
,
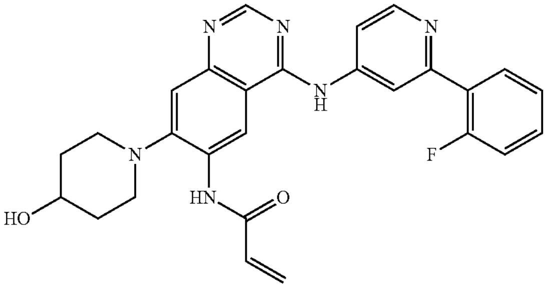
,
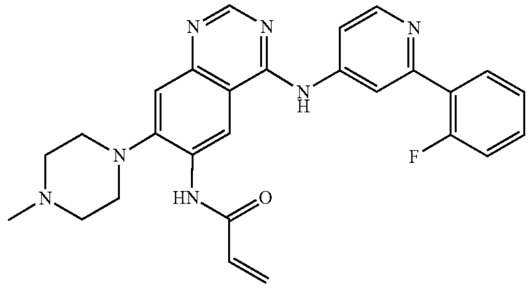
,
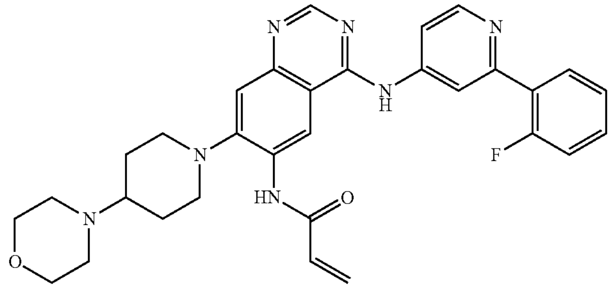
,
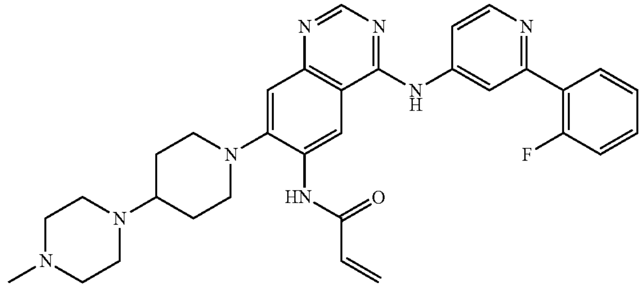
, -continued
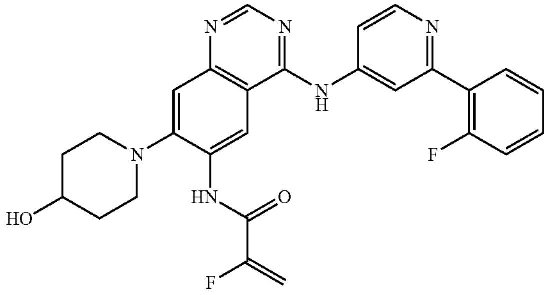,
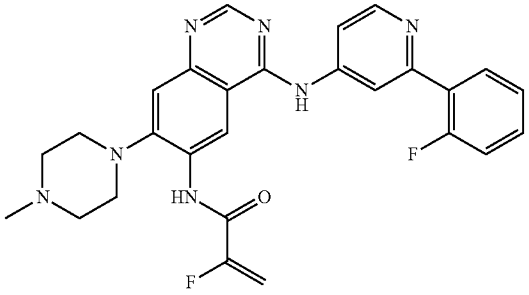,
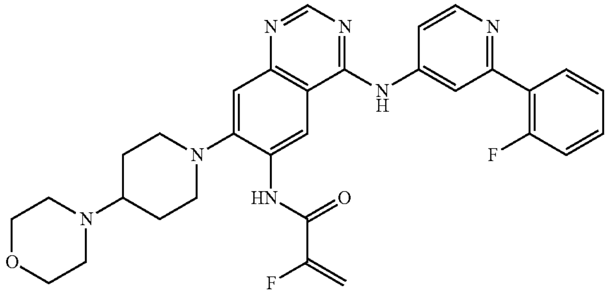,
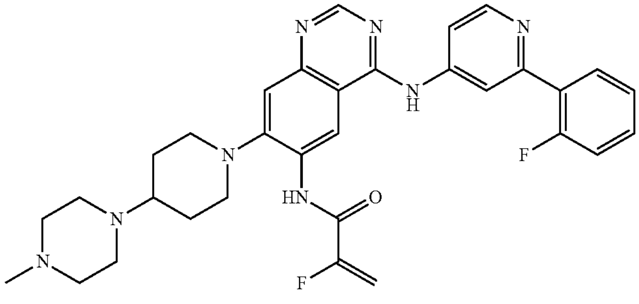,
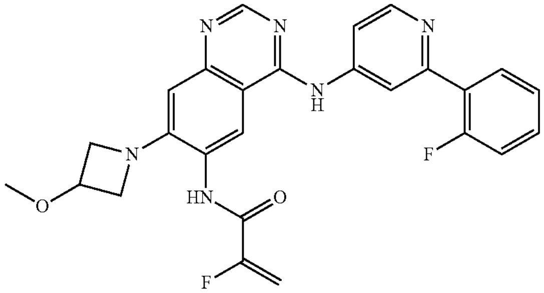,
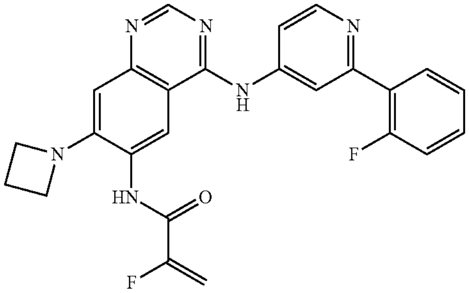, -continued
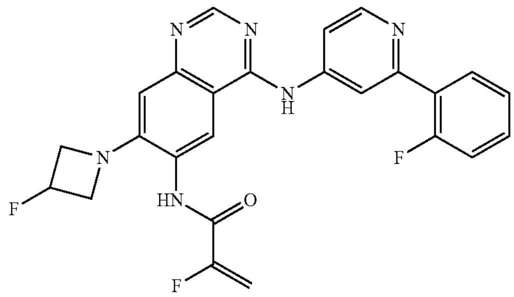
,
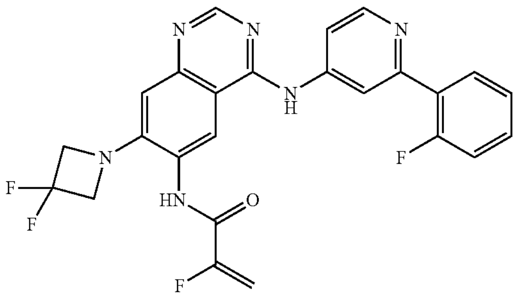
,
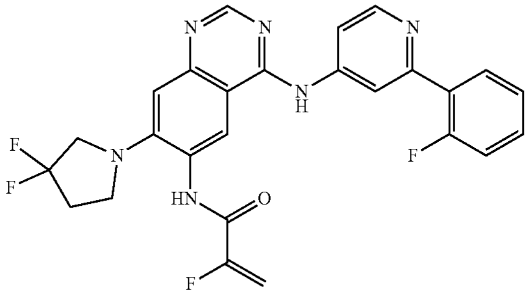
,
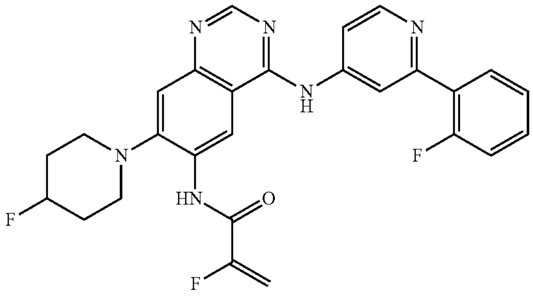
,
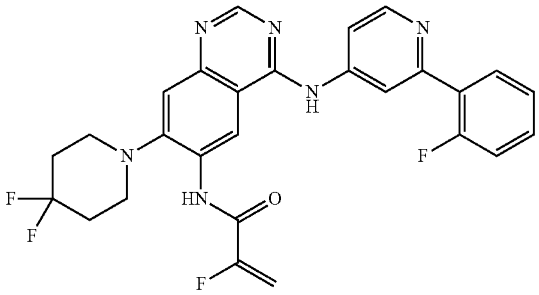
,
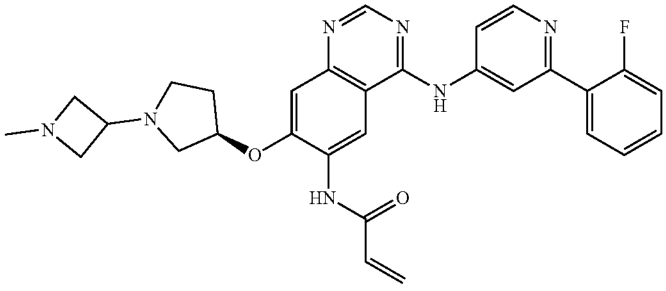
,
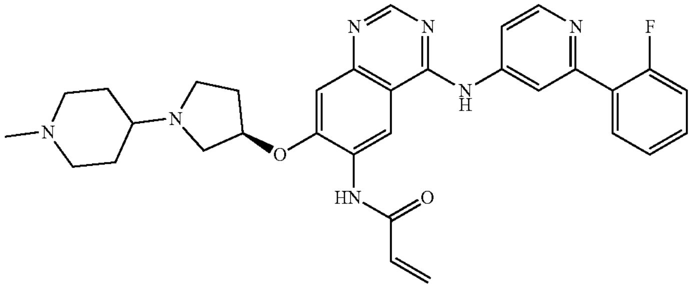
, -continued
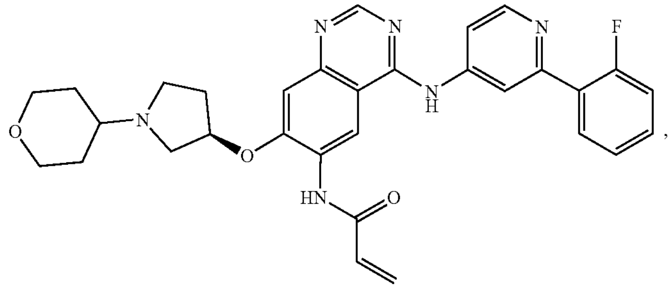
,
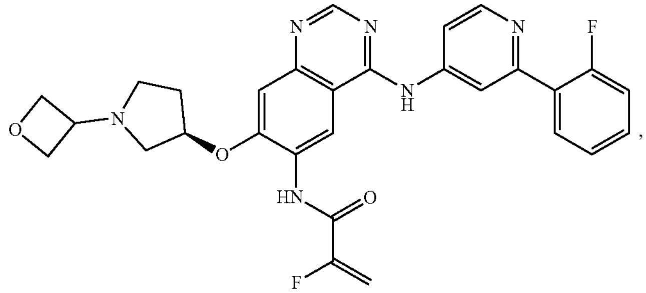
,
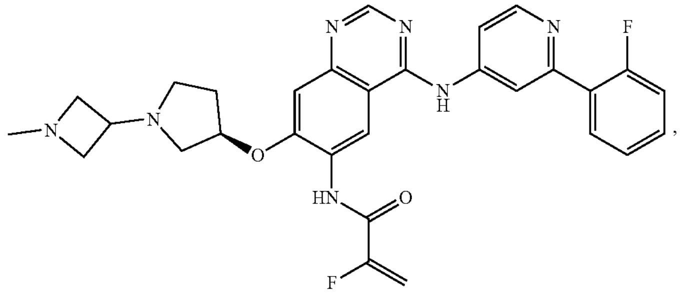
,
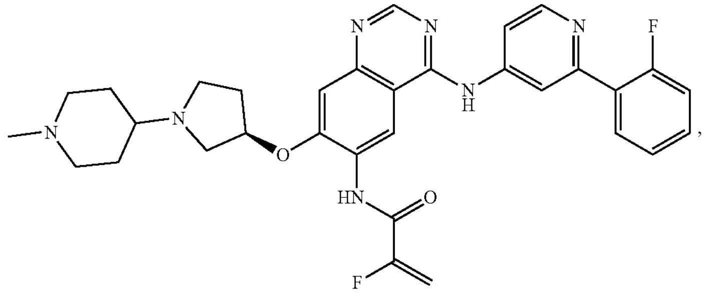
,
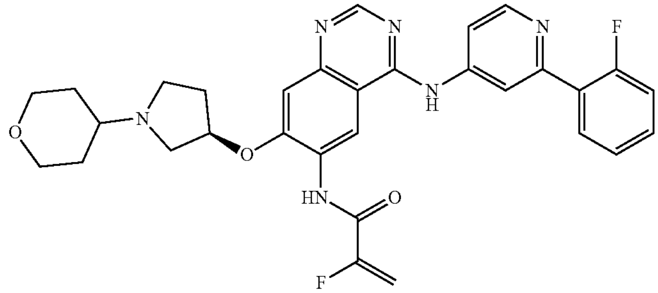
, -continued
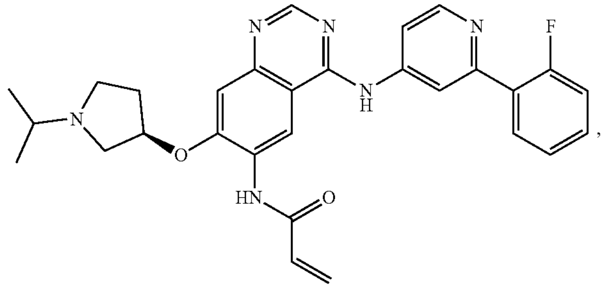
,
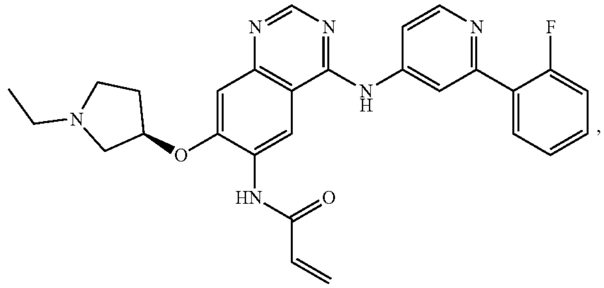
,
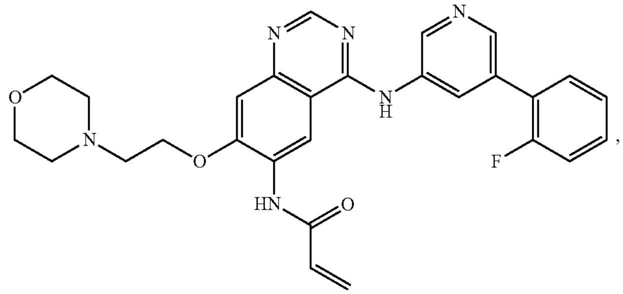
,
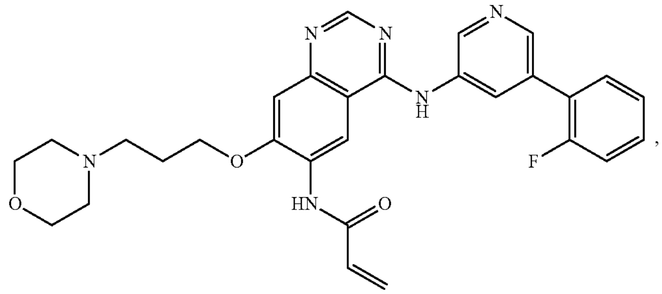
,
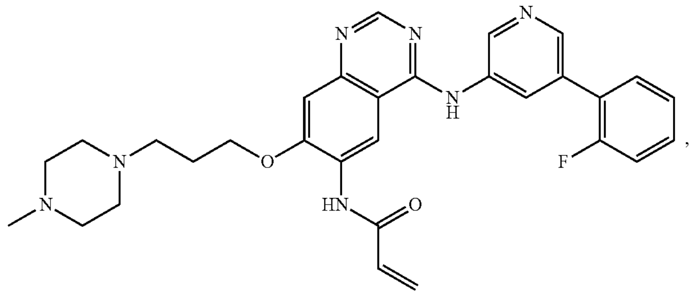
, -continued
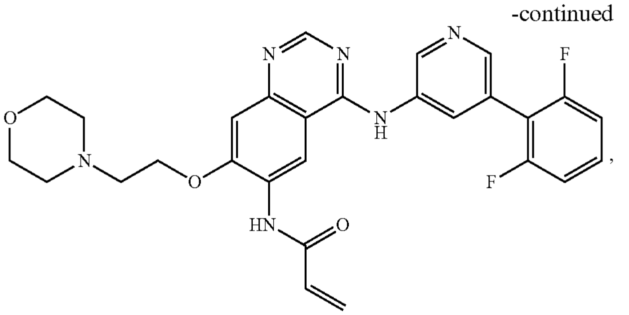
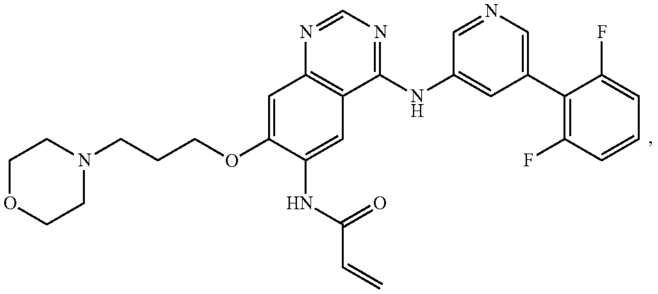
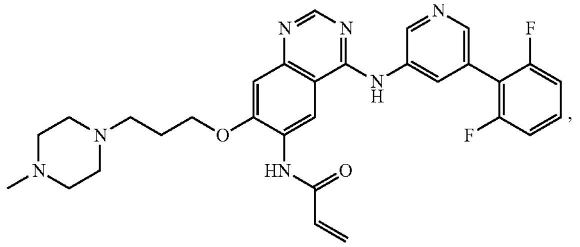
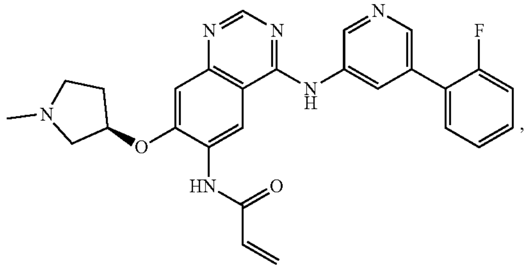
and
-continued
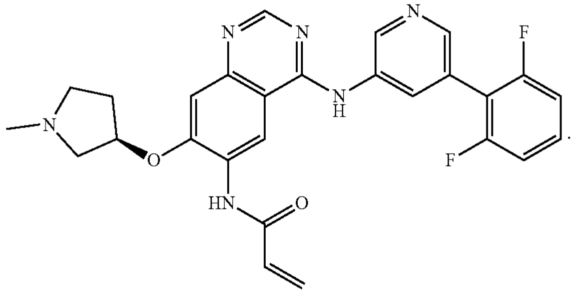
3. A pharmaceutical composition, comprising the compound of formula (IIb) or formula (IIc), the stereoisomer thereof, or the pharmaceutically acceptable salt thereof of claim 1 and a pharmaceutically acceptable carrier.
* * * * *